United States Patent
Aron et al.

(10) Patent No.: US 11,241,417 B2
(45) Date of Patent: Feb. 8, 2022

(54) COMPOSITIONS AND METHODS FOR THE TREATMENT AND PREVENTION OF NEUROLOGICAL DISORDERS

(71) Applicant: Yumanity Therapeutics, Inc., Cambridge, MA (US)

(72) Inventors: Rebecca Aron, Cambridge, MA (US); Bhaumik Pandya, Bedford, MA (US); Daniel Tardiff, Arlington, MA (US); Jeff Piotrowski, Somerville, MA (US); Matthew Lucas, Lexington, MA (US); Bertrand Le Bourdonnec, Northborough, MA (US); Kenneth Rhodes, Belmont, MA (US); Robert Scannevin, Hopkinton, MA (US)

(73) Assignee: Yumanity Therapeutics, Inc., Boston, MA (US)

( * ) Notice: Subject to any disclaimer, the term of this patent is extended or adjusted under 35 U.S.C. 154(b) by 0 days.

(21) Appl. No.: 16/448,439

(22) Filed: Jun. 21, 2019

(65) Prior Publication Data
US 2019/0388397 A1    Dec. 26, 2019

Related U.S. Application Data

(60) Provisional application No. 62/688,115, filed on Jun. 21, 2018.

(51) Int. Cl.
| | |
|---|---|
| *A61K 31/4196* | (2006.01) |
| *C12N 15/113* | (2010.01) |
| *C07K 16/40* | (2006.01) |
| *A61K 31/496* | (2006.01) |
| *A61K 31/4178* | (2006.01) |
| *A61K 31/4164* | (2006.01) |
| *A61K 31/704* | (2006.01) |
| *A61K 31/575* | (2006.01) |
| *A61K 31/506* | (2006.01) |

(52) U.S. Cl.
CPC ...... *A61K 31/4196* (2013.01); *A61K 31/4164* (2013.01); *A61K 31/4178* (2013.01); *A61K 31/496* (2013.01); *A61K 31/506* (2013.01); *A61K 31/575* (2013.01); *A61K 31/704* (2013.01); *C07K 16/40* (2013.01); *C12N 15/1137* (2013.01)

(58) Field of Classification Search
CPC .......................... C07D 233/56; A61K 31/4196
See application file for complete search history.

(56) References Cited

U.S. PATENT DOCUMENTS

| | | | |
|---|---|---|---|
| 3,321,366 A | 5/1967 | Mussell et al. | |
| 3,912,752 A | 10/1975 | Meiser et al. | |
| 4,079,062 A | 3/1978 | Van Reet et al. | |
| 4,080,462 A | 3/1978 | Brookes et al. | |
| 4,144,346 A | 3/1979 | Heeres et al. | |
| 4,404,216 A | 9/1983 | Richardson | |
| 4,416,682 A | 11/1983 | Worthington | |
| 4,432,989 A | 2/1984 | Spencer | |
| 4,439,196 A | 3/1984 | Higuchi | |
| 4,444,887 A | 4/1984 | Hoffmann | |
| 4,447,224 A | 5/1984 | DeCant, Jr. et al. | |
| 4,447,233 A | 5/1984 | Mayfield | |
| 4,464,381 A | 8/1984 | Janssen et al. | |
| 4,475,196 A | 10/1984 | La Zor | |
| 4,486,194 A | 12/1984 | Ferrara | |
| 4,487,603 A | 12/1984 | Harris | |
| 4,503,055 A | 3/1985 | Heeres et al. | |
| 4,507,140 A | 3/1985 | Sugavanam | |
| 4,596,556 A | 6/1986 | Morrow et al. | |
| 4,664,696 A | 5/1987 | Schaub | |
| 4,676,980 A | 6/1987 | Segal et al. | |

(Continued)

FOREIGN PATENT DOCUMENTS

| | | |
|---|---|---|
| EP | 0003089 A1 | 7/1979 |
| EP | 0239400 A2 | 9/1987 |

(Continued)

OTHER PUBLICATIONS

Hum et al., Journal of Pharmacology and Experimental Therapeutics, 2010, 334(3): 981-987.*
Bird et al., "Single-chain antigen-binding proteins," Science. 242(4877):423-426 (1988).
Borel et al., "Recombinant AAV as a platform for translating the therapeutic potential of RNA interference," Mol Ther. 22(4):692-701 (2014).

(Continued)

*Primary Examiner* — Rei Tsang Shiao
(74) *Attorney, Agent, or Firm* — Clark & Elbing LLP

(57) ABSTRACT

The invention provides compositions and methods for treating neurological disorders, such as amyotrophic lateral sclerosis, frontotemporal degeneration, and Alzheimer's disease, among others. Using the compositions and methods described herein, a patient having a neurological disorder, such as a neurological disorder associated with TAR-DNA binding protein (TDP)-43 aggregation, may be administered an inhibitor of cytochrome P450 (CYP450) isoform 51A1 (CYP51A1), also referred to herein as lanosterol 14-alpha demethylase, so as to treat an underlying etiology of the disorder and/or to alleviate one or more symptoms of the disease. The inhibitor of CYP51A1 may be a small molecule, anti-CYP51A1 antibody or antigen-binding fragment thereof, or a compound, such as an interfering RNA molecule, that attenuates CYP51A1 expression. Patients that may be treated using the compositions and methods described herein include those that express a mutant TDP-43 isoform containing a mutation associated with TDP-43-promoted aggregation and toxicity.

8 Claims, 9 Drawing Sheets
Specification includes a Sequence Listing.

(56) References Cited

U.S. PATENT DOCUMENTS

| | | |
|---|---|---|
| 4,716,111 A | 12/1987 | Osband et al. |
| 4,790,824 A | 12/1988 | Morrow et al. |
| 4,800,206 A | 1/1989 | Alig et al. |
| 4,816,397 A | 3/1989 | Boss et al. |
| 4,816,567 A | 3/1989 | Cabilly et al. |
| 4,940,717 A | 7/1990 | Seele et al. |
| 4,941,880 A | 7/1990 | Burns |
| 5,039,676 A | 8/1991 | Saksena et al. |
| 5,064,413 A | 11/1991 | McKinnon et al. |
| 5,116,844 A | 5/1992 | Dickinson et al. |
| 5,158,949 A | 10/1992 | Walker et al. |
| 5,225,539 A | 7/1993 | Winter |
| 5,312,335 A | 5/1994 | McKinnon et al. |
| 5,383,851 A | 1/1995 | McKinnon, Jr. et al. |
| 5,399,163 A | 3/1995 | Peterson et al. |
| 5,413,923 A | 5/1995 | Kucherlapati et al. |
| 5,496,549 A | 3/1996 | Yamazaki et al. |
| 5,530,101 A | 6/1996 | Queen et al. |
| 5,545,806 A | 8/1996 | Lonberg et al. |
| 5,569,825 A | 10/1996 | Lonberg et al. |
| 5,582,996 A | 12/1996 | Curtis |
| 5,585,089 A | 12/1996 | Queen et al. |
| 5,601,819 A | 2/1997 | Wong et al. |
| 5,625,126 A | 4/1997 | Lonberg et al. |
| 5,633,425 A | 5/1997 | Lonberg et al. |
| 5,643,759 A | 7/1997 | Pfreundschuh |
| 5,658,570 A | 8/1997 | Newman et al. |
| 5,661,016 A | 8/1997 | Lonberg et al. |
| 5,661,151 A | 8/1997 | Saksena et al. |
| 5,681,722 A | 10/1997 | Newman et al. |
| 5,693,761 A | 12/1997 | Queen et al. |
| 5,693,762 A | 12/1997 | Queen et al. |
| 5,693,780 A | 12/1997 | Newman et al. |
| 5,789,430 A | 8/1998 | Jautelat et al. |
| 5,807,706 A | 9/1998 | Carter et al. |
| 5,807,715 A | 9/1998 | Morrison et al. |
| 5,814,318 A | 9/1998 | Lonberg et al. |
| 5,821,333 A | 10/1998 | Carter et al. |
| 5,833,985 A | 11/1998 | Ball et al. |
| 5,885,793 A | 3/1999 | Griffiths et al. |
| 5,892,019 A | 4/1999 | Schlom et al. |
| 5,916,771 A | 6/1999 | Hori et al. |
| 5,932,448 A | 8/1999 | Tso et al. |
| 5,939,598 A | 8/1999 | Kucherlapati et al. |
| 5,959,083 A | 9/1999 | Bosslet et al. |
| 5,959,084 A | 9/1999 | Ring et al. |
| 5,989,530 A | 11/1999 | Lorenz et al. |
| 6,010,902 A | 1/2000 | Ledbetter et al. |
| 6,037,453 A | 3/2000 | Jardieu et al. |
| 6,060,285 A | 5/2000 | Lenz et al. |
| 6,106,833 A | 8/2000 | Ring et al. |
| 6,132,992 A | 10/2000 | Ledbetter et al. |
| 6,180,370 B1 | 1/2001 | Queen et al. |
| 6,193,967 B1 | 2/2001 | Morganelli |
| 6,210,668 B1 | 4/2001 | Lindhofer et al. |
| 6,277,877 B1 | 8/2001 | Hoover et al. |
| 6,964,859 B2 | 11/2005 | Rajbhandary et al. |
| 7,560,474 B2 | 7/2009 | Rode et al. |
| 2010/0298394 A1 | 11/2010 | Steiner et al. |
| 2011/0319459 A1* | 12/2011 | Gupta ............... A61P 25/00 514/397 |
| 2012/0172453 A1 | 7/2012 | Barres et al. |

FOREIGN PATENT DOCUMENTS

| | | |
|---|---|---|
| EP | 0519596 A1 | 12/1992 |
| EP | 0592106 A1 | 4/1994 |
| WO | WO-91/00360 A1 | 1/1991 |
| WO | WO-91/09967 A1 | 7/1991 |
| WO | WO-91/10741 A1 | 7/1991 |
| WO | WO-92/00373 A1 | 1/1992 |
| WO | WO-92/01047 A1 | 1/1992 |
| WO | WO-93/08829 A1 | 5/1993 |
| WO | WO-96/33735 A1 | 10/1996 |
| WO | WO-96/34096 A1 | 10/1996 |
| WO | WO-98/16654 A1 | 4/1998 |
| WO | WO-98/24893 A2 | 6/1998 |
| WO | WO-98/46645 A2 | 10/1998 |
| WO | WO-98/50433 A2 | 11/1998 |
| WO | WO-2010/015040 A1 | 2/2010 |
| WO | WO-2011/084714 A2 | 7/2011 |

OTHER PUBLICATIONS

Gillies et al., "High-level expression of chimeric antibodies using adapted cDNA variable region cassettes," J Immunol Methods. 125(1-2):191-202 (1989).

Ho et al., "Site-directed mutagenesis by overlap extension using the polymerase chain reaction," Gene. 77(1):51-9 (1989).

Holliger et al., ""Diabodies": small bivalent and bispecific antibody fragments," Proc Natl Acad Sci USA. 90(14):6444-8 (1993).

Hudson et al., "Engineered Antibodies," *Nat Med.* 9(1): 129-134 (2003).

Huston et al., "Protein engineering of antibody binding sites: recovery of specific activity in an antidigoxin single-chain Fv analogue produced in *Escherichia coli*," Proc Natl Acad Sci U.S.A. 85(16):5879-83 (1988).

Huttunen et al., "Prodrugs-from serendipity to rational design," Pharmacol Rev. 63(3):750-71 (2011).

International Search Report and Written Opinion for International Patent Application No. PCT/US19/38426, dated Sep. 20, 2019 (9 pages).

Jagtap et al., "Multipoint incremental motor unit number estimation versus amyotrophic lateral sclerosis functional rating scale and the medical research council sum score as an outcome measure in amyotrophic lateral sclerosis," Ann Indian Acad Neurol. 17(3):336-9 (2014).

Kabat et al., *Sequences of Proteins of Immunological Interest, Fourth Edition.* National Institutes of Health, 530-535(1987).

Klein et al., "Progress in overcoming the chain association issue in bispecific heterodimeric IgG antibodies," MAbs. 4(6):653-63 (2012).

Kontermann, "Dual targeting strategies with bispecific antibodies," MAbs. 4(2):182-97 (2012).

Lam et al., "siRNA Versus miRNA as Therapeutics for Gene Silencing," Mol Ther Nucleic Acids. 4:e252:1-20 (2015) (20 pages).

Milenic et al., "Construction, binding properties, metabolism, and tumor targeting of a single-chain Fv derived from the pancarcinoma monoclonal antibody CC49," Cancer Res. 51 (23 Pt 1):6363-71 (1991).

Milstein et al., "Hybrid Hybridomas and Their Use in Immunohistochemistry," Nature. 305(5934):537-540 (1983).

Morrison, "Transfectomas provide novel chimeric antibodies," Science. 229(4719):1202-7 (1985).

Oi et al., "Chimeric Antibodies," BioTechniques. 4(3):214-221 (1986) (8 pages).

Pantoliano et al., "Conformational stability, folding, and ligand-binding affinity of single-chain Fv immunoglobulin fragments expressed in *Escherichia coli*," Biochemistry. 30(42):10117-25 (1991).

Rao et al., "siRNA vs. shRNA: similarities and differences," Adv Drug Deliv Rev. 61(9):746-59 (2009).

Riechmann et al., "Reshaping human antibodies for therapy," Nature. 332(6162):323-7 (1988).

Suresh et al., "Bispecific monoclonal antibodies from hybrid hybridomas," Methods Enzymol. 121: 210-28(1986).

Takkinen et al., "An active single-chain antibody containing a cellulose linker domain is secreted by *Escherichia coli*.," Protein Eng. 4(7):837-41 (1991).

Traunecker et al., "Bispecific Single Chain Molecules (Janusins) Target Cytotoxic Lymphocytes on HIV Infected Cells," EMBO J. 10(12): 3655-3659 (1991).

Vig et al., "Amino acids as promoieties in prodrug design and development," Adv Drug Deliv Rev. 65(10):1370-85 (2013).

Ward et al., "Binding activities of a repertoire of single immunoglobulin variable domains secreted from *Escherichia coli*," Nature. 341(6242):544-6 (1989).

(56) References Cited

OTHER PUBLICATIONS

Yazaki et al., "A series of anti-CEA/anti-DOTA bispecific antibody formats evaluated for pretargeting: comparison of tumor uptake and blood clearance," Protein Eng Des Sel. 26(3): 187-93 (2013).

* cited by examiner

Fluconazole

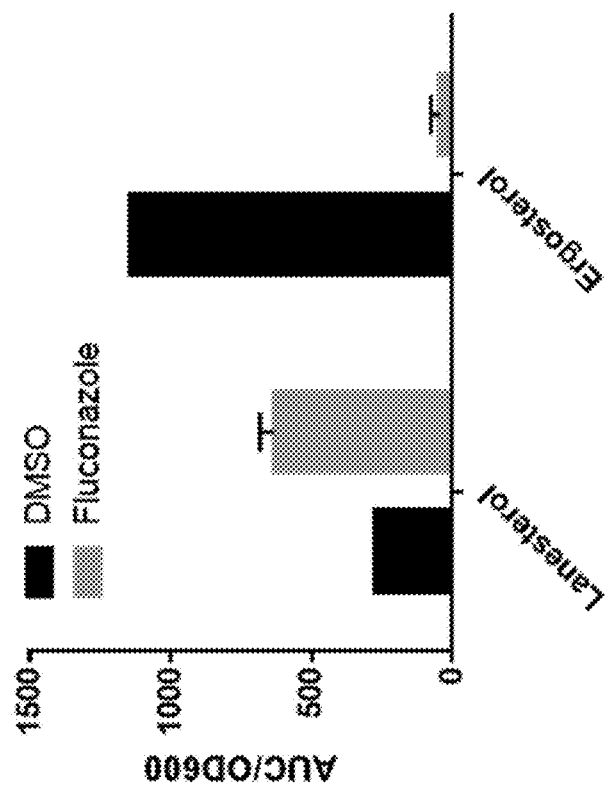

SEQUENCE LISTING

<160> NUMBER OF SEQ ID NOS: 4

<210> SEQ ID NO 1
<211> LENGTH: 503
<212> TYPE: PRT
<213> ORGANISM: Homo sapiens

<400> SEQUENCE: 1

Met Leu Leu Leu Gly Leu Leu Gln Ala Gly Ser Val Leu Gly Gln
1               5                   10                  15

Ala Met Glu Lys Val Thr Gly Gly Asn Leu Leu Ser Met Leu Leu Ile
            20                  25                  30

Ala Cys Ala Phe Thr Leu Ser Leu Val Tyr Leu Ile Arg Leu Ala Ala
                35                  40                  45

Gly His Leu Val Gln Leu Pro Ala Gly Val Lys Ser Pro Pro Tyr Ile
        50                  55                  60

Phe Ser Pro Ile Pro Phe Leu Gly His Ala Ile Ala Phe Gly Lys Ser
65                  70                  75                  80

Pro Ile Glu Phe Leu Glu Asn Ala Tyr Glu Lys Tyr Gly Pro Val Phe
                85                  90                  95

Ser Phe Thr Met Val Gly Lys Thr Phe Thr Tyr Leu Leu Gly Ser Asp
                100                 105                 110

Ala Ala Ala Leu Leu Phe Asn Ser Lys Asn Glu Asp Leu Asn Ala Glu
            115                 120                 125

Asp Val Tyr Ser Arg Leu Thr Thr Pro Val Phe Gly Lys Gly Val Ala
        130                 135                 140

Tyr Asp Val Pro Asn Pro Val Phe Leu Glu Gln Lys Lys Met Leu Lys
145                 150                 155                 160

Ser Gly Leu Asn Ile Ala His Phe Lys Gln His Val Ser Ile Ile Glu
                165                 170                 175

Lys Glu Thr Lys Glu Tyr Phe Glu Ser Trp Gly Glu Ser Gly Glu Lys
                180                 185                 190

Asn Val Phe Glu Ala Leu Ser Glu Leu Ile Ile Leu Thr Ala Ser His
            195                 200                 205

Cys Leu His Gly Lys Glu Ile Arg Ser Gln Leu Asn Glu Lys Val Ala
        210                 215                 220

Gln Leu Tyr Ala Asp Leu Asp Gly Gly Phe Ser His Ala Ala Trp Leu
225                 230                 235                 240

Leu Pro Gly Trp Leu Pro Leu Pro Ser Phe Arg Arg Arg Asp Arg Ala
                245                 250                 255

His Arg Glu Ile Lys Asp Ile Phe Tyr Lys Ala Ile Gln Lys Arg Arg
                260                 265                 270

Gln Ser Gln Glu Lys Ile Asp Ile Leu Gln Thr Leu Leu Asp Ala
            275                 280                 285

Thr Tyr Lys Asp Gly Arg Pro Leu Thr Asp Glu Val Ala Gly Met
        290                 295                 300

Leu Ile Gly Leu Leu Leu Ala Gly Gln His Thr Ser Ser Thr Thr Ser
305                 310                 315                 320

Ala Trp Met Gly Phe Phe Leu Ala Arg Asp Lys Thr Leu Gln Lys Lys
                325                 330                 335

Cys Tyr Leu Glu Gln Lys Thr Val Cys Gly Glu Asn Leu Pro Pro Leu
            340                 345                 350

Thr Tyr Asp Gln Leu Lys Asp Leu Asn Leu Leu Asp Arg Cys Ile Lys
        355                 360                 365

```
Glu Thr Leu Arg Leu Arg Pro Pro Ile Met Ile Met Arg Met Ala
    370                 375                 380
Arg Thr Pro Gln Thr Val Ala Gly Tyr Thr Ile Pro Pro Gly His Gln
385                 390                 395                 400
Val Cys Val Ser Pro Thr Val Asn Gln Arg Leu Lys Asp Ser Trp Val
                405                 410                 415
Glu Arg Leu Asp Phe Asn Pro Asp Arg Tyr Leu Gln Asp Asn Pro Ala
            420                 425                 430
Ser Gly Glu Lys Phe Ala Tyr Val Pro Phe Gly Ala Gly Arg His Arg
        435                 440                 445
Cys Ile Gly Glu Asn Phe Ala Tyr Val Gln Ile Lys Thr Ile Trp Ser
    450                 455                 460
Thr Met Leu Arg Leu Tyr Glu Phe Asp Leu Ile Asp Gly Tyr Phe Pro
465                 470                 475                 480
Thr Val Asn Tyr Thr Thr Met Ile His Thr Pro Glu Asn Pro Val Ile
                485                 490                 495
Arg Tyr Lys Arg Arg Ser Lys
            500

<210> SEQ ID NO 2
<211> LENGTH: 3208
<212> TYPE: RNA
<213> ORGANISM: Homo sapiens

<400> SEQUENCE: 2
gugacgcacg ggguggcgcg cgugggaccc gaggggugggg gcuggguuua guaggagacc     60
uggggcaagg cccccugugg acgaccaucu gccagcuucu cucguuccgu cgauugggag    120
gagcgguggc gaccucggcc uucaguguuu ccgacggagu gaauggcggc ggcggcuggg    180
augcugcugc ugggcuugcu gcaggcgggu ggguucggugc ugggccaggc gauggagaag    240
gugacaggcg gcaaccucuu ugccaugcug cugaucgccu cgccuucac ccucagccug     300
gucuaccuga uccgucuggc cgccggccac cugguccagc ugcccgcagg ggugaaaagu    360
ccuccauaca uuuucucccc aauuccauuc cuugggcaug ccauagcauu ugggaaaagu    420
ccaauugaau uucuagaaaa ugcauaugag aaguauggac cuguauuuag uuuuaccaug    480
guaggcaaga cauuuacuua ccuucugggg agugaugcug cugcacugcu uuuaauagu    540
aaaaaugaag accugaaugc agaagaugu uacagucgcc ugcaacacc uguguuuggg    600
aagggaguug cauacgaugu gccuaaucca guuucuugg agcagaagaa aauguuaaaa    660
aguggccuua acauagccca cuuuaaacag cauguuucua aauugaaaa agaaacaaag    720
gaauacuuug agaguugggg agaaagugga gaaaaaaaug uguuugaagc ucuuucugag    780
cucauaauuu uaacagcuag ccauuguuug cauggaaagg aaaucagaag ucaacucaau    840
gaaaagguag cacagcugua ugcagauuug gauggagguu cagccaugc agccuggcuc    900
uuaccagguu ggcugccuuu gccuaguuuc agacgcaggg acagagcuca ucggaaauc    960
aaggauauuu ucuauaaggc aauccagaaa cgcagacagu cucaagaaaa aauugaugac   1020
auucuccaaa cuuuacuaga ugcuacauac aaggaugggc guccuuugac ugaugaugaa   1080
guagcaggga ugcuuauugg auuacucuug gcagggcagc auacauccuc aacuacuagu   1140
gcuuggaugg gcuucuuuuu ggccagagac aaaacacuuc aaaaaaaaug uuauuagaa    1200
cagaaaacag ucuguggaga gaaucugccu ccuuuaacuu augaccagcu caaggaucua   1260
aauuuacuug aucgcuguau aaaagaaaca uuaagacuua gaccuccuau aaugaucaug   1320
```

```
augagaaugg ccagaacucc ucagacugug gcagggua ua ccauuccucc aggacaucag    1380
guguguguuu cucccacugu caaucaaaga cuuaaagacu caugggua ga acgccuggac    1440 uuuaauccug aucgcuacuu acaggauaac ccagcaucag gggaaaaguu ugccauguag    1500
ccauuuggag cugggcguca ucguuguauu ggggaaaauu uugccuaugu caaauuaag     1560 acaauuuggu ccacuaugcu ucguuuauau gaauuugauc ucauugaugg auacuuuccc    1620
acugugaauu auacaacuau gauucacacc ccugaaaacc cagguauccg uuacaaacga    1680
agaucaaaau gaaaagguu gcaaggaacg aauauaugug auuaucacug uaagccacaa     1740
aggcauucga agagaaugaa guguacaaaa caacucuugu aguuuacugu uuuuuuaagu    1800
guguaauucu aaaagccagu uuaugauuua ggauuuuguu aacugaaugg uucuaucaaa    1860
uauaauagca uuugaaacau uuucuaauag uuaugauacu uaacaugug cuuucaggaa     1920 guuccuuggu gaaacaauug uugaggggg aucuagguaa uggcagauu cuaaauaaua      1980 uaauuuccag auaguaauuu aagagacu caucgcucuu gccaaauaag uucaggguau      2040 ucaaucuug gacuaguccu gcaagguaua aagaauaaaa aucccaguga gauacuugga    2100
aaccacaguu uauuauuauu uaucggggca auuaugugu gugugaggau ggaaggguag    2160
ggaauaaucg aacaucuaaa gccuugaaua agaauacu aauuguuuug guaugaugau      2220
acucagaaau ggagauauua uaggaaaaag aaauccuuug gaauuuuaac uaaaaucacu    2280 gcaauggga aauaagaga uccaggacca uauuugauaa gaguuccuaa aaauaauga      2340 auuauuaaug cuaaagacug cucaugaug uugaucuaau uacuaaauaa uuacauauuu    2400
auuuaccuga uaaaauaugua ucuaguucua caaggucaca uuuaugugga aguccaaagu  2460
caaguccuua ggggauaauu uuguuuggc ucaguuguuc ccugcuuccu uuuuuuuuu     2520 uuuuuuuga gauggagucu cgcucuguug cccaggcugg agugcagugg ucgaucuca     2580 gcucacugca uccucugccu cccggguuca agcaauucuc ugccucagcc ucccaaguag   2640
uugggauuac aggcaccugc caccaugccu ggcuaauuuu uuguauuuu aguagagacg    2700 ggguuucac uauguuggcu aggcuggucu ugaacuccug accucgugau ccacccgccu    2760
uggccuccca aagugcuggg auuacaggca ugagccaccg caccuggccu ucccugcuuc   2820
cucucuagaa uccauuuagg gauguuuguu acuacucaua uugauuaaaa caguuaacaa   2880
acuuuuuucu uuuuaaaaug ugagaucagu gaacucuggu uuuaagauaa ucugaaacaa   2940
gguccuuggg aguaauaaaa uuggucacau ucuguaaagc acauucuguu uaggaaucaa   3000
cuuaucucaa auuguaacuc ggggccuaac uauaugagau ggcugaaaaa auaccacauc   3060
gucuguuuuc acuaggugau gccaaaauau uuugcuuuau guauauuaca guucuuuuua   3120
aaacacugga agacucaugu uaaacucuaa uugugaaggc agaaucucug cuaauuuuuc   3180
agauuaaaau ucucuuugaa aaaauaca                                      3208
```

<210> SEQ ID NO 3
<211> LENGTH: 414
<212> TYPE: PRT
<213> ORGANISM: Homo sapiens

<400> SEQUENCE: 3

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser

```
            35                  40                  45
Gln Cys Met Arg Gly Val Arg Leu Val Glu Gly Ile Leu His Ala Pro
 50                  55                  60

Asp Ala Gly Trp Gly Asn Leu Val Tyr Val Asn Tyr Pro Lys Asp
 65                  70                  75                  80

Asn Lys Arg Lys Met Asp Glu Thr Asp Ala Ser Ser Ala Val Lys Val
                 85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
            115                 120                 125

Glu Val Leu Met Val Gln Val Lys Lys Asp Leu Lys Thr Gly His Ser
            130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
            195                 200                 205

Glu Phe Phe Ser Gln Tyr Gly Asp Val Met Asp Val Phe Ile Pro Lys
            210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
            275                 280                 285

Phe Gly Asn Ser Arg Gly Gly Gly Ala Gly Leu Gly Asn Asn Gln Gly
            290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
            355                 360                 365

Ser Gly Asn Asn Ser Tyr Ser Gly Ser Asn Ser Gly Ala Ala Ile Gly
            370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 4
<211> LENGTH: 4236
<212> TYPE: RNA
<213> ORGANISM: Homo sapiens

<400> SEQUENCE: 4
```

```
ggugggcggg gggaggaggc ggcccuagcg ccauuuugug ggagcgaagc gguggcuggg    60
cugcgcuugg guccgucgcu gcuucggugu cccugucggg cucccagca gcggccuagc   120 gggaaaagua aaagaugucu gaauauauuc ggguaaccga agaugagaac gaugagccca   180
uugaaauacc aucggaagac gaugggacgg ugcugcucuc cacgguuaca gcccaguuuc   240
caggggcgug ugggcuucgc uacaggaauc cagugucuca guguaugaga ggugucccggc  300 ugguagaagg aauucugcau gccccagaug cuggcugggg aaaucgggug uauguuguca   360
acuauccaaa agauaacaaa agaaaaaugg augagacaga ugcuucauca gcagugaaag   420
ugaaaagagc aguccagaaa acauccgauu aaauaguguu gggucuccca uggaaaacaa   480
ccgaacagga ccugaaagag uauuuuagua ccuuuggaga aguucuuaug gugcaggauca  540 agaaagaucu uaagacuggu cauucaaagg gguuuggcuu uguucguuuu acggaauaug   600
aaacacaagu gaaaguaaug ucacagcgac auaugauaga uggacgaugg ugugacugca   660
aacuuccuaa uucuaagcaa agccaagaug agccuuugag aagcagaaaa uguuuugugg   720
ggcgcuguac agaggacaug acugaggaug agcugcggga guucuucucu caguacgggg   780
augugaugga ugucuucauc cccaagccau ucagggccuu ugccuuuguu acauuugcag   840
augaucagau ugcgcagucu cuuugguggag aggacuugaa cauuaaagga aucagcguuc  900
auauauccaa ugccgaaccu aagcacaaua gcaauagaca guuagaaaga aguggaagau   960
uuggugguaa uccaggugggc uuuggaauc agguggauu ugguauagc agagggggug  1020 gagcugguuu gggaaacaau caaggaguaa auaugggugg ugggaugaac uuuggugcgu  1080
ucagcauuaa uccagccaug auggcugccg cccaggcagc acuacagagc aguugggua   1140 ugaugggcau guuagccagc cagcagaacc agucaggccc aucggguaau aaccaaaacc  1200
aaggcaacau gcagagggag ccaaaccagg ccuucguuc uggaaauaac ucuuauagug  1260
gcucuaauuc uggugcagca auugguuggg gaucagcauc caaugcaggg ucgggcagug  1320
guuuuaaugg aggcuuuggc ucaagcaugg auucuaaguc uucuggcugg ggaauguaga  1380
cagugggguu guggugguu gguauagaau ggugggaauu caaauuuuuc uaaacucaug  1440
guaaguauau uguaaaauac auauguacua agaauuuuca aaauuggugu guucagugug  1500
gaguauauuc agcaguauuu uugacauuuu ucuuagaaaa aggaagagc uaaggaauu  1560 uuauaaguuu uguuacauga aagguugaaa auugagugg uugaaaguga acugcuguuu  1620
gccugauugg uaaccaaca cacuacaauu gauaucaaaa gguucccu guaauauuuu  1680 aucccuggac uugucaagug aaucuuugc auguucaaaa cggaaaccau ugauuagaac  1740
uacauucuuu accccuuguu uuaauuugaa ccccaccaua uggauuuuuu ccuuaagaa  1800 aaucuccuuu uaggagauca uggugucaca guguuugguu cuuuuguuuu guuuuuuaac  1860
acuugucucc ccucauacac aaaaguacaa uaugaagccu ucauuaauc ucugcaguuc  1920 aucucauuuc aaauguuuau ggaagaagca cuucauugaa aguagugcug uaaauauucu  1980
gccauaggaa uacugucuac augcuuucuc auucaagaau cgucaucac gcaucacagg  2040 ccgcgucuuu gacggugggu gucccauuuu uauccgcuac ucuuuauuuc auggagucgu  2100
aucaacgcua ugaacgcaag gcugugauau ggaaccagaa ggcugucuga acuuuugaaa  2160
ccuugugugg gaugauggu ggugccgagg caugaaaggc uaguaugagc gagaaaagga  2220
gagagcgcgu gcagagacuu ggguggugcau aauggauauu uuuaacuug gcgagaugug  2280 ucucucaauc cugugggcuuu ggugagagag ugucagaga gcaaugauag caaauaaugu  2340
acgaauguuu uuugcauuca aaggacaucc acaucuguug gaagacuuuu aaguugaguuu  2400
```

-continued

```
uuguucuuag auaacccaca uuagaugaau uguuaagug aaaugauacu uguacucccc    2460
cuaccccuuu gucaacugcu gugaaugcug uauggugugu guucucuucu guuacugaua    2520
uguaagugug gcaugugaa cugaagcuga ugggcugaga acauggacug agcuuguggu    2580
gugcuuugca ggaggacuug aagcagaguu caccagugag cucaggguc ucaaagaagg    2640 guggaaguuc uaaugucugu uagcuaccca uaagaaugcu guuugcugca guucugguc    2700 cugugcuugg augcuuuuua uaagaguugu cauguugga aauucuuaaa uaaaacugau    2760
uuaaauaaua ugugucuuug uuuugcagcc cugaaugcaa agaauucaua gcaguuaauu    2820
ccccuuuuuu gacccuuuug agauggaacu uucauaaagu uucuuggcag uaguuuauuu    2880
ugcuucaaau aaacuuauuu gaaaaguugu cucaagucaa auggauucau caccugucau    2940 gcaugacac cugauaccca gacuuaauug guauuuguuc uugcauuggc caaagugaaa    3000 auuuuuuuu uucuuuugaa aucaguuuu gaauaagucu ggugaccgc accuaaaaug      3060 guaagcagua ccuccggcu uuucuuagu gccucugugc auuuuggguga guucuauuu      3120 acauggccug uguaaaucuc cauugggaag ucaugccuuc uaaaaagauu cuuauuuggg    3180 ggaguggca aaauguugau uauuucuaa ugcuuguag caaagcauau caauugaaaa      3240
gggaauauca gcaccuuccu aguuugggau uugaaagug gaauuaauug caguagggau     3300
aaaguagaag aaaccacaaa uuaucuugug ccugaaaucc auuaagaggc cugauagcuu    3360
uaagaauuag gguggguugu cugucuggaa uguuaagug gaaugggcuu guccuccag     3420 gaggugggg aauguggua cauugaauac aguugaauaa aaucgcuuac aaaacucaca     3480
cucucacaau gcauuguuaa guauguaaaa gcaauaacau ugauucucug uuguacuuuu    3540
uuguaacuaa uucugugaga guugagcuca uuuucuaguu ggaagaaugu gauauuuguu    3600
guguugguag uuuaccuaau gcccuuaccu aauuagauua ugauaaauag guuugucauu    3660
uugcaaguua cauaaacauu uaucaaugaa gucauccuuu agacuuguaa ucgccacauu    3720
guuucauuau ucaguuuccu cuguaagggg aucugaguu guuuuaauuu uuuuuuucug    3780
caucugaauc ugcaugauuu ccaaacccug uaccaucuga auuugcauu uuagcacuug    3840 cacuauuacu cagcagcagu aacauggua acauuaaaau ggacucggg gaccuccaaa    3900 gacuaaacug acaagccuuc aaggagccca gggguaaguu aacuugucaa cggcaugguu    3960
uaaucccuuc uuuacacuug uguaaauuuc aguuacuggu cauagaaggc uuucaauguu    4020
gaguggccuu uuauuaacau guuuaggua cugcauagau acggguauuu auuuacccu     4080 aagaagauuu ugaaguuuaa aaguacuuaa acuauuggc aaagauuugu uuuuaaaau    4140 cuauuugguc aaucuaaaug cauucauucu aaaaauuuu uugaaccaga uaaauaaaau    4200 uuuuuuuga caccacaaaa aaaaaaaaaa aaaaaa                               4236
```

COMPOSITIONS AND METHODS FOR THE TREATMENT AND PREVENTION OF NEUROLOGICAL DISORDERS

SEQUENCE LISTING

The instant application contains a Sequence Listing which has been submitted electronically in ASCII format and is hereby incorporated by reference in its entirety. Said ASCII copy, created on Jun. 19, 2019, is named 51061-029002_Sequence_Listing_6.19.19_ST25 and is 18,129 bytes in size.

FIELD OF THE INVENTION

The invention relates to the field of therapeutic treatment of neurological disorders in patients, such as human patients.

BACKGROUND OF THE INVENTION

Amyotrophic lateral sclerosis (ALS), also known as Lou Gehrig's disease, is an aggressive, debilitating neurological disorder in which affected patients succumb within 2 to 5 years after diagnosis. ALS presents with heterogeneous clinical features but has a common underlying pathology of motor neuron loss that limits the central nervous system's ability to effectively regulate voluntary and involuntary muscle activity. Additionally, without neuronal trophic support muscles being to atrophy, further exacerbating motor deterioration. Cellular and tissue degeneration results in motor impairment such as fasciculations and weakening in the arms, legs and neck, difficulty swallowing, slurred speech and ultimately failure of the diaphragm muscles that control breathing. There remains a need for a treatment paradigm for ALS, as well as various other neurological disorders.

SUMMARY OF THE INVENTION

The present disclosure relates to compositions and methods for treating neurological disorders, such as amyotrophic lateral sclerosis, among others, including neuromuscular disorders and various other neurological conditions. Using the compositions and methods described herein, a patient having a neurological disorder, such as amyotrophic lateral sclerosis, frontotemporal degeneration (also referred to as frontotemporal lobar degeneration and frontotemporal dementia), Alzheimer's disease, Parkinson's disease, dementia with Lewy Bodies, corticobasal degeneration, progressive supranuclear palsy, dementia parkinsonism ALS complex of Guam, Huntington's disease, Inclusion body myopathy with early-onset Paget disease and frontotemporal dementia (IBMPFD), sporadic inclusion body myositis, myofibrillar myopathy, dementia pugilistica, chronic traumatic encephalopathy, Alexander disease, or hereditary inclusion body myopathy may be administered an inhibitor of cytochrome P450 (CYP450) isoform 51A1 (CYP51A1), also referred to herein as lanosterol 14-alpha demethylase, so as to treat an underlying etiology of the disorder and/or to alleviate one or more symptoms of the disease.

The inhibitor of CYP51A1 may be, e.g., a small molecule, such as LEK-935, CP-320626, itraconazole, posaconazole, cyproconazole, voriconazole, fluconazole, clotrimazol, fenticonazole, epoxiconazole, ketoconazole, ravuconazole, isavuconazole, holothurin A, theasaponin, capsicosine, betulafolientriol, prochloraz, propiconazole, prothioconazole, prothioconazole-desthio, tebuconazole, triadimenol, azalanstat, or a variant thereof. In some embodiments, the CYP51A1 inhibitor is an anti-CYP51A1 antibody or antigen-binding fragment thereof, or a compound, such as an interfering RNA molecule, that attenuates CYP51A1 expression.

Patients that may be treated using the compositions and methods described herein include those that exhibit, and/or that are prone to develop, aggregation of TAR-DNA binding protein (TDP)-43. Example of patients that may exhibit or may be prone to exhibit TDP-43 aggregation are those that express a mutant TDP-43 isoform containing a mutation that renders this protein susceptible to aggregation. For example, patients that may be treated using the compositions and methods described herein include those expressing a TDP-43 isoform having a mutation selected from Q331K, M337V, Q343R, N345K, R361S, and N390D, among others that are associated with TDP-43 aggregation and toxicity in vivo.

In a first aspect, the invention features a method of treating a neurological disorder in a patient, such as a human patient, by providing to the patient a therapeutically effective amount of a CYP51A1 inhibitor.

In another aspect, the invention features a method of treating a neurological disorder in a patient, such as a human patient, identified as likely to benefit from treatment with a CYP51A1 inhibitor on the basis of TDP-43 aggregation. In this aspect, the method may include (i) determining that the patient exhibits, or is prone to develop, TDP-43 aggregation, and (ii) providing to the patient a therapeutically effective amount of a CYP51A1 inhibitor. In some embodiments, the patient has previously been determined to exhibit, or to be prone to developing, TDP-43 aggregation, and the method includes providing to the patient a therapeutically effective amount of a CYP51A1 inhibitor. The susceptibility of the patient to developing TDP-43 aggregation may be determined, e.g., by determining whether the patient expresses a mutant isoform of TDP-43 containing a mutation that is associated with TDP-43 aggregation and toxicity, such as a mutation selected from Q331K, M337V, Q343R, N345K, R361S, and N390D. This may be performed, for example, by determining the amino acid sequence of a TDP-43 isoform isolated from a sample obtained from the patient or by determining the nucleic acid sequence of a TDP-43 gene isolated from a sample obtained from the patient. In some embodiments, the method includes the step of obtaining the sample from the patient.

In an additional aspect, the invention features a method of treating a neurological disorder in a patient, such as a human patient, identified as likely to benefit from treatment with a CYP51A1 inhibitor on the basis of TDP-43 expression. In this aspect, the method includes (i) determining that the patient expresses a mutant form of TDP-43 having a mutation associated with TDP-43 aggregation (e.g., a mutation selected from Q331K, M337V, Q343R, N345K, R361S, and N390D), and (ii) providing to the patient a therapeutically effective amount of a CYP51A1 inhibitor. In some embodiments, the patient has previously been determined to express a mutant form of TDP-43 having a mutation associated with TDP-43 aggregation, such as a Q331K, M337V, Q343R, N345K, R361S, or N390D mutation, and the method includes providing to the patient a therapeutically effective amount of a CYP51A1 inhibitor.

In another aspect, the invention features a method of determining whether a patient (e.g., a human patient) having a neurological disorder is likely to benefit from treatment with a CYP51A1 inhibitor by (i) determining whether the patient exhibits, or is prone to develop, TDP-43 aggregation and (ii) identifying the patient as likely to benefit from treatment with a CYP51A1 inhibitor if the patient exhibits, or is prone to develop, TDP-43 aggregation. In some embodiments, the method further includes the step of (iii) informing the patient whether he or she is likely to benefit from treatment with a CYP51A1 inhibitor. The susceptibility of the patient to developing TDP-43 aggregation may be determined, e.g., by determining whether the patient expresses a mutant isoform of TDP-43 containing a mutation that is associated with TDP-43 aggregation and toxicity, such as a mutation selected from Q331K, M337V, Q343R, N345K, R361S, and N390D. This may be performed, for example, by determining the amino acid sequence of a TDP-43 isoform isolated from a sample obtained from the patient or by determining the nucleic acid sequence of a TDP-43 gene isolated from a sample obtained from the patient. In some embodiments, the method includes the step of obtaining the sample from the patient.

In another aspect, the invention features a method of determining whether a patient (e.g., a human patient) having a neurological disorder is likely to benefit from treatment with a CYP51A1 inhibitor by (i) determining whether the patient expresses a TDP-43 mutant having a mutation associated with TDP-43 aggregation (e.g., a mutation selected from Q331K, M337V, Q343R, N345K, R361 S, and N390D) and (ii) identifying the patient as likely to benefit from treatment with a CYP51A1 inhibitor if the patient expresses a TDP-43 mutant. In some embodiments, the method further includes the step of (iii) informing the patient whether he or she is likely to benefit from treatment with a CYP51A1 inhibitor. The TDP-43 isoform expressed by the patient may be assessed, for example, by isolated TDP-43 protein from a sample obtained from the patient and sequencing the protein using molecular biology techniques described herein or known in the art. In some embodiments, the TDP-43 isoform expressed by the patient is determined by analyzing the patient's genotype at the TDP-43 locus, for example, by sequencing the TDP-43 gene in a sample obtained from the patient. In some embodiments, the method includes the step of obtaining the sample from the patient.

In some embodiments of any of the above aspects, the CYP51A1 inhibitor is provided to the patient by administration of the CYP51A1 inhibitor to the patient. In some embodiments, the CYP51A1 inhibitor is provided to the patient by administration of a prodrug that is converted in vivo to the CYP51A1 inhibitor.

In some embodiments of any of the above aspects, the neurological disorder is a neuromuscular disorder, such as a neuromuscular disorder selected from amyotrophic lateral sclerosis, congenital myasthenic syndrome, congenital myopathy, cramp fasciculation syndrome, Duchenne muscular dystrophy, glycogen storage disease type II, hereditary spastic paraplegia, inclusion body myositis, Isaac's Syndrome, Kearns-Sayre syndrome, Lambert-Eaton myasthenic syndrome, mitochondrial myopathy, muscular dystrophy, myasthenia gravis, myotonic dystrophy, peripheral neuropathy, spinal and bulbar muscular atrophy, spinal muscular atrophy, Stiff person syndrome, Troyer syndrome, and Guillain-Barré syndrome. In some embodiments, the neurological disorder is amyotrophic lateral sclerosis.

In some embodiments of any of the above aspects, the neurological disorder is selected from frontotemporal degeneration (also referred to as frontotemporal lobar degeneration and frontotemporal dementia), Alzheimer's disease, Parkinson's disease, dementia with Lewy Bodies, corticobasal degeneration, progressive supranuclear palsy, dementia parkinsonism ALS complex of Guam, Hunting-ton's disease, Inclusion body myopathy with early-onset Paget disease and frontotemporal dementia (IBMPFD), sporadic inclusion body myositis, myofibrillar myopathy, dementia pugilistica, chronic traumatic encephalopathy, Alexander disease, and hereditary inclusion body myopathy.

In some embodiments of any of the above aspects, the CYP51A1 inhibitor is a small molecule antagonist of CYP51A1 activity. The CYP51A1 inhibitor may be, for example, a compound represented by formula (I)

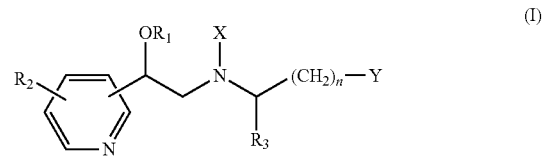

wherein n is 1 or 2;
X is hydrogen, lower alkyl, lower alkoxy-lower alkyl, or a group $X_a$ of the formula:

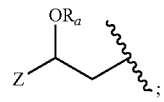

Z is a group of the formula:

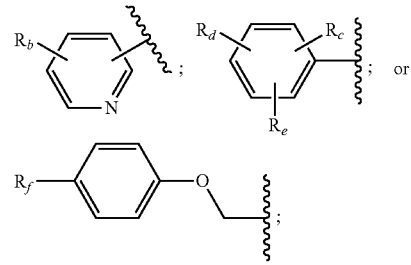

Y is a group of the formula:

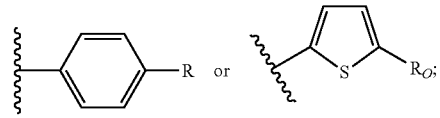

$R_O$ is lower alkyl, $COR_4$ or $C(R_5)$=$CHCOR_4$;
R is $R_o$ or is OR";
R" is hydrogen, lower-alkyl, lower alkanoyl, $(CH_2)_{1-6}$—OH, $(CH_2)_{1-6}$—O$(CH_2)_{1-6}$—$R_6$, or $(CH_2)_{1-6}$—$COR_4$;
$R_1$ and $R_a$ are hydrogen, lower alkanoyl, benzoyl or $(CH_2)_{1-6}$—OH;
$R_2$ and $R^b$ are hydrogen, Cl, Br or $CF_3$;
$R_3$ and $R_5$ are hydrogen or $CH_3$;
$R_4$ is hydroxy, lower-alkoxy or $N(R_7, R_8)$;
$R_6$ is hydrogen, $R_g$, OH or $COR_4$;
$R_7$ and $R_8$ are hydrogen or lower alkyl;
$R_c$ and $R_e$ are hydrogen, Cl, F, Br or $CF_3$;
$R_d$ is hydrogen or $NH_2$;
$R_f$ is hydrogen, $CH_3CONH$—, $NH_2COCH_2$— or $R_9CH_2CH_2OCH_2CH_2O$—;

$R_8$ and $R_9$ are phenyl or phenyl substituted by Cl, F or Br;

or a pharmaceutically acceptable salt, ester, or ether thereof.

In some embodiments of formula (I), n is 1, $R_1$ is hydrogen, $R_2$ is chlorine in the 6-position of a 2-pyridyl residue and Y is phenyl substituted in the p-position by R.

In some embodiments of formula (I), X is $X^a$; $R^a$ is hydrogen; Z is 6-chloro-2-pyridyl, and Y is phenyl substituted in the p-position by 2-ethoxyethoxy, 2-phenethoxyethoxy or methoxycarbonylmethoxy.

In some embodiments of formula (I), the compound is methyl α,α'-[[[(R)-p-(2-ethoxyethoxy)-α-methylphenethyl]imino]dimethylene]bis[(RS)-6-chloro-2-pyridinemethanol]; (RS)-6-chloro-α-[[[(R)-p-(2-ethoxyethoxy)-α-methyl-phenethyl]amino]methyl]-2-pyridinemethanol; α,α'-[[[p-(2-ethoxyethoxy)phenethyl]imino]dimethylene]bis[(RS)-6-chloro-2-pyridinemethanol]; (R)-6-bromo-α-[[[(RS)-2-(6-bromo-2-pyridyl)-2-hydroxyethyl][(R)-p-(2-ethoxyethoxy)-α-methylphenethyl]amino]methyl]-2-pyridimidinemethanol; (R)-6-chloro-α[[[(S)-2-(6-chloro-2-pyridyl)-2-hydroxyethyl][(R)-.alpha.-methyl-p-(2-phenethoxyethoxy)phenethyl]amino]methyl]-2-pyridinemethanol, or a pharmaceutically acceptable salt, ester, or ether thereof.

In some embodiments, the CYP51 A1 inhibitor is a compound represented by formula (II)

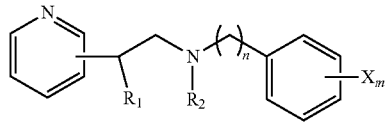

(II)

wherein n is 1, 2, 3, or 4 and m is 0, 1, 2, 3, 4, or 5;

$R_1$ is a hydrogen atom, hydroxyl group, or lower $C_{1-6}$ alkoxy group;

$R_2$ is a hydrogen atom or an optionally substituted straight or branched lower $C_{1-6}$ alkyl group (e.g., an aryl lower alkyl group, such as a phenyl lower alkyl group); and each X is independently fluorine, chlorine, bromine, hydroxyl group, trifluoromethyl group, 3,4-di-Cl, 2,4-di-Cl or lower $C_{1-6}$ alkoxy group, and wherein the phenyl ring containing the X is optionally fused (so as to form, e.g., a naphthyl ring);

or a pharmaceutically acceptable salt, ester, or ether thereof.

In some embodiments, the CYP51A1 inhibitor is a compound represented by formula (1), (2), (3), (13), (14), (15), or (16)

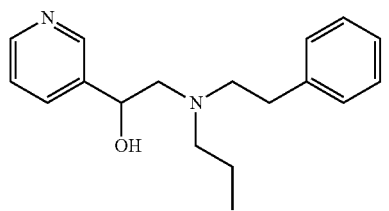

(1)

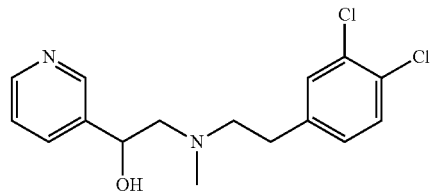

(2)

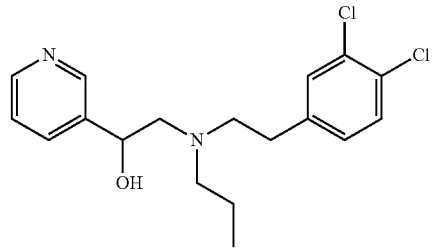

(3)

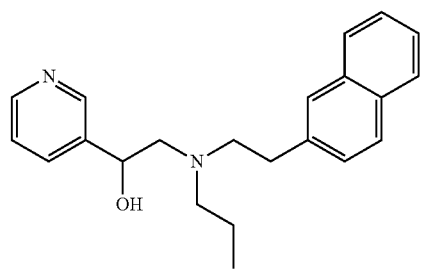

(13)

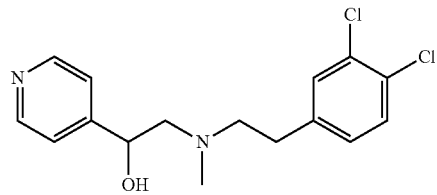

(14)

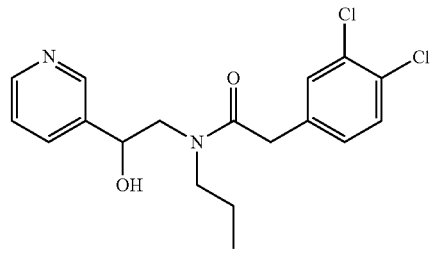

(15)

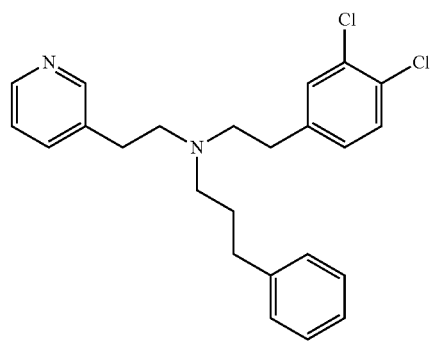

(16)

or a pharmaceutically acceptable salt, ester, or ether thereof.

In some embodiments, n is an integer 2, $R_1$ is a hydroxyl group, $R_2$ a methyl, ethyl, n-propyl, isopropyl, n-butyl or isobutyl group and X is a hydrogen atom or phenyl disubstituted with two chlorine atoms in the positions 3 and 4 or in the positions 2 and 4.

In some embodiments, the CYP51A1 inhibitor is a compound represented by formula (III)

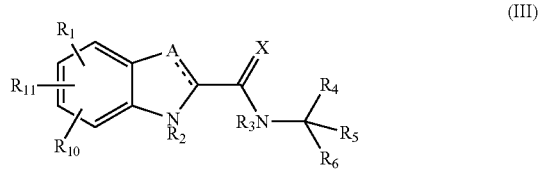

wherein the dotted line (⋯) is an optional bond;

X is O or S;

A is —C(H)═, —C(($C_1$-$C_4$)alkyl)═, —C(halo)═ or —N═, when the dotted line (⋯) is a bond, or A is methylene or —CH(($C_1$-$C_4$)alkyl)—, when the dotted line (⋯) is not a bond;

$R_1$, $R_{10}$ and $R_{11}$ are each independently H, halo, cyano, 4-, 6-, or 7-nitro, ($C_1$-$C_4$)alkyl, ($C_1$-$C_4$)alkoxy, fluoromethyl, difluoromethyl or trifluoromethyl;

$R_2$ is H;

$R_3$ is H or ($C_1$-$C_6$)alkyl;

$R_4$ is H, methyl, ethyl, n-propyl, hydroxy($C_1$-$C_3$)alkyl, ($C_1$-$C_3$)alkoxy($C_1$-$C_3$)alkyl, phenyl($C_1$-$C_4$)alkyl, phenylhydroxy($C_1$-$C_4$)alkyl, (phenyl)(($C_1$-$C_4$)-alkoxy)($C_1$-$C_4$)alkyl, thien-2- or -3-yl($C_1$-$C_4$)alkyl or fur-2- or 3-yl($C_1$-$C_4$)alkyl wherein the $R_4$ rings are mono-, di- or tri-substituted independently on carbon with H, halo, ($C_1$-$C_4$)alkyl, ($C_1$-$C_4$)alkoxy, trifluoromethyl, hydroxy, amino, cyano or 4,5-dihydro-1H-imidazol-2-yl; or $R_4$ is pyrid-2-, -3- or -4-yl($C_1$-$C_4$)alkyl, thiazol-2-, -4- or -5-yl($C_1$-$C_4$)alkyl, imidazol-2-, -4- or -5-yl($C_1$-$C_4$)alkyl, pyrrol-2- or -3-yl($C_1$-$C_4$)alkyl, oxazol-2-, -4- or -5-yl($C_1$-$C_4$)alkyl, pyrazol-3-, -4- or -5-yl($C_1$-$C_4$)alkyl, isoxazol-3-, -4- or -5-yl($C_1$-$C_4$)alkyl, isothiazol-3-, -4- or -5-yl($C_1$-$C_4$)alkyl, pyridazin-3- or -4-yl($C_1$-$C_4$)alkyl, pyrimidin-2-, -4-, -5- or -6-yl($C_1$-$C_4$)alkyl, pyrazin-2- or -3-yl($C_1$-$C_4$)alkyl, 1,3,5-triazin-2-yl($C_1$-$C_4$)alkyl; or indol-2-($C_1$-$C_4$)alkyl, wherein the preceding $R_4$ heterocycles are optionally mono- or di-substituted independently with halo, trifluoromethyl, ($C_1$-$C_4$)alkyl, ($C_1$-$C_4$)alkoxy, amino, hydroxy or cyano and the substituents are bonded to carbon; or $R_4$ is $R_{15}$-carbonyloxymethyl, wherein the $R_{15}$ is phenyl, thiazolyl, imidazolyl, 1H-indolyl, furyl, pyrrolyl, oxazolyl, pyrazolyl, isoxazolyl, isothiazolyl, pyridyl, pyridazinyl, pyrimidinyl, pyrazinyl or 1,3,5-triazinyl and wherein the preceding $R_{15}$ rings are optionally mono- or di-substituted independently with halo, amino, hydroxy, ($C_1$-$C_4$)alkyl, ($C_1$-$C_4$)alkoxy or trifluoromethyl and the mono- or di-substituents are bonded to carbon;

$R_5$ is H, methyl, ethyl, n-propyl, hydroxymethyl or hydroxyethyl;

$R_6$ is carboxy, ($C_1$-$C_8$)alkoxycarbonyl, benzyloxycarbonyl, C(O)NR$_8$R$_9$ or C(O)R$_{12}$ wherein $R_8$ is H, ($C_1$-$C_6$)alkyl, cyclo($C_3$-$C_6$)alkyl, cyclo($C_3$-$C_6$)alkyl($C_1$-$C_5$)alkyl, hydroxy or ($C_1$-$C_8$)alkoxy; and $R_9$ is H, cyclo($C_3$-$C_8$)alkyl, cyclo($C_3$-$C_8$)alkyl($C_1$-$C_5$)alkyl, cyclo($C_4$-$C_7$)alkenyl, cyclo($C_3$-$C_7$)alkyl($C_1$-$C_5$)alkoxy, cyclo($C_3$-$C_7$)alkyloxy, hydroxy, methylene-perfluorinated ($C_1$-$C_8$)alkyl, phenyl, or a heterocycle wherein the heterocycle is pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl, 1,3,5-triazinyl, benzothiazolyl, benzoxazolyl, benzimidazolyl, thiochromanyl or tetrahydrobenzothiazolyl wherein the heterocycle rings are carbon-nitrogen linked; or $R_9$ is ($C_1$-$C_6$)alkyl or ($C_1$-$C_6$)alkoxy wherein the ($C_1$-$C_6$)alkyl or ($C_1$-$C_8$)alkoxy is optionally monosubstituted with cyclo($C_4$-$C_7$)alken-1-yl, phenyl, thienyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, thiomorpholinyl, 1-oxothiomorpholinyl, 1,1-dioxothiomorpholinyl, pyridazinyl, pyrimidinyl, pyrazinyl, piperazinyl, 1,3,5-triazinyl or indolyl and wherein the ($C_1$-$C_6$)alkyl or ($C_1$-$C_8$)alkoxy are optionally additionally independently mono- or di-substituted with halo, hydroxy, ($C_1$-$C_5$)alkoxy, amino, mono-N— or di-N,N—($C_1$-$C_5$)alkylamino, cyano, carboxy, or ($C_1$-$C_4$)alkoxycarbonyl; and wherein the $R_9$ rings are optionally mono- or di-substituted independently on carbon with halo, ($C_1$-$C_4$)alkyl, ($C_1$-$C_4$)alkoxy, hydroxy, hydroxy($C_1$-$C_4$)alkyl, amino($C_1$-$C_4$)alkyl, mono-N— or di-N,N—($C_1$-$C_4$)alkylamino($C_1$-$C_4$)alkyl, ($C_1$-$C_4$)alkoxy($C_1$C$_4$)alkyl, amino, mono-N— or di-N,N—($C_1$-$C_4$)alkylamino, cyano, carboxy, ($C_1$-$C_5$)alkoxycarbonyl, carbamoyl, formyl or trifluoromethyl and the $R_9$ rings may optionally be additionally mono- or di-substituted independently with ($C_1$-$C_5$)alkyl or halo;

optionally with the proviso that no quaternized nitrogen on any $R_9$ heterocycle is included;

$R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan-2-yl, pyrazolidin-1-yl, isoxazolidin-2-yl, isothiazolidin-2-yl, 1,2-oxazetidin-2-yl, oxazolidin-3-yl, 3,4dihydroisoquinolin-2-yl, 1,3-dihydrolsoindol-2-yl, 3,4-dihydro-2H-quinol-1-yl, 2,3-dihydro-benzo[1,4]oxazin-4-yl, 2,3-dihydro-benzo[1,4]-thiazine-4-yl, 3,4-dihydro-2H-quinoxalin-1-yl, 3,4-dihydro-benzo[c][1,2]oxazin-1-yl, 1,4-dihydro-benzo[d][1,2]oxazin-3-yl, 3,4-dihydro-benzo[e][1,2]-oxazin-2-yl, 3H-benzo[d]isoxazol-2-yl, 3H-benzo[c]isoxazol-1-yl or azepan-1-yl, wherein the $R_{12}$ rings are optionally mono-, di- or tri-substituted independently with halo, ($C_1$-$C_5$)alkyl, ($C_1$-$C_5$)alkoxy, hydroxy, amino, mono-N— or di-N,N—($C_1$-$C_5$)alkylamino, formyl, carboxy, carbamoyl, mono-N— or di-N,N—($C_1$-$C_5$)alkylcarbamoyl, ($C_1$-$C_6$)alkoxy($C_1$-$C_3$)alkoxy, ($C_1$-$C_5$)alkoxycarbonyl, benzyloxycarbonyl, ($C_1$-$C_5$)alkoxycarbonyl($C_1$C$_5$)alkyl, ($C_1$C$_4$)alkoxycarbonylamino, carboxy($C_1$-$C_5$)alkyl, carbamoyl($C_1$-$C_5$)alkyl, mono-N— or di-N,N—($C_1$-$C_5$)alkylcarbamoyl($C_1$-$C_5$)alkyl, hydroxy($C_1$-$C_5$)alkyl, ($C_1$-$C_4$)alkoxy($C_{1-4}$)alkyl, amino($C_1$C$_4$)alkyl, mono-N— or di-N,N—($C_1$-$C_4$)alkylamino($C_1$-$C_4$)alkyl, oxo, hydroxylmino or ($C_1$-$C_6$)alkoxylmino and wherein no more than two substituents are selected from oxo, hydroxylmino or ($C_1$-$C_6$)alkoxylmino and oxo, hydroxylmino or ($C_1$-$C_6$)alkoxyimino are on nonaromatic carbon; and the $R_{12}$ rings are optionally additionally mono- or di-substituted independently with ($C_1$-$C_5$)alkyl or halo;

or a pharmaceutically acceptable salt, ester, or ether thereof.

In some embodiments of formula (III), $R_8$ and $R_9$, together with the nitrogen to which they are bound, form an optionally fused, optionally substituted 5 or 6-membered heterocyclic ring, such as an optionally substituted piperazine ring (e.g., a 4-hydroxypiperazine ring).

In some embodiments of formula (III), when $R_6$ is $(C_1-C_5)$alkoxycarbonyl or benzyloxycarbonyl then $R_1$ is 5-halo, 5-$(C_1-C_4)$alkyl or 5-cyano and $R_4$ is (phenyl)(hydroxy)$(C_1-C_4)$alkyl, (phenyl)($(C_1-C_4)$alkoxy)$(C_1-C_4)$alkyl, hydroxymethyl or Ar$(C_1-C_2)$alkyl, wherein Ar is thien-2- or -3-yl, fur-2- or -3-yl or phenyl wherein the Ar is optionally mono- or di-substituted independently with halo; with the provisos that when $R_4$ is benzyl and $R_5$ is methyl, $R_{12}$ is not 4-hydroxy-piperidin-1-yl or when $R_4$ is benzyl and $R_5$ is methyl $R_6$ is not $C(O)N(CH_3)_2$.

In some embodiments of formula (III), when $R_1$, $R_{10}$, and $R_{11}$ are H, $R_4$ is not imidazol-4-ylmethyl, 2-phenylethyl or 2-hydroxy-2-phenylethyl.

In some embodiments of formula (III), when both $R_8$ and $R_9$ are n-pentyl, none of $R_1$ is 5-chloro, 5-bromo, 5-cyano, $5(C_1-C_5)$alkyl, $5(C_1-C_5)$alkoxy or trifluoromethyl.

In some embodiments of formula (III), when $R_{12}$ is 3,4dihydroisoquinol-2-yl, the 3,4-dihydroisoquinol-2-yl is not substituted with carboxy($(C_1-C_4)$alkyl.

In some embodiments of formula (III), when $R_8$ is H and $R_9$ is $(C_1-C_6)$alkyl, $R_9$ is not substituted with carboxy or $(C_1-C_4)$alkoxycarbonyl on the carbon which is attached to the nitrogen atom N of $NHR_9$.

In some embodiments of formula (III), when $R_6$ is carboxy and $R_1$, $R_{10}$, $R_{11}$ and $R_5$ are all H, then $R_4$ is not benzyl, H, (phenyl)(hydroxy)methyl, methyl, ethyl or n-propyl.

Exemplary compounds of formula (III) are those belonging to a first group of compounds in which:

$R_1$ is 5H, 5-halo, 5-methyl, 5-cyano or 5-trifluoromethyl;
$R_{10}$ and $R_{11}$ are each independently H or halo;
A is —C(H)=;
$R_2$ and $R_3$ are H;
$R_4$ is H, methyl, phenyl$(C_1C_2)$alkyl, wherein the phenyl groups are mono- or di-substituted independently with H, halo, $(C_1-C_4)$alkyl, $(C_1C_4)$alkoxy, trifluoromethyl, hydroxy, amino or cyano and wherein the $R_4$ groups are optionally additionally mono-substituted with halo; or
$R_4$ is thien-2- or -3-yl$(C_1-C_2)$alkyl, pyrid-2-, -3- or -4-yl $(C_1-C_2)$alkyl, thiazol-2-, -4- or -5-yl$(C_1-C_2)$alkyl, imidazol-2-, -4- or -5-yl$(C_1-C_2)$alkyl, fur-2- or -3-yl$(C_1-C_2)$alkyl, pyrrol-2- or -3-yl$(C_1-C_2)$alkyl, oxazol-2-, -4- or -5-yl$(C_1-C_2)$alkyl, pyrazol-3-, -4- or -5-yl$(C_1-C_2)$alkyl, isoxazol-3-, -4- or -5-yl$(C_1-C_2)$alkyl, isothiazol-3-, -4- or -5-yl$(C_1-C_2)$alkyl, pyridazin-3- or -4-yl$(C_1-C_2)$alkyl, pyrimidin-2-, -4-, -5- or -6-yl$(C_1-C_2)$alkyl, pyrazin-2- or -3-yl$(C_1-C_2)$alkyl or 1,3,5-triazin-2-yl$(C_1-C_2)$alkyl wherein the preceding $R_4$ heterocycles are optionally mono- or di-substituted independently with halo, trifluoromethyl, $(C_1-C_4)$alkyl, $(C_1-C_4)$alkoxy, amino or hydroxy and the mono- or di-substituents are bonded to cabin;

$R_5$ is H; and
$R_6$ is $C(O)NR_8R_9$ or $C(O)R_{12}$.

For example, compounds of formula (III) that may be used in conjunction with the compositions and methods described herein include those in which:

$R_4$ is H, phenyl$(C_1-C_2)$alkyl, thien-2- or -3-yl$(C_1-C_2)$ alkyl, fur-2- or -3-yl$(C_1-C_2)$alkyl wherein the $R_4$ rings are mono- or di-substituted independently with H or fluoro;
$R_6$ is $C(O)R_{12}$; and
$R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2oxazinan-2-yl, isoxazolidin-2-yl, isothiazolidin-2-yl, 1,2-oxazetidin-2-yl, oxazolidin-3-yl, 1,3-dihydroisoindol-2-yl, or azepan-1-yl, the $R_{12}$ rings are optionally mono- or di-substituted independently with halo, $(C_1-C_5)$alkyl, $(C_1-C_5)$alkoxy, hydroxy, amino, mono-N— or di-N,N—$(C_1-C_5)$alkylamino, formyl, carboxy, carbamoyl, mono-N— or di-N,N—$(C_1-C_5)$alkylcarbamoyl, $(C_1-C_5)$alkoxycarbonyl, hydroxy$(C_1-C_5)$alkyl, amino$(C_1-C_4)$alkyl, mono-N— or di-N,N—$(C_1C_4)$alkylamino$(C_1-C_4)$alkyl, oxo, hydroxylmino or $(C_1-C_6)$alkoxylmino with the proviso that only the $R_{12}$ heterocycles thiazolidin-3-yl, pyrrolidin-1-yl, piperidin-1-yl, piperazin-1-yl, piperazin-4-yl, azetidin-1-yl, 1,2-oxazinan-2-yl, isoxazolidin-2-yl, or oxazolidin-3-yl are optionally mono- or di-substituted with oxo, hydroxylmino, or $(C_1-C_6)$ alkoxylmino; and the $R_{12}$ rings are optionally additionally mono- or di-substituted independently with $(C_1-C_5)$alkyl.

Further exemplary compounds of formula (III) that may be used in conjunction with the compositions and methods described herein include: 5-Chloro-1H-indole-2-carboxylic acid [(1S)-benzyl-2-(3-hydroxylmino-pyrrolidin-1-yl)-2-oxo-ethyl]-amide, 5-Chloro-1H-indole-2-carboxylic acid [2-(cis-3,4-dihydroxy-pyrrolidin-1-yl)-2-oxo-ethyl]-amide, 5-Chloro-1H-indole-2-carboxylic acid [2-((3S,4S)-dihydroxy-pyrrolidin-1-yl)-2-oxo-ethyl]-amide, 5-Chloro-1H-indole-2-carboxylic acid [(1S)-benzyl-2-(cis-3,4-dihydroxy-pyrrolidin-1-yl)-2-oxo-ethyl]-amide, 5-Chloro-1H-indole-2-carboxylic acid [2-(1,1-dioxo-thiazoildin-3-yl)-2-oxo-ethyl]-amide, 5-Chloro-1H-indole-2-carboxylic acid (2-oxo-2-thiazolidin-3-yl-ethyl)-amide, 5-Chloro-1H-indole-2-carboxylic acid [(1S)-(4-fluoro-benzyl)-2-(4-hydroxy-piperidin-1-yl)-2-oxo-ethyl]-amide, 5-Chloro-1H-indole-2-carboxylic acid [(1S)-benzyl-2-((3RS)-hydroxy-piperidin-1-yl)-2-oxo-ethyl]-amide, 5Chloro-1H-indole-2-carboxylic acid [2-oxo-2-((1RS)-oxo-1-thiazolidin-3-yl)-ethyl]-amide, 5-Chloro-1H-indole-2-carboxylic acid [(1S)-(2-fluoro-benzyl)-2-(4-hydroxy-piperidin-1-yl)-2-oxo-ethyl]-amide, 5-Chloro-1H-indole-2-carboxylic acid [(1S)-benzyl-2-((3S,4S)-dihydroxy-pyrrolidin-1-yl)-2-oxo-ethyl]-amide, 5-Chloro-1H-indole-2-carboxylic acid [(1S)-benzyl-2-(3-hydroxy-azetidin-1-yl)-2-oxo-ethyl]-amide, 5-Chloro-1H-indole-2-carboxylic acid [(1S)-benzyl-2-(3-hydroxyimino-azetidin-1-yl)-2-oxo-ethyl]-amide, and 5-Chloro-1H-indole-2-carboxylic acid [(1S)-benzyl-2-(4-hydroxyimino-piperidin-1-yl)-2-oxo-ethyl]-amide.

Further exemplary compounds of formula (III) that may be used in conjunction with the compositions and methods described herein include those in which:

$R_4$ is H; and
$R_{12}$ is thiazolidin-3-yl, 1-oxo-thiazolidin-3-yl, 1,1-dioxothiazolidin-3-yl or oxazolidin-3-yl or the $R_{12}$ substituents optionally mono- or di-substituted independently with carboxy, $(C_1-C_5)$alkoxycarbonyl, hydroxy$(C_1-C_3)$alkyl, amino $(C_1-C_3)$alkyl, mono-N— or di-N,N—$(C_1-C_3)$alkylamino $(C_1-C_3)$alkyl or $R_{12}$ is mono- or di-substituted pyrrolidin-1-yl wherein the substituents are independently carboxy, $(C_1-C_5)$alkoxycarbonyl, $(C_1-C_5)$alkoxy, hydroxy, hydroxy$(C_1-C_3)$alkyl, amino, amino$(C_1-C_3)$alkyl, mono-N— or di-N,N—$(C_1-C_3)$ alkylamino$(C_1-C_3)$alkyl or mono-N— or di-N,N—$(C_1-C_4)$ alkylamino; and the $R_{12}$ rings are optionally additionally, independently, disubstituted with $(C_1-C_5)$alkyl.

Further exemplary compounds of formula (III) that may be used in conjunction with the compositions and methods described herein include those in which:

(a) $R_1$ is 5-chloro;
$R_{10}$ and $R_{11}$ are H; and
$R_{12}$ is cis-3,4-dihydroxy-pyrrolidin-1-yl;
(b) $R_1$ is 5-chloro;

$R_{10}$ and $R_{11}$ are H; and
$R_{12}$ is (3S,4S)-dihydroxy-pyrrolidin-1-yl;
(c) $R_1$ is 5-chloro;
$R_{10}$ and $R_{11}$ are H; and
$R_{12}$ is 1,1-dioxo-thiazolidin-3-yl;
(d) $R_1$ is 5-chloro;
$R_{10}$ and $R_{11}$ are H; and
$R_{12}$ is thiazolidin-3-yl; and
(e) $R_1$ is 5-chloro;
$R_{10}$ and $R_{11}$ are H; and
$R_{12}$ is 1-oxo-thiazolidin-3-yl.

Further exemplary compounds of formula (III) that may be used in conjunction with the compositions and methods described herein include those in which:

$R_4$ is phenylmethyl, thien-2- or -3-ylmethyl wherein the $R_4$ rings are optionally mono- or di-substituted with fluoro; and
$R_{12}$ is thiazolidin-3-yl, 1-oxo-thiazolidin-3-yl, 1,1-dioxo-thiazolidin-3-yl or oxazolidin-3-yl or the $R_{12}$ substituents optionally mono- or di-substituted independently with carboxy or ($C_1$-$C_5$)alkoxycarbonyl, hydroxy($C_1$-$C_3$)alkyl, amino($C_1$-$C_3$)alkyl or mono-N— or di-N,N—($C_1$-$C_3$)alkylamino($C_1$-$C_3$)alkyl or
$R_{12}$ is mono- or di-substituted azetidin-1-yl or mono- or di-substituted pyrrolidin-1-yl or mono- or di-substituted piperidin-1-yl wherein the substituents are independently carboxy, ($C_1$-$C_5$)alkoxycarbonyl, hydroxy($C_1$-$C_3$)alkyl, amino($C_1$-$C_3$)alkyl, mono-N— or di-N,N—($C_1$-$C_3$)alkylamino($C_1$-$C_3$)alkyl, hydroxy, ($C_1$-$C_5$)alkoxy, amino, mono-N— or di-N,N—($C_1$-$C_5$)alkylamino, oxo, hydroxylmino or ($C_1$-$C_5$)alkoxylmino; and
the $R_{12}$ rings are optionally additionally mono- or di-substituted independently with ($C_1$-$C_5$)alkyl.

Further exemplary compounds of formula (III) that may be used in conjunction with the compositions and methods described herein include those in which:

(a) $R_1$ is 5-chloro;
$R_{10}$ and $R_{11}$ are H;
$R_4$ is 4-fluorobenzyl;
$R_{12}$ is 4-hydroxypiperidin-1-yl; and
the stereochemistry of carbon (a) is (S);
(b) $R_1$ is 5-chloro;
$R_{10}$ and $R_{11}$ are H;
$R_4$ is benzyl;
$R_{12}$ is 3-hydroxypiperidin-1-yl; and
the stereochemistry of carbon (a) is (S);
(c) $R_1$ is 5-chloro;
$R_{10}$ and $R_{11}$ are H;
$R_4$ is benzyl;
$R_{12}$ is cis-3,4-dihydroxy-pyrrolidin-1-yl; and
the stereochemistry of carbon (a) is S;
(d) $R_1$ is 5-chloro;
$R_{10}$ and $R_{11}$ are H; $R_4$ is benzyl;
$R_{12}$ is 3-hydroxyimino-pyrrolidin-1-yl; and
the stereochemistry of carbon (a) is (S);
(e) $R_1$ is 5-chloro;
$R_{10}$ and $R_{11}$ are H;
$R_4$ is 2-fluorobenzyl;
$R_{12}$ is 4-hydroxypiperidin-1-yl; and
the stereochemistry of carbon (a) is (S);
(f) $R_1$ is 5-chloro;
$R_{10}$ and $R_{11}$ are H;
$R_4$ is benzyl;
$R_{12}$ is (3S,4S)-dihydroxy-pyrrolidin-1-yl; and
the stereochemistry of carbon (a) is (S);
(g) $R_1$ is 5-chloro;
$R_{10}$ and $R_{11}$ are H;
$R_4$ is benzyl;
$R_{12}$ is 3-hydroxy-azetidin-1-yl; and
the stereochemistry of carbon (a) is (S);
(h) $R_1$ is 5-chloro;
$R_{10}$ and $R_{11}$ are H;
$R_4$ is benzyl;
$R_{12}$ is 3-hydroxyimino-azetidin-1-yl; and
the stereochemistry of carbon (a) is (S); and
(i) $R_1$ is 5chloro;
$R_{10}$ and $R_{11}$ are H;
$R_4$ is benzyl;
$R_{12}$ is 4-hydroxyimino-piperidin-1-yl; and
the stereochemistry of carbon (a) is (S).

Additionally, exemplary compounds of formula (III) are those belonging to a second group of compounds in which:

$R_4$ is H, phenyl($C_1$-$C_2$)alkyl, thien-2- or -3-yl($C_1$-$C_2$)alkyl, fur-2- or -3-yl($C_1$-$C_2$)alkyl wherein the $R_4$ rings are mono- or di-substituted independently with H or fluoro;
$R_6$ is C(O)$NR_8R_9$; and
$R_8$ is H, ($C_1$-$C_5$)alkyl, hydroxy or ($C_1$-$C_4$)alkoxy; and
$R_9$ is H, cyclo($C_4$-$C_6$)alkyl, cyclo($C_3$-$C_6$)alkyl($C_1$-$C_5$)alkyl, methylene-perfluorinated($C_1$-$C_3$)alkyl, pyridyl, pyrrolidinyl, oxazolyl, thiazolyl, imidazolyl, piperidinyl, benzothiazolyl or thiochromanyl; or
$R_9$ is ($C_1$-$C_5$)alkyl wherein the ($C_1$-$C_5$)alkyl is optionally substituted with cyclo($C_4$-$C_6$)alkenyl, phenyl, thienyl, pyridyl, pyrrolidinyl, oxazolyl, thiazolyl, imidazolyl, pyrazolyl, piperidinyl, morpholinyl, thiomorpholinyl, 1-oxothiomorpholinyl, or 1,1-dioxothiomorpholinyl and wherein the ($C_1$-$C_5$)alkyl or ($C_1$-$C_4$)alkoxy is optionally additionally independently mono- or di-substituted with halo, hydroxy, ($C_1$—$C_5$)alkoxy, amino, mono-N— or di-N,N—($C_1$-$C_5$)alkylamino, cyano, carboxy, or ($C_1$-$C_4$)alkoxycarbonyl; wherein the $R_9$ rings are optionally mono- or di-substituted independently on carbon with halo, ($C_1$-$C_4$)alkyl, ($C_1$-$C_4$)alkoxy, hydroxy, amino, mono-N— or di-N,N—($C_1$-$C_4$)alkylamino, carbamoyl, ($C_1$-$C_5$)alkoxycarbonyl or carbamoyl.

Further exemplary compounds of formula (III) that may be used in conjunction with the compositions and methods described herein include those in which:

(a) $R_1$ is 5-chloro;
$R_{10}$ and $R_{11}$ are H;
$R_4$ is benzyl;
$R_8$ is methyl; and
$R_9$ is 3-(dimethylamino)propyl;
(b) the stereochemistry of carbon (a) is (S);
$R_1$ is 5-chloro;
$R_{10}$ and $R_{11}$ are H;
$R_4$ is benzyl;
$R_8$ is methyl; and
$R_9$ is 3-pyridyl;
(c) the stereochemistry of carbon (a) is (S);
$R_1$ is 5-chloro;
$R_{10}$ and $R_{11}$ are H;
$R_4$ is benzyl;
$R_8$ is methyl; and
$R_9$ is 2-hydroxyethyl; and
(d) the stereochemistry of carbon (a) is (S);
$R_1$ is 5-fluoro;
$R_{10}$ and $R_{11}$ are H;
$R_4$ is 4-fluorophenylmethyl;
$R_8$ is methyl; and
$R_9$ is 2-morpholinoethyl.

Additionally, exemplary compounds of formula (III) are those belonging to a third group of compounds in which:

$R_4$ is H, phenyl($C_1$-$C_2$)alkyl, thien-2- or -3-yl($C_1$-$C_2$)alkyl, fur-2- or -3-yl($C_1$-$C_2$)alkyl wherein the $R_4$ rings are mono- or di-substituted independently with H or fluoro;

$R_6$ is C(O)NR$_8$R$_9$; and $R_8$ is H, ($C_1$-$C_5$)alkyl, hydroxy or ($C_1$-$C_4$)alkoxy; and $R_9$ is ($C_1$-$C_4$)alkoxy wherein the ($C_1$-$C_4$)alkoxy is optionally substituted with cyclo($C_4$-$C_6$)alkenyl, phenyl, thienyl, pyridyl, pyrrolidinyl, oxazolyl, thiazolyl, imidazolyl, pyrazolyl, piperidinyl, morpholinyl, thiomorpholinyl, 1-oxothiomorpholinyl, or 1,1-dioxothiomorpholinyl and wherein the ($C_1$-$C_5$)alkyl or ($C_1$-$C_4$)alkoxy is optionally additionally independently mono- or di-substituted with halo, hydroxy, ($C_1$-$C_5$)alkoxy, amino, mono-N— or di-N,N—($C_1$-$C_5$)alkylamino, cyano, carboxy, or ($C_1$-$C_4$)alkoxycarbonyl; wherein the $R_9$ rings are optionally mono- or di-substituted independently on carbon with halo, ($C_1$-$C_4$)alkyl, ($C_1$-$C_4$)alkoxy, hydroxy, amino, mono-N— or di-N,N—($C_1$-$C_4$)alkylamino, carbamoyl, ($C_1$-$C_5$)alkoxycarbonyl or carbamoyl.

Further exemplary compounds of formula (III) that may be used in conjunction with the compositions and methods described herein include those in which:

(a) $R_1$ is 5-chloro;
$R_{10}$ and $R_{11}$ are H;
$R_4$ is benzyl;
$R_8$ is methyl; and
$R_9$ is 2-hydroxyethoxy;
(b) the stereochemistry of carbon (a) is (S);
$R_1$ is 5-chloro;
$R_{10}$ and $R_{11}$ are H;
$R_4$ is 4-fluorophenylmethyl;
$R_8$ is methyl; and
$R_9$ is methoxy;
(c) the stereochemistry of carbon (a) is (S);
$R_1$ is 5-chloro;
$R_{10}$ and $R_{11}$ are H;
$R_4$ is benzyl;
$R_8$ is methyl; and
$R_9$ is methoxy;

Further exemplary compounds of formula (III) that may be used in conjunction with the compositions and methods described herein include those in which:

$R_1$ is 5-halo, 5-methyl, 5-cyano or trifluoromethyl;
$R_{10}$ and $R_{11}$ are each independently H or halo;
A is —C(H)=;
$R_2$ and $R_3$ are H;
$R_4$ is H, phenyl($C_1$-$C_2$)alkyl, thien-2- or -3-yl($C_1$-$C_2$)alkyl, fur-2- or 3-yl($C_1$-$C_2$)alkyl wherein the rings are mono- or di-substituted Independently with H or fluoro;
$R_5$ is H; and
$R_6$ is ($C_1$-$C_5$)alkoxycarbonyl.

Further exemplary compounds of formula (III) that may be used in conjunction with the compositions and methods described herein include those in which:

$R_1$ is 5-halo, 5-methyl, 5-cyano or trifluoromethyl;
$R_{10}$ and $R_{11}$ are each independently H or halo;
A is —C(H)=;
$R_2$ and $R_3$ are H;
$R_4$ is H, methyl or phenyl($C_1$-$C_2$)alkyl, wherein the phenyl groups are mono- or di-substituted independently with H, halo, ($C_1$-$C_4$)alkyl, ($C_1$-$C_4$)alkoxy, trifluoromethyl, hydroxy, amino or cyano and wherein the phenyl groups are additionally mono- or di-substituted independently H or halo; or $R_4$ is thien-2- or -3yl($C_1$-$C_2$)alkyl, pyrid-2-, -3- or -4-yl ($C_1$-$C_2$)alkyl, thiazol-2-, -4- or -5-yl($C_1$-$C_2$)alkyl, imidazol-2-, -4- or -5-yl($C_1$-$C_2$)alkyl, fur-2- or -3-yl($C_1$-$C_2$)alkyl, pyrrol-2- or -3-yl($C_1$-$C_2$)alkyl, oxazol-2-, -4- or -5-yl($C_1$-$C_2$)alkyl, pyrazol-3-, -4- or -5-yl($C_1$-$C_2$)alkyl, isoxazol-3-, -4- or -5-yl($C_1$-$C_2$)alkyl, isothiazol-3-, -4- or -5-yl($C_1$-$C_2$)alkyl, pyridazin-3- or -4yl($C_1$-$C_2$)alkyl, pyrimidin-2-, -4-, -5- or -6-yl($C_1$-$C_2$)alkyl, pyrazin-2- or -3-yl($C_1$-$C_2$)alkyl or 1,3,5-triazin-2-yl($C_1$-$C_2$)alkyl wherein the preceding $R_4$ heterocycles are optionally mono- or di-substituted independently with halo, trifluoromethyl, ($C_1$-$C_4$)alkyl, ($C_1$-$C_4$)alkoxy, amino or hydroxy and the mono- or di-substituents are bonded to carbon;

$R_5$ is H; and
$R_6$ is carboxy.

Further exemplary compounds of formula (III) that may be used in conjunction with the compositions and methods described herein include those in which:

$R_{10}$ and $R_{11}$ are H; and
$R_4$ is H.

Further exemplary compounds of formula (III) that may be used in conjunction with the compositions and methods described herein include those in which $R_1$ is 5-chloro.

In some embodiments, the CYP51A1 inhibitor is a compound represented by formula (IV)

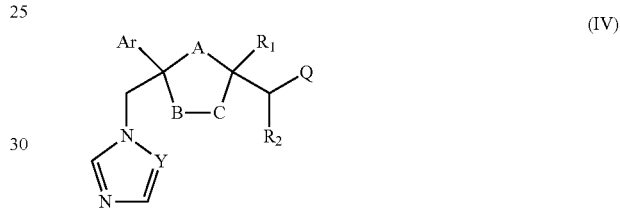

(IV)

wherein Ar is thienyl, pyridyl, biphenyl, phenyl or phenyl substituted by one or more of halo, nitro, cyano, lower alkyl, lower alkoxy or perhalo(lower)alkyl;

Y is CH or N;

either one of A, B and C is oxygen and the remaining two of A, B and C are $CH_2$; or A is oxygen, B is $CH_2$, and C is a direct bond;

Q is:

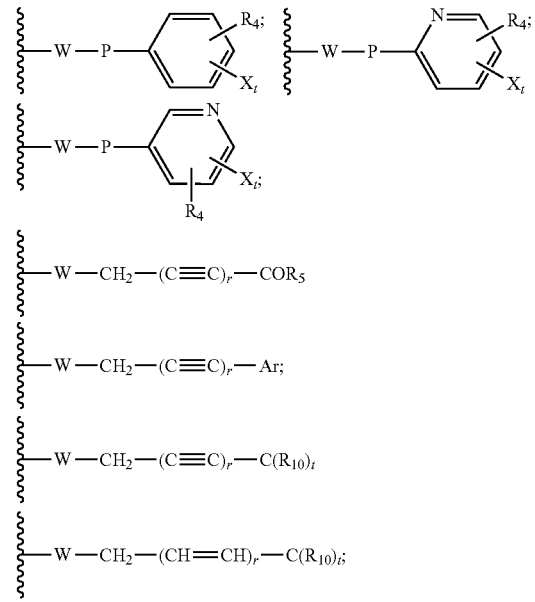

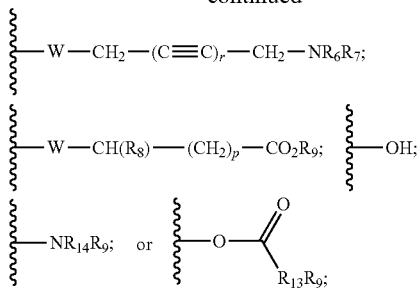

W is —NR$_5$—, —O—, or —S(O)$_n$—;
X is —NO$_2$, —P—NR$_6$R$_7$,

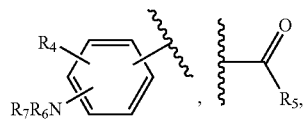

Ar, OR$_3$ or halogen;
P is a direct bond, —CHR$_{11}$— or —CHR$_{11}$CHR$_{12}$—;
R$_1$, R$_8$, R$_9$ and R$_{10}$ are independently hydrogen, lower alkyl or lower alkyl substituted by one or more hydroxy groups;
R$_2$, R$_4$, R$_{11}$, R$_{12}$ and R$_{14}$ are hydrogen, hydroxy, lower alkyl or lower alkyl substituted by one or more hydroxy groups;
R$_3$ and R$_{13}$ are independently hydrogen, lower alkyl, (C$_2$-C$_8$) perhaloalkanoyl or (C$_2$-C$_8$) alkanoyl;
R$_6$ and R$_7$ are independently hydrogen, lower alkyl, phenyl or phenyl substituted by one or more of halo, perhalo (lower)alkyl, (C$_2$-C$_8$)alkanoyl, lower alkyl, lower alkyl substituted by one or more hydroxy groups, lower alkoxy, or 2-(lower)alkyl-3-oxo-1,2,4-triazol-4-yl, or R$_6$ and R$_7$ taken together with the nitrogen atom in NR$_6$R$_7$ form unsubstituted or substituted 5- or 6-membered heterocyclyl ring systems containing carbon and one to four heteroatoms chosen from N, O and S, the heterocyclyl substituents being (C$_1$-C$_8$)alkanoyl, lower alkyl, lower alkoxycarbonyl, aminocarbonyl, N-lower alkylaminocarbonyl, N,N-di(lower alkyl)amino carbonyl, aminothiocarbonyl, N-lower alkylaminothiocarbonyl, N,N-di(lower alkyl)aminothiocarbonyl, lower alkyl sulfonyl, phenyl-substituted lower alkyl sulfonyl, N-lower alkylamino, N,N-di(lower alkyl)amino, 1,3-imidazol-1-yl, 2-loweralkylsulfenyl-1,3-imidazol-1-yl, 2-pyridinyl, 2-thiazolyl, 2-lower alkyl-3-oxo-1,2,4-triazol-4-yl, 1-lower alkylbenzimidazol-2-yl, phenyl or phenyl substituted by one or more of halo, perhalo lower alkyl, (C$_2$-C$_8$) alkanoyl, lower alkyl, lower alkyl substituted by one or more hydroxy group, lower alkoxy, 1H,2,4-triazol-1-yl, 2-lower alkyl-3-oxo-1,2,4-triazol-4-yl, or a substituent represented by the formula:

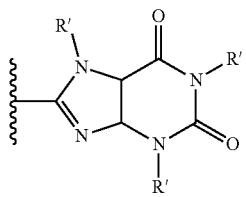

R$_5$ is a lower alkyl, lower alkoxy, amino, N,N-dilower alkylamino, phenyl or phenyl substituted by one or more of halo, perhalo lower alkyl, lower alkoxy, nitro, cyano, (C$_2$-C$_8$)alkanoyl;
p is 0, 1, 2, 3, 4 or 5;
n is 0, 1 or 2;
r is 1 or 2; and
t is 0, 1, 2 or 3;
or a pharmaceutically acceptable salt, ester, or ether thereof.

In some embodiments of formula (IV), when R$_2$, R$_{11}$, or R$_{12}$ is attached to a carbon atom adjacent to —NR$_5$, —S(O)$_n$ or —O—, the R$_2$, R$_{11}$, or R$_{12}$ is not hydroxy.

In some embodiments, the CYP51A1 inhibitor is a compound represented by formula (V)

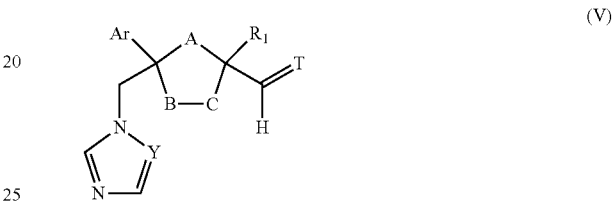

(V)

wherein Y and Ar are as defined for formula (IV) herein;
one of A, B or C is oxygen and the remaining two of A, B, or C are —CH$_2$—;
T is =O, =NOR$_1$, =NNR$_1$R$_2$ or

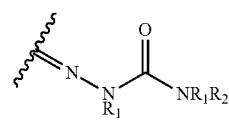

wherein R$_1$ is hydrogen, lower alkyl or lower alkyl substituted by one or more hydroxy groups; and
R$_2$ is hydrogen, hydroxy, lower alkyl or lower alkyl substituted by one or more hydroxy groups;
or a pharmaceutically acceptable salt, ester, or ether thereof.

In some embodiments, the CYP51A1 inhibitor is a compound represented by formula (VI)

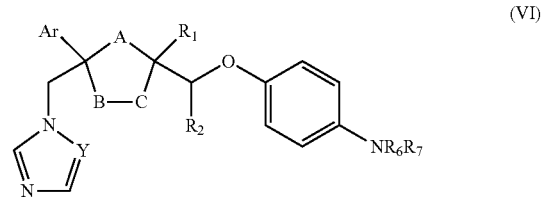

(VI)

wherein Y, Ar, R$_1$, R$_2$, R$_6$ and R$_7$ are as previously defined for formula (IV) herein, and either one of A, B and C is oxygen and the remaining two of A, B and C are CH$_2$, or A is oxygen, B is CH$_2$, and C is a direct bond;
or a pharmaceutically acceptable salt, ester, or ether thereof.

Exemplary compound of formula (VI) for use in conjunction with the compositions and methods described herein are those in which NR$_6$R$_7$ form unsubstituted or substituted 5- or 6-membered heterocyclyl ring systems containing carbon and one to four heteroatoms chosen from N, O and S, the heterocyclyl substituents being (C$_1$-C$_8$) alkanoyl, lower alkyl, lower alkoxycarbonyl, aminocarbonyl, N-lower alkylaminocarbonyl, N,N-di(lower alkyl)aminocarbonyl, aminothiocarbonyl, N-lower alkylaminothiocarbonyl, N,N-di (lower alkyl)aminothiocarbonyl, lower alkyl sulfonyl, phenyl-substituted lower alkyl sulfonyl, N-lower alkylamino, N,N-di(lower alkyl)amino, 1,3-imidazol-1-yl, 2-loweralkylsulfenyl-1,3-imidazol-1-yl, 2-pyridinyl, 2-thiazolyl, 2-lower alkyl-3-oxo-1,2,4-triazol-4-yl, 1-lower alkylbenzimidazol-2-yl, phenyl, phenyl substituted by one or more of halo, perhalo lower alkyl, (C$_2$-C$_8$)alkanoyl, lower alkyl, lower alkyl substituted by one or more hydroxy groups, lower alkoxy, 1H,2,4-triazol-1-yl or 2-lower alkyl-3-oxo-1, 2,4-triazol-4-yl; R$_5$ is a lower alkyl, amino, N,N-dilower alkylamino, or

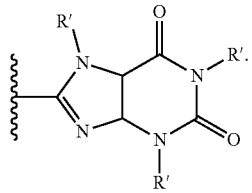

In some embodiments of formula (VI), the NR$_6$R$_7$ is:

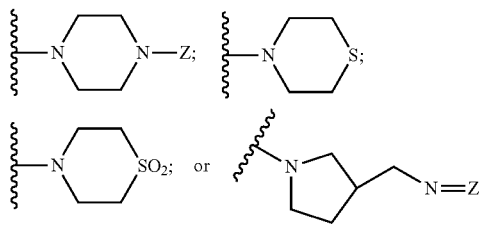

wherein Z is hydrogen, (C$_1$-C$_8$) alkanoyl, lower alkyl, (C$_1$-C$_8$) perhaloalkanoyl or phenyl substituted by 2-loweralkyl-3-oxo-1,2,4-triazol-4-yl.

In some embodiments, the CYP51A1 inhibitor is a compound represented by formula (VII)

(VII)

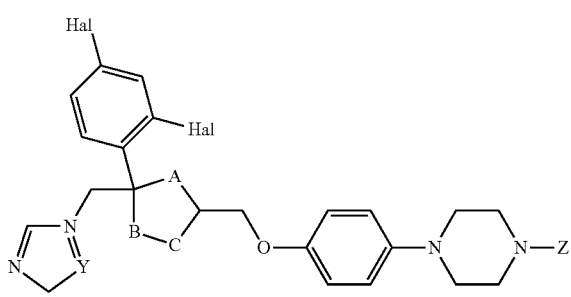

wherein one of A, B and C is oxygen and the remaining two of A, B and C are —CH$_2$—, or two of A, B and C are —CH$_2$—;

each Hal is independently a halogen, such as Cl or F; and

Z is lower alkyl, (C$_2$-C$_8$)alkanoyl, or optionally substituted phenyl, such as phenyl substituted by 2-loweralkyl-3-oxo-1,2,4triazol-4-yl;

or a pharmaceutically acceptable salt, ester, or ether thereof.

In some embodiments of formula (VII), the compound is selected from:

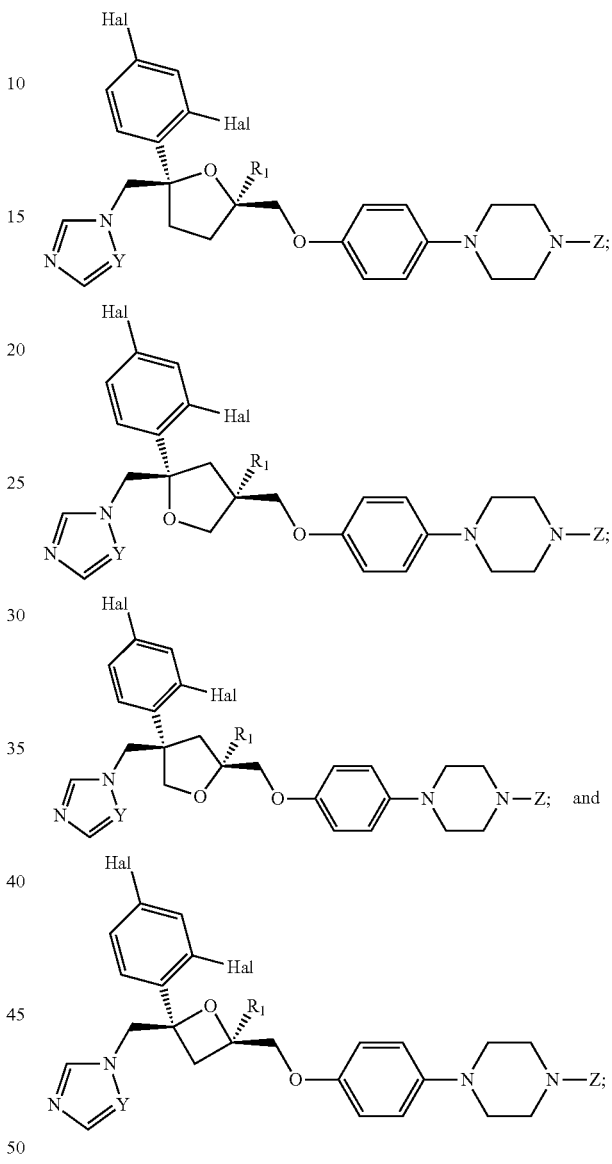

or a pharmaceutically acceptable salt, ester, or ether thereof.

In some embodiments, the CYP51A1 inhibitor is a compound represented by formula (VIII)

(VIII)

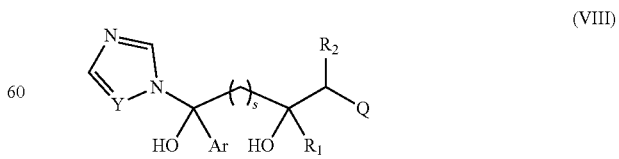

wherein Ar is thienyl, pyridyl, biphenyl, phenyl, or phenyl substituted by one or more of halo, nitro, cyano, lower alkyl, lower alkoxy or perhalo(lower)alkyl;

Q is:

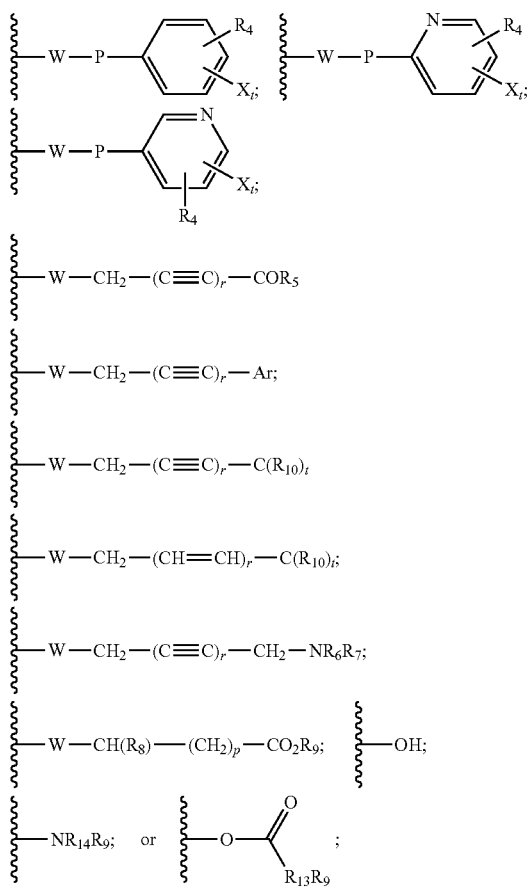

W is —$NR_5$—, —O—, or —$S(O)_n$—;
X is —$NO_2$, —P—$NR_6R_7$,

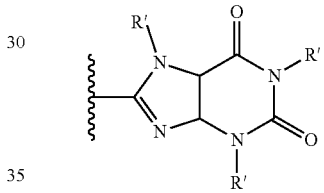

Ar, $OR_3$ or halogen;
P is a direct bond, —$CHR_{11}$— or —$CHR_{11}CHR_{12}$—;
$R_8$, $R_9$ and $R_{10}$ are independently hydrogen, lower alkyl or lower alkyl substituted by one or more hydroxy groups;

$R_4$, $R_{11}$, $R_{12}$ and $R_{14}$ are hydrogen, hydroxy, lower alkyl or lower alkyl substituted by one or more hydroxy groups;
$R_3$ and $R_{13}$ are independently hydrogen, lower alkyl, ($C_2$-$C_8$) perhaloalkanoyl or ($C_2$-$C_8$) alkanoyl;
$R_6$ and $R_7$ are independently hydrogen, lower alkyl, phenyl or phenyl substituted by one or more of halo, perhalo (lower)alkyl, ($C_2$-$C_8$)alkanoyl, lower alkyl, lower alkyl substituted by one or more hydroxy groups, lower alkoxy, or 2-(lower)alkyl-3-oxo-1,2,4-triazol-4-yl, or $R_6$ and $R_7$ taken together with the nitrogen atom in $NR_6$ $R_7$ form unsubstituted or substituted 5- or 6-membered heterocyclyl ring systems containing carbon and one to four heteroatoms chosen from N, O and S, the heterocyclyl substituents being ($C_1$-$C_8$)alkanoyl, lower alkyl, lower alkoxycarbonyl, aminocarbonyl, N-lower alkylaminocarbonyl, N,N-di(lower alkyl)amino carbonyl, aminothiocarbonyl, N-lower alkylaminothiocarbonyl, N,N-di(lower alkyl)aminothiocarbonyl, lower alkyl sulfonyl, phenyl-substituted lower alkyl sulfonyl, N-lower alkylamino, N,N-di(lower alkyl)amino, 1,3-imidazol-1-yl, 2-loweralkylsulfenyl-1,3-imidazol-1-yl, 2-pyridinyl, 2-thiazolyl, 2-lower alkyl-3-oxo-1,2,4-triazol-4-yl, 1-lower alkylbenzimidazol-2-yl, phenyl or phenyl substituted by one or more of halo, perhalo lower alkyl, ($C_2$-$C_8$) alkanoyl, lower alkyl, lower alkyl substituted by one or more hydroxy group, lower alkoxy, 1H,2,4-triazol-1-yl, 2-lower alkyl-3-oxo-1,2,4-triazol-4-yl, or a substituent represented by the formula:

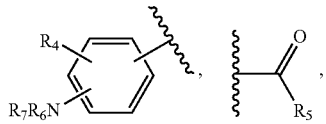

$R_5$ is a lower alkyl, lower alkoxy, amino, N,N-dilower alkylamino, phenyl or phenyl substituted by one or more of halo, perhalo lower alkyl, lower alkoxy, nitro, cyano, ($C_2$-$C_8$)alkanoyl;
p is 0, 1, 2, 3, 4 or 5;
n is 0, 1 or 2;
r is 1 or 2; and
t is 0, 1, 2 or 3;
$R_1$ is hydrogen, lower alkyl or lower alkyl substituted by one or more hydroxy groups; and
$R_2$ is hydrogen, hydroxy, lower alkyl or lower alkyl substituted by one or more hydroxy groups;
or a pharmaceutically acceptable salt, ester, or ether thereof.

In some embodiments, the CYP51A1 inhibitor is a compound represented by formula (IX)

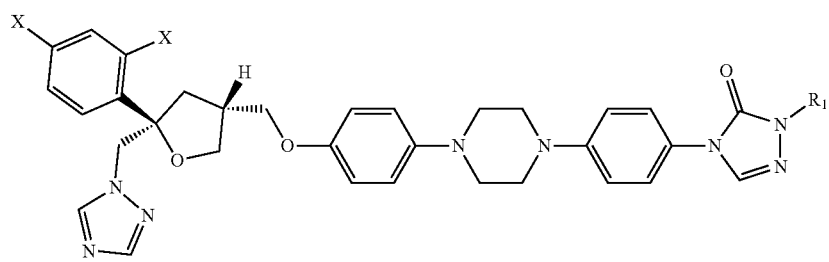

wherein each X is independently a halogen, such as F or Cl; and

R₁ is a straight or branched chain ($C_3$ to $C_8$) alkyl group optionally substituted by one or two hydroxy moieties or by one or two groups convertible in vivo into hydroxy moieties;

or a pharmaceutically acceptable salt, ester, or ether thereof.

In some embodiments of formula (IX), the compound is represented by formula (X)

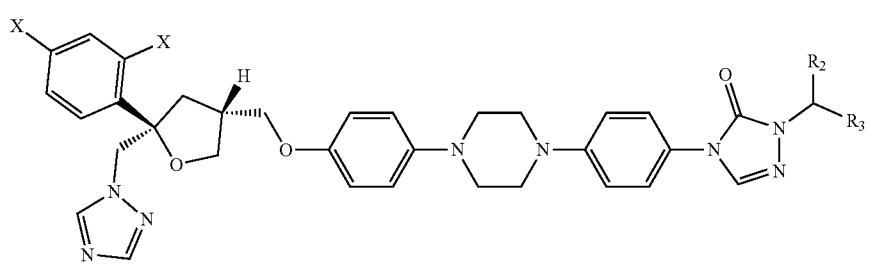

(X)

wherein each X is independently a halogen, such as F or Cl; and

R₂ is H or ($C_1$-$C_3$) alkyl and R₃ is ($C_1$-$C_3$) alkyl optionally substituted by one hydroxy moiety or by a group convertible in vivo into a hydroxy moiety;

or a pharmaceutically acceptable salt, ester, or ether thereof.

In some embodiments of formula (X), the compound is represented by formula (XI)

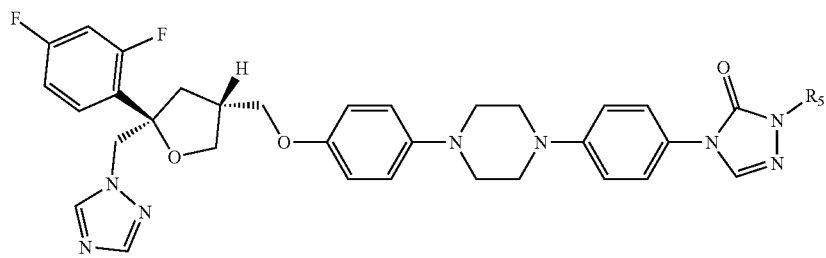

(XI)

wherein R₅ is:

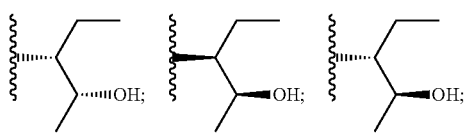

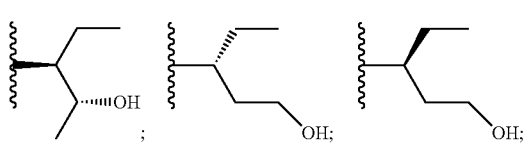

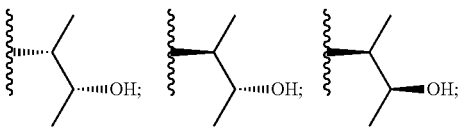

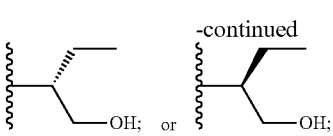

or a pharmaceutically acceptable salt, ester, or ether thereof.

In some embodiments of formula (XI), the compound is represented by formula (XII)

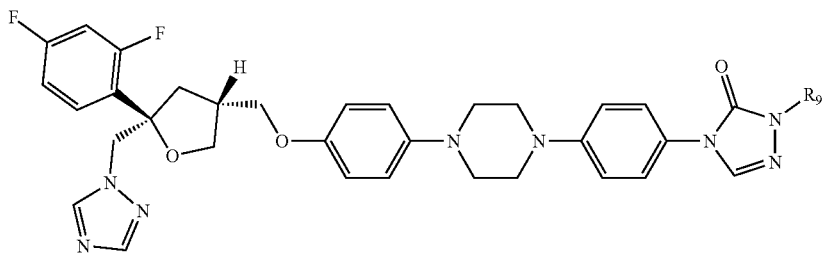

(XII)

wherein $R_9$ is —$H(C_2H_5)CH(R_6)CH_3$ or —$H(CH_3)CH(R_6)CH_3$;
$R_6$ is OH or a group convertible in vivo into OH;
or a pharmaceutically acceptable salt, ester, or ether thereof.

In some embodiments of formula (XII), the compound is:

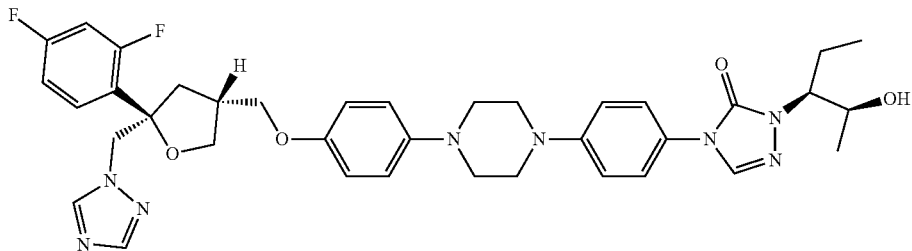 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

or a pharmaceutically acceptable salt, ester, or ether thereof.

In some embodiments of formulas (IX)-(XII), the compound is an ester of the corresponding structural formula, such as a phosphate ester. The phosphate ester may be, for example, a phosphate ester selected from

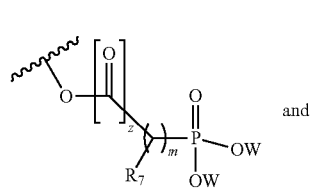 and

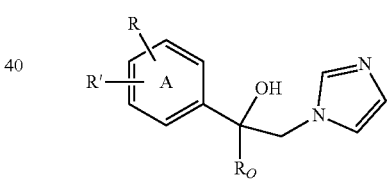

wherein z is 0 or 1, $R_7$ is a ($C_1$-$C_6$) straight or branched chain alkyl group or H, f and n are independently an integer from 0 to 6, m is zero or 1 and W is H, $CH_2$ Ar or and Ar is phenyl, phenyl substituted by halo, nitro, cyano or trihalomethyl.

In some embodiments, the CYP51A1 inhibitor is a compound represented by formula (XIII)

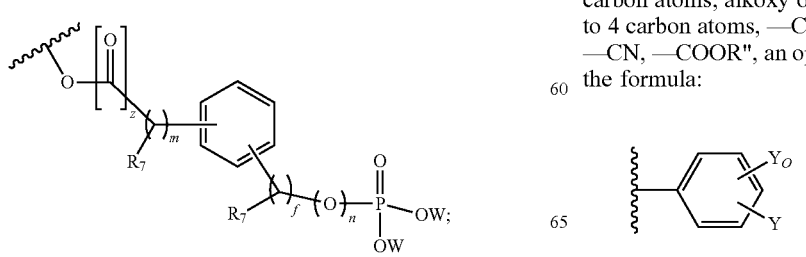

(XIII)

wherein $R_O$ is alkyl of 2 to 6 carbon atoms, cycloalkyl of 3 to 6 carbon atoms, cycloalkyl-alkyl in which the cycloalkyl is of 3 to 6 carbon atoms and the alkyl portion of 1 to 3 carbon atoms, the cycloalkyl and cycloalkyl-alkyl being optionally ring substituted by one or two alkyl groups of 1 to 3 carbon atoms;

R is hydrogen, fluoro, chloro, bromo, alkyl of 1 to 4 carbon atoms, alkoxy of 1 to 4 carbon atoms, alkylthio of 1 to 4 carbon atoms or nitro;

R' is hydrogen, fluoro, chloro, bromo, alkyl of 1 to 4 carbon atoms, alkoxy of 1 to 4 carbon atoms, alkylthio of 1 to 4 carbon atoms, —$CF_3$ in the 3-position of Ring A, nitro, —CN, —COOR", an optionally substituted phenyl group of the formula:

or an optionally substituted phenoxy group in the 4-position of Ring A and having the formula:

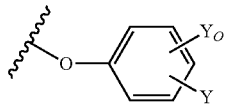

R" is hydrogen, alkyl of 1 to 4 carbon atoms or a cation, preferably an agriculturally acceptable cation, or R and R' together represent alkylenedioxy of 1 or 2 carbon atoms substituted onto adjacent carbon atoms of the phenyl Ring A; and $Y_O$ and Y are independently hydrogen, fluoro, chloro, bromo, alkyl of 1 to 4 carbon atoms or alkoxy of 1 to 4 carbon atoms;

or a pharmaceutically acceptable salt, ester, or ether thereof.

In some embodiments of formula (XIII), when $R_O$ is n-butyl: (a) at least one of R and R' is other than hydrogen and (b) R and R' are not both halo.

In some embodiments, the CYP51A1 inhibitor is an α-[aryl(alkylene)$_m$]-α-[CR$_1$R$_2$—(CHR$_3$)$_n$-R$_4$]1H-1,2,4-triazole-1-ethanol (formula (XIV-A)) or an α-[aryl(alkylene)$_m$]-α-[CR$_1$R$_2$—(CHR$_3$)$_n$-R$_4$]1H-imidazole-1-ethanol (formula (XIV-B)), or a pharmaceutically acceptable salt, ester, or ether thereof, wherein:

$R_1$ is $C_{1-5}$ alkyl, unsubstituted or substituted by halogen, by $C_{1-5}$-alkoxy, by phenyl-$C_{1-3}$ alkoxy, by phenoxy, by $C_{1-5}$ alkylthio, by phenyl-$C_{1-3}$ alkylthio or by phenylthio, whereby optional phenyl groups may be substituted by $C_{1-5}$ alkyl, halogen, halogen substituted $C_{1-5}$ alkyl, $C_{1-5}$ alkoxy or halogen substituted $C_{1-5}$ alkoxy; or is $C_{2-5}$ alkenyl or $C_{2-5}$ alkynyl, unsubstituted or substituted by halogen; or is cycloalkyl, unsubstituted or substituted by $C_{1-5}$ alkyl; or is phenyl, unsubstituted or substituted by substituents selected from the group consisting of halogen and $C_{1-5}$ alkyl;

$R_2$ and $R_3$, independently, are H or have an $R_1$ significance, whereby $R_1$ and $R_2$ may be linked together to form a $C_{3-7}$ cycloalkyl group;

m is 0 or 1;

n is 0, 1 or 2; and $R_4$ is $C_{3-7}$ cycloalkyl, unsubstituted or substituted by $C_{1-5}$ alkyl.

The aryl portion in the α-[aryl(alkylen)$_m$] moiety of formula (XIV-A) or (XIV-B) (collectively "formula (XIV)") may be an aromatic hydrocarbon (e.g. naphthyl, preferably phenyl) unsubstituted or substituted, or a heteroaromatic ring linked by one of its ring carbon atoms (e.g. a 5- or 6-membered ring with 1 or 2 heteroatoms from the group O, N and S, preferably furyl, thienyl or pyridyl), and may be unsubstituted or substituted.

Examples of suitable α-[aryl(alkylene)$_m$] groups that may be present in formula (XIV) are phenyl, benzyl and α-$C_{1-5}$ alkylbenzyl (e.g., unsubstituted, mono- or multiple-substituted in the phenyl moiety by $NO_2$, halogen, $C_{1-5}$ alkyl, $C_{2-5}$ alkenyl, $C_{2-5}$ alkynyl, or $C_{1-5}$ alkoxy (unsubstituted or halogenated), phenyl, or phenoxy, unsubstituted or substituted). Further examples of suitable α-aryl groups are the heteroaromatic 3-pyridyl group and 2-thienyl and 2-furyl, which may be, for example, unsubstituted or singly substituted by halogen or lower alkyl (e.g. 5-Cl-2-thienyl and 5-tert.butyl-2-furyl).

For example, the α-[aryl(alkylene)$_m$] group may be phenyl, benzyl, or α-$C_{1-5}$ alkylbenzyl substituted in the phenyl moiety by $R_5$, $R_6$ and/or $R_7$, wherein:

$R_5$ and $R_6$, independently, are H; halogen, $C_{1-5}$ alkyl, $C_{2-5}$ alkenyl, $C_{2-5}$ alkynyl, or $C_{1-5}$ alkoxy, (e.g., unsubstituted or halogenated), phenyl or phenoxy (e.g., unsubstituted or substituted), or $NO_2$; and $R_7$ is H, $C_{1-5}$ alkyl or halogen.

In some embodiments, the compound represented by formula (XIV) is a compound represented by formula (XV)

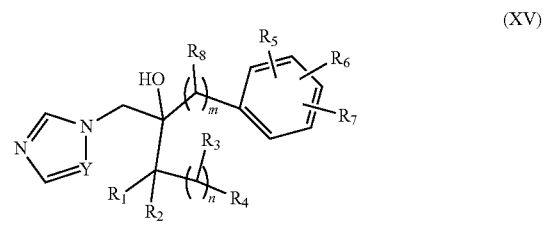

(XV)

wherein $R_1$, $R_2$, $R_3$, $R_4$, $R_5$, $R_6$, $R_7$, m and n are as defined for formula (XIV) herein, $R_8$ is H or $C_{1-5}$ alkyl, and Y is CH or N;

or a pharmaceutically acceptable salt, ester, or ether thereof.

In some embodiments, the compound represented by formula (XV) is a compound represented by formula (XVI)

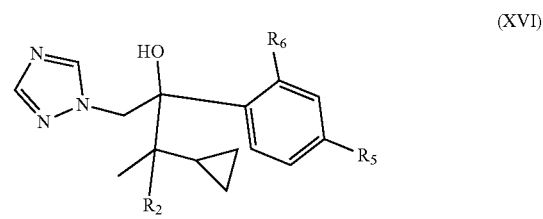

(XVI)

wherein $R_2$ is hydrogen or optionally substituted alkyl, such as optionally substituted lower alkyl (e.g., methyl, ethyl, n-propyl, iso-propyl, n-butyl, iso-butyl, sec-butyl, tert-butyl, n-pentyl, n-hexyl, or the like); and $R_5$ and $R_6$ are each independently hydrogen or a halogen atom, such as chloro;

or a pharmaceutically acceptable salt, ester, or ether thereof.

In some embodiments, the CYP51A1 inhibitor is 2-(4-chlorophenyl)-3-cyclopropyl-1-(1H-1,2,4-triazol-1-yl)-butan-2-ol, 2-(4-chlorophenyl)-3-cyclopropyl-3-methyl-1-(1H-1,2,4-triazol-1-yl)-butan-2-ol, 2-(2,4-diclorophenyl)-3-cyclopropyl-1-(1H-1,2,4-triazol-1-yl) butan-2-ol, or 2-(2,4-dichlorophenyl)-3-cyclopropyl-3-methyl-1-(1H-1,2,4-triazol-1-yl)butan-2-ol.

In some embodiments, the CYP51A1 inhibitor is a compound represented by formula (XVII)

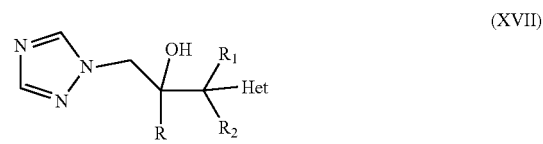

(XVII)

wherein R is phenyl optionally substituted by 1 to 3 substituents each independently selected from halo and $CF_3$;

$R^1$ is $C_1$-$C_4$ alkyl;

$R_2$ is H or $C_1$-$C_4$ alkyl; and

"Het", which is attached to the adjacent carbon atom by a ring carbon atom, is selected from pyridinyl, pyridazinyl, pyrimidinyl, pyrazinyl and triazinyl. "Het" may be optionally substituted by $C_1$-$C_4$ alkyl, $C_1$-$C_4$ alkoxy, halo, $CF_3$, CN, $NO_2$, $NH_2$, —NH($C_1$-$C_4$ alkanoyl) or —NHCO$_2$ ($C_1$-$C_4$ alkyl);

or a pharmaceutically acceptable salt, ester, or ether thereof.

In some embodiments of formula (XVII), "Het" is selected from 2- and 4-pyridinyl, pyridazinyl, 2- and 4-pyrimidinyl, pyrazinyl and triazinyl, and may be optionally substituted by $C_1$-$C_4$ alkyl, $C_1$-$C_4$ alkoxy, halo, $CF_3$, CN, $NO_2$, $NH_2$, —NH($C_1$-$C_4$ alkanoyl) or —NHCO$_2$ ($C_1$-$C_4$ alkyl). In some embodiments, "Het" is pyridinyl, pyridazinyl, pyrimidinyl, pyrazinyl or triazinyl, and may be optionally substituted by $C_1$-$C_4$ alkyl, $C_1$-$C_4$ alkoxy, halo, $CF_3$, $NO_2$, $NH_2$ or —NH($C_1$-$C_4$ alkanoyl).

In some embodiments of formula (XVII), R is a substituted phenyl moiety, such as 2-fluorophenyl, 2-chlorophenyl, 2-bromophenyl, 2-iodophenyl, 2-trifluoromethylphenyl, 2,4-dichlorophenyl, 2,4-difluorophenyl, 2-chloro-4-fluorophenyl, 2-fluoro-4-chlorophenyl, 2,5-difluorophenyl, 2,4,6-trifluorophenyl, or 4-bromo-2,5-difluorophenyl. In some embodiments, R is a phenyl group substituted by from 1 to 3 halo (preferably F or Cl) substituents. In some embodiments, R is a phenyl group substituted by from 1 or 2 halo (preferably F or Cl) substituents. In some embodiments, R is 2,4-difluorophenyl, 2,4-dichlorophenyl, 2-fluorophenyl or 2-chlorophenyl.

In some embodiments, the CYP51A1 inhibitor is 2-(2,4-difluorophenyl)-3-(pyridin-2-yl)-1-(1H-1,2,4-triazol-1-yl)butan-2-ol, 2-(2,4-difluorophenyl)-3-(pyridin-4-yl)-1-(1H-1,2,4-triazol-1-yl)butan-2-ol, or 2-(2,4-difluorophenyl)-3-(pyrimidin-4-yl)-1-(1H,1,2,4-triazol-1-yl)butan-2-ol.

In some embodiments, the CYP51A1 inhibitor is a compound represented by formula (XVIII)

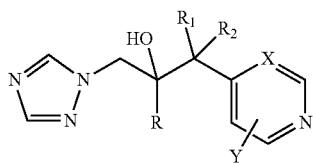

(XVIII)

wherein R is optionally substituted phenyl (e.g., substituted by from 1 to 3 substituents each independently selected from halo, —$CF_3$ and —$OCF_3$);

$R^1$ is optionally substituted alkyl, such as optionally substituted lower alkyl (e.g., $C_1$-$C_4$ alkyl);

$R_2$ is H or optionally substituted alkyl, such as optionally substituted lower alkyl (e.g., $C_1$-$C_4$ alkyl);

X is CH or N; and

Y is a halogen, such as F or Cl;

or a pharmaceutically acceptable salt, ester, or ether thereof.

Examples of R in formula (XVIII) are 2-fluorophenyl, 4-fluorophenyl, 2-chlorophenyl, 4-chlorophenyl, 2-bromophenyl, 2-iodophenyl, 2-trifluoromethylphenyl, 2,4-dichlorophenyl, 2,4-difluorophenyl, 2-chloro-4-fluorophenyl, 2-fluoro-4-chlorophenyl, 2,5-difluorophenyl, 2,4,6-trifluorophenyl, 4-bromo-2,5-difluorophenyl, and 2-trifluoromethoxyphhenyl.

In some embodiments of formula (XVIII), the compound is represented by formula (XIX)

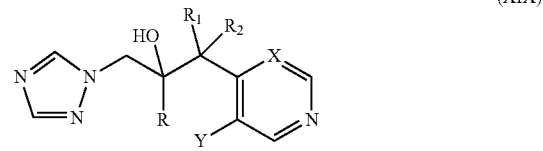

(XIX)

wherein R, $R_1$, $R_2$, X, and Y are as defined for formula (XVIII);

or a pharmaceutically acceptable salt, ester, or ether thereof.

In some embodiments of formula (XVIII), the compound is represented by formula (XX)

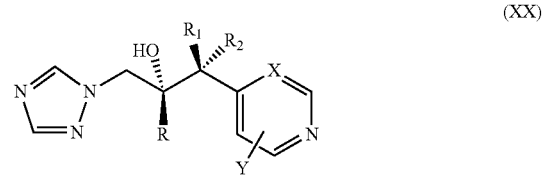

(XX)

wherein R, $R_1$, $R_2$, X, and Y are as defined for formula (XVIII);

or a pharmaceutically acceptable salt, ester, or ether thereof.

In some embodiments of formula (XVIII), the compound is represented by formula (XXI)

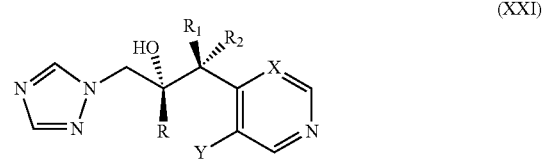

(XXI)

wherein R, $R_1$, $R_2$, X, and Y are as defined for formula (XVIII);

or a pharmaceutically acceptable salt, ester, or ether thereof.

In some embodiments, the CYP51A1 inhibitor is 2-(2,4-difluorophenyl)-3-(5-fluoropyrimidin-4-yl)-1-(1H-1,2,4-triazol-1-yl)butan-2-ol, or a pharmaceutically acceptable salt, ester, or ether thereof. In some embodiments, the CYP51A1 inhibitor is (2R,3S)-2-(2,4-difluorophenyl)-3-(5-fluoropyrimidin-4-yl)-1-(1H-1,2,4-triazol-1-yl)butan-2-ol, or a pharmaceutically acceptable salt, ester, or ether thereof.

In some embodiments, the CYP51A1 inhibitor is a compound represented by formula (XXII)

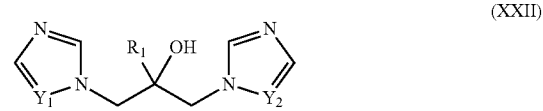

(XXII)

wherein $R_1$ is an optionally substituted alkyl, cycloalkyl (e.g. cyclopentyl or cyclohexyl), aryl (e.g. phenyl) or arylalkyl (e.g. benzyl) group; and $Y_1$ and $Y_2$ are each independently =CH— or =N—;

or a pharmaceutically acceptable salt, ester, or ether thereof.

In some embodiments of formula (XXII), $R_1$ is alkyl, cycloalkyl, optionally substituted aryl, or optionally substituted arylalkyl; and $Y^1$ and $Y^2$ are either both =CH— or both =N—.

In some embodiments of formula (XXII), $R_1$ is phenyl or benzyl, optionally substituted with one or more of halogen, alkyl or haloalkyl each containing from 1 to 5 carbon atoms, alkoxy or haloalkoxy each containing from 1 to 4 carbon atoms, nitro, cyano, hydroxy, alkylthio containing from 1 to 40 carbon atoms, vinyl, phenyl or phenoxy. In some embodiments, the alkyl moiety of the benzyl is unsubstituted, or substituted with alkyl containing from 1 to 4 carbon atoms, phenyl or chlorophenyl.

In some embodiments, the CYP51A1 inhibitor is selected from:

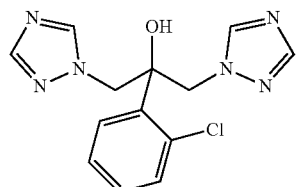

and

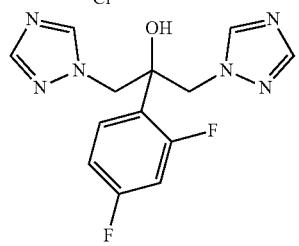

or a pharmaceutically acceptable salt, ester, or ether thereof.

In some embodiments, the CYP51A1 inhibitor is a compound represented by formula (XXIII)

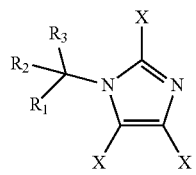

(XXIII)

wherein each of $R_1$, $R_2$, and $R_3$ is independently an aryl group represented by the formula:

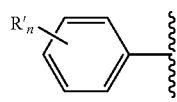

n is 0, 1, 2, 3, 4, or 5 (e.g., 0, 1, or 2) and each R' is independently halogen or optionally substituted alkyl (e.g., optionally substituted lower alkyl); and each X is independently selected from hydrogen, optionally substituted alkyl (e.g., optionally substituted lower alkyl), or optionally substituted aryl (e.g., optionally substituted phenyl);

or a pharmaceutically acceptable salt, ester, or ether thereof. In some embodiments, the total number of carbon atoms in all X substituents is an integer of from 0 to 15.

In some embodiments, the CYP51A1 inhibitor is a compound selected from I-(tris(m-tert-butylphenyl)methyl) imidazole, 1-(tris(p-tert-butylphenyl methyl) imidazole, 1-(his (2,4-difiourophenyl)methyl)-2,4,5-trimethylimidazole, 1-(tris(p-chlorophenyl)methyl)-2-methyl-4,5-diphenylimidazone, 1-(tris(m-tolyl)methyl)-2-n-propylimidaz-ole, and 1-trityl-2-methylimidazole.

In some embodiments, the CYP51A1 inhibitor is a compound represented by formula (XXIV)

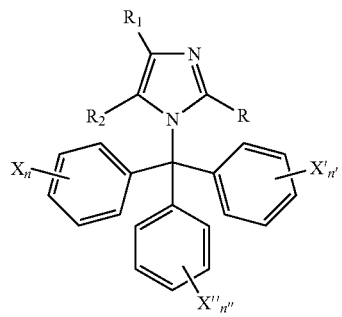

(XXIV)

wherein each of R, $R_1$, and $R_2$ is independently hydrogen, optionally substituted alkyl (e.g., optionally substituted lower alkyl), or optionally substituted and optionally fused aryl (e.g., optionally substituted phenyl);

each of X, X', and X''' is independently hydrogen, halogen, optionally substituted alkyl (e.g., optionally substituted lower alkyl), or optionally substituted and optionally fused aryl (e.g., optionally substituted phenyl); and each of n, n', and n" is independently 1, 2, 3, 4, or 5 (e.g., 1, 2, or 3);

or a pharmaceutically acceptable salt, ester, or ether thereof.

In some embodiments of formula (XXIV), the compound is represented by formula (XXV)

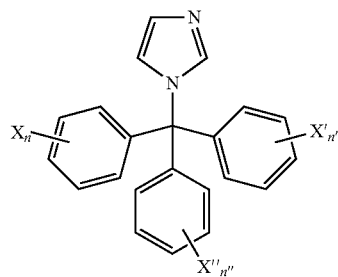

(XXV)

wherein X, X', X''', n, n', and n" are as defined for formula (XXIV);

or a pharmaceutically acceptable salt, ester, or ether thereof.

In some embodiments of formula (XXIV), the compound is represented by formula (XXVI)

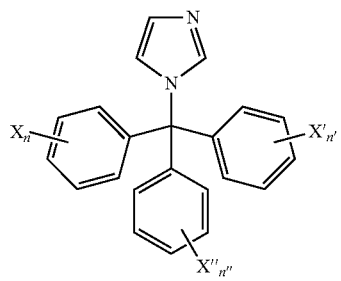

(XXVI)

wherein X, X', X''', n, n', and n'' are as defined for formula (XXIV);

or a pharmaceutically acceptable salt, ester, or ether thereof.

In some embodiments, the CYP51A1 inhibitor is 1-(3,4-Dimethylphenyl-phenyl-2-pyridyl)-methyl-imidazole, 1-(2,4-dimethylphenyl-phenyl-2-pyridyl)-methyl-imidazole, 1-(2,6-dimethylphenyl-phenyl-2-pyridyl)-methyl-imidazole, 1-(2,4-dimethylphenyl-phenyl-4-pyridyl)-methyl-imidazole, 1-(3,4-dimethylphenyl-phenyl-4-pyridyl)-methyl-imidazole, 1-(2,5-dimethylphenyl-phenyl-4-pyridyl)-methyl-imidazole, 1-(2,3-dimethylphenyl-phenyl-2-pyridyl)-methyl-imidazole, 1-(2,3-dimethylphenyl-phenyl-2-pyridyl)-methyl-imidazole, 1-(2,3-dimethylphenyl-phenyl-2-pyridyl)-methyl-imidazole, 1-(2,3-dimethylphenyl-phenyl-4-pyridyl)-methyl-imidazole, 1-(3,4-dimethylphenyl-phenyl-4-pyridyl)-methyl-imidazole, or a pharmaceutically acceptable salt thereof, such as the 1,5-naphthalene-disulphonate salt thereof or the hydrochloride salt thereof.

In some embodiments, the CYP51A1 inhibitor is a compound represented by formula (XXVII)

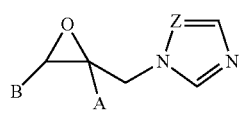

(XXVII)

wherein A and B are independently selected from optionally substituted alkyl (e.g., optionally substituted lower alkyl, such as alkyl of 1 to 4 carbon atoms), optionally substituted naphthyl, optionally substituted biphenyl, and optionally substituted phenyl, and Z is CH or N;

or a pharmaceutically acceptable salt, ester, or ether thereof.

In some embodiments of formula (XXVII), A and/or B is an optionally substituted phenyl group, such as a phenyl group substituted by one or more of halogen, nitro, alkyl (e.g., of from 1 to 4 carbon atoms), alkoxy (e.g., of from 1 to 4 carbon atoms), haloalkyl (e.g., of from 1 to 4 carbon atoms), phenoxy, or phenylsulyfonyl.

In some embodiments, the CYP51A1 inhibitor is a compound represented by formula (XXVIII)

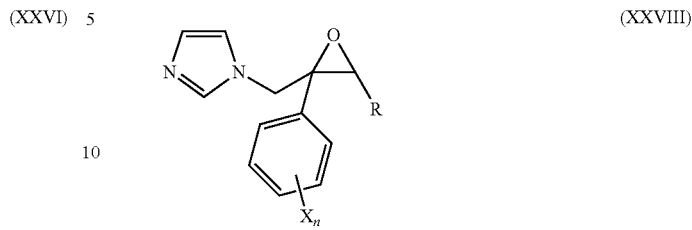

(XXVIII)

wherein R is optionally substituted aryl, such as phenyl, pyridyl, tetrahydropyranyl, norbornyl, $C_3$-$C_{12}$ cycloalkyl or $C_5$-$C_8$ cycloalkenyl, each of which may be unsubstituted or monosubstituted to trisubstituted by halogen, nitro, phenoxy, alkyl, amino, alkoxy (e.g., of from 1 to 4 carbon atoms), haloalkoxy (e.g., of from 1 to 4 carbon atoms), or haloalkyl (e.g., of from 1 to 4 carbon atoms);

each X is independently fluorine, chlorine, bromine, or iodine; and each n is independently 1, 2, 3, 4, or 5 (e.g., 1, 2, or 3);

or a pharmaceutically acceptable salt, ester, or ether thereof.

In some embodiments of formula (XXVIII), the compound is represented by formula (XXIX)

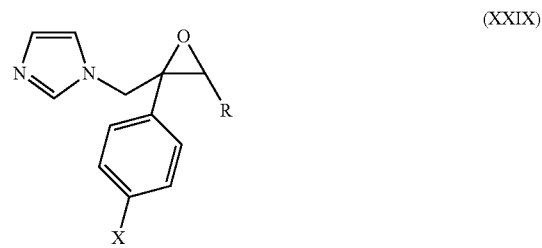

(XXIX)

wherein R and X are as defined for formula (XXVIII);

or a pharmaceutically acceptable salt, ester, or ether thereof.

In some embodiments of formula (XXVIII), the compound is represented by formula (XXX)

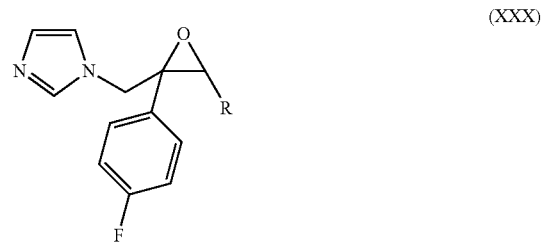

(XXX)

wherein R is as defined for formula (XXVIII);

or a pharmaceutically acceptable salt, ester, or ether thereof.

In some embodiments, the CYP51A1 inhibitor is a compound represented by formula (XXXI)

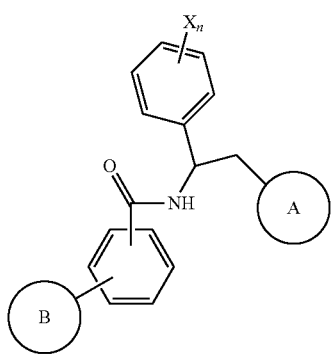

(XXXI)

wherein each of rings A and B are independently optionally substituted and optionally fused aryl, heteroaryl, cycloalkyl, or heterocycloalkyl;

each X is independently halogen or optionally substituted alkyl (e.g., optionally substituted lower alkyl); and n is 1, 2, 3, 4, or 5 (e.g., 1, 2, or 3);

or a pharmaceutically acceptable salt, ester, or ether thereof.

In some embodiments of formula (XXXI), the compound is represented by formula (XXXII)

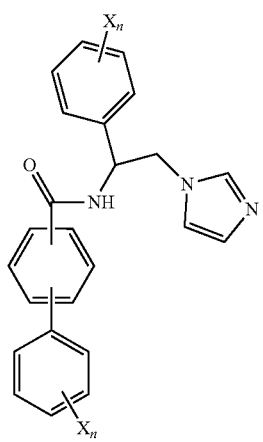

(XXXII)

wherein each X is independently halogen or optionally substituted alkyl (e.g., optionally substituted lower alkyl); and each n is independently 1, 2, 3, 4, or 5 (e.g., 1, 2, or 3);

or a pharmaceutically acceptable salt, ester, or ether thereof.

In some embodiments of formula (XXXII), the compound is represented by formula (XXXIII)

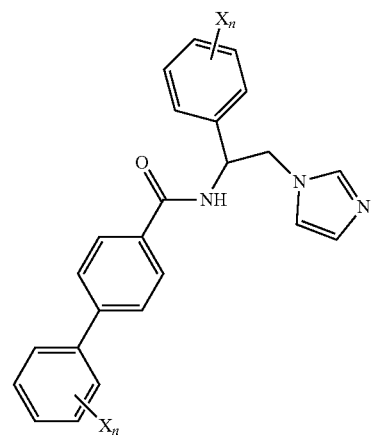

(XXXIII)

wherein each X and n are as defined for formula (XXXII);

or a pharmaceutically acceptable salt, ester, or ether thereof.

In some embodiments, the CYP51A1 inhibitor is represented by the formula:

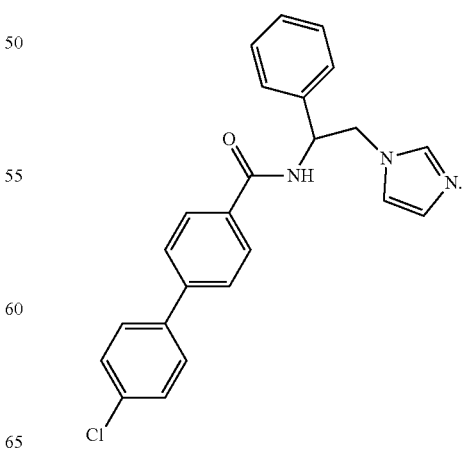

In some embodiments, the CYP51A1 inhibitor is a compound represented by formula (XXXIV)

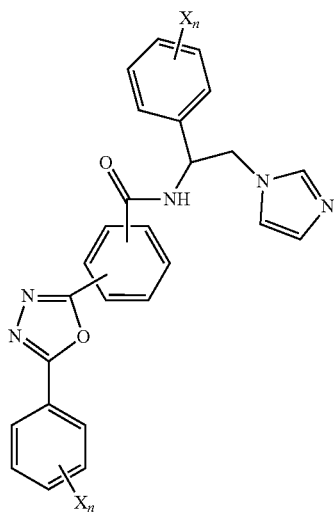

(XXXIV)

wherein each X is independently halogen or optionally substituted alkyl (e.g., optionally substituted lower alkyl); and each n is independently 1, 2, 3, 4, or 5 (e.g., 1, 2, or 3);

or a pharmaceutically acceptable salt, ester, or ether thereof.

In some embodiments of formula (XXXIV), the compound is represented by formula (XXXV)

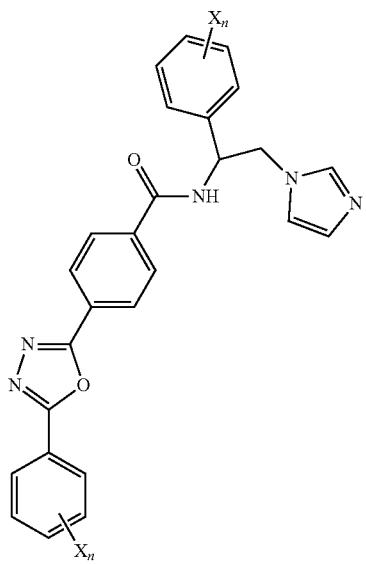

(XXXV)

wherein each X and n are as defined for formula (XXXIV);

or a pharmaceutically acceptable salt, ester, or ether thereof.

In some embodiments, the CYP51A1 inhibitor is represented by the formula:

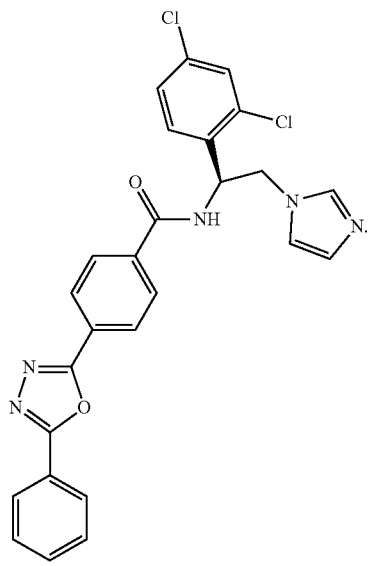 [SMILES: O=C(N[C@H](Cn1ccnc1)c1ccc(Cl)cc1Cl)c1ccc(-c2nnc(-c3ccccc3)o2)cc1]

In some embodiments, the CYP51A1 inhibitor is a compound represented by formula (XXXVI)

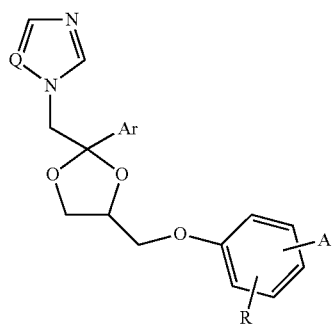

(XXXVI)

wherein Q is selected from the group consisting of CH and N;

Ar is an optionally substituted, optionally fused aryl group, such as an optionally fused, optionally substituted phenyl group, for example, a phenyl group having from 1 to 3 substituents, such as from 1 to 3 substituents independently selected from the group consisting of halo, lower alkyl and lower alkyloxy;

A is selected from the group consisting of:
(a) an isothiocyanato group —N=C=S;
(b) an amino group of the formula

wherein $R_1$ and $R_2$ are each independently selected from the group consisting of hydrogen and lower alkyl;

(c) a group of the formula

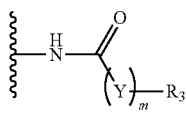

wherein X is selected from the group consisting of O and S, Y is selected from the group consisting of O and NH, m is the integer 0 or 1, and $R_3$ is selected from the group consisting of hydrogen, lower alkyl, mono- and dihalo-(lower alkyl), phenyl and substituted phenyl, said substituted phenyl having from 1 to 2 substituents independently selected from the group consisting of halo, lower alkyl and lower alkyloxy, optionally provided that:
i) when said X is S, then said Y is NH and said m is 1; and
ii) when said Y is O and said m is 1, then said $R_3$ is other than hydrogen; and
(d) a group of the formula

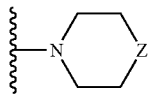

wherein Z is selected from the group consisting of a direct bond, $CH_2$, O and N—$R_4$, wherein $R_4$ is selected from the group consisting of hydrogen, lower alkyl, hydroxy-(lower alkyl), (lower alkyloxy)-lower alkyl, lower alkanoyl, lower alkylsulfonyl, phenylmethylsulfonyl, lower alkyloxycarbonyl, lower alkyloxycarbonylmethyl, phenoxycarbonyl, aminocarbonyl, mono- and di(lower alkyl)aminocarbonyl, aminocarbonylmethyl, (lower alkyl)aminocarbonylmethyl, (lower alkyl)aminothioxomethyl, (lower alkylthio)thioxomethyl, phenyl, phenylmethyl, benzoyl and substituted benzoyl, said substituted benzoyl being benzoyl having from 1 to 2 substituents independently selected from the group consisting of halo, lower alkyl and lower alkyloxy; and R is selected from the group consisting of hydrogen and nitro, optionally provided that when said R is nitro, then said A is amino;
or a pharmaceutically acceptable salt, ester, or ether thereof.

In some embodiments, the CYP51A1 inhibitor is a compound represented by formula (XXXVII)

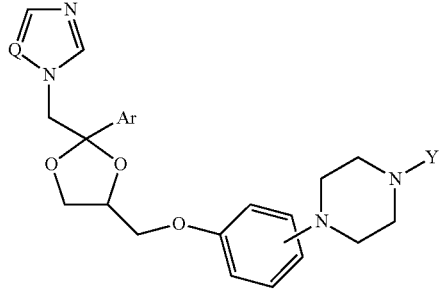

(XXXVII)

wherein Q is selected from the group consisting of N and CH;
Ar is selected from the group consisting of phenyl, thienyl, halothienyl and substituted phenyl, the substituted phenyl having from 1 to 3 substituents each independently selected from the group consisting of halo, lower alkyl, lower alkyloxy and trifluoromethyl; and
the group Y is selected from the group consisting of:
a group of the formula —$SO_2R_1$, wherein $R_1$ is selected from the group consisting of trifluoromethyl and aryl;
a group of formula -alk-$R_2$, wherein alk is selected from the group consisting of lower alkylene and lower alkenylene and $R_2$ is selected from the group consisting of cyano, amino, mono- and di(lower alkyl)amino, arylamino, mono- and di(aryllower alkyl)amino, 1-pyrrolidinyl, 1-morpholinyl, 1-piperidinyl, aryloxy and aryl, provided that alk is other than methylene when $R_2$ is phenyl;
a group of formula

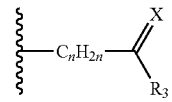

wherein n is an integer of from 0 to 6 inclusive, X is O or S and $R_3$ is selected from the group consisting of hydrogen, mono-, di- and trihalo lower alkyl, amino, mono- and di(lower alkyl)amino, arylamino, mono- and di(aryllower alkyl)amino, amino lower alkyl, mono- and di(lower alkyl)amino lower alkyl, (1-pyrrolidinyl)lower alkyl, (1-morpholinyl)lower alkyl, (1-piperidinyl)lower alkyl, aryl, aryllower alkyl, aryllower alkenyl and lower alkyloxycarbonyl lower alkyloxy, optionally provided that:
(i) said n is other than 0 or 1 when said $R_3$ is amino or lower alkylamino; and
(ii) said n is other than 0 when said $R_3$ is di(lower alkyl)amino or aryl; and
a group of formula

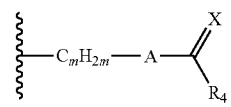

wherein m is an integer of from 1 to 6 inclusive, A is O or NH, X is O or S and $R_4$ is selected from the group consisting of hydrogen, lower alkyl, lower alkyloxy, aryl, aryloxy, aryllower alkyl, amino, mono- and di(lower alkyl)amino, arylamino, mono- and di(aryllower alkyl)amino, 1-pyrrolidinyl, 1-morpholinyl and 1-piperidinyl;
wherein said aryl, as used in the foregoing definitions, is selected from the group consisting of phenyl, substituted phenyl, thienyl, halothienyl, lower alkylthienyl and pyridinyl, said substituted phenyl optionally being a phenyl ring having from 1 to 3 substituents each independently selected from the group consisting of lower alkyl, lower alkyloxy, halo, amino, mono- and di(lower alkyl)amino, lower alkylcarbonylamino, nitro and trifluoromethyl;
or a pharmaceutically acceptable salt, ester, or ether thereof.

In some embodiments, the CYP51A1 inhibitor is a compound represented by formula (XXXVIII)

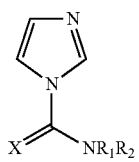

(XXXVIII)

wherein X is oxygen or sulfur, $R_1$ is optionally substituted alkyl, alkenyl, alkynyl, cycloalkyl, phenyl, phenylalkyl, phenylalkenyl, phenoxyalkyl or phenylthioalkyl and $R_2$ is optionally substituted phenyl, phenylalkyl, phenylalkenyl, phenoxyalkyl or phenylthioalkyl, provided that when $R_1$ is methyl or phenyl $R_2$ is substituted phenyl or optionally substituted phenylalkyl, phenylalkenyl, phenoxyalkyl or phenylthioalkyl;

or a pharmaceutically acceptable salt, ester, or ether thereof.

In some embodiments of formula (XXXVIII), X is selected from the group consisting of oxygen and sulfur, $R_1$ is selected from the group consisting of alkyl of 1 to 10 carbon atoms, alkenyl of 3 or 4 carbon atoms, alkynyl of 3 to 5 carbon atoms, cycloalkyl of 3 to 10 carbon atoms, optionally substituted phenyl, phenylalkyl, of the formula $Ph(CH_2)_n$ where n is 1 to 5, phenylalkenyl of 9 to 11 carbon atoms, phenoxyalkyl of the formula $PhO(CH_2)_n$ where n is 2 to 5 and phenylthioalkyl of the formula $PhS(CH_2)_n$ where n is 2 to 5, wherein the substituted phenyl nucleus has at least one substituent selected from the group consisting of halo, alkoxy of 1 or 2 carbon atoms, alkyl of 1 to 4 carbon atoms, trihalomethyl, cyano, methylthio, nitro and methylsulphonyl, and $R_2$ is selected from the group consisting of optionally substituted phenylalkyl, of the formula $Ph(CH_2)_n$ where n is 1 to 5, phenylalkenyl of 9 to 11 carbon atoms, phenoxyalkyl of the formula $PhO(CH_2)_n$ where n is 2 to 5 and phenylthioalkyl of the formula $PhS(CH_2)_n$ where n is 2 to 5, wherein the substituted phenyl nucleus has at least one substituent selected from the group consisting of halo, alkoxy of 1 or 2 carbon atoms, alkyl of 1 to 4 carbon atoms, trihalomethyl, cyano, methylthio, nitro and methylsulphonyl.

In some embodiments, the CYP51A1 inhibitor is prochloraz, represented by formula (7)

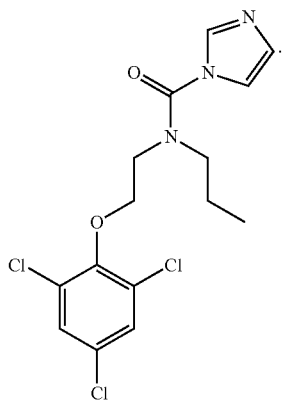

(7)

In some embodiments, the CYP51A1 inhibitor is a compound represented by formula (XXXIX)

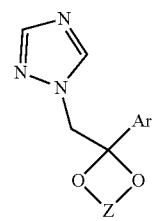

(XXXIX)

wherein Z is an alkylene selected from the group consisting of —$CH_2CH_2$—, —$CH_2$—$CH_2CH_2$—, —$CH(CH_3)CH(CH_3)$—, and —$CH_2CH(alkyl)$-, wherein the alkyl has from 1 to about 10 carbon atoms; and Ar is an optionally fused, optionally substituted aryl group, such as an optionally fused, optionally substituted phenyl, thienyl, naphthyl, or fluorenyl, for example, phenyl, thienyl, halothienyl, naphthyl and fluorenyl, each optionally containing one or more (e.g., from 1 to 3) substituents, such as substituents selected independently from the group consisting of halo, lower alkyl, lower alkyloxy, cyano, and nitro;

or a pharmaceutically acceptable salt, ester, or ether thereof.

In some embodiments, the CYP51A1 inhibitor is propiconazole, represented by formula (8)

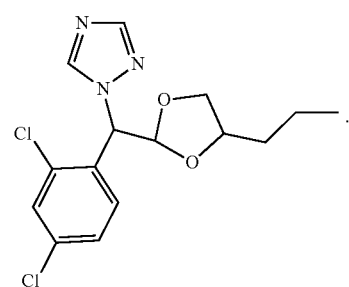

(8)

In some embodiments, the CYP51A1 inhibitor is a compound represented by formula (XL)

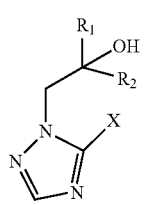

(XL)

wherein $R_1$ and $R_2$ are each independently selected from optionally substituted alkyl, optionally substituted alkenyl, optionally substituted cycloalkyl, optionally substituted aralkyl, optionally substituted aralkenyl, optionally substituted aroxyalkyl, optionally substituted aryl, and optionally substituted heteroaryl; and X is —SH, —$SR_3$, —SO—$R_3$, —$SO_2$—$R_3$, or —$SO_3H$, wherein $R_3$ is alkyl which is optionally substituted by one or more halogen moieties (e.g., fluorine and/or chlorine), alkenyl which is optionally substituted by one or more halogen moieties (e.g., fluorine and/or chlorine), optionally substituted aralkyl or optionally substituted aryl;

or a pharmaceutically acceptable salt, ester, or ether thereof.

In some embodiments, the CYP51A1 inhibitor is prothioconazole, represented by formula (8)

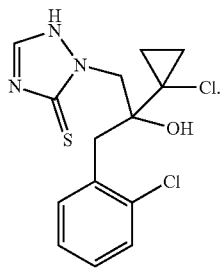

(8)

In some embodiments, the CYP51A1 inhibitor is prothioconazole-desthio, represented by formula (9)

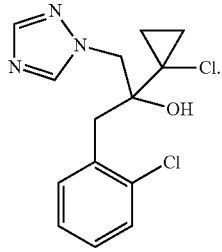

(9)

In some embodiments, the CYP51A1 inhibitor is a compound represented by formula (XLI)

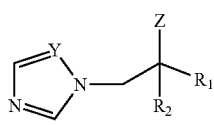

(XLI)

wherein $R_1$ is —CH=CH—X, —C≡C—X, or —CH$_2$—CH$_2$—X, wherein X is hydrogen, alkyl, hydroxyalkyl, alkoxyalkyl, cycloalkyl or optionally substituted aryl, aralkyl, aryloxy alkyl, or heterocycle;

$R_2$ is alkyl, cycloalkyl (e.g. cyclopropyl, cyclopentyl, or cyclohexyl) or optionally substituted aryl;

Z is Cl, CN, or $OR_3$, wherein $R_3$ is hydrogen, acetyl, alkyl, alkenyl or aralkyl; and Y is =N— or =CH—, or a pharmaceutically acceptable salt, ester, or ether thereof.

In some embodiments, the CYP51A1 inhibitor is tebuconazole, represented by formula (10)

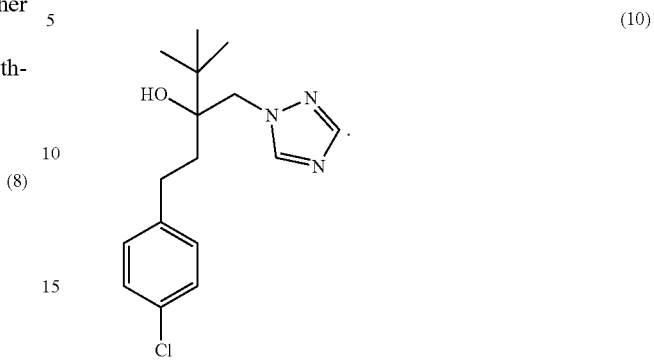

(10)

In some embodiments, the CYP51A1 inhibitor is a compound represented by formula (XLII)

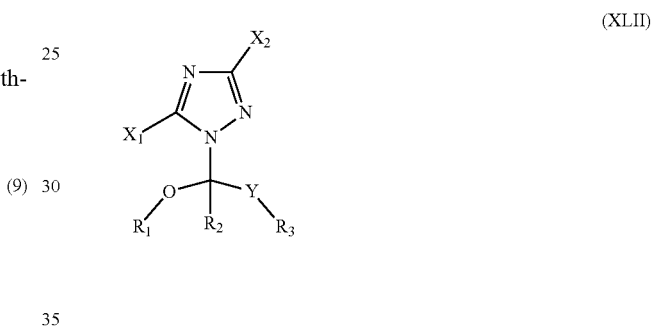

(XLII)

wherein $X_1$ is hydrogen or an alkyl group, $X_2$ is hydrogen or an alkyl group, $R_1$ is an alkyl, alkenyl, alkynyl, cycloalkyl, cycloalkenyl or optionally substituted aryl or aralkyl group, $R_2$ is hydrogen or an alkyl, alkenyl, alkynyl, cycloalkyl, cycloalkenyl or optionally substituted aryl or aralkyl group, $R_3$ is hydrogen or an alkyl, alkenyl, alkynyl, cycloalkyl, cycloalkenyl or optionally substituted aryl or aralkyl group, and Y is a keto group or a functional keto derivative.

or a pharmaceutically acceptable salt, ester, or ether thereof.

In some embodiments, the CYP51A1 inhibitor is triadimenol, represented by formula (11)

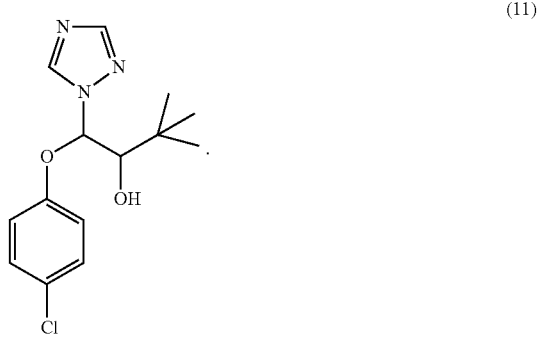 [SMILES: CC(C)(C)C(O)C(Oc1ccc(Cl)cc1)n1cncn1]

(11)

In some embodiments, the CYP51A1 inhibitor is a compound represented by formula (XLIII)

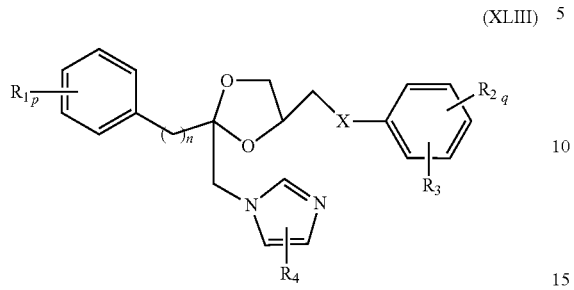

(XLIII)

wherein n is 2 or 3;

p is 0, 1 or 2;

q is 0, 1 or 2;

X is oxygen or $S(O)_t$ wherein t is 0, 1, or 2;

each $R_1$ is independently halo, lower alkyl, lower alkoxy, or trifluoromethyl;

each $R_2$ is independently halo or lower alkyl;

$R_3$ is nitro or $-N(R_5)R_6$ where $R_5$ is hydrogen or lower alkyl;

$R_6$ is hydrogen, lower alkyl, lower alkylsulfonyl or $-C(Y)R_7$ where Y is oxygen or sulfur and $R_7$ is hydrogen, lower alkyl, lower alkoxy or $-N(R_8)R_9$ where $R_8$ is hydrogen or lower alkyl and $R_9$ is hydrogen, lower alkyl or lower alkoxycarbonyl; or $R_5$ and $R_6$ together with N is pyrrolidino, piperidino, morpholino, thiomorpholino or piperazino, wherein the piperazino is optionally substituted at the 4-position by $-C(O)R_{10}$ where $R_{10}$ is hydrogen, lower alkyl, lower alkoxy or amino; and $R_4$ is hydrogen or optionally substituted lower alkyl;

or a pharmaceutically acceptable salt, ester, or ether thereof.

In some embodiments of formula (XLIII), the compound is represented by formula (XLIV)

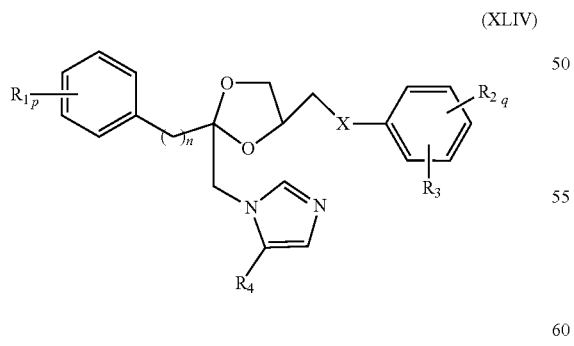

(XLIV)

wherein $R_1$, $R_2$, $R_3$, $R_4$, X, n, p, and q are as defined for formula (XLIII);

or a pharmaceutically acceptable salt, ester, or ether thereof.

In some embodiments of formula (XLIII), the compound is represented by formula (XLV)

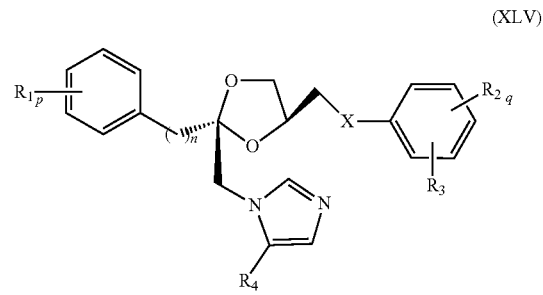

(XLV)

wherein $R_1$, $R_2$, $R_3$, $R_4$, X, n, p, and q are as defined for formula (XLIII);

or a pharmaceutically acceptable salt, ester, or ether thereof.

In some embodiments of formula (XLIII), the compound is represented by formula (XLVI)

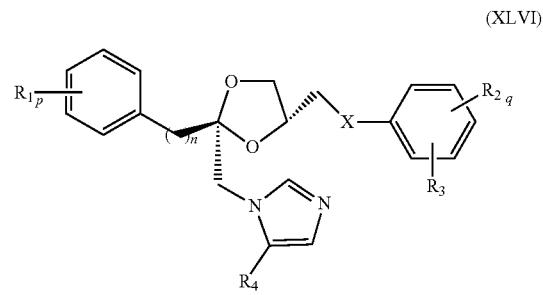

(XLVI)

wherein $R_1$, $R_2$, $R_3$, $R_4$, X, n, p, and q are as defined for formula (XLIII);

or a pharmaceutically acceptable salt, ester, or ether thereof.

In some embodiments of formula (XLIII), the compound is represented by formula (XLVII)

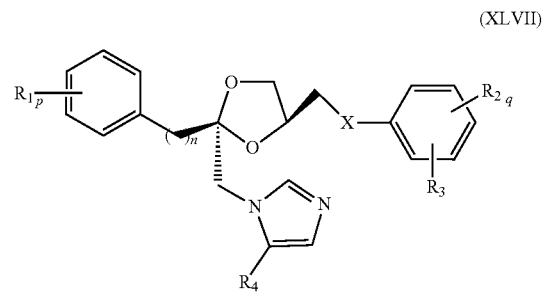

(XLVII)

wherein $R_1$, $R_2$, $R_3$, $R_4$, X, n, p, and q are as defined for formula (XLIII);

or a pharmaceutically acceptable salt, ester, or ether thereof.

In some embodiments of formula (XLIII), the compound is represented by formula (XLVIII)

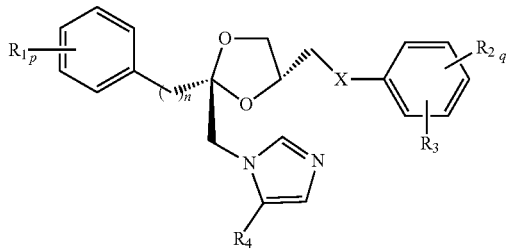

(XLVIII)

wherein R₁, R₂, R₃, R₄, X, n, p, and q are as defined for formula (XLIII);

or a pharmaceutically acceptable salt, ester, or ether thereof.

In some embodiments, the CYP51A1 inhibitor is azalanstat, represented by formula (12)

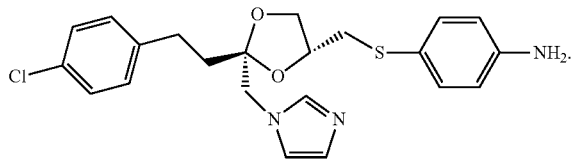

(12)

In some embodiments, the CYP51A1 inhibitor is LEK-935, CP-320626, itraconazole, posaconazole, cyproconazole, voriconazole, fluconazole, clotrimazol, fenticonazole, epoxiconazole, ketoconazole, ravuconazole, isavuconazole, holothurin A, theasaponin, capsicosine, betulafolientriol, prochloraz, propiconazole, prothioconazole, prothioconazole-desthio, tebuconazole, triadimenol, azalanstat, or a variant thereof.

In some embodiments, the CYP51A1 inhibitor is an antibody or antigen-binding fragment thereof, such as one that specifically binds to CYP51A1 and/or inhibits CYP51A1 catalytic activity. In some embodiments, the antibody or antigen-binding fragment thereof is a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')₂ molecule, and a tandem di-scFv. In some embodiments, the antibody has an isotype selected from IgG, IgA, IgM, IgD, and IgE.

In some embodiments, the CYP51A1 inhibitor is an interfering RNA molecule, such as a short interfering RNA (siRNA), micro RNA (miRNA), or short hairpin RNA (shRNA). The interfering RNA may suppress expression of a CYP51A1 mRNA transcript, for example, by way of (i) annealing to a CYP51A1 mRNA or pre-mRNA transcript, thereby forming a nucleic acid duplex; and (ii) promoting nuclease-mediated degradation of the CYP51A1 mRNA or pre-mRNA transcript and/or (iii) slowing, inhibiting, or preventing the translation of a CP51A1 mRNA transcript, such as by sterically precluding the formation of a functional ribosome-RNA transcript complex or otherwise attenuating formation of a functional protein product from the target RNA transcript.

In some embodiments, the interfering RNA molecule, such as the siRNA, miRNA, or shRNA, contains an antisense portion that anneals to a segment of a CYP51A1 RNA transcript (e.g., mRNA or pre-mRNA transcript), such as a portion that anneals to a segment of a CYP51A1 RNA transcript having a nucleic acid sequence that is at least 85% identical to the nucleic acid sequence of SEQ ID NO: 2 (e.g., 85%, 86%, 87%, 88%, 89%, 90%, 91%, 92%, 93%, 94%, 95%<96%, 97%, 98%, 99%, 99.9%, or 100% identical to the nucleic acid sequence of SEQ ID NO: 2).

In some embodiments, the interfering RNA molecule, such as the siRNA, miRNA, or shRNA, contains a sense portion having at least 85% sequence identity to the nucleic acid sequence of a segment of SEQ ID NO: 2 (e.g., 85%, 86%, 87%, 88%, 89%, 90%, 91%, 92%, 93%, 94%, 95%<96%, 97%, 98%, 99%, 99.9%, or 100% identical to the nucleic acid sequence of a segment of SEQ ID NO: 2).

In some embodiments, the neurological disorder is amyotrophic lateral sclerosis, and following administration of the CYP51A1 inhibitor to the patient, the patient exhibits one or more, or all, of the following responses:

(i) an improvement in condition as assessed using the amyotrophic lateral sclerosis functional rating scale (ALSFRS) or the revised ALSFRS (ALSFRS-R), such as an improvement in the patient's ALSFRS or ALSFRS-R score within one or more days, weeks, or months following administration of the CYP51A1 inhibitor (e.g., an improvement in the patient's ALSFRS or ALSFRS-R score within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient);

(ii) an increase in slow vital capacity, such as an increase in the patient's slow vital capacity within one or more days, weeks, or months following administration of the CYP51A1 inhibitor (e.g., an increase in the patient's slow vital capacity within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient);

(iii) a reduction in decremental responses exhibited by the patient upon repetitive nerve stimulation, such as a reduction that is observed within one or more days, weeks, or months following administration of the CYP51A1 inhibitor (e.g., a reduction that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient);

(iv) an improvement in muscle strength, as assessed, for example, by way of the Medical Research Council muscle testing scale (as described, e.g., in Jagtap et al., Ann. Indian. Acad. Neurol. 17:336-339 (2014), the disclosure of which is incorporated herein by reference as it pertains to measuring patient response to neurological disease treatment), such as an improvement that is observed within one or more days, weeks, or months following administration of the CYP51A1 inhibitor (e.g., an improvement that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient);

(v) an improvement in quality of life, as assessed, for example, using the amyotrophic lateral sclerosis-specific quality of life (ALS-specific QOL) questionnaire, such as an improvement in the patient's quality of life that is observed within one or more days, weeks, or months following administration of the CYP51A1 inhibitor (e.g., an improvement in the subject's quality of life that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient);

(vi) a decrease in the frequency and/or severity of muscle cramps, such as a decrease in cramp frequency and/or severity within one or more days, weeks, or months following administration of the CYP51A1 inhibitor (e.g., a decrease in cramp frequency and/or severity within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient); and/or (vii) a decrease in TDP-43 aggregation, such as a decrease in TDP-43 aggregation within one or more days, weeks, or months following administration of the CYP51A1 inhibitor (e.g., a decrease in TDP-43 aggregation within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient.

In another aspect, the invention features a kit containing a CYP51A1 inhibitor. The kit may further contain a package insert, such as one that instructs a user of the kit to perform the method of any of the above aspects or embodiments of the invention. The CYP51A1 inhibitor in the kit may be a small molecule, antibody, antigen-binding fragment thereof, or interfering RNA molecule, such as a small molecule, antibody, antigen-binding fragment thereof, or interfering RNA molecule described above and herein.

Definitions

As used herein, the term "about" refers to a value that is within 10% above or below the value being described. For instance, a value of "about 5 mg" refers to a quantity that is from 4.5 mg to 5.5 mg.

As used herein, the term "affinity" refers to the strength of a binding interaction between two molecules, such as a ligand and a receptor. The term "$K_i$", as used herein, is intended to refer to the inhibition constant of an antagonist for a particular molecule of interest, and is expressed as a molar concentration (M). $K_i$ values for antagonist-target interactions can be determined, e.g., using methods established in the art. The term "$K_d$", as used herein, is intended to refer to the dissociation constant, which can be obtained, e.g., from the ratio of the rate constant for the dissociation of the two molecules ($k_d$) to the rate constant for the association of the two molecules ($k_a$) and is expressed as a molar concentration (M). $K_d$ values for receptor-ligand interactions can be determined, e.g., using methods established in the art. Methods that can be used to determine the $K_d$ of a receptor-ligand interaction include surface plasmon resonance, e.g., through the use of a biosensor system such as a BIACORE® system.

As used herein, the terms "benefit" and "response" are used interchangeably in the context of a subject, such as a human subject undergoing therapy for the treatment of a neurological disorder, for example, amyotrophic lateral sclerosis, frontotemporal degeneration (also referred to as frontotemporal lobar degeneration and frontotemporal dementia), Alzheimer's disease, Parkinson's disease, dementia with Lewy Bodies, corticobasal degeneration, progressive supranuclear palsy, dementia parkinsonism ALS complex of Guam, Huntington's disease, Inclusion body myopathy with early-onset Paget disease and frontotemporal dementia (IBMPFD), sporadic inclusion body myositis, myofibrillar myopathy, dementia pugilistica, chronic traumatic encephalopathy, Alexander disease, and hereditary inclusion body myopathy. The terms "benefit" and "response" refer to any clinical improvement in the subject's condition. Exemplary benefits in the context of a subject undergoing treatment for a neurological disorder using the compositions and methods described herein (e.g., in the context of a human subject undergoing treatment for a neurological disorder described herein, such as amyotrophic lateral sclerosis, with a cytochrome P450 isoform 51A1 (CYP51A1) inhibitor described herein, such as an inhibitory small molecule, antibody, antigen-binding fragment thereof, or interfering RNA molecule) include the slowing and halting of disease progression, as well as suppression of one or more symptoms associated with the disease. Particularly, in the context of a patient (e.g., a human patient) undergoing treatment for amyotrophic lateral sclerosis with a CYP51A1 inhibitor described herein, examples of clinical "benefits" and "responses" are (i) an improvement in the subject's condition as assessed using the amyotrophic lateral sclerosis functional rating scale (ALSFRS) or the revised ALSFRS (ALSFRS-R) following administration of the CYP51A1 inhibitor, such as an improvement in the subject's ALSFRS or ALSFRS-R score within one or more days, weeks, or months following administration of the CYP51A1 inhibitor (e.g., an improvement in the subject's ALSFRS or ALSFRS-R score within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); (ii) an increase in the subject's slow vital capacity following administration of the CYP51A1 inhibitor, such as an increase in the subject's slow vital capacity within one or more days, weeks, or months following administration of the CYP51A1 inhibitor (e.g., an increase in the subject's slow vital capacity within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); (iii) a reduction in decremental responses exhibited by the subject upon repetitive nerve stimulation, such as a reduction that is observed within one or more days, weeks, or months following administration of the CYP51A1 inhibitor (e.g., a reduction that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); (iv) an improvement in the subject's muscle strength, as assessed, for example, by way of the Medical Research Council muscle testing scale (as described, e.g., in Jagtap et al., Ann. Indian. Acad. Neurol. 17:336-339 (2014), the disclosure of which is incorporated herein by reference as it pertains to measuring patient response to neurological disease treatment), such as an improvement that is observed within one or more days, weeks, or months following administration of the CYP51A1 inhibitor (e.g., an improvement that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); (v) an improvement in the subject's quality of life, as assessed, for example, using the amyotrophic lateral sclerosis-specific quality of life (ALS-specific QOL) questionnaire, such as an improvement in the subject's quality of life that is observed within one or more days, weeks, or months following administration of the CYP51A1 inhibitor (e.g., an improvement in the subject's quality of life that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); and (vi) a decrease in the frequency and/or severity of muscle cramps exhibited by the subject, such as a decrease in cramp frequency and/or severity within one or more days, weeks, or months following administration of the CYP51A1 inhibitor (e.g., a decrease in cramp frequency and/or severity within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject).

As used herein, the terms "conservative mutation," "conservative substitution," or "conservative amino acid substitution" refer to a substitution of one or more amino acids for one or more different amino acids that exhibit similar physicochemical properties, such as polarity, electrostatic charge, and steric volume. These properties are summarized for each of the twenty naturally-occurring amino acids in Table 1 below.

TABLE 1

Representative physicochemical properties of naturally-occurring amino acids

| Amino Acid | 3 Letter Code | 1 Letter Code | Side-chain Polarity | Electrostatic character at physiological pH (7.4) | Steric Volume[†] |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | nonpolar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

[†]based on volume in $A^3$: 50-100 is small, 100-150 is intermediate, 150-200 is large, and >200 is bulky From this table it is appreciated that the conservative amino acid families include, e.g., (i) G, A, V, L, I, P, and M; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

As used herein, the terms "cytochrome P450 isoform 51A1," "CYP51A1," and "lanosterol 14-alpha demethylase" are used interchangeably and refer to the enzyme that catalyzes the conversion of lanosterol to 4,4-dimethyl-cholesta-8(9),14,24-trien-3β-ol, for example, in human subjects. The terms "cytochrome P450 isoform 51A1," "CYP51A1," and "lanosterol 14-alpha demethylase" refer not only to wild-type forms of CYP51A1, but also to variants of wild-type CYP51A1 proteins and nucleic acids encoding the same. The amino acid sequence and corresponding mRNA sequence of a wild-type form of human CYP51A1 are provided herein as SEQ ID NOs: 1 and 2, which correspond to GenBank Accession No. AAC50951.1 and NCBI Reference Sequence NO. NM_000786.3, respectively. These sequences are shown in Table 2, below.

TABLE 2

Amino acid and mRNA nucleic acid sequences of wild-type human CYP5A1

| SEQ ID NO. | Sequence |
|---|---|
| 1 | MLLLGLLQAGGSVLGQAMEKVTGGNLLSMLLIACAFTLSLVYLIRLAAGHLVQLPAG VKSPPYIFSPIPFLGHAIAFGKSPIEFLENAYEKYGPVFSFTMVGKTFTYLLGSDAAAL LFNSKNEDLNAEDVYSRLTTPVFGKGVAYDVPNPVFLEQKKMLKSGLNIANFKQHV SIIEKETKEYFESWGESGEKNVFEALSELIILTASHCLHGKEIRSQLNEKVAQLYADL DGGFSHAAWLLPGWLPLPSFRRRDRAHREIKDIFYKAIQKRRQSQEKIDDILQTLLD ATYKDGRPLTDDEVAGMLIGLLLAGQHTSSTTSAWMGFFLARDKTLQKKCYLEQKT |

TABLE 2-continued

Amino acid and mRNA nucleic acid sequences of wild-type human CYP5A1

| SEQ ID NO. | Sequence |
|---|---|
|  | VCGENLPPLTYDQLKDLNLLDRCIKETLRLRPPIMIMMRMARTPQTVAGYTIPPGHQ VCVSPTVNQRLKDSWVERLDFNPDRYLQDNPASGEKFAYVPFGAGRHRCIGENFA YVQIKTIWSTMLRLYEFDLIDGYFPTVNYTTMIHTPENPVIRYKRRSK |
| 2 | GUGACGCACGGGGUGGCGCGCGUGGGACCCGAGGGGUGGGGCUGGGUUUA GUAGGAGACCUGGGGCAAGGCCCCCUGUGGACGACCAUCUGCCAGCUUCUC UCGUUCCGUCGAUUGGGAGGAGCGGUGGCGACCUCGGCCUUCAGUGUUUCC GACGGAGUGAAUGGCGGCGGCGGCUGGGAUGCUGCUGCUGGGCUUGCUGC AGGCGGGUGGGUCGGUGCUGGGCCAGGCGAUGGAGAAGGUGACAGGCGGC AACCUCUUGUCCAUGCUGCUGAUCGCCUGCGCCUUCACCCUCAGCCUGGUC UACCUGAUCCGUCUGGCCGCCGGCCACCUGGUCCAGCUGCCCGCAGGGGUG AAAAGUCCUCCAUACAUUUUCUCCCCAAUUCCAUUCCUUGGGCAUGCCAUAG CAUUUGGGAAAAGUCCAAUUGAAUUUCUAGAAAAUGCAUAUGAGAAGUAUGG ACCUGUAUUUAGUUUUACCAUGGUAGGCAAGACAUUUACUUACCUUCUGGGG AGUGAUGCUGCUGCACUGCUUUUUAAUAGUAAAAAUGAAGACCUGAAUGCAG AAGAUGCUACAGUCGCCUGACAACACCUGUGUUUGGGAAGGGAGUUGCAU ACGAUGUGCCUAAUCCAGUUUUCUUGGAGCAGAAGAAAAUGUUAAAAAGUGG CCUUAACAUAGCCCACUUUAAACAGCAUGUUUCUAUAAUUGAAAAAGAAACAA AGGAAUACUUUGAGAGUUGGGGAGAAAGUGGAGAAAAAAAUGUGUUUGAAGC UCUUUCUGAGCUCAUAAUUUUAACAGCUAGCCAUUGUUUGCAUGGAAAGGAA AUCAGAAGUCAACUCAAUGAAAAGGUAGCACAGCUGUAUGCAGAUUUGGAUG GAGGUUUCAGCCAUGCAGCCUGGCUCUUACCAGGUUGGCUGCCUUUGCCUA GUUUCAGACGCAGGGACAGAGCUCAUCGGGAAAUCAAGGAUAUUUUCUAUAA GGCAAUCCAGAAACGCAGACAGUCUCAAGAAAAAAUUGAUGACAUUCUCCAAA CUUUACUAGAUGCUACAUACAAGGAUGGGCGUCCUUUGACUGAUGAUGAAGU AGCAGGGAUGCUUAUUGGAUUACUCUUGGCAGGGCAGCAUACAUCCUCAACU ACUAGUGCUUGGAUGGGCUUCUUUUUGGCCAGAGACAAAACACUUCAAAAAA AAUGUUAUUUGAACAGAAAACAGUCUGUGGAGAGAAUCUGCCUCCUUUAAC UUAUGACCAGCUCAAGGAUCUAAAUUUACUUGAUCGCUGUAUAAAAGAAACA UUAAGACUUAGACCUCCUAUAAUGAUCAUGAUGAGAAUGGCCAGAACUCCUC AGACUGUGGCAGGGUAUACCAUUCCUCCAGGACAUCAGGUGUGUGUUUCUC CCACUGUCAAUCAAAGACUUAAAGACUCAUGGGUAGAACGCCUGGACUUUAA UCCUGACGCUACUUACAGGAUAACCCAGCAUCAGGGGAAAAGUUUGCCUAU GUGCCAUUUGGAGCUGGGCGUCAUCGUUGUAUUGGGGAAAAUUUUGCCUAU GUUCAAAUUAAGACAAUUUGGUCCACUAUGCUUCGUUUAUAUGAAUUUGAUC UCAUUGAUGGAUACUUUCCCACUGUGAAUUAUACAACUAUGAUUCACACCCC UGAAAACCCAGUUAUCCGUUACAAACGAAGAUCAAAAUGAAAAAGGUUGCAAG GAACGAAUAUAUGUGAUUAUCACUGUAAGCCACAAAGGCAUUCGAAGAGAAU GAAGUGUACAAACAACUCUUGUAGUUUACUGUUUUUUUAAGUGUGUAAUUC UAAAAGCCAGUUUAUGAUUUAGGAUUUUGUUAACUGAAUGGUUCUAUCAAAU AUAAUAGCAUUUGAAACAUUUUCUAAAUAGUUAUGAUACUUAACAUGUGCUU UCAGGAAGUUCCUUGGUGAAACAAUUGUUGAGGGGGGAUCUAGGUAAUUGG CAGAUUCUAAAUAAUAUAAUUUCCAGAUAGUAAUUUUAAGAGUACUCAUCGCU CUUGCCAAAUAAGUUCAGGGUAUUCAAAUCUUGGACUAGUCCUGCAAGGUAU AAAGAAUAAAAAUCCCAGUGAGAUACUUGGAAACCACAGUUUAUUAUUAUUUA UCUGGGCAAUUAUUGUGUGUGUGAGGAUGGAAGGGUAGGGAAUAAUCGAAC AUCUAAAGCCUUGAAUAAGAGAAUACUAAUUGUUUUGGUAUGAUGAUACUCA GAAAUGGAGAUAUUAUAGGAAAAAGAAAUCCUUUGGAAUUUUAACUAAAAUCA CUGCAUAUGGGAAAUUAAGAGAUCCAGGACCAUAUUUGUAAGAGUUCCUAA AAAUAAUGUAAUUAUUAAUGCUAAAGACUGCUCAUGUAUCUUGAUCUAAUUAC UAAAUAAUUACAUAUUUAUUUACCUGAUAAAUAUGUAUCUAGUUCUACAAGGU CACAUUUAUGUGGAAGUCCAAAGUCAAGUCCUUAGGGGAUAAUUUUGUUUUG GCUCAGUUGUUCCCUGCUUCCUUUUUUUUUUUUUUUUUUUGAGAUGGAGUC UCGCUCUGUUGCCCAGGCUGGAGUGCAGUGGUGCGAUCUCAGCUCACUGCA UCCUCUGCCUCCCGGGUUCAAGCAAUUCUCUGCCUCAGCCUCCCAAGUAGU UGGGAUUACAGGCACCUGCCACCAUGCCUGGCUAAUUUUUGUAUUUUUAG UAGAGACGGGGUUUCACUAUGUUGGCUAGGCUGGUCUUGAACUCCUGACC UCGUGAUCCACCCGCCUUGGCCUCCCAAAGUGCUGGGAUUACAGGCAUGAG CCACCGCACCUGGCCUUCCCUGCUUCCUCUCUAGAAUCCAAUUAGGGAUGUU UGUUACUACUCAUAUUGAUUAAAACAGUUAACAAACUUUUUUCUUUUUAAAAU GUGAGAUCAGUGAACUCUGGUUUUAAGAUAAUCUGAAACAAGGUCCUUGGGA GUAAUAAAAUUGGUCACAUUCUGUAAAGCACAUUCUGUUUAGGAAUCAACUU AUCUCAAAUUGUAACUCGGGCCUAACUAUAUGAGAUGGCUGAAAAAAUACC ACAUCGUCUGUUUUCACUAGGUGAUGCCAAAAUAUUUUGCUUUAUGUAUAUU ACAGUUCUUUUUAAAACACUGGAAGACUCAUGUUAAACUCUAAUUGUGAAGG CAGAAUCUCUGCUAAUUUUUCAGAUUAAAAUUCUCUUUGAAAAAAUACA |

The terms "cytochrome P450 isoform 51A1," "CYP51A1," and "lanosterol 14-alpha demethylase" as used herein include, for example, forms of the human CYP51A1 protein that have an amino acid sequence that is at least 85% identical to the amino acid sequence of SEQ ID NO: 1 (e.g., 85%, 86%, 87%, 88%, 89%, 90%, 91%, 92%, 93%, 94%, 95%, 96%, 97%, 98%, 99%, 99.9%, or 100% identical to the amino acid sequence of SEQ ID NO: 1) and/or forms of the human CYP51A1 protein that contain one or more substitutions, insertions, and/or deletions (e.g., one or more conservative and/or nonconservative amino acid substitutions, such as up to 5, 10, 15, 20, 25, or more, conservative or nonconservative amino acid substitutions) relative to a wild-type CYP51A1 protein. Similarly, the terms "cytochrome P450 isoform 51A1," "CYP51A1," and "lanosterol 14-alpha demethylase" as used herein include, for example, forms of the human CYP51A1 gene that encode an mRNA transcript having a nucleic acid sequence that is at least 85% identical to the nucleic acid sequence of SEQ ID NO: 2 (e.g., 85%, 86%, 87%, 88%, 89%, 90%, 91%, 92%, 93%, 94%, 95%, 96%, 97%, 98%, 99%, 99.9%, or 100% identical to the amino acid sequence of SEQ ID NO: 2).

As used herein, the terms "cytochrome P450 isoform 51A1 inhibitor," "CYP51A1 inhibitor," and "lanosterol 14-alpha demethylase inhibitor" are used interchangeably and refer to substances, such as small molecules, peptides, and biologic agents (e.g., antibodies and antigen-binding fragments thereof), that suppress the activity of the CYP51A1 enzyme. Inhibitors of this type may, for example, competitively inhibit CYP51A1 activity by specifically binding the CYP51A1 enzyme (e.g., by virtue of the affinity of the inhibitor for the CYP51A1 active site), thereby precluding, hindering, or halting the entry of one or more endogenous substrates of CYP51A1 into the enzyme's active site. Additional examples of CYP51A1 inhibitors that suppress the activity of the CYP51A1 enzyme include substances, such as small molecules, peptides, and biologic agents (e.g., antibodies and antigen-binding fragments thereof), that may bind CYP51A1 at a site distal from the active site and attenuate the binding of endogenous substrates to the CYP51A1 active site by way of a change in the enzyme's spatial conformation upon binding of the inhibitor. In addition to encompassing substances that modulate CYP51A1 activity, the terms "cytochrome P450 isoform 51A1 inhibitor," "CYP51A1 inhibitor," and "lanosterol 14-alpha demethylase inhibitor" refer to substances that reduce the concentration and/or stability of CYP51A1 mRNA transcripts in vivo, as well as those that suppress the translation of functional CYP51A1 enzyme. Examples of inhibitors of this type are interfering RNA molecules, such as short interfering RNA (siRNA), micro RNA (miRNA), and short hairpin RNA (shRNA). Additional examples of "cytochrome P450 isoform 51A1 inhibitors," "CYP51A1 inhibitors," and "lanosterol 14-alpha demethylase inhibitors" are substances, such as small molecules, peptides, and biologic agents (e.g., antibodies and antigen-binding fragments thereof), that attenuate the transcription of an endogenous gene encoding CYP51A1.

As used herein, the term "dose" refers to the quantity of a therapeutic agent, such as a CYP51A1 inhibitor described herein (e.g., an inhibitory small molecule, antibody, antigen-binding fragment thereof, or interfering RNA molecule described herein) that is administered to a subject for the treatment of a disorder or condition, such as to treat or prevent a neurological disorder in a subject (e.g., a human subject). A therapeutic agent as described herein may be administered in a single dose or in multiple doses for the treatment of a particular indication. In each case, the therapeutic agent may be administered using one or more unit dosage forms of the therapeutic agent. For instance, a single dose of 1 mg of a therapeutic agent may be administered using, e.g., two 0.5 mg unit dosage forms of the therapeutic agent, four 0.25 mg unit dosage forms of the therapeutic agent, one single 1 mg unit dosage form of the therapeutic agent, and the like.

As used herein, the term "endogenous" describes a molecule (e.g., a metabolite, polypeptide, nucleic acid, or cofactor) that is found naturally in a particular organism (e.g., a human) or in a particular location within an organism (e.g., an organ, a tissue, or a cell, such as a human cell).

As used herein, the term "exogenous" describes a molecule (e.g., a small molecule, polypeptide, nucleic acid, or cofactor) that is not found naturally in a particular organism (e.g., a human) or in a particular location within an organism (e.g., an organ, a tissue, or a cell, such as a human cell). Exogenous materials include those that are provided from an external source to an organism or to cultured matter extracted there from.

As used herein, the term "interfering RNA" refers to a RNA, such as a short interfering RNA (siRNA), micro RNA (miRNA), or short hairpin RNA (shRNA) that suppresses the expression of a target RNA transcript, for example, by way of (i) annealing to the target RNA transcript, thereby forming a nucleic acid duplex; and (ii) promoting the nuclease-mediated degradation of the RNA transcript and/or (iii) slowing, inhibiting, or preventing the translation of the RNA transcript, such as by sterically precluding the formation of a functional ribosome-RNA transcript complex or otherwise attenuating formation of a functional protein product from the target RNA transcript. Interfering RNAs as described herein may be provided to a patient, such as a human patient having a neurological disorder described herein, in the form of, for example, a single- or double-stranded oligonucleotide, or in the form of a vector (e.g., a viral vector) containing a transgene encoding the interfering RNA. Exemplary interfering RNA platforms are described, for example, in Lam et al., Molecular Therapy-Nucleic Acids 4:e252 (2015); Rao et al., Advanced Drug Delivery Reviews 61:746-769 (2009); and Borel et al., Molecular Therapy 22:692-701 (2014), the disclosures of each of which are incorporated herein by reference in their entirety.

"Percent (%) sequence complementarity" with respect to a reference polynucleotide sequence is defined as the percentage of nucleic acids in a candidate sequence that are complementary to the nucleic acids in the reference polynucleotide sequence, after aligning the sequences and introducing gaps, if necessary, to achieve the maximum percent sequence complementarity. A given nucleotide is considered to be "complementary" to a reference nucleotide as described herein if the two nucleotides form canonical Watson-Crick base pairs. For the avoidance of doubt, Watson-Crick base pairs in the context of the present disclosure include adenine-thymine, adenine-uracil, and cytosine-guanine base pairs. A proper Watson-Crick base pair is referred to in this context as a "match," while each unpaired nucleotide, and each incorrectly paired nucleotide, is referred to as a "mismatch." Alignment for purposes of determining percent nucleic acid sequence complementarity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal complementarity over the full length of the sequences being compared. As an illustration, the percent sequence complementarity of a given nucleic acid sequence, A, to a given nucleic acid sequence, B, (which can alternatively be phrased as a given nucleic acid sequence, A that has a certain percent complementarity to a given nucleic acid sequence, B) is calculated as follows:

$$100 \text{ multiplied by (the fraction } X/Y)$$

where X is the number of complementary base pairs in an alignment (e.g., as executed by computer software, such as BLAST) in that program's alignment of A and B, and where Y is the total number of nucleic acids in B. It will be appreciated that where the length of nucleic acid sequence A is not equal to the length of nucleic acid sequence B, the percent sequence complementarity of A to B will not equal the percent sequence complementarity of B to A. As used herein, a query nucleic acid sequence is considered to be "completely complementary" to a reference nucleic acid sequence if the query nucleic acid sequence has 100% sequence complementarity to the reference nucleic acid sequence.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction X/Y)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

As used herein in the context of administration of a therapeutic agent, the term "periodically" refers to administration of the agent two or more times over the course of a treatment period (e.g., two or more times daily, weekly, monthly, or yearly).

As used herein, the term "pharmaceutical composition" means a mixture containing a therapeutic compound to be administered to a patient, such as a mammal, e.g., a human, in order to prevent, treat or control a particular disease or condition affecting the mammal, such as a neurological disorder described herein.

As used herein, the term "pharmaceutically acceptable" refers to those compounds, materials, compositions and/or dosage forms, which are suitable for contact with the tissues of a patient, such as a mammal (e.g., a human) without excessive toxicity, irritation, allergic response and other problem complications commensurate with a reasonable benefit/risk ratio.

As used herein in the context of therapeutic treatment, the terms "provide" and "providing" refer to the delivery of a therapeutic agent to a subject (e.g., a mammalian subject, such as a human) in need of treatment, such as a subject experiencing or at risk of developing a neurological disorder described herein. A therapeutic agent may be provided to a subject in need thereof, for instance, by direct administration of the therapeutic agent to the subject, or by administration of a prodrug that is converted in vivo to the therapeutic agent upon administration of the prodrug to the subject. Exemplary prodrugs include, without limitation, esters, phosphates, and other chemical functionalities susceptible to hydrolysis upon administration to a subject. Prodrugs include those known in the art, such as those described, for instance, in Vig et al., Adv. Drug Deliv. Rev. 65:1370-1385 (2013), and Huttunen et al., Pharmacol. Rev. 63:750-771 (2011), the disclosures of each of which are incorporated herein by reference in their entirety.

As used herein, the term "neuromuscular disorder" refers to a disease impairing the ability of one or more neurons to control the activity of an associated muscle. Examples of neuromuscular disorders are amyotrophic lateral sclerosis, congenital myasthenic syndrome, congenital myopathy, cramp fasciculation syndrome, Duchenne muscular dystrophy, glycogen storage disease type II, hereditary spastic paraplegia, inclusion body myositis, Isaac's Syndrome, Kearns-Sayre syndrome, Lambert-Eaton myasthenic syndrome, mitochondrial myopathy, muscular dystrophy, myasthenia gravis, myotonic dystrophy, peripheral neuropathy, spinal and bulbar muscular atrophy, spinal muscular atrophy, Stiff person syndrome, Troyer syndrome, and Guillain-Barré syndrome, among others.

As used herein, the term "sample" refers to a specimen (e.g., blood, blood component (e.g., serum or plasma), urine, saliva, amniotic fluid, cerebrospinal fluid, tissue (e.g., placental or myometrial), pancreatic fluid, chorionic villus sample, and cells) isolated from a patient.

As used herein, the phrases "specifically binds" and "binds" refer to a binding reaction which is determinative of the presence of a particular protein in a heterogeneous population of proteins and other biological molecules that is recognized, e.g., by a ligand with particularity. A ligand (e.g., a protein, proteoglycan, or glycosaminoglycan) that specifically binds to a protein will bind to the protein, e.g., with a $K_D$ of less than 100 nM. For example, a ligand that specifically binds to a protein may bind to the protein with a $K_D$ of up to 100 nM (e.g., between 1 pM and 100 nM). A ligand that does not exhibit specific binding to a protein or a domain thereof will exhibit a $K_D$ of greater than 100 nM (e.g., greater than 200 nM, 300 nM, 400 nM, 500 nM, 600 nm, 700 nM, 800 nM, 900 nM, 1 µM, 100 µM, 500 µM, or 1 mM) for that particular protein or domain thereof. A variety of assay formats may be used to determine the affinity of a ligand for a specific protein. For example, solid-phase ELISA assays are routinely used to identify ligands that specifically bind a target protein. See, e.g., Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of assay formats and conditions that can be used to determine specific protein binding.

As used herein, the terms "subject' and "patient" are used interchangeably and refer to an organism, such as a mammal (e.g., a human) that receives therapy for the treatment or prevention of a neurological disease described herein, for example, for amyotrophic lateral sclerosis. Patients that may receive therapy, or that are considered to be in need of therapy, for the treatment or prevention of a neurological disease described herein include subjects (e.g., human subjects) that have been diagnosed as having the neurological disease and/or that exhibit one or more symptoms of the disease, as well as those at risk of developing the disease. In the context of a neurological disorder described herein, such as amyotrophic lateral sclerosis, examples of patients that may be treated using the compositions and methods of the present disclosure are those that are at risk of developing the disease, as well as those that are classified as having clinically definite, clinically probable, clinically probable (laboratory-supported), or clinically possible amyotrophic lateral sclerosis according to the EI-Escorial diagnostic criteria for this disease. A patient may be diagnosed as having a neurological disorder, for example, by way of (i) electrodiagnostic tests including electomyography (EMG) and nerve conduction velocity (NCV); (ii) blood and urine studies, including high resolution serum protein electrophoresis, thyroid and parathyroid hormone levels, and 24-hour urine collection for heavy metals; (iii) spinal tap; x-rays, including magnetic resonance imaging; (iv) myelogram of cervical spine; (v) muscle and/or nerve biopsy; and/or (vi) thorough neurological evaluation.

A variety of clinical indicators can be used to identify a patient as "at risk" of developing a particular neurological disease. Examples of patients (e.g., human patients) that are "at risk" of developing a neurological disease, such as amyotrophic lateral sclerosis, frontotemporal degeneration, Alzheimer's disease, Parkinson's disease, dementia with Lewy Bodies, corticobasal degeneration, progressive supranuclear palsy, dementia parkinsonism ALS complex of Guam, Huntington's disease, Inclusion body myopathy with early-onset Paget disease and frontotemporal dementia (IBMPFD), sporadic inclusion body myositis, myofibrillar myopathy, dementia pugilistica, chronic traumatic encephalopathy, Alexander disease, and hereditary inclusion body myopathy, include (i) subjects exhibiting or prone to exhibit aggregation of TAR-DNA binding protein (TDP)-43, and (ii) subjects expressing a mutant form of TDP-43 containing a mutation associated with TDP-43 aggregation and toxicity, such as a mutation selected from Q331K, M337V, Q343R, N345K, R361 S, and N390D. Subjects that are "at risk" of developing amyotrophic lateral sclerosis may exhibit one or both of these characteristics, for example, prior to the first administration of a CYP51A1 inhibitor in accordance with the compositions and methods described herein.

As used herein, the terms "TAR-DNA binding protein-43" and "TDP-43" are used interchangeably and refer to the transcription repressor protein involved in modulating HIV-1 transcription and alternative splicing of the cystic fibrosis transmembrane conductance regulator (CFTR) pre-mRNA transcript, for example, in human subjects. The terms "TAR-DNA binding protein-43" and "TDP-43" refer not only to wild-type forms of TDP-43, but also to variants of wild-type TDP-43 proteins and nucleic acids encoding the same. The amino acid sequence and corresponding mRNA sequence of a wild-type form of human TDP-43 are provided herein as SEQ ID NOs: 3 and 4, which correspond to NCBI Reference Sequence NOs. NM_007375.3 and NP_031401.1, respectively. These sequences are shown in Table 3, below.

TABLE 3

| Amino acid and nucleic acid sequences of wild-type human TDP-43 | |
|---|---|
| SEQ ID NO. | Sequence |
| 3 | MSEYIRVTEDENDEPIEIPSEDDGTVLLSTVTAQFPGACGLRYRNPVSQCMRGVRL VEGILHAPDAGWGNLVYVVNYPKDNRKMDETDASSAVKVKRAVQKTSDLIVLGLP WKTTEQDLKEYFSTFGEVLMVQVKKDLKTGHSKGFGFVRFTEYETQVKVMSQRH MIDGRWCDCKLPNSKQSQDEPLRSRKVFVGRCTEDMTEDELREFFSQYGDVMDV FIPKPFRAFAFVTFADDQIAQSLCGEDLIIKGISVHISNAEPKHNSNRQLERSGRFGG NPGGFGNQGGFGNSRGGGAGLGNNQGSNMGGGMNFGAFSINPAMMAAAQAAL QSSWGMMGMLASQQNQSGPSGNNQNQGNMQREPNQAFGSGNNSYSGSNSGA AIGWGSASNAGSGSGFNGGFGSSMDSKSSGWGM |
| 4 | GGUGGGCGGGGGAGGAGGCGGCCCUAGCGCCAUUUGUGGGAGCGAAGC GGUGGCUGGGCUGCGCUUGGGUCCGUCGCUGCUUCGGUGUCCCUGUCGGG CUUCCCAGCAGCGGCCUAGCGGGAAAAGUAAAAGAUGUCUGAAUAUAUUCGG GUAACCGAAGAUGAGAACGAUGAGCCCAUUGAAAUACCAUCGGAAGACGAUG GGACGGUGCUGCUCUCCACGGUUACAGCCCAGUUUCCAGGGGCGUGUGGGC UUCGCUACAGGAAUCCAGUGUCUCAGUGUAUGAGAGGUGUCCGGCUGGUAG AAGGAAUUCUGCAUGCCCCAGAUGCUGGCUGGGGAAAUCUGGUGUAUGUUG UCAACUAUCCAAAAGAUAACAAAAGAAAAAUGGAUGAGACAGAUGCUUCAUCA GCAGUGAAAGUGAAAAGAGCAGUCCAGAAAACAUCCGAUUUAAUAGUGUUGG GUCUCCCAUGGAAAACAACCGAACAGGACCUGAAAGAGUAUUUUAGUACCUU UGGAGAAGUUCUUAUGGUGCAGGUCAAGAAAGAUCUUAAGACUGGUCAUUCA AAGGGGUUUGGCUUUGUUCGUUUUACGGAAUAUGAAACACAAGUGAAAGUAA UGUCACAGCGACAUAUGAUAGAUGGACGAUGGUGUGACUGCAAACUUCCUAA UUCUAAGCAAAGCCAAGAUGAGCCUUUGAGAAGCAGAAAAGUGUUUGUGGGG CGCUGUACAGAGGACAUGACUGAGGAUGAGCUGCGGGAGUUCUUCUCUCAG UACGGGGAUGUGAUGGAUGUCUUCAUCCCCAAGCCAUUCAGGGCCUUUGCC UUUGUUACAUUUGCAGAUGAUCAGAUUGCGCAGUCUCUUUGUGGAGAGGAC UUGAUCAUUAAAGGAAUCAGCGUUCAUAUAUCCAAUGCCGAACCUAAGCACA AUAGCAAUAGACAGUUAGAAAGAAGUGGAAGAUUUGGUGGUAAUCCAGGUGG CUUUGGGAAUCAGGGUGGAUUUGGUAAUAGCAGAGGGGGUGGAGCUGGUUU GGGAAACAAUCAAGGUAGUAAUAUGGGUGGUGGGAUGAACUUUGGUGCGUU CAGCAUUAAUCCAGCCAUGAUGGCUGCCGCCCAGGCAGCACUACAGAGCAGU UGGGGUAUGAUGGGCAUGUUAGCCAGCCAGCAGAACCAGUCAGGCCCAUCG GGUAAUAACCAAAACCAAGGCAACAUGCAGAGGGAGCCAAACCAGGCCUUCG GUUCUGGAAAUAACUCUUAUAGUGGCUCUAAUUCUGGUGCAGCAAUUGGUU GGGGAUCAGCAUCCAAUGCAGGGUCGGGCAGUGGUUUUAAUGGAGGCUUUG GCUCAAGCAUGGAUUCUAAGUCUUCUGGCUGGGGAAUGUAGACAGUGGGGU UGUGGUUGGUUGGUAUAGAAUGGUGGGAAUUCAAAUUUUUCUAAACUCAUG |

TABLE 3-continued

Amino acid and nucleic acid sequences of wild-type human TDP-43

| SEQ ID NO. | Sequence |
|---|---|
| | GUAAGUAUAUUGUAAAAUACAUAUGUACUAAGAAUUUUCAAAAUUGGUUUGU<br>UCAGUGUGGAGUAUAUUCAGCAGUAUUUUUGACAUUUUUCUUUAGAAAAAGG<br>AAGAGCUAAAGGAAUUUUAUAAGUUUUGUUACAUGAAAGGUUGAAAUAUUGA<br>GUGGUUGAAAGUGAACUGCUGUUUGCCUGAUUGGUAAACCAACACACUACAA<br>UUGAUAUCAAAAGGUUUCUCCUGUAAUAUUUUAUCCCUGGACUUGUCAAGUG<br>AAUUCUUUGCAUGUUCAAAACGGAAACCAUUGAUUAGAACUACAUUCUUUAC<br>CCCUUGUUUUAAUUUGAACCCCACCAUAUGGAUUUUUUUCCUUAAGAAAAUC<br>UCCUUUUAGGAGAUCAUGGUGUCACAGUGUUUGGUUCUUUUGUUUUGUUUU<br>UUAACACUUGUCUCCCCUCAUACACAAAAGUACAAUAUGAAGCCUUCAUUUAA<br>UCUCUGCAGUUCAUCUCAUUUCAAAUGUUUAUGGAAGAAGCACUUCAUUGAA<br>AGUAGUGCUGUAAAUAUUCUGCCAUAGGAAUACUGUCUACAUGCUUUCUCAU<br>UCAAGAAUUCGUCAUCACGCAUCACAGGCCGCGUCUUUGACGGUGGGUGUC<br>CCAUUUUUAUCCGCUACUCUUUAUUUCAUGGAGUCGUAUCAACGCUAUGAAC<br>GCAAGGCUGUGAUAUGGAACCAGAAGGCUGUCUGAACUUUUGAAACCUUGU<br>GUGGGAUUGAUGGUGGUGCCGAGGCAUGAAAGGCUAGUAUGAGCGAGAAAA<br>GGAGAGAGCGCGUGCAGAGACUUGGUGGUGCAUAAUGGAUAUUUUUUAACU<br>UGGCGAGAUGUGUCUCUCAAUCCUGUGGCUUUGGUGAGAGAGUGUGCAGAG<br>AGCAAUGAUAGCAAAUAAUGUACGAAUGUUUUUUGCAUUCAAAGGACAUCCA<br>CAUCUGUUGGAAGACUUUUAAGUGAGUUUUUGUUCUUAGAUAACCCACAUUA<br>GAUGAUGUGUUAAGUGAAAUGAUACUUGUACUCCCCCUACCCCUUUGUCAA<br>CUGCUGUGAAUGCUGUAUGGUGUGUGUUCUCUUCUGUUACUGAUAUGUAAG<br>UGUGGCAAUGUGAACUGAAGCUGAUGGGCUGAGAACAUGGACUGAGCUUGU<br>GGUGUGCUUUGCAGGAGGACUUGAAGCAGAGUUCACCAGUGAGCUCAGGUG<br>UCUCAAAGAAGGGUGGAAGUUCUAAUGUCUGUUAGCUACCCAUAAGAAUGCU<br>GUUUGCUGCAGUUCUGUGUCCUGUGCUUGGAUGCUUUUUAUAAGAGUUGUC<br>AUUGUUGGAAAUUCUUAAAUAAAACUGAUUUAAAUAAUAUGUGUCUUUGUUU<br>UGCAGCCCUGAAUGCAAAGAAUUCAUAGCAGUUAAUUCCCCUUUUUUGACCC<br>UUUUGAGAUGGAACUUUCAUAAAGUUUCUUGGCAGUAGUUUAUUUUGCUUCA<br>AAUAAACUUAUUUGAAAAGUUGCUCAAGUCAAAUGGAUUCAUCACCUGUCA<br>UGCAUUGACACCUGAUACCCAGACUUAAUUGGUAUUUGUUCUUGCAUUGGCC<br>AAAGUGAAAAUUUUUUUUUUCUUUUGAAAUCUAGUUUUGAAUAAGUCUGGG<br>UGACCGCACCUAAAAUGGUAAGCAGUACCCUCCGGCUUUUUCUUAGUGCCUC<br>UGUGCAUUUGGGUGAUGUUCUAUUUACAUGGCCUGUGUAAAUCUCCAUUGG<br>GAAGUCAUGCCUUCUAAAAAGAUUCUUAUUUGGGGGAGUGGGCAAAAUGUUG<br>AUUAUUUUCUAAUGCUUUGUAGCAAAGCAUAUCAAUUGAAAAGGGAAUAUCA<br>GCACCUUCCUAGUUUGGGAUUUGAAAAGUGGAAUUAAUUGCAGUAGGGAUAA<br>AGUAGAAGAAACCACAAAUUAUCUUGUGCCUGAAAUCCAUUAAGAGGCCUGA<br>UAGCUUUAAGAAUUAGGGUGGGUUGUCUGUCUGGAAGUGUUAAGUGGAAUG<br>GGCUUUGUCCUCCAGGAGGUGGGGAAUGUGGUAACAUUGAAUACAGUUGA<br>AUAAAAUCGCUUACAAAACUCACACUCUCACAAUGCAUUGUUAAGUAUGUAAA<br>AGCAAUAACAUUGAUUCUCUGUUGUACUUUUUUGUAACUAAUUCUGUGAGAG<br>UUGAGCUCAUUUUCUAGUUGGAAGAAUGUGAUAUUUGUUGUGUUGGUAGUU<br>UACCUAAUGCCCUUACCUAAUUAGAUUAUGAUAAAUAGGUUUGUCAUUUUGC<br>AAGUUACAUAAACAUUUAUCAAUGAAGUCAUCCUUUAGACUUGUAAUCGCCAC<br>AUUGUUUCAUUAUUCAGUUUCCUCUGUAAAGGGAUCUUGAGUUGUUUUAAUU<br>UUUUUUUCUGCAUCUGAAUCUGCAUGAUUUCCAAACCCUGUACCAUCUGAA<br>UUUUGCAUUUUAGCACUUGCACUAUUACUCAGCAGCAGUAACAUGGUAACAC<br>UUAAAAUGGUACUCGGGGACCUCCAAAGACUAAACUGACAAGCCUUCAAGGA<br>GCCCAGGGGUAAGUUAACUUGUCAACGGCAUGGUUUAAUCCCUUCUUUACAC<br>UUGUGUAAAUUUCAGUUACUGGUCAUAGAAGGCUUUCAAUGUUGAGUGGCC<br>UUUUAUUAACAUGUUUAUGGUACUGCAUAGAUACGGGUAUUUAUUUUACCCU<br>AAGAAGAUUUUGAAGUUUAAAAGUACUUAAACUAUUUGGCAAAGAUUUGUUU<br>UUAAAAAUCUAUUGGUCAAUCUAAAUGCAUUCAUUCUAAAAAAUUUUUUGAA<br>CCAGAUAAAUAAAAUUUUUUUUUGACACCACAAAAAAAAAAAAAAAAAAAA |

The terms "TAR-DNA binding protein-43" and "TDP-43" as used herein include, for example, forms of the human TDP-43 protein that have an amino acid sequence that is at least 85% identical to the amino acid sequence of SEQ ID NO: 3 (e.g., 85%, 86%, 87%, 88%, 89%, 90%, 91%, 92%, 93%, 94%, 95%, 96%, 97%, 98%, 99%, 99.9%, or 100% identical to the amino acid sequence of SEQ ID NO: 3) and/or forms of the human TDP-43 protein that contain one or more substitutions, insertions, and/or deletions (e.g., one or more conservative and/or nonconservative amino acid substitutions, such as up to 5, 10, 15, 20, 25, or more, conservative or nonconservative amino acid substitutions) relative to a wild-type TDP-43 protein. For instance, patients that may be treated for a neurological disorder as described herein, such as amyotrophic lateral sclerosis, frontotemporal degeneration, Alzheimer's disease, Parkinson's disease, dementia with Lewy Bodies, corticobasal degeneration, progressive supranuclear palsy, dementia parkinsonism ALS complex of Guam, Huntington's disease, Inclusion body myopathy with early-onset Paget disease and frontotemporal dementia (IBMPFD), sporadic inclusion body myositis, myofibrillar myopathy, dementia pugilistica, chronic traumatic encephalopathy, Alexander disease, and hereditary inclusion body myopathy, include human patients that express a form of TDP-43 having a mutation associated with elevated TDP-43 aggregation and toxicity, such as a mutation selected from Q331K, M337V, Q343R, N345K, R361S, and N390D. Similarly, the terms "TAR-DNA binding protein-43" and "TDP-43" as used herein include, for example, forms of the human TDP-43 gene that encode an mRNA transcript having a nucleic acid sequence that is at least 85% identical to the nucleic acid sequence of SEQ ID NO: 4 (e.g., 85%, 86%, 87%, 88%, 89%, 90%, 91%, 92%, 93%, 94%, 95%, 96%, 97%, 98%, 99%, 99.9%, or 100% identical to the amino acid sequence of SEQ ID NO: 4).

As used herein in the context of a CYP51A1 inhibitor, such as an inhibitory small molecule, antibody, antigen-binding fragment thereof, or interfering RNA molecule described herein, the term "therapeutically effective amount" refers to a quantity of the inhibitor that, optionally when administered in combination with one another agent, achieves a beneficial treatment outcome for a subject that has or is at risk of developing a neurological disease described herein, such as amyotrophic lateral sclerosis, frontotemporal degeneration, Alzheimer's disease, Parkinson's disease, dementia with Lewy Bodies, corticobasal degeneration, progressive supranuclear palsy, dementia parkinsonism ALS complex of Guam, Huntington's disease, Inclusion body myopathy with early-onset Paget disease and frontotemporal dementia (IBMPFD), sporadic inclusion body myositis, myofibrillar myopathy, dementia pugilistica, chronic traumatic encephalopathy, Alexander disease, and hereditary inclusion body myopathy. For example, the term "therapeutically effective amount" of a CYP51A1 inhibitor described herein includes amounts of the inhibitor that, optionally when administered in combination with another agent, is capable of achieving (i) an improvement in the subject's condition as assessed using the amyotrophic lateral sclerosis functional rating scale (ALSFRS) or the revised ALSFRS (ALSFRS-R) following administration of the CYP51A1 inhibitor, such as an improvement in the subject's ALSFRS or ALSFRS-R score within one or more days, weeks, or months following administration of the CYP51A1 inhibitor (e.g., an improvement in the subject's ALSFRS or ALSFRS-R score within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); (ii) an increase in the subject's slow vital capacity following administration of the CYP51A1 inhibitor, such as an increase in the subject's slow vital capacity within one or more days, weeks, or months following administration of the CYP51A1 inhibitor (e.g., an increase in the subject's slow vital capacity within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); (iii) a reduction in decremental responses exhibited by the subject upon repetitive nerve stimulation, such as a reduction that is observed within one or more days, weeks, or months following administration of the CYP51A1 inhibitor (e.g., a reduction that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); (iv) an improvement in the subject's muscle strength, as assessed, for example, by way of the Medical Research Council muscle testing scale (as described, e.g., in Jagtap et al., Ann. Indian. Acad. Neurol. 17:336-339 (2014), the disclosure of which is incorporated herein by reference as it pertains to measuring patient response to neurological disease treatment), such as an improvement that is observed within one or more days, weeks, or months following administration of the CYP51A1 inhibitor (e.g., an improvement that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); (v) an improvement in the subject's quality of life, as assessed, for example, using the amyotrophic lateral sclerosis-specific quality of life (ALS-specific QOL) questionnaire, such as an improvement in the subject's quality of life that is observed within one or more days, weeks, or months following administration of the CYP51A1 inhibitor (e.g., an improvement in the subject's quality of life that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); and/or (vi) a decrease in the frequency and/or severity of muscle cramps exhibited by the subject, such as a decrease in cramp frequency and/or severity within one or more days, weeks, or months following administration of the CYP51A1 inhibitor (e.g., a decrease in cramp frequency and/or severity within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject).

As used herein in the context of a neurological disorder, the terms "treat" or "treatment" refer to therapeutic treatment, in which the object is to slow, delay, or halt the progression or development of a neurological disorder, e.g., in a human subject. Successful treatment of a subject using a CYP51A1 inhibitor as described herein (e.g., using a CYP51A1 inhibitory small molecule, antibody, antigen-binding fragment thereof, or interfering RNA molecule described herein) may manifest in a variety of ways. Desired treatment outcomes that may be achieved using the compositions and methods described herein include, without limitation, (i) an improvement in the subject's condition as assessed using the amyotrophic lateral sclerosis functional rating scale (ALSFRS) or the revised ALSFRS (ALSFRS-R) following administration of the CYP51A1 inhibitor, such as an improvement in the subject's ALSFRS or ALSFRS-R score within one or more days, weeks, or months following administration of the CYP51A1 inhibitor (e.g., an improvement in the subject's ALSFRS or ALSFRS-R score within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); (ii) an increase in the subject's slow vital capacity following administration of the CYP51A1 inhibitor, such as an increase in the subject's slow vital capacity within one or more days, weeks, or months following administration of the CYP51A1 inhibitor (e.g., an increase in the subject's slow vital capacity within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); (iii) a reduction in decremental responses exhibited by the subject upon repetitive nerve stimulation, such as a reduction that is observed within one or more days, weeks, or months following administration of the CYP51A1 inhibitor (e.g., a reduction that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); (iv) an improvement in the subject's muscle strength, as assessed, for example, by way of the Medical Research Council muscle testing scale (as described, e.g., in Jagtap et al., Ann. Indian. Acad. Neurol. 17:336-339 (2014), the disclosure of which is incorporated herein by reference as it pertains to measuring patient response to neurological disease treatment), such as an improvement that is observed within one or more days, weeks, or months following administration of the CYP51A1 inhibitor (e.g., an improvement that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); (v) an improvement in the subject's quality of life, as assessed, for example, using the amyotrophic lateral sclerosis-specific quality of life (ALS-specific QOL) questionnaire, such as an improvement in the subject's quality of life that is observed within one or more days, weeks, or months following administration of the CYP51A1 inhibitor (e.g., an improvement in the subject's quality of life that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); (vi) a decrease in the frequency and/or severity of muscle cramps exhibited by the subject, such as a decrease in cramp frequency and/or severity within one or more days, weeks, or months following administration of the CYP51A1 inhibitor (e.g., a decrease in cramp frequency and/or severity within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject); and (vii) a decrease in TDP-43 aggregation exhibited by the patient, such as a decrease in TDP-43 aggregation within one or more days, weeks, or months following administration of the CYP51A1 inhibitor (e.g., a decrease in TDP-43 aggregation within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the subject, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the subject.

As used herein, the term "treatment period" refers to a duration of time over which a patient may be administered a therapeutic agent, such as a CYP51A1 inhibitor as described herein, so as to treat or prevent a neurological disorder. Treatment periods as described herein may have a duration of several hours, days, weeks, months, or years.

As used herein, the term "alkyl" refers to monovalent, optionally branched alkyl groups, such as those having from 1 to 6 carbon atoms, or more. This term is exemplified by groups such as methyl, ethyl, n-propyl, isopropyl, n-butyl, isobutyl, tert-butyl, n-hexyl and the like.

As used herein, the term "lower alkyl" refers to alkyl groups having from 1 to 6 carbon atoms.

As used herein, the term "aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenanthrenyl and the like.

As used herein, the terms "aralkyl" and "aryl alkyl" are used interchangeably and refer to an alkyl group containing an aryl moiety. Similarly, the terms "aryl lower alkyl" and the like refer to lower alkyl groups containing an aryl moiety.

As used herein, the term "alkyl aryl" refers to alkyl groups having an aryl substituent, including benzyl, phenethyl and the like.

As used herein, the term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, I,3,4-oxadiazolyl,I,3,4-triazinyl, 1,2,3-triazinyl, benzofuryl, [2,3-dihydrojbenzofuryl, isobenzofuryl, benzothienyl, benzotriazolyl, isobenzothienyl, indolyl, isoindolyl, 3H-indolyl, benzimidazolyl, imidazo[I,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, and the like.

As used herein, the term "alkyl heteroaryl" refers to alkyl groups having a heteroaryl substituent, including 2-furylmethyl, 2-thienylmethyl, 2-(1H-indol-3-yl)ethyl and the like.

As used herein, the term "lower alkenyl" refers to alkenyl groups preferably having from 2 to 6 carbon atoms and having at least 1 or 2 sites of alkenyl unsaturation. Exemplary alkenyl groups are ethenyl ($-CH=CH_2$), n-2-propenyl (allyl, $-CH_2CH=CH_2$) and the like.

As used herein, the term "alkenyl aryl" refers to alkenyl groups having an aryl substituent, including 2-phenylvinyl and the like.

As used herein, the term "alkenyl heteroaryl" refers to alkenyl groups having a heteroaryl substituent, including 2-(3-pyridinyl)vinyl and the like.

As used herein, the term "lower alkynyl" refers to alkynyl groups preferably having from 2 to 6 carbon atoms and having at least 1-2 sites of alkynyl unsaturation, preferred alkynyl groups include ethynyl ($-C\equiv CH$), propargyl ($-CH_2C\equiv CH$), and the like.

As used herein, the term "alkynyl aryl" refers to alkynyl groups having an aryl substituent, including phenylethynyl and the like.

As used herein, the term "alkynyl heteroaryl" refers to alkynyl groups having a heteroaryl substituent, including 2-thienylethynyl and the like.

As used herein, the term "cycloalkyl" refers to a monocyclic cycloalkyl group having from 3 to 8 carbon atoms, such as cyclopropyl, cyclobutyl, cyclopentyl, cyclohexyl, cycloheptyl, cyclooctyl, and the like.

As used herein, the term "lower cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

As used herein, the term "heterocycloalkyl" refers to a cycloalkyl group in which one or more ring carbon atoms are replaced with a heteroatom, such as a nitrogen atom, an oxygen atom, a sulfur atom, and the like. Exemplary heterocycloalkyl groups are pyrrolidinyl, piperidinyl, oxopiperidinyl, morpholinyl, piperazinyl, oxopiperazinyl, thiomorpholinyl, azepanyl, diazepanyl, oxazepanyl, thiazepanyl, dioxothiazepanyl, azokanyl, tetrahydrofuranyl, tetrahydropyranyl, and the like.

As used herein, the term "alkyl cycloalkyl" refers to alkyl groups having a cycloalkyl substituent, including cyclohexylmethyl, cyclopentylpropyl, and the like.

As used herein, the term "alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

As used herein, the term "carboxy" refers to the group —C(O)OH.

As used herein, the term "alkyl carboxy" refers to $C_1$-$C_5$-alkyl groups having a carboxy substituent, including 2-carboxyethyl and the like.

As used herein, the term "acyl" refers to the group —C(O)R, wherein R may be, for example, $C_1$-$C_6$-alkyl, aryl, heteroaryl, $C_1$-$C_6$-alkyl aryl, or $C_1$-$C_6$-alkyl heteroaryl, among other substituents. As used herein, the term "acyloxy" refers to the group —OC(O)R, wherein R may be, for example, $C_1$-$C_6$-alkyl, aryl, heteroaryl, $C_1$-$C_6$-alkyl aryl, or $C_1$-$C_6$-alkyl heteroaryl, among other substituents.

As used herein, the term "alkoxy" refers to the group —O—R, wherein R is, for example, an optionally substituted alkyl group, such as an optionally substituted $C_1$-$C_6$-alkyl, aryl, heteroaryl, $C_1$-$C_6$-alkyl aryl, or $C_1$-$C_6$-alkyl heteroaryl, among other substituents. Exemplary alkoxy groups include by way of example, methoxy, ethoxy, phenoxy, and the like.

As used herein, the term "alkoxycarbonyl" refers to the group —C(O)OR, wherein R is, for example, hydrogen, $C_1$-$C_6$-alkyl, aryl, heteroaryl, $C_1$-$C_6$-alkyl aryl, or $C_1$-$C_6$-alkyl heteroaryl, among other possible substituents.

As used herein, the term "alkyl alkoxycarbonyl" refers to alkyl groups having an alkoxycarbonyl substituent, including 2-(benzyloxycarbonyl)ethyl and the like.

As used herein, the term "aminocarbonyl" refers to the group —C(O)NRR', wherein each of R and R' may independently be, for example, hydrogen, $C_1$-$C_6$-alkyl, aryl, heteroaryl, $C_1$-$C_6$-alkyl aryl, or $C_1$-$C_6$-alkyl heteroaryl, among other substituents.

As used herein, the term "alkyl aminocarbonyl" refers to alkyl groups having an aminocarbonyl substituent, including 2-(dimethylaminocarbonyl)ethyl and the like.

As used herein, the term "acylamino" refers to the group —NRC(O)R', wherein each of R and R' may independently be, for example, hydrogen, $C_1$-$C_6$-alkyl, aryl, heteroaryl, $C_1$-$C_6$-alkyl aryl, or $C_1$-$C_6$-alkyl heteroaryl, among other substituents.

As used herein, the term "alkyl acylamino" refers to alkyl groups having an acylamino substituent, including 2-(propionylamino)ethyl and the like.

As used herein, the term "ureido" refers to the group —NRC(O)NR'R", wherein each of R, R', and R" may independently be, for example, hydrogen, $C_1$-$C_6$-alkyl, aryl, heteroaryl, $C_1$-$C_6$-alkyl aryl, $C_1$-$C_6$-alkyl heteroaryl, cycloalkyl, or heterocycloalkyl, among other substituents. Exemplary ureido groups further include moieties in which R' and R", together with the nitrogen atom to which they are attached, form a 3-8-membered heterocycloalkyl ring.

As used herein, the term "alkyl ureido" refers to alkyl groups having an ureido substituent, including 2-(N'-methylureido)ethyl and the like.

As used herein, the term "amino" refers to the group —NRR', wherein each of R and R' may independently be, for example, hydrogen, $C_1$-$C_6$-alkyl, aryl, heteroaryl, $C_1$-$C_6$-alkyl aryl, $C_1$-$C_6$-alkyl heteroaryl, cycloalkyl, or heterocycloalkyl, among other substituents. Exemplary amino groups further include moieties in which R and R', together with the nitrogen atom to which they are attached, can form a 3-8-membered heterocycloalkyl ring.

As used herein, the term "alkyl amino" refers to alkyl groups having an amino substituent, including 2-(1-pyrrolidinyl)ethyl and the like.

As used herein, the term "ammonium" refers to a positively charged group —N+RR'R", wherein each of R, R', and R" may independently be, for example, $C_1$-$C_6$-alkyl, $C_1$-$C_6$-alkyl aryl, $C_1$-$C_6$-alkyl heteroaryl, cycloalkyl, or heterocycloalkyl, among other substituents. Exemplary ammonium groups further include moieties in which R and R', together with the nitrogen atom to which they are attached, form a 3-8-membered heterocycloalkyl ring.

As used herein, the term "halogen" refers to fluoro, chloro, bromo and iodo atoms.

As used herein, the term "sulfonyloxy" refers to a group —OSO₂—R wherein R is selected from hydrogen, $C_1$-$C_6$-alkyl, $C_1$-$C_6$-alkyl substituted with halogens, e.g., an —OSO₂—CF₃ group, aryl, heteroaryl, $C_1$-$C_6$-alkyl aryl, and $C_1$-$C_6$-alkyl heteroaryl.

As used herein, the term "alkyl sulfonyloxy" refers to alkyl groups having a sulfonyloxy substituent, including 2-(methylsulfonyloxy)ethyl and the like.

As used herein, the term "sulfonyl" refers to group "—SO₂—R" wherein R is selected from hydrogen, aryl, heteroaryl, $C_1$-$C_6$-alkyl, $C_1$-$C_6$-alkyl substituted with halogens, e.g., an —SO₂—CF₃ group, $C_1$-$C_6$-alkyl aryl or $C_1$-$C_6$-alkyl heteroaryl.

As used herein, the term "alkyl sulfonyl" refers to alkyl groups having a sulfonyl substituent, including 2-(methylsulfonyl)ethyl and the like.

As used herein, the term "sulfinyl" refers to a group "—S(O)—R" wherein R is selected from hydrogen, $C_1$-$C_6$-alkyl, $C_1$-$C_6$-alkyl substituted with halogens, e.g., a —SO—CF₃ group, aryl, heteroaryl, $C_1$-$C_6$-alkyl aryl or $C_1$-$C_6$-alkyl heteroaryl.

As used herein, the term "alkyl sulfinyl" refers to $C_1$-$C_5$-alkyl groups having a sulfinyl substituent, including 2-(methylsulfinyl)ethyl and the like.

As used herein, the term "sulfanyl" refers to groups —S—R, wherein R is, for example, alkyl, aryl, heteroaryl, $C_1$-$C_6$-alkyl aryl, or $C_1$-$C_6$-alkyl heteroaryl, among other substituents. Exemplary sulfanyl groups are methylsulfanyl, ethylsulfanyl, and the like.

As used herein, the term "alkyl sulfanyl" refers to alkyl groups having a sulfanyl substituent, including 2-(ethylsulfanyl)ethyl and the like.

As used herein, the term "sulfonylamino" refers to a group —NRSO₂—R', wherein each of R and R' may independently be hydrogen, $C_1$-$C_6$-alkyl, aryl, heteroaryl, $C_1$-$C_6$-alkyl aryl, or $C_1$-$C_6$-alkyl heteroaryl, among other substituents.

As used herein, the term "alkyl sulfonylamino" refers to alkyl groups having a sulfonylamino substituent, including 2-(ethylsulfonylamino)ethyl and the like.

Unless otherwise constrained by the definition of the individual substituent, the above set out groups, like "alkyl", "alkenyl", "alkynyl", "aryl" and "heteroaryl" etc. groups can optionally be substituted, for example, with one or more substituents, as valency permits, such as a substituent selected from alkyl (e.g., $C_1$-$C_6$-alkyl), alkenyl (e.g., $C_2$-$C_6$-alkenyl), alkynyl (e.g., $C_2$-$C_6$-alkynyl), cycloalkyl, heterocycloalkyl, alkyl aryl (e.g., $C_1$-$C_6$-alkyl aryl), alkyl heteroaryl (e.g., $C_1$-$C_6$-alkyl heteroaryl, alkyl cycloalkyl (e.g., $C_1$-$C_6$-alkyl cycloalkyl), alkyl heterocyloalyl (e.g., $C_1$-$C_6$-alkyl heterocycloalkyl), amino, ammonium, acyl, acyloxy, acylamino, aminocarbonyl, alkoxycarbonyl, ureido, aryl, heteroaryl, sulfinyl, sulfonyl, alkoxy, sulfanyl, halogen, carboxy, trihalomethyl, cyano, hydroxy, mercapto, nitro, and the like. In some embodiments, the substitution is one in which neighboring substituents have undergone ring closure, such as situations in which vicinal functional substituents are involved, thus forming, e.g., lactams, lactones, cyclic anhydrides, acetals, thioacetals, and aminals, among others.

As used herein, the term "optionally fused" refers to a cyclic chemical group that may be fused with a ring system, such as cycloalkyl, heterocycloalkyl, aryl, or heteroaryl. Exemplary ring systems that may be fused to an optionally fused chemical group include, e.g., indolyl, isoindolyl, benzofuranyl, isobenzofuranyl, benzothiophenyl, benzoxazolyl, benzothiazolyl, benzoisoxazolyl, benzoisothiazolyl, indazolyl, benzimidazolyl, quinolinyl, isoquinolinyl, phthalazinyl, quinoxalinyl, quinazolinyl, cinnolinyl, indolizinyl, naphthyridinyl, pteridinyl, indanyl, naphtyl, 1,2,3,4-tetrahydronaphthyl, indolinyl, isoindolinyl, 2,3,4,5-tetrahydrobenzo[b]oxepinyl, 6,7,8,9-tetrahydro-5H-benzocycloheptenyl, chromanyl, and the like.

As used herein, the term "pharmaceutically acceptable salt" refers to a salt, such as a salt of a compound described herein, that retains the desired biological activity of the non-ionized parent compound from which the salt is formed. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. The compounds can also be administered as pharmaceutically acceptable quaternary salts, such as quaternary ammonium salts of the formula —NR,R',R"+Z$^-$, wherein each of R, R', and R" may independently be, for example, hydrogen, alkyl, benzyl, $C_1$-$C_6$-alkyl, $C_2$-$C_6$-alkenyl, $C_2$-$C_6$-alkynyl, $C_1$-$C_6$-alkyl aryl, $C_1$-$C_6$-alkyl heteroaryl, cycloalkyl, heterocycloalkyl, or the like, and Z is a counterion, such as chloride, bromide, iodide, —O-alkyl, toluenesulfonate, methyl sulfonate, sulfonate, phosphate, carboxylate (such as benzoate, succinate, acetate, glycolate, maleate, malate, fumarate, citrate, tartrate, ascorbate, cinnamoate, mandeloate, and diphenylacetate), or the like.

As used herein in the context of a CYP51A1 inhibitor, the term "variant" refers to an agent containing one or more modifications relative to a reference agent and that (i) retains an ability to inhibit CYP51A1 and/or (ii) is converted in vivo into an agent that inhibits CYP51A1. In the context of small molecule CYP51A1 inhibitors, structural variants of a reference compound include those that differ from the reference compound by the inclusion and/or location of one or more substituents, as well as variants that are isomers of a reference compound, such as structural isomers (e.g., regioisomers) or stereoisomers (e.g., enantiomers or diastereomers), as well as prodrugs of a reference compound. In the context of an antibody or antigen-binding fragment thereof, a variant may contain one or more amino acid substitutions, such as one or more conservative amino acid substitutions, relative to the parent antibody or antigen-binding fragment thereof. In the context of an interfering RNA molecule, a variant may contain one or more nucleic acid substitutions relative to a parent interfering RNA molecule.

The structural compositions described herein also include the tautomers, geometrical isomers (e.g., E/Z isomers and cis/trans isomers), enantiomers, diastereomers, and racemic forms, as well as pharmaceutically acceptable salts thereof. Such salts include, e.g., acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

As used herein, chemical structural formulas that do not depict the stereochemical configuration of a compound having one or more stereocenters will be interpreted as encompassing any one of the stereoisomers of the indicated compound, or a mixture of one or more such stereoisomers (e.g., any one of the enantiomers or diastereomers of the indicated compound, or a mixture of the enantiomers (e.g., a racemic mixture) or a mixture of the diastereomers). As used herein, chemical structural formulas that do specifically depict the stereochemical configuration of a compound having one or more stereocenters will be interpreted as referring to the substantially pure form of the particular stereoisomer shown.

"Substantially pure" forms refer to compounds having a purity of greater than 85%, such as a purity of from 85% to 99%, 85% to 99.9%, 85% to 99.99%, or 85% to 100%, such as a purity of 85%, 86%, 87%, 88%, 89%, 90%, 91%, 92%, 93%, 94%, 95%, 96%, 97%, 98%, 99%, 99.9%, 99.99%, 99.999%, or 100%, as assessed, for example, using chromatography and nuclear magnetic resonance techniques known in the art.

As used herein, the term "antibody" (Ab) refers to an immunoglobulin molecule that specifically binds to, or is immunologically reactive with, a particular antigen, and includes polyclonal, monoclonal, genetically engineered, and otherwise modified forms of antibodies, including, but not limited to, chimeric antibodies, humanized antibodies, heteroconjugate antibodies (e.g., bi- tri- and quad-specific antibodies, diabodies, triabodies, and tetrabodies), and antigen-binding fragments of antibodies, including e.g., Fab', F(ab')$_2$, Fab, Fv, rIgG, and scFv fragments. In some embodiments, two or more portions of an immunoglobulin molecule are covalently bound to one another, e.g., via an amide bond, a thioether bond, a carbon-carbon bond, a disulfide bridge, or by a linker, such as a linker described herein or known in the art. Antibodies also include antibody-like protein scaffolds, such as the tenth fibronectin type III domain ($^{10}$Fn3), which contains BC, DE, and FG structural loops similar in structure and solvent accessibility to antibody complementarity-determining regions (CDRs). The tertiary structure of the $^{10}$Fn3 domain resembles that of the variable region of the IgG heavy chain, and one of skill in the art can graft, e.g., the CDRs of a reference antibody onto the fibronectin scaffold by replacing residues of the BC, DE, and FG loops of $^{10}$Fn3 with residues from the CDR-H1, CDR-H2, or CDR-H3 regions, respectively, of the reference antibody.

The term "antigen-binding fragment," as used herein, refers to one or more fragments of an antibody that retain the ability to specifically bind to a target antigen. The antigen-binding function of an antibody can be performed by fragments of a full-length antibody. The antibody fragments can be a Fab, F(ab')$_2$, scFv, SMIP, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the $V_L$, $V_H$, $C_L$, and $C_H1$ domains; (ii) a F(ab')2 fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment (Ward et al., Nature 341:544-546, 1989), which consists of a $V_H$ domain; (vii) a dAb which consists of a $V_H$ or a $V_L$ domain; (viii) an isolated CDR; and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single-chain Fv (scFv); see, e.g., Bird et al., Science 242:423-426, 1988, and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in some embodiments, by chemical peptide synthesis procedures known in the art.

As used herein, the term "bispecific antibodies" refers to monoclonal, often human or humanized antibodies that have binding specificities for at least two different antigens.

As used herein, the term "chimeric" antibody refers to an antibody having variable domain sequences (e.g., CDR sequences) derived from an immunoglobulin of one source organism, such as rat or mouse, and constant regions derived from an immunoglobulin of a different organism (e.g., a human, another primate, pig, goat, rabbit, hamster, cat, dog, guinea pig, member of the bovidae family (such as cattle, bison, buffalo, elk, and yaks, among others), cow, sheep, horse, or bison, among others). Methods for producing chimeric antibodies are known in the art. See, e.g., Morrison, 1985, Science 229(4719): 1202-7; Oi et al, 1986, BioTechniques 4:214-221; Gillies et al, 1985, J. Immunol. Methods 125:191-202; U.S. Pat. Nos. 5,807,715; 4,816,567; and 4,816,397; incorporated herein by reference.

As used herein, the term "complementarity-determining region" (CDR) refers to a hypervariable region found both in the light chain and the heavy chain variable domains. The more highly conserved portions of variable domains are called the framework regions (FRs). As is appreciated in the art, the amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The antibodies described herein may comprising modifications in these hybrid hypervariable positions. The variable domains of native heavy and light chains each comprise four framework regions that primarily adopt a β-sheet configuration, connected by three CDRs, which form loops that connect, and in some cases form part of, the β-sheet structure. The CDRs in each chain are held together in close proximity by the FR regions in the order FR1-CDR1-FR2-CDR2-FR3-CDR3-FR4 and, with the CDRs from the other antibody chains, contribute to the formation of the target binding site of antibodies (see Kabat et al, Sequences of Proteins of Immunological Interest (National Institute of Health, Bethesda, Md. 1987; incorporated herein by reference). As used herein, numbering of immunoglobulin amino acid residues is done according to the immunoglobulin amino acid residue numbering system of Kabat et al, unless otherwise indicated.

As used herein, the term "derivatized antibodies" refers to antibodies that are modified by a chemical reaction so as to cleave residues or add chemical moieties not native to an isolated antibody. Derivatized antibodies can be obtained by glycosylation, acetylation, pegylation, phosphorylation, amidation, derivatization by addition of known chemical protecting/blocking groups, proteolytic cleavage, linkage to a cellular ligand or other protein. Any of a variety of chemical modifications can be carried out by known techniques, including, without limitation, specific chemical cleavage, acetylation, formylation, metabolic synthesis of tunicamycin, etc. using established procedures. Additionally, the derivative can contain one or more non-natural amino acids, e.g., using amber suppression technology (see, e.g., U.S. Pat. No. 6,964,859; incorporated herein by reference).

As used herein, the term "diabodies" refers to bivalent antibodies comprising two polypeptide chains, in which each polypeptide chain includes $V_H$ and $V_L$ domains joined by a linker that is too short (e.g., a linker composed of five amino acids) to allow for intramolecular association of VH and VL domains on the same peptide chain. This configuration forces each domain to pair with a complementary domain on another polypeptide chain so as to form a homodimeric structure. Accordingly, the term "triabodies" refers to trivalent antibodies comprising three peptide chains, each of which contains one VH domain and one VL domain joined by a linker that is exceedingly short (e.g., a linker composed of 1-2 amino acids) to permit intramolecular association of VH and VL domains within the same peptide chain. In order to fold into their native structure, peptides configured in this way typically trimerize so as to position the VH and VL domains of neighboring peptide chains spatially proximal to one another to permit proper folding (see Holliger et al., Proc. Natl. Acad. Sci. USA 90:6444-48, 1993; incorporated herein by reference).

As used herein, the term "framework region" or "FW region" includes amino acid residues that are adjacent to the CDRs. FW region residues may be present in, for example, human antibodies, rodent-derived antibodies (e.g., murine antibodies), humanized antibodies, primatized antibodies, chimeric antibodies, antibody fragments (e.g., Fab fragments), single-chain antibody fragments (e.g., scFv fragments), antibody domains, and bispecific antibodies, among others.

As used herein, the term "heterospecific antibodies" refers to monoclonal, preferably human or humanized, antibodies that have binding specificities for at least two different antigens. Traditionally, the recombinant production of heterospecific antibodies is based on the co-expression of two immunoglobulin heavy chain-light chain pairs, where the two heavy chains have different specificities (Milstein et al., Nature 305:537, 1983). Similar procedures are disclosed, e.g., in WO 93/08829, U.S. Pat. Nos. 6,210,668; 6,193,967; 6,132,992; 6,106,833; 6,060,285; 6,037,453; 6,010,902; 5,989,530; 5,959,084; 5,959,083; 5,932,448; 5,833,985; 5,821,333; 5,807,706; 5,643,759, 5,601,819; 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986); incorporated herein by reference. Heterospecific antibodies can include Fc mutations that enforce correct chain association in multi-specific antibodies, as described by Klein et al, mAbs 4(6):653-663, 2012; incorporated herein by reference.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A human antibody can be produced in a human cell (e.g., by recombinant expression), or by a non-human animal or a prokaryotic or eukaryotic cell that is capable of expressing functionally rearranged human immunoglobulin (e.g., heavy chain and/or light chain) genes. Further, when a human antibody is a single-chain antibody, it can include a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. See U.S. Pat. Nos. 4,444,887 and 4,716,111; and PCT publications WO 1998/46645; WO 1998/50433; WO 1998/24893; WO 1998/16654; WO 1996/34096; WO 1996/33735; and WO 1991/10741; incorporated herein by reference. Human antibodies can also be produced using transgenic mice that are incapable of expressing functional endogenous immunoglobulins, but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598; incorporated by reference herein.

As used herein, the term "humanized" antibodies refers to forms of non-human (e.g., murine) antibodies that are chimeric immunoglobulins, immunoglobulin chains or fragments thereof (such as Fv, Fab, Fab', F(ab')$_2$ or other target-binding subdomains of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin. All or substantially all of the FR regions may also be those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., Nature 332:323-7, 1988; U.S. Pat. Nos. 5,530,101; 5,585,089; 5,693,761; 5,693,762; and U.S. Pat. No. 6,180,370 to Queen et al; EP239400; PCT publication WO 91/09967; U.S. Pat. No. 5,225,539; EP592106; and EP519596; incorporated herein by reference.

As used herein, the term "monoclonal antibody" refers to an antibody that is derived from a single clone, including any eukaryotic, prokaryotic, or phage clone, and not the method by which it is produced.

As used herein, the term "multi-specific antibodies" refers to antibodies that exhibit affinity for more than one target antigen. Multi-specific antibodies can have structures similar to full immunoglobulin molecules and include Fc regions, for example IgG Fc regions. Such structures can include, but not limited to, IgG-Fv, IgG-(scFv)$_2$, DVD-Ig, (scFv)$_2$-(scFv)$_2$-Fc and (scFv)$_2$-Fc-(scFv)$_2$. In case of IgG-(scFv)$_2$, the scFv can be attached to either the N-terminal or the C-terminal end of either the heavy chain or the light chain. Exemplary multi-specific molecules have been reviewed by Kontermann, 2012, mAbs 4(2):182-197, Yazaki et al, 2013, Protein Engineering, Design & Selection 26(3): 187-193, and Grote et al, 2012, in Proetzel & Ebersbach (eds.), Antibody Methods and Protocols, Methods in Molecular Biology vol. 901, chapter 16:247-263; incorporated herein by reference. In some embodiments, antibody fragments can be components of multi-specific molecules without Fc regions, based on fragments of IgG or DVD or scFv. Exemplary multi-specific molecules that lack Fc regions and into which antibodies or antibody fragments can be incorporated include scFv dimers (diabodies), trimers (triabodies) and tetramers (tetrabodies), Fab dimers (conjugates by adhesive polypeptide or protein domains) and Fab trimers (chemically conjugated), are described by Hudson and Souriau, 2003, Nature Medicine 9:129-134; incorporated herein by reference.

As used herein, the term "primatized antibody" refers to an antibody comprising framework regions from primate-derived antibodies and other regions, such as CDRs and/or constant regions, from antibodies of a non-primate source. Methods for producing primatized antibodies are known in the art. See e.g., U.S. Pat. Nos. 5,658,570; 5,681,722; and 5,693,780; incorporated herein by reference. For instance, a primatized antibody or antigen-binding fragment thereof described herein can be produced by inserting the CDRs of a non-primate antibody or antigen-binding fragment thereof into an antibody or antigen-binding fragment thereof that contains one or more framework regions of a primate.

As used herein, the term "scFv" refers to a single-chain Fv antibody in which the variable domains of the heavy chain and the light chain from an antibody have been joined to form one chain. scFv fragments contain a single polypeptide chain that includes the variable region of an antibody light chain (VL) (e.g., CDR-L1, CDR-L2, and/or CDR-L3) and the variable region of an antibody heavy chain (VH) (e.g., CDR-H1, CDR-H2, and/or CDR-H3) separated by a linker. The linker that joins the VL and VH regions of a scFv fragment can be a peptide linker composed of proteinogenic amino acids. Alternative linkers can be used to so as to increase the resistance of the scFv fragment to proteolytic degradation (e.g., linkers containing D-amino acids), in order to enhance the solubility of the scFv fragment (e.g., hydrophilic linkers such as polyethylene glycol-containing linkers or polypeptides containing repeating glycine and serine residues), to improve the biophysical stability of the molecule (e.g., a linker containing cysteine residues that form intramolecular or intermolecular disulfide bonds), or to attenuate the immunogenicity of the scFv fragment (e.g., linkers containing glycosylation sites). scFv molecules are known in the art and are described, e.g., in U.S. Pat. No.

5,892,019, Flo et al., (Gene 77:51, 1989); Bird et al., (Science 242:423, 1988); Pantoliano et al., (Biochemistry 30:10117, 1991); Milenic et al., (Cancer Research 51:6363, 1991); and Takkinen et al., (Protein Engineering 4:837, 1991). The VL and VH domains of a scFv molecule can be derived from one or more antibody molecules. It will also be understood by one of ordinary skill in the art that the variable regions of the scFv molecules described herein can be modified such that they vary in amino acid sequence from the antibody molecule from which they were derived. For example, in one embodiment, nucleotide or amino acid substitutions leading to conservative substitutions or changes at amino acid residues can be made (e.g., in CDR and/or framework residues). Alternatively or in addition, mutations are made to CDR amino acid residues to optimize antigen binding using art recognized techniques. scFv fragments are described, for example, in WO 2011/084714; incorporated herein by reference.

BRIEF DESCRIPTION OF THE FIGURES

FIGS. 1A-1C demonstrate that the viability of a yeast TDP-43 model is restored by the Erg11 inhibitor, fluconazole. (FIG. 1A) Structure of the Erg11 inhibitor and antifungal, fluconazole. (FIG. 1B) Fluconazole rescues viability of TDP-43-expressing yeast using a resazurin-reduction endpoint. A 2-fold serial dilution of fluconazole was applied to TDP-43-expressing yeast for 24 hours prior to analysis. (FIG. 1C) Wild-type yeast cultures were treated with fluconazole for eight hours prior to HPLC analysis for lanosterol and ergosterol. Data are expressed as the area under the curve (AUC) normalized to cell mass based on optical density of cultures at 600 nm. Fluconazole treatment reduces ergosterol, while simultaneously leading to an increase in the Erg11 substrate, lanosterol.

(FIG. 3A) Risk of neuron death plots. The lifetime of each neuron was determined by either loss of RFP signal or morphological indicators of death such as loss of neurites and cell blebbing and used to generate cumulative hazard plots of risk of death over time (hrs) post-transfection. (FIG. 3B) Forest plots. Hazard ratios for each treatment group (relative to TDP-43 DMSO group) were determined by cox regression analysis and used to generate forest plots. Hazard ratios (HR)<1 in which the confidence interval (CI) does not encompass 1 represent treatments that significantly reduce probability of neuron death relative to the TDP-43 DMSO control. P, p-value.

(FIG. 4A) Risk of neuron death plots. The lifetime of each neuron was determined by either loss of RFP signal or morphological indicators of death such as loss of neurites and cell blebbing and used to generate cumulative hazard plots of risk of death over time (hrs) post-transfection. (FIG. 4B) Forest plots. Hazard ratios for each treatment group (relative to TDP-43 DMSO group) were determined by cox regression analysis and used to generate forest plots. Hazard ratios (HR)<1 in which the confidence interval (CI) does not encompass 1 represent treatments that significantly reduce probability of neuron death relative to the TDP-43 DMSO control. P, p-value.

(FIG. 5A) Risk of neuron death plots. The lifetime of each neuron was determined by either loss of RFP signal or morphological indicators of death such as loss of neurites and cell blebbing and used to generate cumulative hazard plots of risk of death over time (hrs) post-transfection. (FIG. 5B) Forest plots. Hazard ratios for each treatment group (relative to TDP-43 DMSO group) were determined by cox regression analysis and used to generate forest plots. Hazard ratios (HR)<1 in which the confidence interval (CI) does not encompass 1 represent treatments that significantly reduce probability of neuron death relative to the TDP-43 DMSO control. P, p-value.

DETAILED DESCRIPTION

Figure 1A:
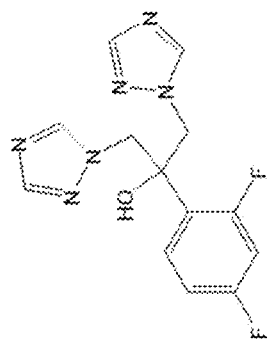

The present invention features compositions and methods for treating neurological disorders, such as amyotrophic lateral sclerosis and other neuromuscular disorders, as well as frontotemporal degeneration, Alzheimer's disease, Parkinson's disease, dementia with Lewy Bodies, corticobasal degeneration, progressive supranuclear palsy, dementia parkinsonism ALS complex of Guam, Huntington's disease, Inclusion body myopathy with early-onset Paget disease and frontotemporal dementia (IBMPFD), sporadic inclusion body myositis, myofibrillar myopathy, dementia pugilistica, chronic traumatic encephalopathy, Alexander disease, and hereditary inclusion body myopathyamong others. Particularly, the invention provides inhibitors of cytochrome P450 isoform 51A1 (CYP51A1), also referred to herein as lanosterol 14-alpha demethylase, that may be administered to a patient (e.g., a human patient) so as to treat or prevent a neurological disorder, such as one or more of the foregoing conditions. In the context of therapeutic treatment, the CYP51A1 inhibitor may be administered to the patient to alleviate one or more symptoms of the disorder and/or to remedy an underlying molecular pathology associated with the disease, such as to suppress or prevent aggregation of TAR-DNA binding protein (TDP)-43.

The disclosure herein is based, in part, on the discovery that CYP51A1 inhibition modulates TDP-43 aggregation in vivo. Suppression of TDP-43 aggregation exerts beneficial effects in patients suffering from a neurological disorder. Many pathological conditions have been correlated with TDP-43-promoted aggregation and toxicity, such as amyotrophic lateral sclerosis, frontotemporal degeneration, Alzheimer's disease, Parkinson's disease, dementia with Lewy Bodies, corticobasal degeneration, progressive supranuclear palsy, dementia parkinsonism ALS complex of Guam, Huntington's disease, IBMPFD, sporadic inclusion body myositis, myofibrillar myopathy, dementia pugilistica, chronic traumatic encephalopathy, Alexander disease, and hereditary inclusion body myopathy. Without being limited by mechanism, by administering an inhibitor of CYP51A1, patients suffering from diseases associated with TDP-43 aggregation and toxicity may be treated, for example, due to the suppression of TDP-43 aggregation induced by the CYP51A1 inhibitor.

Patients that are likely to respond to CYP51A1 inhibition as described herein include those that have or are at risk of developing TDP-43 aggregation, such as those that express a mutant form of TDP-43 associated with TDP-43 aggregation and toxicity in vivo. Examples of such mutations in TDP-43 that have been correlated with elevated TDP-43 aggregation and toxicity include Q331K, M337V, Q343R, N345K, R361 S, and N390D, among others. The compositions and methods described herein thus provide the additional clinical benefit of enabling the identification of patients that are likely to respond to CYP51A1 inhibitor therapy, as well as processes for treating these patients accordingly.

As described in further detail below, CYP51A1 inhibitors useful in conjunction with the compositions and methods of the invention include inhibitory small molecules, such as LEK-935, CP-320626, itraconazole, posaconazole, cyproconazole, voriconazole, fluconazole, clotrimazol, fenticonazole, epoxiconazole, ketoconazole, ravuconazole, isavuconazole, holothurin A, theasaponin, capsicosine, betulafolientriol, prochloraz, propiconazole, prothioconazole, prothioconazole-desthio, tebuconazole, triadimenol, azalanstat, and variants thereof. In some embodiments, the CYP51A1 inhibitor is an anti-CYP51A1 antibody or antigen-binding fragment thereof, or a compound, such as an interfering RNA molecule, that attenuates CYP51A1 expression.

The sections that follow provide a description of exemplary CYP51A1 inhibitors that may be used in conjunction with the compositions and methods disclosed herein. The sections below additionally provide a description of various exemplary routes of administration and pharmaceutical compositions that may be used for delivery of these substances for the treatment of a neurological disorder.

Small Molecule CYP51A1 Inhibitors
LEK-935 and Variants Thereof

CYP51A1 inhibitors that may be used in conjunction with the compositions and methods described herein include small molecule antagonists of CYP51A1 activity. The CYP51A1 inhibitor may be, for example, LEK-935, represented by formula (3), herein.

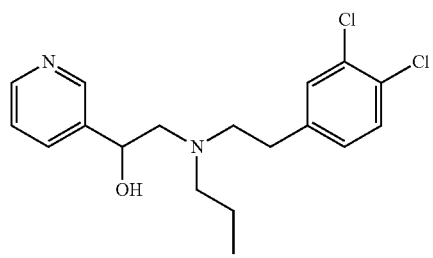
(3)

In some embodiments, the CYP51A1 inhibitor is a variant of LEK-835 that retains CYP51A1 inhibitory activity. For example, CYP51A1 inhibitors useful in conjunction with the compositions and methods described herein include those represented by formula (I)

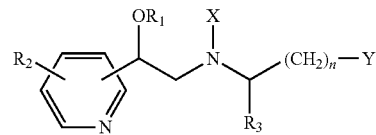
(I)

wherein n is 1 or 2;
X is hydrogen, lower alkyl, lower alkoxy-lower alkyl, or a group $X^a$ of the formula:

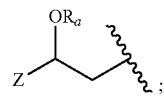

Z is a group of the formula:

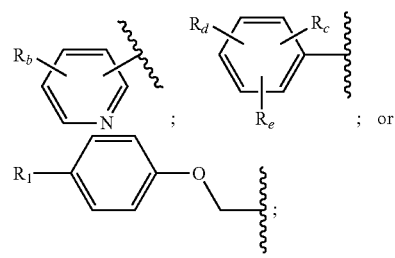

Y is a group of the formula:

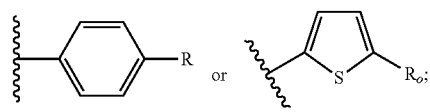

$R_O$ is lower alkyl, $COR_4$ or $C(R_5)=CHCOR_4$;
R is $R_o$ or is OR";
R" is hydrogen, lower-alkyl, lower alkanoyl, $(CH_2)_{1-6}$—OH, $(CH_2)_{1-6}$—O$(CH_2)_{1-6}R_6$, or $(CH_2)_{1-6}$—$COR_4$;
$R_1$ and $R_a$ are hydrogen, lower alkanoyl, benzoyl or $(CH_2)_{1-6}$—OH;
$R_2$ and $R_b$ are hydrogen, Cl, Br or $CF_3$;
$R_3$ and $R_5$ are hydrogen or $CH_3$;
$R_4$ is hydroxy, lower-alkoxy or $N(R_7, R_8)$;
$R_6$ is hydrogen, $R_g$, OH or $COR_4$;
$R_7$ and $R_8$ are hydrogen or lower alkyl;
$R_c$ and $R_e$ are hydrogen, Cl, F, Br or $CF_3$;
$R_d$ is hydrogen or $NH_2$;
$R_f$ is hydrogen, $CH_3CONH$—, $NH_2COCH_2$— or $R_9CH_2CH_2OCH_2CH_2O$—;
$R_g$ and $R_9$ are phenyl or phenyl substituted by Cl, F or Br;
or a pharmaceutically acceptable salt, ester, or ether thereof.

In some embodiments of formula (I), n is 1, $R_1$ is hydrogen, $R_2$ is chlorine in the 6-position of a 2-pyridyl residue and Y is phenyl substituted in the p-position by R.

In some embodiments of formula (I), X is $X^a$; $R^a$ is hydrogen; Z is 6-chloro-2-pyridyl, and Y is phenyl substituted in the p-position by 2-ethoxyethoxy, 2-phenethoxyethoxy or methoxycarbonylmethoxy.

In some embodiments of formula (I), the compound is methyl α,α'-[[[(R)-p-(2-ethoxyethoxy)-α-methylphenethyl]imino]dimethylene]bis[(RS)-6-chloro-2-pyridinemethanol]; (RS)-6-chloro-α-[[[(R)-p-(2-ethoxyethoxy)-α-methyl-phenethyl]amino]methyl]-2-pyridinemethanol; α,α'-[[[p-(2-ethoxyethoxy)phenethyl]imino]dimethylene]bis[(RS)-6-chloro-2-pyridinemethanol]; (R)-6-bromo-α-[[[(RS)-2-(6-bromo-2-pyridyl)-2-hydroxyethyl][(R)-p-(2-ethoxyethoxy)-α-methylphenethyl]-amino]methyl]-2-pyridimidinemethanol; (R)-6-chloro-α[[[(S)-2-(6-chloro-2-pyridyl)-2-hydroxyethyl][(R)-.alpha.-methyl-p-(2-phenethoxyethoxy)phenethyl]amino]methyl]-2-pyridinemethanol.

In some embodiments, the CYP51A1 inhibitor is a compound represented by formula (II)

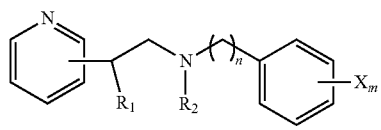

(II)

wherein n is an integer from 1 to 4 and m is an integer from 0 to 5;

$R_1$ is a hydrogen atom, hydroxyl group, or lower $C_{1-6}$ alkoxy group;

$R_2$ is a hydrogen atom or an optionally substituted straight or branched lower $C_{1-6}$ alkyl group (e.g., an aryl lower alkyl group, such as a phenyl lower alkyl group); and each X is independently fluorine, chlorine, bromine, hydroxyl group, trifluoromethyl group, 3,4-di-Cl, 2,4-di-Cl or lower $C_{1-6}$ alkoxy group, and wherein the phenyl ring containing the X is optionally fused (so as to form, e.g., a naphthyl ring);

or a pharmaceutically acceptable salt, ester, or ether thereof.

In some embodiments, the CYP51A1 inhibitor is a compound represented by formula (1), (2), (3), (13), (14), (15), or (16), or a pharmaceutically acceptable salt, ester, or ether thereof.

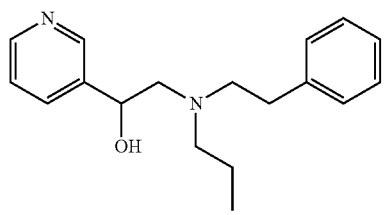

(1)

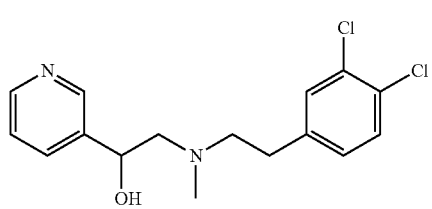

(2)

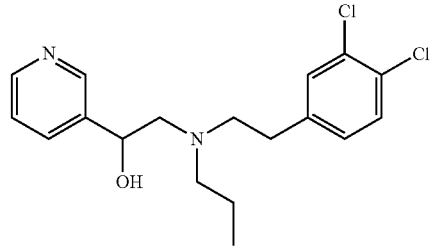

(3)

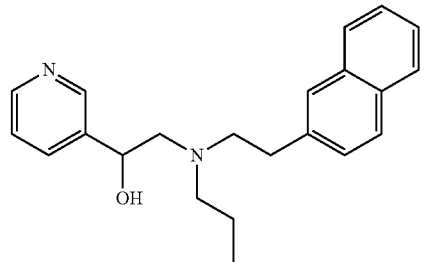

(13)

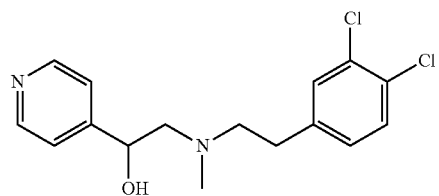

(14)

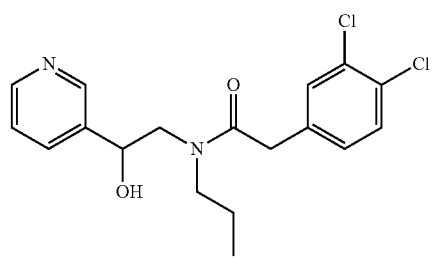

(15)

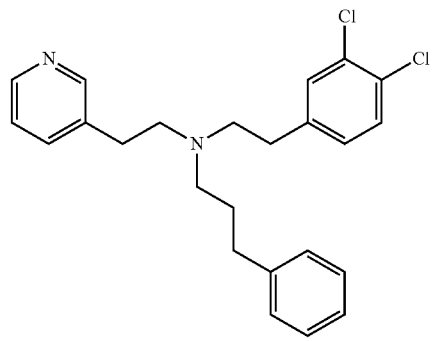

(16)

In some embodiments, n is an integer 2, $R_1$ is a hydroxyl group, $R_2$ a methyl, ethyl, n-propyl, isopropyl, n-butyl or isobutyl group and X is a hydrogen atom or phenyl disubstituted with 2 chlorine atoms in the positions 3 and 4 or in the positions 2 and 4.

Exemplary variants of LEK-935 that may be used in conjunction with the compositions and methods described herein are those compounds described in U.S. Pat. Nos. 4,800,206 and 7,560,474, the disclosures of each of which are incorporated herein by reference in their entirety.

CP-320626 and Variants Thereof

In some embodiments, the CYP51A1 inhibitor is CP-320626, represented by formula (4) herein.

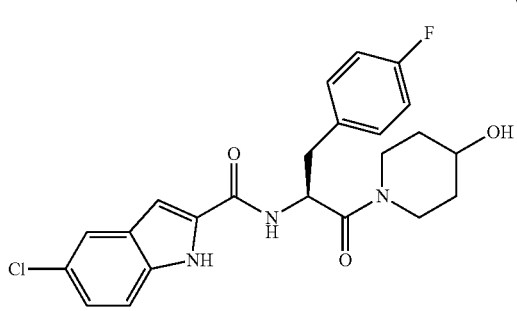

(4)

In some embodiments, the CYP51A1 inhibitor is a variant of CP-320626 that retains CYP51A1 inhibitory activity, such as a compound represented by formula (III)

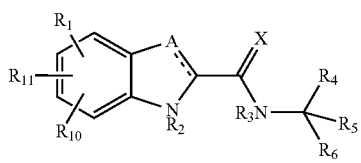

(III)

wherein the dotted line ( -- ) is an optional bond;
X is O or S;
A is —C(H)═, —C(($C_1$-$C_4$)alkyl)═, —C(halo)═ or —N═, when the dotted line ( -- ) is a bond, or A is methylene or —CH(($C_1$-$C_4$)alkyl)—, when the dotted line ( -- ) is not a bond;
$R_1$, $R_{10}$ or $R_{11}$ are each independently H, halo, cyano, 4-, 6-, or 7-nitro, ($C_1$-$C_4$)alkyl, ($C_1$-$C_4$)alkoxy, fluoromethyl, difluoromethyl or trifluoromethyl;
$R_2$ is H;
$R_3$ is H or ($C_1$-$C_6$)alkyl;
$R_4$ is H, methyl, ethyl, n-propyl, hydroxy($C_1$-$C_3$)alkyl, ($C_1$-$C_3$)alkoxy($C_1$-$C_3$)alkyl, phenyl($C_1$-$C_4$)alkyl, phenylhydroxy($C_1$-$C_4$)alkyl, (phenyl)(($C_1$-$C_4$)-alkoxy)($C_1$-$C_4$)alkyl, thien-2- or -3-yl($C_1$-$C_4$)alkyl or fur-2- or 3-yl($C_1$-$C_4$)alkyl wherein the $R_4$ rings are mono-, di- or tri-substituted independently on carbon with H, halo, ($C_1$-$C_4$)alkyl, ($C_1$-$C_4$)alkoxy, trifluoromethyl, hydroxy, amino, cyano or 4,5-dihydro-1H-imidazol-2-yl; or
$R_4$ is pyrid-2-, -3- or -4-yl($C_1$-$C_4$)alkyl, thiazol-2-, -4- or -5-yl($C_1$-$C_4$)alkyl, imidazol-2-, -4- or -5-yl($C_1$-$C_4$)alkyl, pyrrol-2- or -3-yl($C_1$-$C_4$)alkyl, oxazol-2-, -4- or -5-yl($C_1$-$C_4$)alkyl, pyrazol-3-, -4- or -5-yl($C_1$-$C_4$)alkyl, isoxazol-3-, -4- or -5-yl($C_1$-$C_4$)alkyl, isothiazol-3-, -4- or -5-yl($C_1$-$C_4$)alkyl, pyridazin-3- or -4-yl($C_1$-$C_4$)alkyl, pyrimidin-2-, -4-, -5- or -6-yl($C_1$-$C_4$)alkyl, pyrazin-2- or -3-yl($C_1$-$C_4$)alkyl, 1,3,5-triazin-2-yl($C_1$-$C_4$)alkyl; or indol-2-($C_1$-$C_4$)alkyl, wherein the preceding $R_4$ heterocycles are optionally mono- or di-substituted independently with halo, trifluoromethyl, ($C_1$-$C_4$)alkyl, ($C_1$-$C_4$)alkoxy, amino, hydroxy or cyano and the substituents are bonded to carbon; or
$R_4$ is $R_{15}$-carbonyloxymethyl, wherein the $R_{15}$ is phenyl, thiazolyl, imidazolyl, 1H-indolyl, furyl, pyrrolyl, oxazolyl, pyrazolyl, isoxazolyl, pyridyl, pyridazinyl, pyrimidinyl, pyrazinyl or 1,3,5-triazinyl and wherein the preceding $R_{15}$ rings are optionally mono- or di-substituted independently with halo, amino, hydroxy, ($C_1$-$C_4$)alkyl, ($C_1$-$C_4$)alkoxy or trifluoromethyl and the mono- or di-substituents are bonded to carbon;
$R_5$ is H, methyl, ethyl, n-propyl, hydroxymethyl or hydroxyethyl;
$R_6$ is carboxy, ($C_1$-$C_8$)alkoxycarbonyl, benzyloxycarbonyl, C(O)NR$_8$R$_9$ or C(O)R$_{12}$ wherein
$R_8$ is H, ($C_1$-$C_6$)alkyl, cyclo($C_3$-$C_6$)alkyl, cyclo($C_3$-$C_6$)alkyl($C_1$-$C_5$)alkyl, hydroxy or ($C_1$-$C_8$)alkoxy; and
$R_9$ is H, cyclo($C_3$-$C_8$)alkyl, cyclo($C_3$-$C_8$)alkyl($C_1$-$C_5$)alkyl, cyclo($C_4$-$C_7$)alkenyl, cyclo($C_3$-$C_7$)alkyl($C_1$-$C_5$)alkoxy, cyclo($C_3$-$C_7$)alkyloxy, hydroxy, methylene-perfluorinated ($C_1$-$C_8$)alkyl, phenyl, or a heterocycle wherein the heterocycle is pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl, 1,3,5-triazinyl, benzothiazolyl, benzoxazolyl, benzimidazolyl, thiochromanyl or tetrahydrobenzothiazolyl wherein the heterocycle rings are carbon-nitrogen linked; or
$R_9$ is ($C_1$-$C_6$)alkyl or ($C_1$-$C_8$)alkoxy wherein the ($C_1$-$C_6$)alkyl or ($C_1$-$C_8$)alkoxy is optionally monosubstituted with cyclo($C_4$-$C_7$)alken-1-yl, phenyl, thienyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, thiomorpholinyl, 1-oxothiomorpholinyl, 1,1-dioxothiomorpholinyl, pyridazinyl, pyrimidinyl, pyrazinyl, piperazinyl, 1,3,5-triazinyl or indolyl and wherein the ($C_1$-$C_6$)alkyl or ($C_1$-$C_8$)alkoxy are optionally additionally independently mono- or di-substituted with halo, hydroxy, ($C_1$-$C_5$)alkoxy, amino, mono-N— or di-N,N—($C_1$-$C_5$)alkylamino, cyano, carboxy, or ($C_1$-$C_4$)alkoxycarbonyl; and
wherein the $R_9$ rings are optionally mono- or di-substituted independently on carbon with halo, ($C_1$-$C_4$)alkyl, ($C_1$-$C_4$)alkoxy, hydroxy, hydroxy($C_1$-$C_4$)alkyl, amino($C_1$-$C_4$)alkyl, mono-N— or di-N,N—($C_1$-$C_4$)alkylamino($C_1$-$C_4$)alkyl, ($C_1$-$C_4$)alkoxy($C_1$-$C_4$)alkyl, amino, mono-N— or di-N,N—($C_1$-$C_4$)alkylamino, cyano, carboxy, ($C_1$-$C_5$)alkoxycarbonyl, carbamoyl, formyl or trifluoromethyl and the $R_9$ rings may optionally be additionally mono- or di-substituted independently with ($C_1$-$C_5$)alkyl or halo;
with the proviso that no quaternized nitrogen on any $R_9$ heterocycle is included;
$R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan-2-yl, pyrazolidin-1-yl, isoxazolidin-2-yl, isothiazolidin-2-yl, 1,2-oxazetidin-2-yl, oxazolidin-3-yl, 3,4dihydroisoquinolin-2-yl, 1,3-dihydrolsoindol-2-yl, 3,4-dihydro-2H-quinol-1-yl, 2,3-dihydro-benzo[1,4]oxazin-4-yl, 2,3-dihydro-benzo[1,4]-thiazine-4-yl, 3,4-dihydro-2H-quinoxalin-1-yl, 3,4-dihydro-benzo[c][1,2]oxazin-1-yl, 1,4-dihydro-benzo[d][1,2]oxazin-3-yl, 3,4-dihydro-benzo[e][1, 2]-oxazin-2-yl, 3H-benzo[d]isoxazol-2-yl, 3H-benzo[c]isoxazol-1-yl or azepan-1-yl,
wherein the $R_{12}$ rings are optionally mono-, di- or tri-substituted independently with halo, ($C_1$-$C_5$)alkyl, ($C_1$-$C_5$)alkoxy, hydroxy, amino, mono-N— or di-N,N—($C_1$-$C_5$)alkylamino, formyl, carboxy, carbamoyl, mono-N— or di-N,N—($C_1$-$C_5$)alkylcarbamoyl, ($C_1$-$C_6$)alkoxy($C_1$-$C_3$)alkoxy, ($C_1$-$C_5$)alkoxycarbonyl, benzyloxycarbonyl, ($C_1$-$C_5$)alkoxycarbonyl($C_1$-$C_5$)alkyl, ($C_1$-$C_4$)alkoxycarbonylamino, carboxy($C_1$-$C_5$)alkyl, carbamoyl($C_1$-$C_5$)alkyl, mono-N— or di-N,N—($C_1$-$C_5$)alkylcarbamoyl($C_1$-$C_5$)alkyl, hydroxy($C_1$-$C_5$)alkyl, ($C_1$-$C_4$)alkoxy($C_{1-4}$)alkyl, amino ($C_1C_4$)alkyl, mono-N— or di-N,N—($C_1$-$C_4$)alkylamino($C_1$-$C_4$)alkyl, oxo, hydroxylmino or ($C_1$-$C_6$)alkoxylmino and wherein no more than two substituents are selected from oxo, hydroxylmino or ($C_1$-$C_6$)alkoxylmino and oxo, hydroxylmino or ($C_1$-$C_6$)alkoxyimino are on nonaromatic carbon; and the $R_{12}$ rings are optionally additionally mono- or di-substituted independently with ($C_1$-$C_5$)alkyl or halo.

In some embodiments of formula (III), when $R_6$ is ($C_1$-$C_5$)alkoxycarbonyl or benzyloxycarbonyl then $R_1$ is 5-halo, 5-($C_1$-$C_4$)alkyl or 5-cyano and $R_4$ is (phenyl)(hydroxy)($C_1$-$C_4$)alkyl, (phenyl)(($C_1$-$C_4$)alkoxy)($C_1$-$C_4$)alkyl, hydroxymethyl or Ar($C_1$-$C_2$)alkyl, wherein Ar is thien-2- or -3-yl, fur-2- or -3-yl or phenyl wherein the Ar is optionally mono- or di-substituted independently with halo; with the provisos that when $R_4$ is benzyl and $R_5$ is methyl, $R_{12}$ is not 4-hydroxy-piperidin-1-yl or when $R_4$ is benzyl and $R_5$ is methyl $R_6$ is not $C(O)N(CH_3)_2$.

In some embodiments of formula (III), when $R_1$, $R_{10}$, and $R_{11}$ are H, $R_4$ is not imidazol-4-ylmethyl, 2-phenylethyl or 2-hydroxy-2-phenylethyl.

In some embodiments of formula (III), when both $R_8$ and $R_9$ are n-pentyl, none of $R_1$ is 5-chloro, 5-bromo, 5-cyano, 5($C_1$-$C_5$)alkyl, 5($C_1$-$C_5$)alkoxy or trifluoromethyl.

In some embodiments of formula (III), when $R_{12}$ is 3,4dihydroisoquinol-2-yl, the 3,4-dihydroisoquinol-2-yl is not substituted with carboxy(($C_1$-$C_4$)alkyl.

In some embodiments of formula (III), when $R_8$ is H and $R_9$ is ($C_1$-$C_6$)alkyl, $R_9$ is not substituted with carboxy or ($C_1$-$C_4$)alkoxycarbonyl on the carbon which is attached to the nitrogen atom N of $NHR_9$.

In some embodiments of formula (III), when $R_6$ is carboxy and $R_1$, $R_{10}$, $R_{11}$ and $R_5$ are all H, then $R_4$ is not benzyl, H, (phenyl)(hydroxy)methyl, methyl, ethyl or n-propyl.

Exemplary compounds of formula (III) are those belonging to a first group of compounds in which:

$R_1$ is 5H, 5-halo, 5-methyl, 5-cyano or 5-trifluoromethyl;
$R_{10}$ and $R_{11}$ are each independently H or halo;
A is —C(H)=;
$R_2$ and $R_3$ are H;
$R_4$ is H, methyl, phenyl($C_1C_2$)alkyl, wherein the phenyl groups are mono- or di-substituted independently with H, halo, ($C_1$-$C_4$)alkyl, ($C_1C_4$)alkoxy, trifluoromethyl, hydroxy, amino or cyano and wherein the $R_4$ groups are optionally additionally mono-substituted with halo; or
$R_4$ is thien-2- or -3-yl($C_1$-$C_2$)alkyl, pyrid-2-, -3- or -4-yl ($C_1$-$C_2$)alkyl, thiazol-2-, -4- or -5-yl($C_1$-$C_2$)alkyl, imidazol-2-, -4- or -5-yl($C_1$-$C_2$)alkyl, fur-2- or -3-yl($C_1$-$C_2$)alkyl, pyrrol-2- or -3-yl($C_1$-$C_2$)alkyl, oxazol-2-, -4- or -5-yl($C_1$-$C_2$)alkyl, pyrazol-3-, -4- or -5-yl($C_1$-$C_2$)alkyl, isoxazol-3-, -4- or -5-yl($C_1$-$C_2$)alkyl, isothiazol-3-, -4- or -5-yl($C_1$-$C_2$)alkyl, pyridazin-3- or -4-yl($C_1$-$C_2$)alkyl, pyrimidin-2-, -4-, -5- or -6-yl($C_1$-$C_2$)alkyl, pyrazin-2- or -3-yl($C_1$-$C_2$)alkyl or 1,3,5-triazin-2-yl($C_1$-$C_2$)alkyl wherein the preceding $R_4$ heterocycles are optionally mono- or di-substituted independently with halo, trifluoromethyl, ($C_1$-$C_4$)alkyl, ($C_1$-$C_4$)alkoxy, amino or hydroxy and the mono- or di-substituents are bonded to cabin;
$R_5$ is H; and
$R_6$ is $C(O)NR_8R_9$ or $C(O)R_{12}$.

For example, compounds of formula (III) that may be used in conjunction with the compositions and methods described herein include those in which:

$R_4$ is H, phenyl($C_1$-$C_2$)alkyl, thien-2- or -3-yl($C_1$-$C_2$) alkyl, fur-2- or -3-yl($C_1$-$C_2$)alkyl wherein the $R_4$ rings are mono- or di-substituted independently with H or fluoro;

$R_6$ is $C(O)R_{12}$; and
$R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2oxazinan-2-yl, isoxazolidin-2-yl, isothiazolidin-2-yl, 1,2-oxazetidin-2-yl, oxazolidin-3-yl, 1,3-dihydroisoindol-2-yl, or azepan-1-yl, the $R_{12}$ rings are optionally mono- or di-substituted independently with halo, ($C_1$-$C_5$)alkyl, ($C_1$-$C_5$)alkoxy, hydroxy, amino, mono-N— or di-N,N—($C_1$-$C_5$)alkylamino, formyl, carboxy, carbamoyl, mono-N— or di-N,N—($C_1$-$C_5$)alkylcarbamoyl, ($C_1$-$C_5$)alkoxycarbonyl, hydroxy($C_1$-$C_5$)alkyl, amino($C_1$-$C_4$)alkyl, mono-N— or di-N,N—($C_1C_4$)alkylamino($C_1$-$C_4$)alkyl, oxo, hydroxylmino or ($C_1$-$C_6$)alkoxylmino with the proviso that only the $R_{12}$ heterocycles thiazolidin-3-yl, pyrrolidin-1-yl, piperidin-1-yl, piperazin-1-yl, piperazin-4-yl, azetidin-1-yl, 1,2-oxazinan-2-yl, isoxazolidin-2-yl, or oxazolidin-3-yl are optionally mono- or di-substituted with oxo, hydroxylmino, or ($C_1$-$C_6$) alkoxylmino; and the $R_{12}$ rings are optionally additionally mono- or di-substituted independently with ($C_1$-$C_5$)alkyl.

Further exemplary compounds of formula (III) that may be used in conjunction with the compositions and methods described herein include: 5-Chloro-1H-indole-2-carboxylic acid [(1S)-benzyl-2-(3-hydroxylmino-pyrrolidin-1-yl)-2-oxo-ethyl]-amide, 5-Chloro-1H-indole-2-carboxylic acid [2-(cis-3,4-dihydroxy-pyrrolidin-1-yl)-2-oxo-ethyl]amide, 5-Chloro-1H-indole-2-carboxylic acid [2-((3S,4S)-dihydroxy-pyrrolidin-1-yl)-2-oxo-ethyl]amide, 5-Chloro-1H-indole-2-carboxylic acid [(1S)-benzyl-2-(cis-3,4-dihydroxy-pyrrolidin-1-yl)-2-oxo-ethyl]-amide, 5-Chloro-1H-indole-2-carboxylic acid [2-(1,1-dioxo-thiazoildin-3-yl)-2-oxo-ethyl] amide, 5-Chloro-1H-indole-2-carboxylic acid (2-oxo-2-thiazolidin-3-yl-ethyl)-amide, 5-Chloro-1H-indole-2-carboxylic acid [(1S)-(4-fluoro-benzyl)-2-(4-hydroxy-piperidin-1-yl)-2-oxo-ethyl]amide, 5-Chloro-1H-indole-2-carboxylic acid [(1S)-benzyl-2-((3RS)-hydroxy-piperidin-1-yl)-2-oxo-ethyl]-amide, 5Chloro-1H-indole-2-carboxylic acid [2-oxo-2-((1RS)-oxo-1-thiazolidin-3-yl)-ethyl]-amide, 5-Chloro-1H-indole-2-carboxylic acid [(1S)-(2-fluoro-benzyl)-2-(4-hydroxy-piperidin-1-yl)-2-oxo-ethyl]-amide, 5-Chloro-1H-indole-2-carboxylic acid [(1S)-benzyl-2-((3S, 4S)-dihydroxy-pyrrolidin-1-yl)-2-oxo-ethyl]-amide, 5-Chloro-1H-indole-2-carboxylic acid [(1S)-benzyl-2-(3-hydroxy-azetidin-1-yl)-2-oxo-ethyl]amide, 5-Chloro-1H-indole-2-carboxylic acid [(1S)-benzyl-2-(3-hydroxyimino-azetidin-1-yl)-2-oxo-ethyl]-amide, and 5-Chloro-1H-indole-2-carboxylic acid [(1S)-benzyl-2-(4-hydroxyimino-piperidin-1-yl)-2-oxo-ethyl]-amide.

Further exemplary compounds of formula (III) that may be used in conjunction with the compositions and methods described herein include those in which:

$R_4$ is H; and
$R_{12}$ is thiazolidin-3-yl, 1-oxo-thiazolidin-3-yl, 1,1-dioxo-thiazolidin-3-yl or oxazolidin-3-yl or the $R_{12}$ substituents optionally mono- or di-substituted independently with carboxy, ($C_1$-$C_5$)alkoxycarbonyl, hydroxy($C_1$-$C_3$)alkyl, amino ($C_1$-$C_3$)alkyl, mono-N— or di-N,N—($C_1$-$C_3$)alkylamino ($C_1$-$C_3$)alkyl or
$R_{12}$ is mono- or di-substituted pyrrolidin-1-yl wherein the substituents are independently carboxy, ($C_1$-$C_5$)alkoxycarbonyl, ($C_1$-$C_5$)alkoxy, hydroxy, hydroxy($C_1$-$C_3$)alkyl, amino, amino($C_1$-$C_3$)alkyl, mono-N— or di-N,N—($C_1$-$C_3$) alkylamino($C_1$-$C_3$)alkyl or mono-N— or di-N,N—($C_1$-$C_4$)

alkylamino; and the $R_{12}$ rings are optionally additionally independently disubstituted with $(C_1-C_5)$alkyl.

Further exemplary compounds of formula (III) that may be used in conjunction with the compositions and methods described herein include those in which:
(a) $R_1$ is 5-chloro;
$R_{10}$ and $R_{11}$ are H; and
$R_{12}$ is cis-3,4-dihydroxy-pyrrolidin-1-yl;
(b) $R_1$ is 5-chloro;
$R_{10}$ and $R_{11}$ are H; and
$R_{12}$ is (3S,4S)-dihydroxy-pyrrolidin-1-yl;
(c) $R_1$ is 5-chloro;
$R_{10}$ and $R_{11}$ are H; and
$R_{12}$ is 1,1-dioxo-thiazolidin-3-yl;
(d) $R_1$ is 5-chloro;
$R_{10}$ and $R_{11}$ are H; and
$R_{12}$ is thiazolidin-3-yl; and
(e) $R_1$ is 5-chloro;
$R_{10}$ and $R_{11}$ are H; and
$R_{12}$ is 1-oxo-thiazolidin-3-yl.

Further exemplary compounds of formula (III) that may be used in conjunction with the compositions and methods described herein include those in which:
$R_4$ is phenylmethyl, thien-2- or -3-ylmethyl wherein the $R_4$ rings are optionally mono- or di-substituted with fluoro; and
$R_{12}$ is thiazolidin-3-yl, 1-oxo-thiazolidin-3-yl, 1,1-dioxo-thiazolidin-3-yl or oxazolidin-3-yl or the $R_{12}$ substituents optionally mono- or di-substituted independently with carboxy or $(C_1-C_5)$alkoxycarbonyl, hydroxy$(C_1-C_3)$alkyl, amino$(C_1-C_3)$alkyl or mono-N— or di-N,N—$(C_1-C_3)$alkylamino$(C_1-C_3)$alkyl or
$R_{12}$ is mono- or di-substituted azetidin-1-yl or mono- or di-substituted pyrrolidin-1-yl or mono- or di-substituted piperidin-1-yl wherein the substituents are independently carboxy, $(C_1-C_5)$alkoxycarbonyl, hydroxy$(C_1-C_3)$alkyl, amino$(C_1-C_3)$alkyl, mono-N— or di-N,N—$(C_1-C_3)$alkylamino$(C_1-C_3)$alkyl, hydroxy, $(C_1-C_5)$alkoxy, amino, mono-N— or di-N,N—$(C_1-C_5)$alkylamino, oxo, hydroxylmino or $(C_1-C_5)$alkoxylmino; and
the $R_{12}$ rings are optionally additionally mono- or di-substituted independently with $(C_1-C_5)$alkyl.

Further exemplary compounds of formula (III) that may be used in conjunction with the compositions and methods described herein include those in which:
(a) $R_1$ is 5-chloro;
$R_{10}$ and $R_{11}$ are H;
$R_4$ is 4-fluorobenzyl;
$R_{12}$ is 4-hydroxypiperidin-1-yl; and
the stereochemistry of carbon (a) is (S);
(b) $R_1$ is 5-chloro;
$R_{10}$ and $R_{11}$ are H;
$R_4$ is benzyl;
$R_{12}$ is 3-hydroxypiperidin-1-yl; and
the stereochemistry of carbon (a) is (S);
(c) $R_1$ is 5-chloro;
$R_{10}$ and $R_{11}$ are H;
$R_4$ is benzyl;
$R_{12}$ is cis-3,4-dihydroxy-pyrrolidin-1-yl; and
the stereochemistry of carbon (a) is S;
(d) $R_1$ is 5-chloro;
$R_{10}$ and $R_{11}$ are H; $R_4$ is benzyl;
$R_{12}$ is 3-hydroxyimino-pyrrolidin-1-yl; and
the stereochemistry of carbon (a) is (S);
(e) $R_1$ is 5-chloro;
$R_{10}$ and $R_{11}$ are H;
$R_4$ is 2-fluorobenzyl;
$R_{12}$ is 4-hydroxypiperidin-1-yl; and
the stereochemistry of carbon (a) is (S);
(f) $R_1$ is 5-chloro;
$R_{10}$ and $R_{11}$ are H;
$R_4$ is benzyl;
$R_{12}$ is (3S,4S)-dihydroxy-pyrrolidin-1-yl; and
the stereochemistry of carbon (a) is (S);
(g) $R_1$ is 5-chloro;
$R_{10}$ and $R_{11}$ are H;
$R_4$ is benzyl;
$R_{12}$ is 3-hydroxy-azetidin-1-yl; and
the stereochemistry of carbon (a) is (S);
(h) $R_1$ is 5-chloro;
$R_{10}$ and $R_{11}$ are H;
$R_4$ is benzyl;
$R_{12}$ is 3-hydroxyimino-azetidin-1-yl; and
the stereochemistry of carbon (a) is (S); and
(i) $R_1$ is 5chloro;
$R_{10}$ and $R_{11}$ are H;
$R_4$ is benzyl;
$R_{12}$ is 4-hydroxyimino-piperidin-1-yl; and
the stereochemistry of carbon (a) is (S).

Additionally, exemplary compounds of formula (III) are those belonging to a second group of compounds in which:
$R_4$ is H, phenyl$(C_1-C_2)$alkyl, thien-2- or -3-yl$(C_1-C_2)$alkyl, fur-2- or -3-yl$(C_1-C_2)$alkyl wherein the $R_4$ rings are mono- or di-substituted independently with H or fluoro;
$R_6$ is $C(O)NR_8R_9$; and
$R_8$ is H, $(C_1-C_5)$alkyl, hydroxy or $(C_1-C_4)$alkoxy; and
$R_9$ is H, cyclo$(C_4-C_6)$alkyl, cyclo$(C_3-C_6)$alkyl$(C_1-C_5)$alkyl, methylene-perfluorinated$(C_1-C_3)$alkyl, pyridyl, pyrrolidinyl, oxazolyl, thiazolyl, imidazolyl, piperidinyl, benzothiazolyl or thiochromanyl; or $R_9$ is $(C_1-C_5)$alkyl wherein the $(C_1-C_5)$alkyl is optionally substituted with cyclo$(C_4-C_6)$alkenyl, phenyl, thienyl, pyridyl, pyrrolidinyl, oxazolyl, thiazolyl, imidazolyl, pyrazolyl, piperidinyl, morpholinyl, thiomorpholinyl, 1-oxothiomorpholinyl, or 1,1-dioxothiomorpholinyl and wherein the $(C_1-C_5)$alkyl or $(C_1-C_4)$alkoxy is optionally additionally independently mono- or di-substituted with halo, hydroxy, $(C_1-C_5)$alkoxy, amino, mono-N— or di-N,N—$(C_1-C_5)$alkylamino, cyano, carboxy, or $(C_1-C_4)$alkoxycarbonyl; wherein the $R_9$ rings are optionally mono- or di-substituted independently on carbon with halo, $(C_1-C_4)$alkyl, $(C_1-C_4)$alkoxy, hydroxy, amino, mono-N— or di-N,N—$(C_1-C_4)$alkylamino, carbamoyl, $(C_1-C_5)$alkoxycarbonyl or carbamoyl.

Further exemplary compounds of formula (III) that may be used in conjunction with the compositions and methods described herein include those in which:
(a) $R_1$ is 5-chloro;
$R_{10}$ and $R_{11}$ are H;
$R_4$ is benzyl;
$R_8$ is methyl; and
$R_9$ is 3-(dimethylamino)propyl;
(b) the stereochemistry of carbon (a) is (S);
$R_1$ is 5-chloro;
$R_{10}$ and $R_{11}$ are H;
$R_4$ is benzyl;
$R_8$ is methyl; and
$R_9$ is 3-pyridyl;
(c) the stereochemistry of carbon (a) is (S);
$R_1$ is 5-chloro;
$R_{10}$ and $R_{11}$ are H;
$R_4$ is benzyl;
$R_8$ is methyl; and
$R_9$ is 2-hydroxyethyl; and (d) the stereochemistry of carbon (a) is (S);
$R_1$ is 5-fluoro;
$R_{10}$ and $R_{11}$ are H;
$R_4$ is 4-fluorophenylmethyl;
$R_8$ is methyl; and
$R_9$ is 2-morpholinoethyl.

Additionally, exemplary compounds of formula (III) are those belonging to a third group of compounds in which:

$R_4$ is H, phenyl($C_1$-$C_2$)alkyl, thien-2- or -3-yl($C_1$-$C_2$) alkyl, fur-2- or -3-yl($C_1$-$C_2$)alkyl wherein the $R_4$ rings are mono- or di-substituted independently with H or fluoro;
$R_6$ is C(O)$NR_8R_9$; and
$R_8$ is H, ($C_1$-$C_5$)alkyl, hydroxy or ($C_1$-$C_4$)alkoxy; and
$R_9$ is ($C_1$-$C_4$)alkoxy wherein the ($C_1$-$C_4$)alkoxy is optionally substituted with cyclo($C_4$-$C_6$)alkenyl, phenyl, thienyl, pyridyl, pyrrolidinyl, oxazolyl, thiazolyl, imidazolyl, pyrazolyl, piperidinyl, morpholinyl, thiomorpholinyl, 1-oxothiomorpholinyl, or 1,1-dioxothiomorpholinyl and wherein the ($C_1$-$C_5$)alkyl or ($C_1$-$C_4$)alkoxy is optionally additionally independently mono- or di-substituted with halo, hydroxy, ($C_1$-$C_5$)alkoxy, amino, mono-N— or di-N,N—($C_1$-$C_5$)alkylamino, cyano, carboxy, or ($C_1$-$C_4$)alkoxycarbonyl; wherein the $R_9$ rings are optionally mono- or di-substituted independently on carbon with halo, ($C_1$-$C_4$)alkyl, ($C_1$-$C_4$)alkoxy, hydroxy, amino, mono-N— or di-N,N—($C_1$-$C_4$)alkylamino, carbamoyl, ($C_1$-$C_5$)alkoxycarbonyl or carbamoyl.

Further exemplary compounds of formula (III) that may be used in conjunction with the compositions and methods described herein include those in which:

(a) $R_1$ is 5-chloro;
$R_{10}$ and $R_{11}$ are H;
$R_4$ is benzyl;
$R_8$ is methyl; and
$R_9$ is 2-hydroxyethoxy;
(b) the stereochemistry of carbon (a) is (S);
$R_1$ is 5-chloro;
$R_{10}$ and $R_{11}$ are H;
$R_4$ is 4-fluorophenylmethyl;
$R_8$ is methyl; and
$R_9$ is methoxy;
(c) the stereochemistry of carbon (a) is (S);
$R_1$ is 5-chloro;
$R_{10}$ and $R_{11}$ are H;
$R_4$ is benzyl;
$R_8$ is methyl; and
$R_9$ is methoxy;

Further exemplary compounds of formula (III) that may be used in conjunction with the compositions and methods described herein include those in which:

$R_1$ is 5-halo, 5-methyl, 5-cyano or trifluoromethyl;
$R_{10}$ and $R_{11}$ are each independently H or halo;
A is —C(H)═;
$R_2$ and $R_3$ are H;
$R_4$ is H, phenyl($C_1$-$C_2$)alkyl, thien-2- or -3-yl($C_1$-$C_2$) alkyl, fur-2- or 3-yl($C_1$-$C_2$)alkyl wherein the rings are mono- or di-substituted Independently with H or fluoro;
$R_5$ is H; and
$R_6$ is ($C_1$-$C_5$)alkoxycarbonyl.

Further exemplary compounds of formula (III) that may be used in conjunction with the compositions and methods described herein include those in which:

$R_1$ is 5-halo, 5-methyl, 5-cyano or trifluoromethyl;
$R_{10}$ and $R_{11}$ are each independently H or halo;
A is —C(H)═;
$R_2$ and $R_3$ are H;
$R_4$ is H, methyl or phenyl($C_1$-$C_2$)alkyl, wherein the phenyl groups are mono- or di-substituted independently with H, halo, ($C_1$-$C_4$)alkyl, ($C_1$-$C_4$)alkoxy, trifluoromethyl, hydroxy, amino or cyano and wherein the phenyl groups are additionally mono- or di-substituted independently H or halo; or $R_4$ is thien-2- or -3yl($C_1$-$C_2$)alkyl, pyrid-2-, -3- or -4-yl ($C_1$-$C_2$)alkyl, thiazol-2-, -4- or -5-yl($C_1$-$C_2$)alkyl, imidazol-2-, -4- or -5-yl($C_1$-$C_2$)alkyl, fur-2- or -3-yl($C_1$-$C_2$)alkyl, pyrrol-2- or -3-yl($C_1$-$C_2$)alkyl, oxazol-2-, -4- or -5-yl($C_1$-$C_2$)alkyl, pyrazol-3-, -4- or -5-yl($C_1$-$C_2$)alkyl, isoxazol-3-, -4- or -5-yl($C_1$-$C_2$)alkyl, isothiazol-3-, -4- or -5-yl($C_1$-$C_2$) alkyl, pyridazin-3- or -4yl($C_1$-$C_2$)alkyl, pyrimidin-2-, -4-, -5- or -6-yl($C_1$-$C_2$)alkyl, pyrazin-2- or -3-yl($C_1$-$C_2$)alkyl or 1,3,5-triazin-2-yl($C_1$-$C_2$)alkyl wherein the preceding $R_4$ heterocycles are optionally mono- or di-substituted independently with halo, trifluoromethyl, ($C_1$-$C_4$)alkyl, ($C_1$-$C_4$) alkoxy, amino or hydroxy and the mono- or di-substituents are bonded to carbon;
$R_5$ is H; and
$R_6$ is carboxy.

Further exemplary compounds of formula (III) that may be used in conjunction with the compositions and methods described herein include those in which:
$R_{10}$ and $R_{11}$ are H; and
$R_4$ is H.

Further exemplary compounds of formula (III) that may be used in conjunction with the compositions and methods described herein include those in which $R_1$ is 5-chloro.

Exemplary variants of CP-320606 that may be used in conjunction with the compositions and methods described herein are those compounds described in U.S. Pat. No. 6,277,877, the disclosure of which is incorporated herein by reference in its entirety.

Itraconazole, Posaconazole, and Variants Thereof

In some embodiments, the CYP51A1 inhibitor itraconazole, posaconazole, or a variant thereof that retains CYP51A1 inhibitory activity. For example, the CYP51A1 inhibitor may be a compound represented by formula (IV)

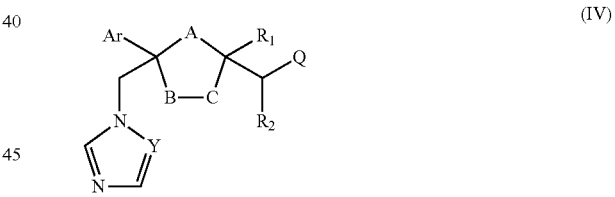

(IV)

wherein Ar is thienyl, pyridyl, biphenyl, phenyl or phenyl substituted by one or more of halo, nitro, cyano, lower alkyl, lower alkoxy or perhalo(lower)alkyl;
Y is CH or N;
either one of A, B and C is oxygen and the remaining two of A, B and C are $CH_2$; or A is oxygen, B is $CH_2$, and C is a direct bond;
Q is:

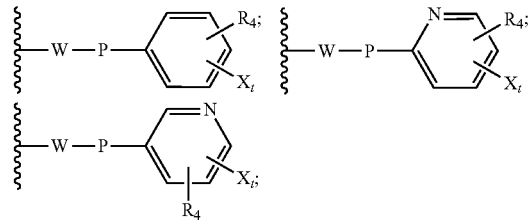

91

-continued

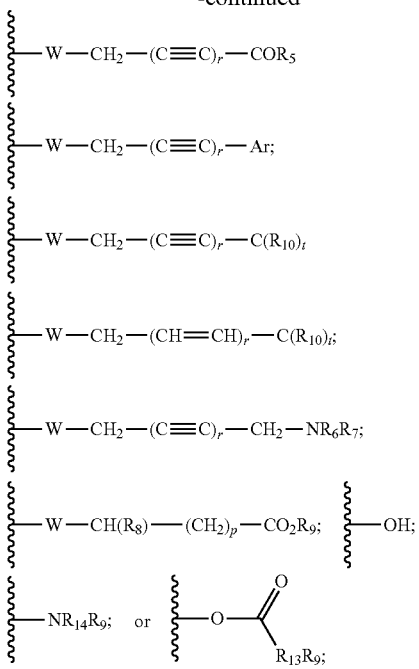

W is —NR₅—, —O—, or —S(O)$_n$—;
X is —NO₂, —P—NR₆R₇,

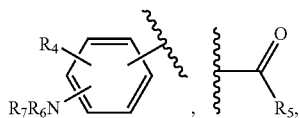

Ar, OR₃ or halogen;

P is a direct bond, —CHR₁₁— or —CHR₁₁CHR₁₂—;

R₁, R₈, R₉ and R₁₀ are independently hydrogen, lower alkyl or lower alkyl substituted by one or more hydroxy groups;

R₂, R₄, R₁₁, R₁₂ and R₁₄ are hydrogen, hydroxy, lower alkyl or lower alkyl substituted by one or more hydroxy groups;

R₃ and R₁₃ are independently hydrogen, lower alkyl, (C₂-C₈) perhaloalkanoyl or (C₂-C₈) alkanoyl;

R₆ and R₇ are independently hydrogen, lower alkyl, phenyl or phenyl substituted by one or more of halo, perhalo (lower)alkyl, (C₂-C₈)alkanoyl, lower alkyl, lower alkyl substituted by one or more hydroxy groups, lower alkoxy, or 2-(lower)alkyl-3-oxo-1,2,4-triazol-4-yl, or R₆ and R₇ taken together with the nitrogen atom in NR₆ R₇ form unsubstituted or substituted 5- or 6-membered heterocyclyl ring systems containing carbon and one to four heteroatoms chosen from N, O and S, the heterocyclyl substituents being (C₁-C₈)alkanoyl, lower alkyl, lower alkoxycarbonyl, aminocarbonyl, N-lower alkylaminocarbonyl, N,N-di(lower alkyl)amino carbonyl, aminothiocarbonyl, N-lower alkylaminothiocarbonyl, N,N-di(lower alkyl)aminothiocarbonyl, lower alkyl sulfonyl, phenyl-substituted lower alkyl sulfonyl, N-lower alkylamino, N,N-di(lower alkyl)amino, 1,3-imidazol-1-yl, 2-loweralkylsulfenyl-1,3-imidazol-1-yl,

92

2-pyridinyl, 2-thiazolyl, 2-lower alkyl-3-oxo-1,2,4-triazol-4-yl, 1-lower alkylbenzimidazol-2-yl, phenyl or phenyl substituted by one or more of halo, perhalo lower alkyl, (C₂-C₈) alkanoyl, lower alkyl, lower alkyl substituted by one or more hydroxy group, lower alkoxy, 1H,2,4-triazol-1-yl, 2-lower alkyl-3-oxo-1,2,4-triazol-4-yl, or a substituent represented by the formula:

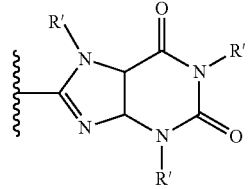

R₅ is a lower alkyl, lower alkoxy, amino, N,N-dilower alkylamino, phenyl or phenyl substituted by one or more of halo, perhalo lower alkyl, lower alkoxy, nitro, cyano, (C₂-C₈)alkanoyl;

p is 0, 1, 2, 3, 4 or 5;

n is 0, 1 or 2;

r is 1 or 2; and t is 0, 1, 2 or 3;

or a pharmaceutically acceptable salt, ester, or ether thereof.

In some embodiments of formula (IV), when R₂, R₁₁, or R₁₂ is attached to a carbon atom adjacent to —NR₅—, —S(O)$_n$— or —O—, the R₂, R₁₁, or R₁₂ is not hydroxy.

In some embodiments, the CYP51A1 inhibitor is represented by formula (V)

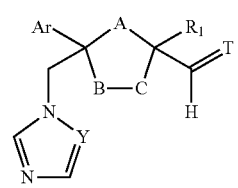

(V)

Wherein Y and Ar are as defined for formula (IV) herein;

one of A, B or C is oxygen and the remaining two of A, B, or C are —CH₂—;

T is =O, =NOR₁, =NNR₁ R₂ or

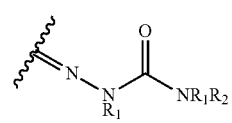

wherein R₁ is hydrogen, lower alkyl or lower alkyl substituted by one or more hydroxy groups; and R₂ is hydrogen, hydroxy, lower alkyl or lower alkyl substituted by one or more hydroxy groups.

In some embodiments, the CYP51A1 inhibitor is represented by formula (VI)

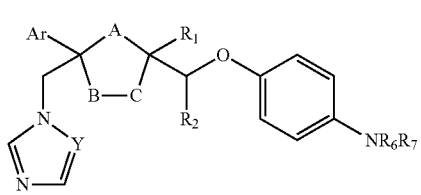

(VI)

wherein Y, Ar, $R_1$, $R_2$, $R_6$ and $R_7$ are as previously defined for formula (IV) herein, and either one of A, B and C is oxygen and the remaining two of A, B and C are $CH_2$, or A is oxygen, B is $CH_2$, and C is a direct bond.

Exemplary compound of formula (VI) for use in conjunction with the compositions and methods described herein are those in which $NR_6R_7$ form unsubstituted or substituted 5- or 6-membered heterocyclyl ring systems containing carbon and one to four heteroatoms chosen from N, O and S, the heterocyclyl substituents being ($C_1$-$C_8$) alkanoyl, lower alkyl, lower alkoxycarbonyl, aminocarbonyl, N-lower alkylaminocarbonyl, N,N-di(lower alkyl)aminocarbonyl, aminothiocarbonyl, N-lower alkylaminothiocarbonyl, N,N-di(lower alkyl)aminothiocarbonyl, lower alkyl sulfonyl, phenyl-substituted lower alkyl sulfonyl, N-lower alkylamino, N,N-di(lower alkyl)amino, 1,3-imidazol-1-yl, 2-loweralkylsulfenyl-1,3-imidazol-1-yl, 2-pyridinyl, 2-thiazolyl, 2-lower alkyl-3-oxo-1,2,4-triazol-4-yl, 1-lower alkylbenzimidazol-2-yl, phenyl, phenyl substituted by one or more of halo, perhalo lower alkyl, ($C_2$-$C_8$)alkanoyl, lower alkyl, lower alkyl substituted by one or more hydroxy groups, lower alkoxy, 1H,2,4-triazol-1-yl or 2-lower alkyl-3-oxo-1, 2,4-triazol-4-yl; $R_5$ is a lower alkyl, amino, N,N-dilower alkylamino, or

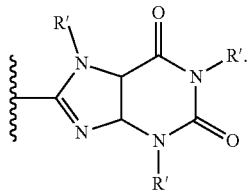

In some embodiments of formula (VI), the $NR_6R_7$ is:

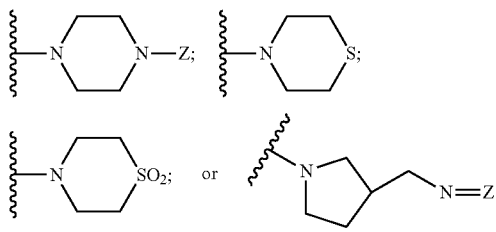

wherein Z is hydrogen, ($C_1$-$C_8$) alkanoyl, lower alkyl, ($C_1$-$C_8$) perhaloalkanoyl or phenyl substituted by 2-loweralkyl-3-oxo-1,2,4-triazol-4-yl.

In some embodiments, the CYP51A1 inhibitor is represented by formula (VII)

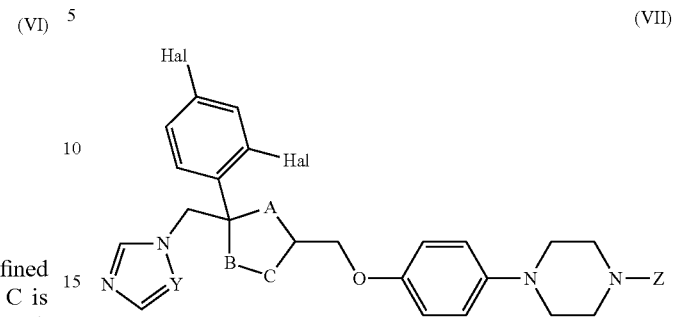

(VII)

wherein one of A, B and C is oxygen and the remaining two of A, B and C are —$CH_2$—, or two of A, B and C are —$CH_2$—;

each Hal is independently a halogen, such as Cl or F; and

Z is lower alkyl, ($C_2$-$C_8$)alkanoyl, or phenyl substituted by 2-loweralkyl-3-oxo-1,2,4triazol-4-yl.

In some embodiments of formula (VII), the compound is selected from:

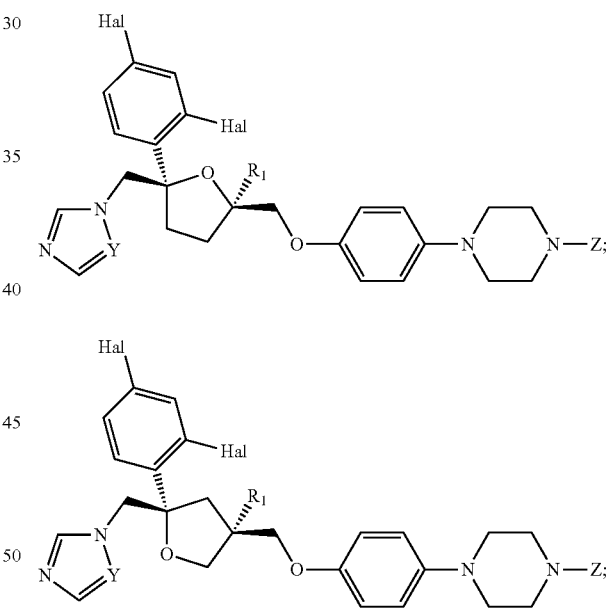

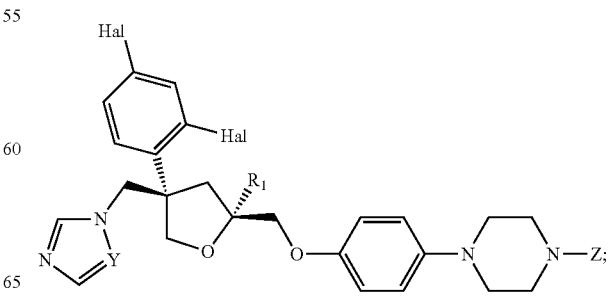

-continued and

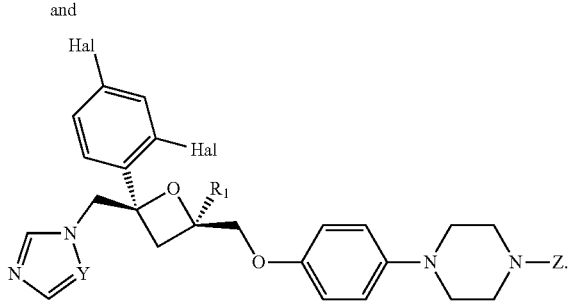

In some embodiments, the CYP51A1 inhibitor is represented by formula (VIII)

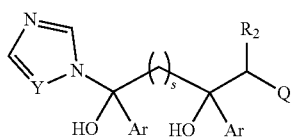
(VIII)

wherein Ar is thienyl, pyridyl, biphenyl, phenyl or phenyl substituted by one or more of halo, nitro, cyano, lower alkyl, lower alkoxy or perhalo(lower)alkyl;

Q is:

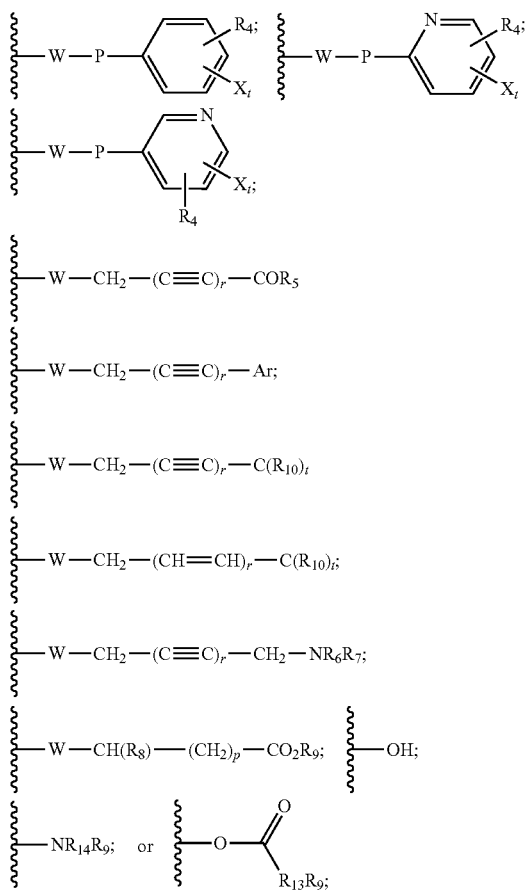

W is $-NR_5-$, $-O-$, or $-S(O)_n-$;

X is $-NO_2$, $-P-NR_6R_7$,

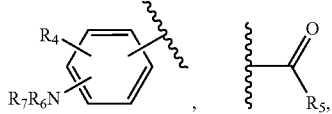, $\text{\{}\!\!\!-C(O)R_5\text{\}}$,

Ar, $OR_3$ or halogen;

P is a direct bond, $-CHR_{11}-$ or $-CHR_{11}CHR_{12}-$;

$R_8$, $R_9$ and $R_{10}$ are independently hydrogen, lower alkyl or lower alkyl substituted by one or more hydroxy groups;

$R_4$, $R_{11}$, $R_{12}$ and $R_{14}$ are hydrogen, hydroxy, lower alkyl or lower alkyl substituted by one or more hydroxy groups;

$R_3$ and $R_{13}$ are independently hydrogen, lower alkyl, ($C_2$-$C_8$) perhaloalkanoyl or ($C_2$-$C_8$) alkanoyl;

$R_6$ and $R_7$ are independently hydrogen, lower alkyl, phenyl or phenyl substituted by one or more of halo, perhalo (lower)alkyl, ($C_2$-$C_8$)alkanoyl, lower alkyl, lower alkyl substituted by one or more hydroxy groups, lower alkoxy, or 2-(lower)alkyl-3-oxo-1,2,4-triazol-4-yl, or $R_6$ and $R_7$ taken together with the nitrogen atom in $NR_6 R_7$ form unsubstituted or substituted 5- or 6-membered heterocyclyl ring systems containing carbon and one to four heteroatoms chosen from N, O and S, the heterocyclyl substituents being ($C_1$-$C_8$)alkanoyl, lower alkyl, lower alkoxycarbonyl, aminocarbonyl, N-lower alkylaminocarbonyl, N,N-di(lower alkyl)amino carbonyl, aminothiocarbonyl, N-lower alkylaminothiocarbonyl, N,N-di(lower alkyl)aminothiocarbonyl, lower alkyl sulfonyl, phenyl-substituted lower alkyl sulfonyl, N-lower alkylamino, N,N-di(lower alkyl)amino, 1,3-imidazol-1-yl, 2-loweralkylsulfenyl-1,3-imidazol-1-yl, 2-pyridinyl, 2-thiazolyl, 2-lower alkyl-3-oxo-1,2,4-triazol-4-yl, phenyl or phenyl substituted by one or more of halo, perhalo lower alkyl, ($C_2$-$C_8$) alkanoyl, lower alkyl, lower alkyl substituted by one or more hydroxy group, lower alkoxy, 1H,2,4-triazol-1-yl, 2-lower alkyl-3-oxo-1,2,4-triazol-4-yl, or a substituent represented by the formula:

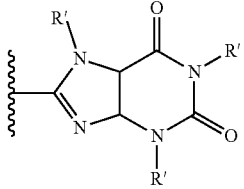

$R_5$ is a lower alkyl, lower alkoxy, amino, N,N-dilower alkylamino, phenyl or phenyl substituted by one or more of halo, perhalo lower alkyl, lower alkoxy, nitro, cyano, ($C_2$-$C_8$)alkanoyl;

p is 0, 1, 2, 3, 4 or 5;

n is 0, 1 or 2;

r is 1 or 2; and t is 0, 1, 2 or 3;

$R_1$ is hydrogen, lower alkyl or lower alkyl substituted by one or more hydroxy groups; and $R_2$ is hydrogen, hydroxy, lower alkyl or lower alkyl substituted by one or more hydroxy groups.

In some embodiments, the CYP51A1 inhibitor is a compound represented by formula (IX)

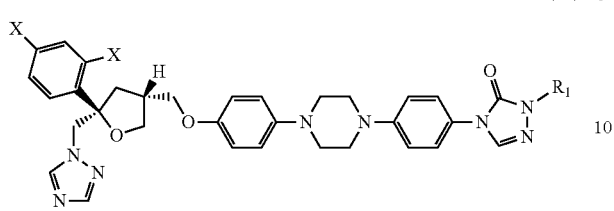

(IX)

wherein each X is independently a halogen, such as F or Cl; and $R_1$ is a straight or branched chain ($C_3$ to $C_8$) alkyl group optionally substituted by one or two hydroxy moieties or by one or two groups convertible in vivo into hydroxy moieties;

or a pharmaceutically acceptable salt, ester, or ether thereof.

In some embodiments of formula (IX), the compound is represented by formula (X)

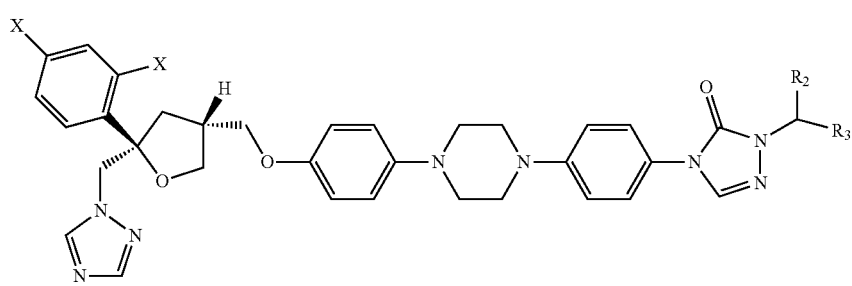

(X)

wherein each X is independently a halogen, such as F or Cl; and $R_2$ is H or ($C_1$-$C_3$) alkyl and $R_3$ is ($C_1$-$C_3$) alkyl optionally substituted by one hydroxy moiety or by a group convertible in vivo into a hydroxy moiety;

or a pharmaceutically acceptable salt, ester, or ether thereof.

In some embodiments of formula (X), the compound is represented by formula (XI)

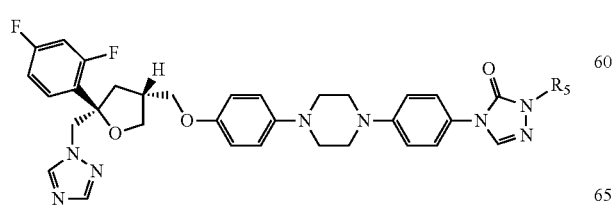

(XI)

wherein $R_5$ is:

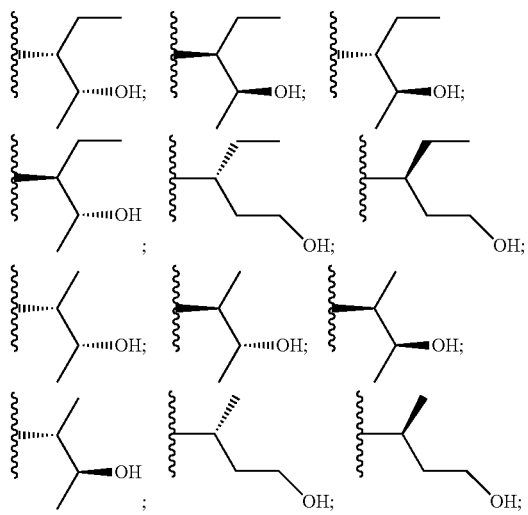

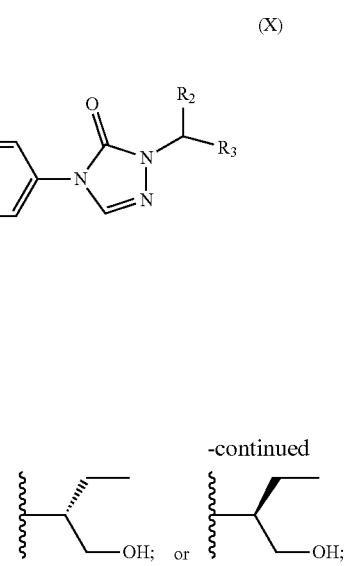

-continued or a pharmaceutically acceptable salt, ester, or ether thereof.

In some embodiments of formula (XI), the compound is represented by formula (XII)

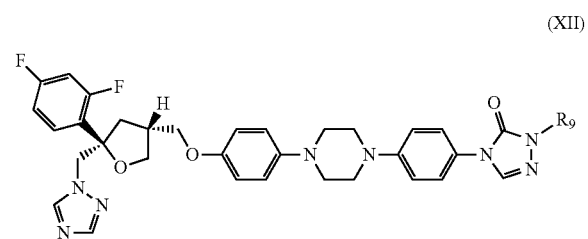

(XII)

wherein $R_9$ is —H($C_2H_5$)CH($R_6$)$CH_3$ or —H($CH_3$)CH($R_6$)$CH_3$;

$R_6$ is OH or a group convertible in vivo into OH;

or a pharmaceutically acceptable salt, ester, or ether thereof.

In some embodiments of formula (XII), the compound is:

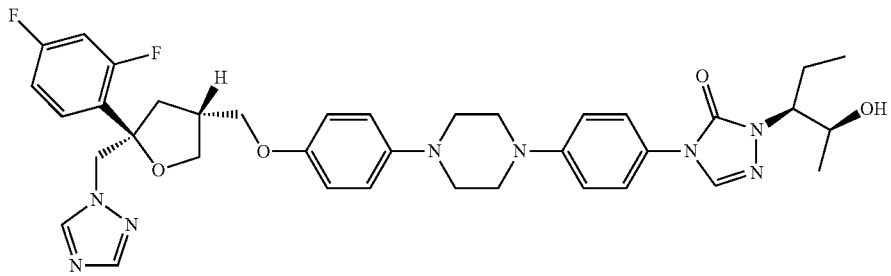 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

or a pharmaceutically acceptable salt, ester, or ether thereof.

In some embodiments of formulas (IX)-(XII), the compound is an ester of the corresponding structural formula, such as a phosphate ester. The phosphate ester may be, for example, a phosphate ester selected from

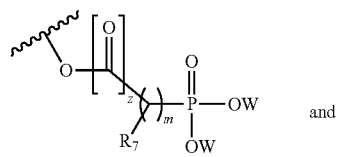 and

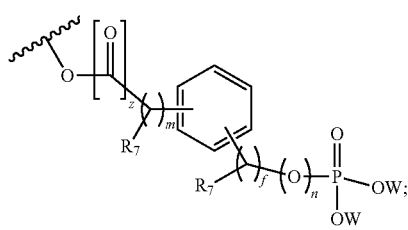

wherein z is 0 or 1, $R_7$ is a ($C_1$-$C_6$) straight or branched chain alkyl group or H, f and n are independently an integer from 0 to 6, m is zero or 1 and W is H, $CH_2$ Ar or and Ar is phenyl, phenyl substituted by halo, nitro, cyano or trihalomethyl.

Exemplary variants of itraconazole and posaconazole useful in conjunction with the compositions and methods described herein are described in U.S. Pat. Nos. 5,039,676, and 5,661,151, the disclosures of each of which are incorporated herein by reference in their entirety.

Cyproconazole and Variants Thereof

In some embodiments, the CYP51A1 inhibitor cyproconazole or a variant thereof that retains CYP51A1 inhibitory activity, such as a compound represented by formula (XIII)

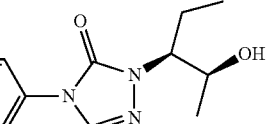

(XIII)

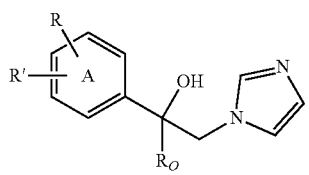

wherein $R_O$ is alkyl of 2 to 6 carbon atoms, cycloalkyl of 3 to 6 carbon atoms, cycloalkyl-alkyl in which the cycloalkyl is of 3 to 6 carbon atoms and the alkyl portion of 1 to 3 carbon atoms, the cycloalkyl and cycloalkyl-alkyl being optionally ring substituted by one or two alkyl groups of 1 to 3 carbon atoms;

R is hydrogen, fluoro, chloro, bromo, alkyl of 1 to 4 carbon atoms, alkoxy of 1 to 4 carbon atoms, alkylthio of 1 to 4 carbon atoms or nitro;

R' is hydrogen, fluoro, chloro, bromo, alkyl of 1 to 4 carbon atoms, alkoxy of 1 to 4 carbon atoms, alkylthio of 1 to 4 carbon atoms, —$CF_3$ in the 3-position of Ring A, nitro, —CN, —COOR", an optionally substituted phenyl group of the formula:

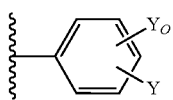

or an optionally substituted phenoxy group in the 4-position of Ring A and having the formula:

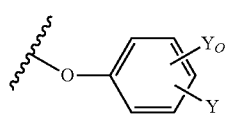

R" is hydrogen, alkyl of 1 to 4 carbon atoms or a cation, preferably an agriculturally acceptable cation, or R and R' together represent alkylenedioxy of 1 or 2 carbon atoms substituted onto adjacent carbon atoms of the phenyl Ring A; and $Y_O$ and Y are independently hydrogen, fluoro, chloro, bromo, alkyl of 1 to 4 carbon atoms or alkoxy of 1 to 4 carbon atoms.

In some embodiments of formula (XIII), when $R_O$ is n-butyl: (a) at least one of R and R' is other than hydrogen and (b) R and R' are not both halo.

In some embodiments, the CYP51A1 inhibitor is an α-[aryl(alkylene)$_m$]-α-[CR$_1$R$_2$—(CHR$_3$)$_n$—R$_4$]1H-1,2,4-triazole-1-ethanol (formula (XIV-A)) or an α-[aryl(alkylene)$_m$]-α-[CR$_1$R$_2$—(CHR$_3$)$_n$—R$_4$]1H-imidazole-1-ethanol (formula (XIV-B)), or a pharmaceutically acceptable salt or ester thereof, wherein:

$R_1$ is $C_{1-5}$ alkyl, unsubstituted or substituted by halogen, by $C_{1-5}$-alkoxy, by phenyl-$C_{1-3}$ alkoxy, by phenoxy, by $C_{1-5}$ alkylthio, by phenyl-$C_{1-3}$ alkylthio or by phenylthio, whereby optional phenyl groups may be substituted by $C_{1-5}$ alkyl, halogen, halogen substituted $C_{1-5}$ alkyl, $C_{1-5}$ alkoxy or halogen substituted $C_{1-5}$ alkoxy; or is $C_{2-5}$ alkenyl or $C_{2-5}$ alkynyl, unsubstituted or substituted by halogen; or is cycloalkyl, unsubstituted or substituted by $C_{1-5}$ alkyl; or is phenyl, unsubstituted or substituted by substituents selected from the group consisting of halogen and $C_{1-5}$ alkyl;

$R_2$ and $R_3$, independently, are H or have an $R_1$ significance, whereby $R_1$ and $R_2$ may be linked together to form a $C_{3-7}$ cycloalkyl group;

m is 0 or 1;

n is 0, 1 or 2; and $R_4$ is $C_{3-7}$ cycloalkyl, unsubstituted or substituted by $C_{1-5}$ alkyl.

The aryl portion in the α-[aryl(alkylen)$_m$] moiety of formula (XIV) may be an aromatic hydrocarbon (e.g. naphthyl, preferably phenyl) unsubstituted or substituted, or a heteroaromatic ring linked by one of its ring carbon atoms (e.g. a 5- or 6-membered ring with 1 or 2 heteroatoms from the group O, N and S, preferably furyl, thienyl or pyridyl), and may be unsubstituted or substituted.

Examples of suitable α-[aryl(alkylene)$_m$] groups that may be present in formula (XIV) are phenyl, benzyl and α-$C_{1-5}$ alkylbenzyl (e.g., unsubstituted, mono- or multiple-substituted in the phenyl moiety by NO$_2$, halogen, $C_{1-5}$ alkyl, $C_{2-5}$ alkenyl, $C_{2-5}$ alkynyl, or $C_{1-5}$ alkoxy (unsubstituted or halogenated), phenyl, or phenoxy, unsubstituted or substituted). Further examples of suitable α-aryl groups are the heteroaromatic 3-pyridyl group and 2-thienyl and 2-furyl, which may be, for example, unsubstituted or singly substituted by halogen or lower alkyl (e.g. 5-Cl-2-thienyl and 5-tert.butyl-2-furyl).

For example, the α-[aryl(alkylene)$_m$] group may be phenyl, benzyl, or α-$C_{1-5}$ alkylbenzyl substituted in the phenyl moiety by $R_5$, $R_6$ and/or $R_7$, wherein:

$R_5$ and $R_6$, independently, are H; halogen, $C_{1-5}$ alkyl, $C_{2-5}$ alkenyl, $C_{2-5}$ alkynyl, or $C_{1-5}$ alkoxy, (e.g., unsubstituted or halogenated), phenyl or phenoxy (e.g., unsubstituted or substituted), or NO$_2$; and $R_7$ is H, $C_{1-5}$ alkyl or halogen.

In some embodiments, the compound represented by formula (XIV) is a compound represented by formula (XV)

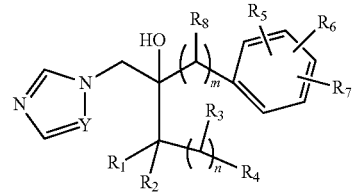

(XV)

wherein $R_1$, $R_2$, $R_3$, $R_4$, $R_5$, $R_6$, $R_7$, m and n are as defined for formula (XIV) herein, $R_8$ is H or $C_{1-5}$ alkyl, and Y is CH or N;

or a pharmaceutically acceptable salt, ester, or ether thereof.

In some embodiments, the compound represented by formula (XV) is a compound represented by formula (XVI)

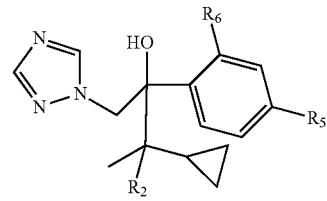

(XVI)

wherein $R_2$ is hydrogen or optionally substituted alkyl, such as optionally substituted lower alkyl (e.g., methyl, ethyl, n-propyl, iso-propyl, n-butyl, iso-butyl, sec-butyl, tert-butyl, n-pentyl, n-hexyl, or the like); and $R_5$ and $R_6$ are each independently hydrogen or a halogen atom, such as chloro;

or a pharmaceutically acceptable salt, ester, or ether thereof.

In some embodiments, the CYP51A1 inhibitor is 2-(4-chlorophenyl)-3-cyclopropyl-1-(1H-1,2,4-triazol-1-yl)-butan-2-ol, 2-(4-chlorophenyl)-3-cyclopropyl-3-methyl-1-(1H-1,2,4-triazol-1-yl)-butan-2-ol, 2-(2,4-diclorophenyl)-3-cyclopropyl-1-(1H-1,2,4-triazol-1-yl) butan-2-ol, or 2-(2,4-dichlorophenyl)-3-cyclopropyl-3-methyl-1-(1H-1,2,4-triazol-1-yl)butan-2-ol.

Exemplary variants of cyproconazole useful in conjunction with the compositions and methods described herein are described in U.S. Pat. Nos. 4,432,989 and 4,664,696, the disclosures of each of which are incorporated herein by reference in their entirety.

Voriconazole and Variants Thereof

In some embodiments, the CYP51A1 inhibitor is voriconazole or a variant thereof that retains CYP51A1 inhibitory activity, such as a compound represented by formula (XVII)

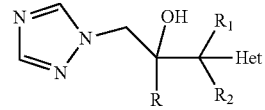

(XVII)

wherein R is phenyl optionally substituted by 1 to 3 substituents each independently selected from halo and CF$_3$;

$R^1$ is $C_1$-$C_4$alkyl;

$R_2$ is H or $C_1$-$C_4$ alkyl; and

"Het", which is attached to the adjacent carbon atom by a ring carbon atom, is selected from pyridinyl, pyridazinyl, pyrimidinyl, pyrazinyl and triazinyl. "Het" may be optionally substituted by $C_1$-$C_4$ alkyl, $C_1$-$C_4$ alkoxy, halo, $CF_3$, CN, $NO_2$, $NH_2$, —NH($C_1$-$C_4$ alkanoyl) or —$NHCO_2$ ($C_1$-$C_4$alkyl);

or a pharmaceutically acceptable salt, ester, or ether thereof.

In some embodiments of formula (XVII), "Het" is selected from 2- and 4-pyridinyl, pyridazinyl, 2- and 4-pyrimidinyl, pyrazinyl and triazinyl, and may be optionally substituted by $C_1$-$C_4$ alkyl, $C_1$-$C_4$ alkoxy, halo, $CF_3$, CN, $NO_2$, $NH_2$, —NH($C_1$-$C_4$ alkanoyl) or —$NHCO_2$ ($C_1$-$C_4$ alkyl). In some embodiments, "Het" is pyridinyl, pyridazinyl, pyrimidinyl, pyrazinyl or triazinyl, and may be optionally substituted by $C_1$-$C_4$ alkyl, $C_1$-$C_4$ alkoxy, halo, $CF_3$, $NO_2$, $NH_2$ or —NH($C_1$-$C_4$ alkanoyl).

In some embodiments of formula (XVII), R is a substituted phenyl moiety, such as 2-fluorophenyl, 2-chlorophenyl, 2-bromophenyl, 2-iodophenyl, 2-trifluoromethylphenyl, 2,4-dichlorophenyl, 2,4-difluorophenyl, 2-chloro-4-fluorophenyl, 2-fluoro-4-chlorophenyl, 2,5-difluorophenyl, 2,4,6-trifluorophenyl, or 4-bromo-2,5-difluorophenyl. In some embodiments, R is a phenyl group substituted by from 1 to 3 halo (preferably F or Cl) substituents. In some embodiments, R is a phenyl group substituted by from 1 or 2 halo (preferably F or Cl) substituents. In some embodiments, R is 2,4-difluorophenyl, 2,4-dichlorophenyl, 2-fluorophenyl or 2-chlorophenyl.

In some embodiments, the CYP51A1 inhibitor is 2-(2,4-difluorophenyl)-3-(pyridin-2-yl)-1-(1H-1,2,4-triazol-1-yl)butan-2-ol, 2-(2,4-difluorophenyl)-3-(pyridin-4-yl)-1-(1H-1,2,4-triazol-1-yl)butan-2-ol, or 2-(2,4-difluorophenyl)-3-(pyrimidin-4-yl)-1H,1,2,4-triazol-1-yl)butan-2-ol.

In some embodiments, the CYP51A1 inhibitor is a compound represented by formula (XVIII)

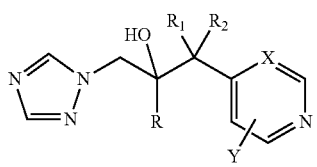

(XVIII)

wherein R is optionally substituted phenyl (e.g., substituted by from 1 to 3 substituents each independently selected from halo, —$CF_3$ and —$OCF_3$);

$R^1$ is optionally substituted alkyl, such as optionally substituted lower alkyl (e.g., $C_1$-$C_4$ alkyl);

$R_2$ is H or optionally substituted alkyl, such as optionally substituted lower alkyl (e.g., $C_1$-$C_4$ alkyl);

X is CH or N; and

Y is a halogen, such as F or Cl;

or a pharmaceutically acceptable salt, ester, or ether thereof.

Examples of R in formula (XVIII) are 2-fluorophenyl, 4-fluorophenyl, 2-chlorophenyl, 4-chlorophenyl, 2-bromophenyl, 2-iodophenyl, 2-trifluoromethylphenyl, 2,4-dichlorophenyl, 2,4-difluorophenyl, 2-chloro-4-fluorophenyl, 2-fluoro-4-chlorophenyl, 2,5-difluorophenyl, 2,4,6-trifluorophenyl, 4-bromo-2,5-difluorophenyl, and 2-trifluoromethoxyphhenyl.

In some embodiments of formula (XVIII), the compound is represented by formula (XIX)

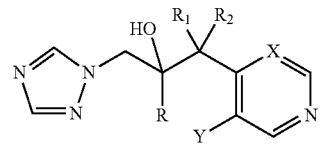

(XIX)

wherein R, $R_1$, $R_2$, X, and Y are as defined for formula (XVIII).

In some embodiments of formula (XVIII), the compound is represented by formula (XX)

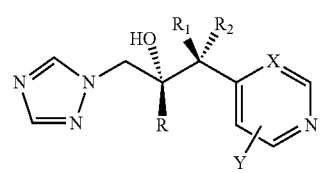

(XX)

wherein R, $R_1$, $R_2$, X, and Y are as defined for formula (XVIII).

In some embodiments of formula (XVIII), the compound is represented by formula (XXI)

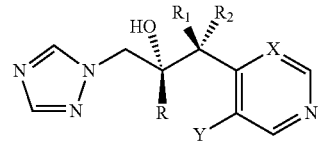

(XXI)

wherein R, $R_1$, $R_2$, X, and Y are as defined for formula (XVIII).

In some embodiments, the CYP51A1 inhibitor is 2-(2,4-difluorophenyl)-3-(5-fluoropyrimidin-4-yl)-1-(1H-1,2,4-triazol-1-yl)butan-2-ol, or a pharmaceutically acceptable salt, ester, or ether thereof. In some embodiments, the CYP51A1 inhibitor is (2R,3S)-2-(2,4-difluorophenyl)-3-(5-fluoropyrimidin-4-yl)-1-(1H-1,2,4-triazol-1-yl)butan-2-ol, or a pharmaceutically acceptable salt, ester, or ether thereof.

Exemplary variants of voriconazole that may be used in conjunction with the compositions and methods described herein are described, for example, in U.S. Pat. No. 5,116,844, the disclosure of which is incorporated herein by reference in its entirety.

Fluconazole and Variants Thereof

In some embodiments, the CYP51A1 inhibitor is fluconazole or a variant thereof that retains CYP51A1 inhibitory activity, such as a compound represented by formula (XXII)

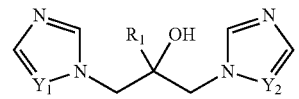

(XXII)

wherein $R_1$ is an optionally substituted alkyl, cycloalkyl (e.g. cyclopentyl or cyclohexyl), aryl (e.g. phenyl) or arylalkyl (e.g. benzyl) group; and $Y_1$ and $Y_2$ are each independently =CH— or =N—;

or a pharmaceutically acceptable salt, ester, or ether thereof.

In some embodiments of formula (XXII), $R_1$ is alkyl, cycloalkyl, optionally substituted aryl, or optionally substituted arylalkyl; and $Y^1$ and $Y^2$ are either both =CH— or both =N—.

In some embodiments of formula (XXII), $R_1$ is phenyl or benzyl, optionally substituted with one or more of halogen, alkyl or haloalkyl each containing from 1 to 5 carbon atoms, alkoxy or haloalkoxy each containing from 1 to 4 carbon atoms, nitro, cyano, hydroxy, alkylthio containing from 1 to 40 carbon atoms, vinyl, phenyl or phenoxy. In some embodiments, the alkyl moiety of the benzyl is unsubstituted, or substituted with alkyl containing from 1 to 4 carbon atoms, phenyl or chlorophenyl.

In some embodiments, the CYP51A1 inhibitor is selected from:

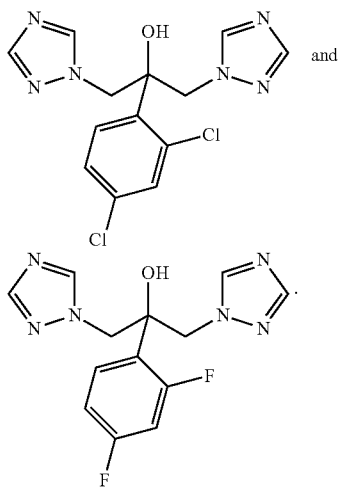

Exemplary variants of fluconazole that may be used in conjunction with the compositions and methods described herein are described, for example, in U.S. Pat. Nos. 4,416,682 and 4,404,216, the disclosures of each of which are incorporated herein by reference in their entirety.

Clotrimazole and Variants Thereof

In some embodiments, the CYP51A1 inhibitor is clotrimazole or a variant thereof that retains CYP51A1 inhibitory activity, such as a compound represented by formula (XXIII)

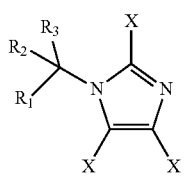
(XXIII)

wherein each of $R_1$, $R_2$, and $R_3$ is independently an aryl group represented by the formula:

n is an integer of from 0 to 5 (e.g., an integer of from 0 to 2) and each R' is independently halogen or optionally substituted alkyl (e.g., optionally substituted lower alkyl); and each X is independently selected from hydrogen, optionally substituted alkyl (e.g., optionally substituted lower alkyl), or optionally substituted aryl (e.g., optionally substituted phenyl);

or a pharmaceutically acceptable salt thereof. In some embodiments, the total number of carbon atoms in all X substituents is an integer of from 0 to 15.

In some embodiments, the CYP51A1 inhibitor is a compound selected from I-(tris(m-tert-butylphenyl)methyl) imidazole, 1-(tris(p-tert-butylphenyl methyl) imidazole, 1-(his(2,4-difiourophenyl)methyl)-2,4,5-trimethylimidazole, 1-(tris(p-chlorophenyl)methyl)-2-methyl-4,5-diphenylimidazone, 1-(tris(m-tolyl)methyl)-2-n-propylimidaz-ole, and 1-trityl-2-methylimidazole.

In some embodiments, the CYP51A1 inhibitor is a compound represented by formula (XXIV)

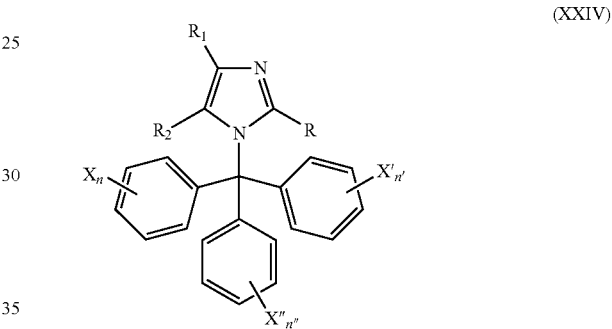
(XXIV)

wherein each of R, $R_1$, and $R_2$ is independently hydrogen, optionally substituted alkyl (e.g., optionally substituted lower alkyl), or optionally substituted and optionally fused aryl (e.g., optionally substituted phenyl);

each of X, X', and X''' is independently hydrogen, halogen, optionally substituted alkyl (e.g., optionally substituted lower alkyl), or optionally substituted and optionally fused aryl (e.g., optionally substituted phenyl); and each of n, n', and n'' is independently 1, 2, 3, 4, or 5 (e.g., 1, 2, or 3).

In some embodiments of formula (XXIV), the compound is represented by formula (XXV)

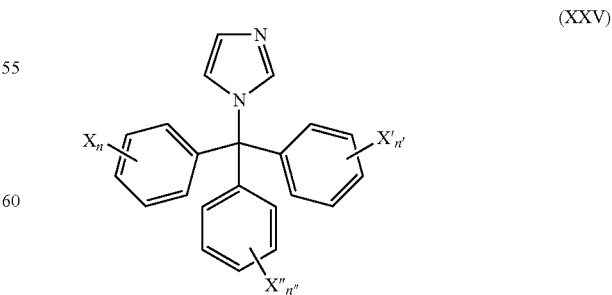
(XXV)

wherein X, X', X''', n, n', and n'' are as defined for formula (XXIV).

In some embodiments of formula (XXIV), the compound is represented by formula (XXVI)

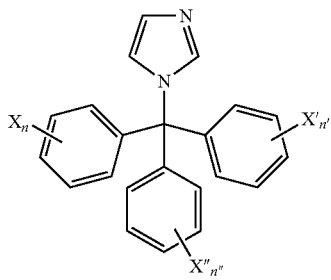

(XXVI)

wherein X, X', X''', n, n', and n'' are as defined for formula (XXIV).

In some embodiments, the CYP51A1 inhibitor is 1-(3,4-Dimethylphenyl-phenyl-2-pyridyl)-methyl-imidazole, 1-(2,4-dimethylphenyl-phenyl-2-pyridyl)-methyl-imidazole, 1-(2,6-dimethylphenyl-phenyl-2-pyridyl)-methyl-imidazole, 1-(2,4-dimethylphenyl-phenyl-4-pyridyl)-methyl-imidazole, 1-(3,4-dimethylphenyl-phenyl-4-pyridyl)-methyl-imidazole, 1-(2,5-dimethylphenyl-phenyl-4-pyridyl)-methyl-imidazole, 1-(2,3-dimethylphenyl-phenyl-2-pyridyl)-methyl-imidazole, 1-(2,3-dimethylphenyl-phenyl-2-pyridyl)-methyl-imidazole, 1-(2,3-dimethylphenyl-phenyl-2-pyridyl)-methyl-imidazole, 1-(2,3-dimethylphenyl-phenyl-4-pyridyl)-methyl-imidazole, 1-(3,4-dimethylphenyl-phenyl-4-pyridyl)-methyl-imidazole, or a pharmaceutically acceptable salt thereof, such as the 1,5-naphthalene-disulphonate salt thereof or the hydrochloride salt thereof.

Exemplary variants of clotrimazole that may be used in conjunction with the compositions and methods described herein are described, for example, in U.S. Pat. No. 3,321,366, the disclosure of which is incorporated herein by reference in its entirety.

Epoxiconazole and Variants Thereof

In some embodiments, the CYP51A1 inhibitor is epoxiconazole or a variant thereof that retains CYP51A1 inhibitory activity, such as a compound represented by formula (XXVII)

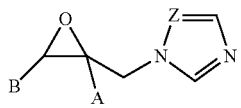

(XXVII)

wherein A and B are independently selected from optionally substituted alkyl (e.g., optionally substituted lower alkyl, such as alkyl of 1 to 4 carbon atoms), optionally substituted naphthyl, optionally substituted biphenyl, and optionally substituted phenyl, and Z is CH or N. In some embodiments, A and/or B is an optionally substituted phenyl group, such as a phenyl group substituted by one or more of halogen, nitro, alkyl (e.g., of from 1 to 4 carbon atoms), alkoxy (e.g., of from 1 to 4 carbon atoms), haloalkyl (e.g., of from 1 to 4 carbon atoms), phenoxy, or phenylsulyfonyl.

In some embodiments, the CYP51A1 inhibitor is a compound represented by formula (XXVIII)

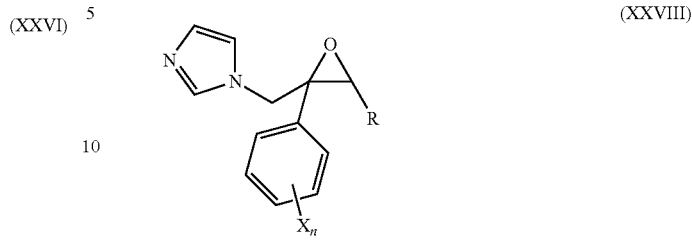

(XXVIII)

wherein R is optionally substituted aryl, such as phenyl, pyridyl, tetrahydropyranyl, norbornyl, $C_3$-$C_{12}$ cycloalkyl or $C_5$-$C_8$ cycloalkenyl, each of which may be unsubstituted or monosubstituted to trisubstituted by halogen, nitro, phenoxy, alkyl, amino, alkoxy (e.g., of from 1 to 4 carbon atoms), haloalkoxy (e.g., of from 1 to 4 carbon atoms), or haloalkyl (e.g., of from 1 to 4 carbon atoms);

each X is independently fluorine, chlorine, bromine, or iodine; and each n is independently an integer of from 1 to 5 (e.g., an integer of from 1 to 3).

In some embodiments of formula (XXVIII), the compound is represented by formula (XXIX)

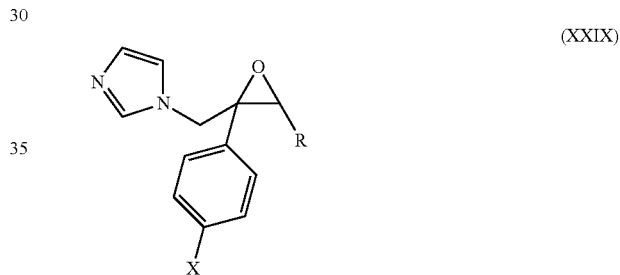

(XXIX)

wherein R and X are as defined for formula (XXVIII).

In some embodiments of formula (XXVIII), the compound is represented by formula (XXX)

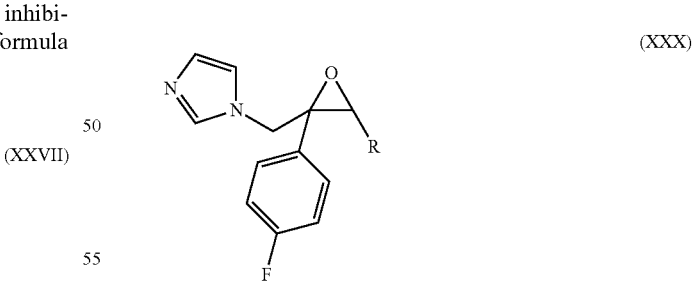

(XXX)

wherein R is as defined for formula (XXVIII).

Exemplary variants of epoxiconazole that may be used in conjunction with the compositions and methods described herein are described, for example, in U.S. Pat. Nos. 4,464,381 and 4,940,717, the disclosures of each of which are incorporated herein by reference in their entirety.

VNI, VNF, and Variants Thereof

In some embodiments, the CYP51A1 inhibitor is VNI, represented by formula (5), herein, or VNF, represented by formula (6), herein.

(5)

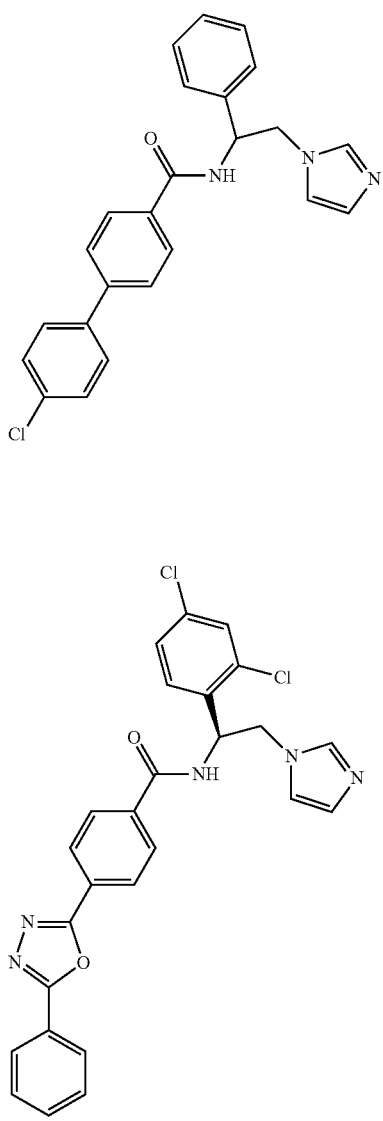

(6)

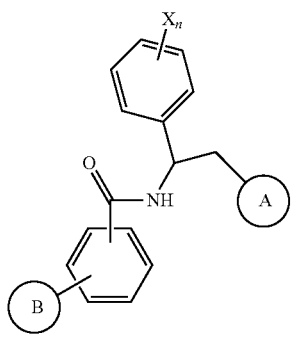

In some embodiments, the CYP51A1 inhibitor is a variant of VNI or VNF that retains CYP51A1 inhibitory activity. For example, the CYP51A1 inhibitor may be a compound represented by formula (XXXI)

wherein each of rings A and B are independently optionally substituted and optionally fused aryl, heteroaryl, cycloalkyl, or heterocycloalkyl;

each X is independently halogen or optionally substituted alkyl (e.g., optionally substituted lower alkyl); and n is an integer of from 1 to 5 (e.g., an integer of from 1 to 3).

In some embodiments of formula (XXXI), the compound is represented by formula (XXXII)

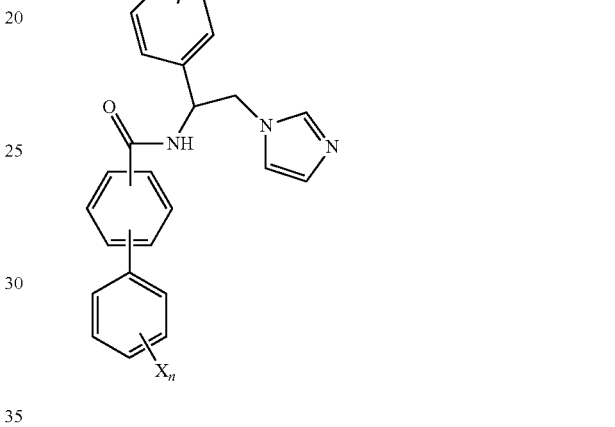

(XXXII)

wherein each X is independently halogen or optionally substituted alkyl (e.g., optionally substituted lower alkyl); and each n is independently an integer of from 1 to 5 (e.g., an integer of from 1 to 3).

In some embodiments of formula (XXXII), the compound is represented by formula (XXXIII)

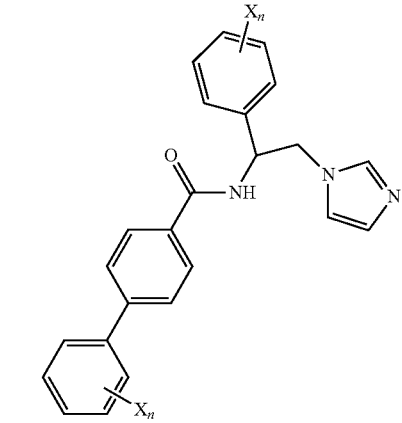

(XXXIII)

wherein each X and n are as defined for formula (XXXII).

In some embodiments, the CYP51A1 inhibitor is a compound represented by formula (XXXIV)

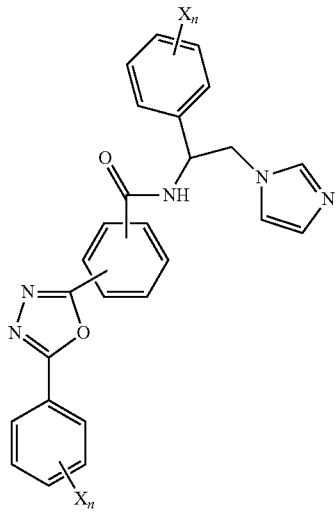
(XXXIV)

wherein each X is independently halogen or optionally substituted alkyl (e.g., optionally substituted lower alkyl); and each n is independently an integer of from 1 to 5 (e.g., an integer of from 1 to 3).

In some embodiments of formula (XXXIV), the compound is represented by formula (XXXV)

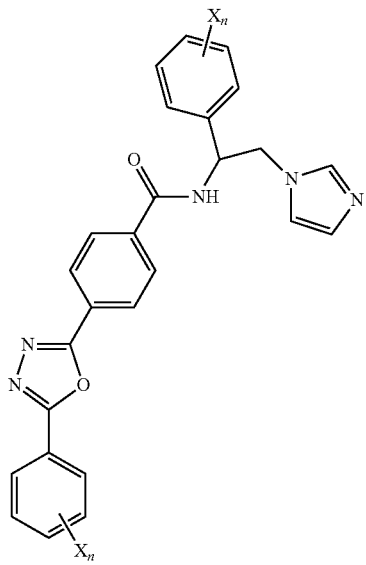
(XXXV)

wherein each X and n are as defined for formula (XXXIV).

Ketoconazole and Variants Thereof

In some embodiments, the CYP51A1 inhibitor is ketoconazole or a variant thereof that retains CYP51A1 inhibitory activity, such as a compound represented by formula (XXXVI)

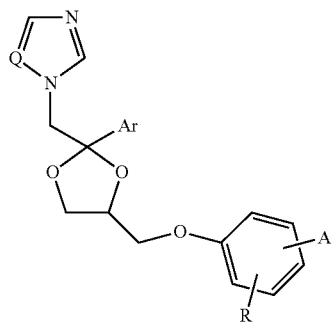
(XXXVI)

wherein Q is selected from the group consisting of CH and N;

Ar is an optionally substituted, optionally fused aryl group, such as an optionally fused, optionally substituted phenyl group, for example, a phenyl group having from 1 to 3 substituents, such as from 1 to 3 substituents independently selected from the group consisting of halo, lower alkyl and lower alkyloxy;

A is selected from the group consisting of:
(a) an isothiocyanato group —N=C=S;
(b) an amino group of the formula

wherein $R_1$ and $R_2$ are each independently selected from the group consisting of hydrogen and lower alkyl;
(c) a group of the formula

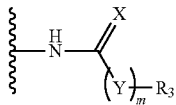

wherein X is selected from the group consisting of O and S, Y is selected from the group consisting of O and NH, m is the integer 0 or 1, and $R_3$ is selected from the group consisting of hydrogen, lower alkyl, mono- and dihalo-(lower alkyl), phenyl and substituted phenyl, said substituted phenyl having from 1 to 2 substituents independently selected from the group consisting of halo, lower alkyl and lower alkyloxy, optionally provided that:
i) when said X is S, then said Y is NH and said m is 1; and
ii) when said Y is O and said m is 1, then said $R_3$ is other than hydrogen; and
(d) a group of the formula

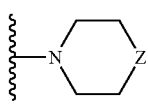

wherein Z is selected from the group consisting of a direct bond, $CH_2$, O and N—$R_4$, wherein $R_4$ is selected from the group consisting of hydrogen, lower alkyl, hydroxy-(lower alkyl), (lower alkyloxy)-lower alkyl, lower alkanoyl, lower alkylsulfonyl, phenylmethylsulfonyl, lower alkyloxycarbonyl, lower alkyloxycarbonylmethyl, phenoxycarbonyl, aminocarbonyl, mono- and di(lower alkyl)aminocarbonyl, aminocarbonylmethyl, (lower alkyl)aminocarbonylmethyl, (lower alkyl)aminothioxomethyl, (lower alkylthio)thioxomethyl, phenyl, phenylmethyl, benzoyl and substituted benzoyl, said substituted benzoyl being benzoyl having from 1 to 2 substituents independently selected from the group consisting of halo, lower alkyl and lower alkyloxy; and R is selected from the group consisting of hydrogen and nitro, optionally provided that when said R is nitro, then said A is amino.

In some embodiments, the CYP51A1 inhibitor is a compound represented by formula (XXXVII)

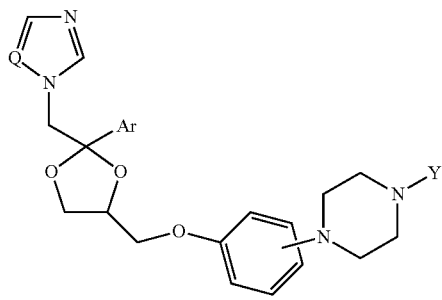

(XXXVII)

wherein Q is selected from the group consisting of N and CH;

Ar is selected from the group consisting of phenyl, thienyl, halothienyl and substituted phenyl, the substituted phenyl having from 1 to 3 substituents each independently selected from the group consisting of halo, lower alkyl, lower alkyloxy and trifluoromethyl; and the group Y is selected from the group consisting of:

a group of the formula $-SO_2R_1$, wherein $R_1$ is selected from the group consisting of trifluoromethyl and aryl;

a group of formula -alk-$R_2$, wherein alk is selected from the group consisting of lower alkylene and lower alkenylene and $R_2$ is selected from the group consisting of cyano, amino, mono- and di(lower alkyl)amino, arylamino, mono- and di(aryllower alkyl)amino, 1-pyrrolidinyl, 1-morpholinyl, 1-piperidinyl, aryloxy and aryl, provided that alk is other than methylene when $R_2$ is phenyl;

a group of formula

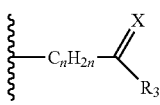

wherein n is an integer of from 0 to 6 inclusive, X is O or S and $R_3$ is selected from the group consisting of hydrogen, mono-, di- and trihalolower alkyl, amino, mono- and di(lower alkyl)amino, arylamino, mono- and di(aryllower alkyl)amino, amino lower alkyl, mono- and di(lower alkyl)amino lower alkyl, (1-pyrrolidinyl)lower alkyl, (1-morpholinyl)lower alkyl, (1-piperidinyl)lower alkyl, aryl, aryllower alkyl, aryllower alkenyl and lower alkyloxycarbonyl lower alkyloxy, optionally provided that:

(i) said n is other than 0 or 1 when said $R_3$ is amino or lower alkylamino; and (ii) said n is other than 0 when said $R_3$ is di(lower alkyl)amino or aryl; and a group of formula

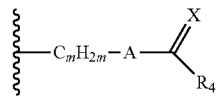

wherein m is an integer of from 1 to 6 inclusive, A is O or NH, X is O or S and $R_4$ is selected from the group consisting of hydrogen, lower alkyl, lower alkyloxy, aryl, aryloxy, aryllower alkyl, amino, mono- and di(lower alkyl)amino, arylamino, mono- and di(aryllower alkyl)amino, 1-pyrrolidinyl, 1-morpholinyl and 1-piperidinyl;

wherein said aryl, as used in the foregoing definitions, is selected from the group consisting of phenyl, substituted phenyl, thienyl, halothienyl, lower alkylthienyl and pyridinyl, said substituted phenyl having from 1 to 3 substituents each independently selected from the group consisting of lower alkyl, lower alkyloxy, halo, amino, mono- and di(lower alkyl)amino, lower alkylcarbonylamino, nitro and trifluoromethyl.

Exemplary variants of ketoconazole that may be used in conjunction with the compositions and methods described herein are described, for example, in U.S. Pat. Nos. 4,144, 346 and 4,503,055, the disclosures of each of which are incorporated herein by reference in their entirety.

Prochloraz and Variants Thereof

In some embodiments, the CYP51A1 inhibitor is prochloraz, represented by formula (7), below.

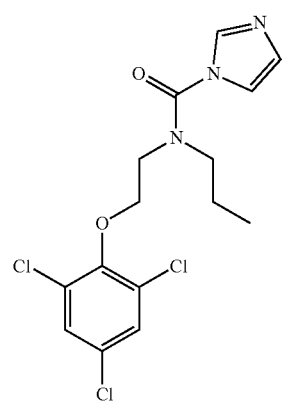

(7)

In some embodiments, the CYP51A1 inhibitor is a variant of prochloraz that retains CYP51A1 inhibitory activity, such as a compound represented by formula (XXXVIII)

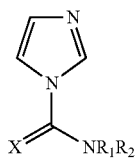

(XXXVIII)

wherein X is oxygen or sulfur, $R_1$ is optionally substituted alkyl, alkenyl, alkynyl, cycloalkyl, phenyl, phenylalkyl, phenylalkenyl, phenoxyalkyl or phenylthioalkyl and $R_2$ is optionally substituted phenyl, phenylalkyl, phenylalkenyl, phenoxyalkyl or phenylthioalkyl, provided that when $R_1$ is methyl or phenyl $R_2$ is substituted phenyl or optionally substituted phenylalkyl, phenylalkenyl, phenoxyalkyl or phenylthioalkyl.

In some embodiments of formula (XXXVIII), X is selected from the group consisting of oxygen and sulfur, $R_1$ is selected from the group consisting of alkyl of 1 to 10 carbon atoms, alkenyl of 3 or 4 carbon atoms, alkynyl of 3 to 5 carbon atoms, cycloalkyl of 3 to 10 carbon atoms, optionally substituted phenyl, phenylalkyl, of the formula $Ph(CH_2)_n$ where n is 1 to 5, phenylalkenyl of 9 to 11 carbon atoms, phenoxyalkyl of the formula $PhO(CH_2)_n$ where n is 2 to 5 and phenylthioalkyl of the formula $PhS(CH_2)_n$ where n is 2 to 5, wherein the substituted phenyl nucleus has at least one substituent selected from the group consisting of halo, alkoxy of 1 or 2 carbon atoms, alkyl of 1 to 4 carbon atoms, trihalomethyl, cyano, methylthio, nitro and methylsulphonyl, and $R_2$ is selected from the group consisting of optionally substituted phenylalkyl, of the formula $Ph(CH_2)_n$ where n is 1 to 5, phenylalkenyl of 9 to 11 carbon atoms, phenoxyalkyl of the formula $PhO(CH_2)_n$ where n is 2 to 5 and phenylthioalkyl of the formula $PhS(CH_2)_n$ where n is 2 to 5, wherein the substituted phenyl nucleus has at least one substituent selected from the group consisting of halo, alkoxy of 1 or 2 carbon atoms, alkyl of 1 to 4 carbon atoms, trihalomethyl, cyano, methylthio, nitro and methylsulphonyl.

Exemplary variants of prochloraz that may be used in conjunction with the compositions and methods described herein are described, for example, in U.S. Pat. No. 4,080,462, the disclosure of which is incorporated herein by reference in its entirety.

Propiconazole and Variants Thereof

In some embodiments, the CYP51A1 inhibitor is propiconazole, represented by formula (8), below.

(8)

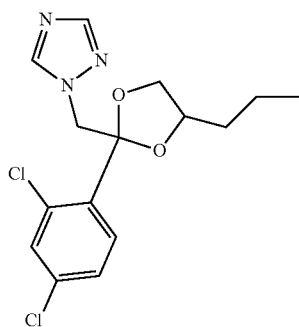

In some embodiments, the CYP51A1 inhibitor is a variant of propiconazole that retains CYP51A1 inhibitory activity, such as a compound represented by formula (XXXIX)

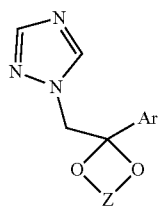

(XXXIX)

wherein Z is an alkylene selected from the group consisting of —$CH_2CH_2$—, —$CH_2$—$CH_2CH_2$—, —$CH(CH_3)$ $CH(CH_3)$—, and —$CH_2CH(alkyl)$-, wherein the alkyl has from 1 to about 10 carbon atoms; and Ar is an optionally fused, optionally substituted aryl group, such as an optionally fused, optionally substituted phenyl, thienyl, naphthyl, or fluorenyl, for example, phenyl, thienyl, halothienyl, naphthyl and fluorenyl, each optionally containing one or more (e.g., from 1 to 3) substituents selected independently from the group consisting of halo, lower alkyl, lower alkyloxy, cyano, and nitro.

Exemplary variants of propiconazole that may be used in conjunction with the compositions and methods described herein are described, for example, in U.S. Pat. No. 4,079,062, the disclosure of which is incorporated herein by reference in its entirety.

Prothioconazole, Prothioconazole-desthio, and Variants Thereof

In some embodiments, the CYP51A1 inhibitor is prothioconazole, represented by formula (8), below.

(8)

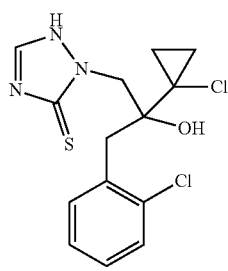

In some embodiments, the CYP51A1 inhibitor is prothioconazole-desthio, represented by formula (9), below.

(9)

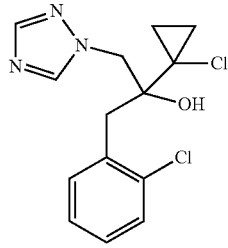

In some embodiments, the CYP51A1 inhibitor is a variant of prothioconazole or prothioconazole-desthio that retains CYP51A1 inhibitory activity, such as a compound represented by formula (XL)

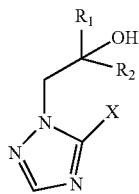

(XL)

wherein $R_1$ and $R_2$ are each independently selected from optionally substituted alkyl, optionally substituted alkenyl, optionally substituted cycloalkyl, optionally substituted aralkyl, optionally substituted aralkenyl, optionally substituted aroxyalkyl, optionally substituted aryl, and optionally substituted heteroaryl; and X is —SH, —$SR_3$, —SO—$R_3$, —$SO_2$—$R_3$, or —$SO_3H$, wherein $R_3$ is alkyl which is optionally substituted by one or more halogen moieties (e.g., fluorine and/or chlorine), alkenyl which is optionally substituted by one or more halogen moieties (e.g., fluorine and/or chlorine), optionally substituted aralkyl or optionally substituted aryl.

Exemplary variants of prothioconazole and prothioconazole-desthio that may be used in conjunction with the compositions and methods described herein are described, for example, in U.S. Pat. No. 5,789,430, the disclosure of which is incorporated herein by reference in its entirety.

Tebuconazole and Variants Thereof

In some embodiments, the CYP51A1 inhibitor is tebuconazole, represented by formula (10), below.

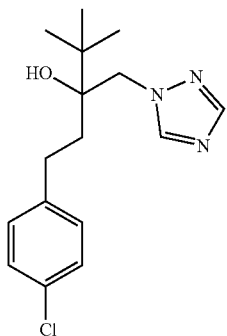

(10)

In some embodiments, the CYP51A1 inhibitor is a variant of tebuconazole that retains CYP51A1 inhibitory activity, such as a compound represented by formula (XLI)

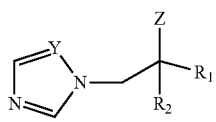

(XLI)

wherein $R_1$ is —CH=CH—X, —C≡C—X, or —$CH_2$—$CH_2$—X, wherein X is hydrogen, alkyl, hydroxyalkyl, alkoxyalkyl, cycloalkyl or optionally substituted aryl, aralkyl, aryloxy alkyl, or heterocycle;

$R_2$ is alkyl, cycloalkyl (e.g. cyclopropyl, cyclopentyl, or cyclohexyl) or optionally substituted aryl;

Z is Cl, CN, or $OR_3$, wherein $R_3$ is hydrogen, acetyl, alkyl, alkenyl or aralkyl; and Y is =N— or =CH—, or a pharmaceutically acceptable salt, ester, or ether thereof.

Exemplary variants of tebuconazole that may be used in conjunction with the compositions and methods described herein are described, for example, in U.S. Pat. No. 4,507,140, the disclosure of which is incorporated herein by reference in its entirety.

Triadimenol and Variants Thereof

In some embodiments, the CYP51A1 inhibitor is triadimenol, represented by formula (11), below.

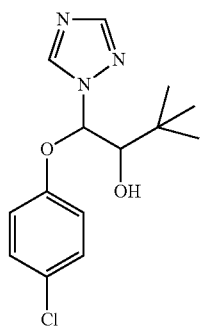

(11)

In some embodiments, the CYP51A1 inhibitor is a variant of triadimenol that retains CYP51A1 inhibitory activity, such as a compound represented by formula (XLII)

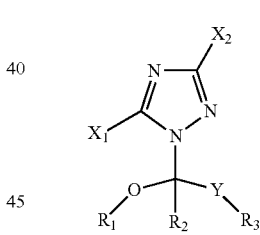

(XLII)

wherein $X_1$ is hydrogen or an alkyl group, $X_2$ is hydrogen or an alkyl group, $R_1$ is an alkyl, alkenyl, alkynyl, cycloalkyl, cycloalkenyl or optionally substituted aryl or aralkyl group, $R_2$ is hydrogen or an alkyl, alkenyl, alkynyl, cycloalkyl, cycloalkenyl or optionally substituted aryl or aralkyl group, $R_3$ is hydrogen or an alkyl, alkenyl, alkynyl, cycloalkyl, cycloalkenyl or optionally substituted aryl or aralkyl group, and Y is a keto group or a functional keto derivative.

or a pharmaceutically acceptable salt, ester, or ether thereof.

Exemplary variants of triadimenol that may be used in conjunction with the compositions and methods described herein are described, for example, in U.S. Pat. No. 3,912,752, the disclosure of which is incorporated herein by reference in its entirety.

Azalanstat and Variants Thereof

In some embodiments, the CYP51A1 inhibitor is azalanstat, represented by formula (12), below.

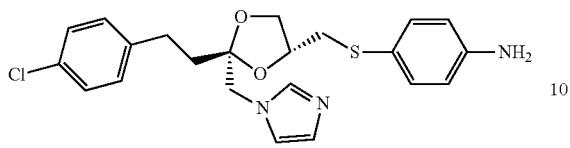

(12)

In some embodiments, the CYP51A1 inhibitor is a variant of azalanstat that retains CYP51A1 inhibitory activity, such as a compound represented by formula (XLIII)

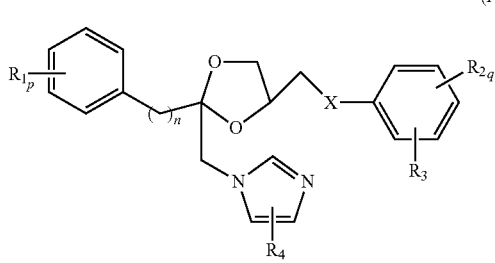

(XLIII)

wherein n is 2 or 3;
p is 0, 1 or 2;
q is 0, 1 or 2;
X is oxygen or $S(O)_t$ wherein t is 0, 1, or 2;
each $R_1$ is independently halo, lower alkyl, lower alkoxy, or trifluoromethyl;
each $R_2$ is independently halo or lower alkyl;
$R_3$ is nitro or —$N(R_5)R_6$ where
$R_5$ is hydrogen or lower alkyl;
$R_6$ is hydrogen, lower alkyl, lower alkylsulfonyl or —$C(Y)R_7$ where Y is oxygen or sulfur and $R_7$ is hydrogen, lower alkyl, lower alkoxy or —$N(R_8)R_9$ where $R_8$ is hydrogen or lower alkyl and $R_9$ is hydrogen, lower alkyl or lower alkoxycarbonyl; or
$R_5$ and $R_6$ together with N is pyrrolidino, piperidino, morpholino, thiomorpholino or piperazino, wherein the piperazino is optionally substituted at the 4-position by —C(O)$R_{10}$ where $R_{10}$ is hydrogen, lower alkyl, lower alkoxy or amino; and
$R_4$ is hydrogen or optionally substituted lower alkyl;
or a pharmaceutically acceptable salt, ester, or ether thereof.

In some embodiments of formula (XLIII), the compound is represented by formula (XLIV)

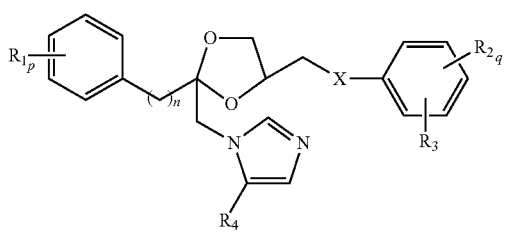

(XLIV)

wherein $R_1$, $R_2$, $R_3$, $R_4$, X, n, p, and q are as defined for formula (XLIII).

In some embodiments of formula (XLIII), the compound is represented by formula (XLV)

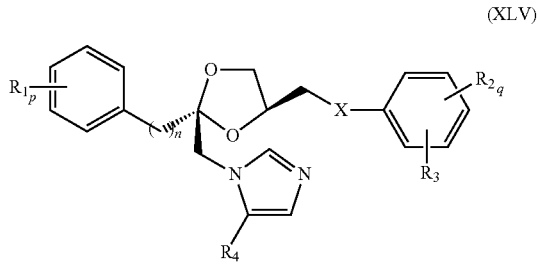

(XLV)

wherein $R_1$, $R_2$, $R_3$, $R_4$, X, n, p, and q are as defined for formula (XLIII).

In some embodiments of formula (XLIII), the compound is represented by formula (XLVI)

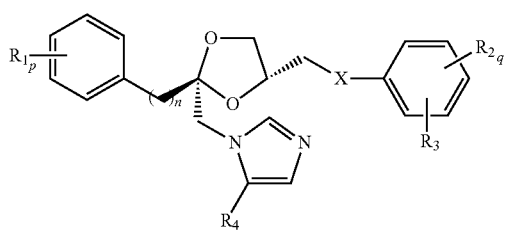

(XLVI)

wherein $R_1$, $R_2$, $R_3$, $R_4$, X, n, p, and q are as defined for formula (XLIII).

In some embodiments of formula (XLIII), the compound is represented by formula (XLVII)

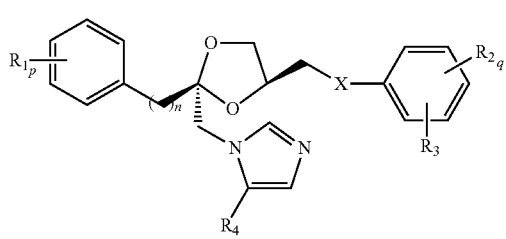

(XLVII)

wherein $R_1$, $R_2$, $R_3$, $R_4$, X, n, p, and q are as defined for formula (XLIII).

In some embodiments of formula (XLIII), the compound is represented by formula (XLVIII)

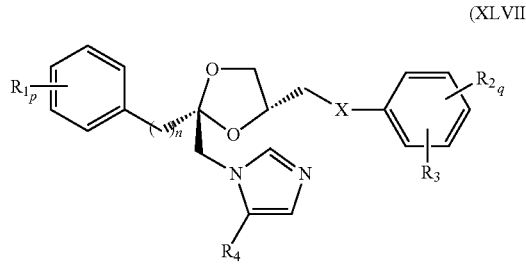

(XLVIII)

wherein $R_1$, $R_2$, $R_3$, $R_4$, X, n, p, and q are as defined for formula (XLIII).

Exemplary variants of azalanstat that may be used in conjunction with the compositions and methods described herein are described, for example, in U.S. Pat. No. 5,158,949, the disclosure of which is incorporated herein by reference in its entirety.

Antibody Inhibitors of CYP51A1

CYP51A1 inhibitors useful in conjunction with the compositions and methods described herein include antibodies and antigen-binding fragments thereof, such as those that specifically bind to CYP51A1 and/or inhibit CYP51A1 catalytic activity. In some embodiments, the antibody or antigen-binding fragment thereof is a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv. In some embodiments, the antibody has an isotype selected from IgG, IgA, IgM, IgD, and IgE.

Interfering RNA Inhibitors of CYP51A1

CYP51A1 inhibitors useful in conjunction with the compositions and methods described herein include interfering RNA molecules, such as short interfering RNA (siRNA) molecules, micro RNA (miRNA) molecules, or short hairpin RNA (shRNA) molecules. The interfering RNA may suppress expression of a CYP51A1 mRNA transcript, for example, by way of (i) annealing to a CYP51A1 mRNA or pre-mRNA transcript, thereby forming a nucleic acid duplex; and (ii) promoting nuclease-mediated degradation of the CYP51A1 mRNA or pre-mRNA transcript and/or (iii) slowing, inhibiting, or preventing the translation of a CP51A1 mRNA transcript, such as by sterically precluding the formation of a functional ribosome-RNA transcript complex or otherwise attenuating formation of a functional protein product from the target RNA transcript.

In some embodiments, the interfering RNA molecule, such as the siRNA, miRNA, or shRNA, contains an antisense portion that anneals to a segment of a CYP51A1 RNA transcript (e.g., mRNA or pre-mRNA transcript), such as a portion that anneals to a segment of a CYP51A1 RNA transcript having a nucleic acid sequence that is at least 85% identical to the nucleic acid sequence of SEQ ID NO: 2 (e.g., 85%, 86%, 87%, 88%, 89%, 90%, 91%, 92%, 93%, 94%, 95%<96%, 97%, 98%, 99%, 99.9%, or 100% identical to the nucleic acid sequence of SEQ ID NO: 2).

In some embodiments, the interfering RNA molecule, such as the siRNA, miRNA, or shRNA, contains a sense portion having at least 85% sequence identity to the nucleic acid sequence of a segment of SEQ ID NO: 2 (e.g., 85%, 86%, 87%, 88%, 89%, 90%, 91%, 92%, 93%, 94%, 95%<96%, 97%, 98%, 99%, 99.9%, or 100% identical to the nucleic acid sequence of a segment of SEQ ID NO: 2).

Interfering RNAs as described herein may be provided to a patient, such as a human patient having a neurological disorder described herein, in the form of, for example, a single- or double-stranded oligonucleotide, or in the form of a vector (e.g., a viral vector) containing a transgene encoding the interfering RNA. Exemplary interfering RNA platforms are described, for example, in Lam et al., Molecular Therapy -Nucleic Acids 4:e252 (2015); Rao et al., Advanced Drug Delivery Reviews 61:746-769 (2009); and Borel et al., Molecular Therapy 22:692-701 (2014), the disclosures of each of which are incorporated herein by reference in their entirety.

Methods of Treatment

Suppression of CYP51A1 Activity and TDP-43 Aggregation to Treat Neurological Disorders Using the compositions and methods described herein, a patient suffering from a neurological disorder may be administered a CYP51A1 inhibitor, such as a small molecule, antibody, antigen-binding fragment thereof, or interfering RNA molecule described herein, so as to treat the disorder and/or to suppress one or more symptoms associated with the disorder. Exemplary neurological disorders that may be treated using the compositions and methods described herein are, without limitation, amyotrophic lateral sclerosis, frontotemporal degeneration, Alzheimer's disease, Parkinson's disease, dementia with Lewy Bodies, corticobasal degeneration, progressive supranuclear palsy, dementia parkinsonism ALS complex of Guam, Huntington's disease, IBMPFD, sporadic inclusion body myositis, myofibrillar myopathy, dementia pugilistica, chronic traumatic encephalopathy, Alexander disease, and hereditary inclusion body myopathy, as well as neuromuscular diseases such as congenital myasthenic syndrome, congenital myopathy, cramp fasciculation syndrome, Duchenne muscular dystrophy, glycogen storage disease type II, hereditary spastic paraplegia, inclusion body myositis, Isaac's Syndrome, Kearns-Sayre syndrome, Lambert-Eaton myasthenic syndrome, mitochondrial myopathy, muscular dystrophy, myasthenia gravis, myotonic dystrophy, peripheral neuropathy, spinal and bulbar muscular atrophy, spinal muscular atrophy, Stiff person syndrome, Troyer syndrome, and Guillain-Barré syndrome.

The present disclosure is based, in part, on the discovery that CYP51A1 inhibitors, such as the agents described herein, are capable of attenuating TDP-43 aggregation in vivo. TDP-43-promoted aggregation and toxicity have been associated with various neurological diseases. The discovery that CYP51A1 inhibitors modulate TDP-43 aggregation provides an important therapeutic benefit. Using a CYP51A1 inhibitor, such as a CYP51A1 inhibitor described herein, a patient suffering from a neurological disorder or at risk of developing such a condition may be treated in a manner that remedies an underlying molecular etiology of the disease. Without being limited by mechanism, the compositions and methods described herein can be used to treat or prevent such neurological conditions, for example, by suppressing the TDP-43 aggregation that promotes pathology.

Additionally, the compositions and methods described herein provide the beneficial feature of enabling the identification and treatment of patients that are likely to respond to CYP51A1 inhibitor therapy. For example, in some embodiments, a patient (e.g., a human patient suffering from or at risk of developing a neurological disease described herein, such as amyotrophic lateral sclerosis) is administered a CYP51A1 inhibitor if the patient is identified as likely to respond to this form of treatment. Patients may be identified as such on the basis, for example, of susceptibility to TDP-43 aggregation. In some embodiments, the patient is identified is likely to respond to CYP51A1 inhibitor treatment based on the isoform of TDP-43 expressed by the patient. For example, patients expressing TDP-43 isoforms having a mutation selected from Q331K, M337V, Q343R, N345K, R361S, and N390D, among others, are more likely to develop TDP-43-promoted aggregation and toxicity relative to patients that do not express such isoforms of TDP-43. Using the compositions and methods described herein, a patient may be identified as likely to respond to CYP51A1 inhibitor therapy on the basis of expressing such an isoform of TDP-43, and may subsequently be administered a CYP51A1 inhibitor so as to treat or prevent one or more neurological disorders, such as one or more of the neurological disorders described herein.

Assessing Patient Response

A variety of methods known in the art and described herein can be used to determine whether a patient having a neurological disorder (e.g., a patient at risk of developing TDP-43 aggregation, such as a patient expressing a mutant form of TDP-43 having a mutation associated with elevated TDP-43 aggregation and toxicity, for example, a mutation selected from Q331K, M337V, Q343R, N345K, R361S, and N390D) is responding favorably to CYP51A1 inhibition. For example, successful treatment of a patient having a neurological disease, such as amyotrophic lateral sclerosis, with a CYP51A1 inhibitor described herein may be signaled by:

(i) an improvement in condition as assessed using the amyotrophic lateral sclerosis functional rating scale (ALSFRS) or the revised ALSFRS (ALSFRS-R), such as an improvement in the patient's ALSFRS or ALSFRS-R score within one or more days, weeks, or months following administration of the CYP51A1 inhibitor (e.g., an improvement in the patient's ALSFRS or ALSFRS-R score within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient);

(ii) an increase in slow vital capacity, such as an increase in the patient's slow vital capacity within one or more days, weeks, or months following administration of the CYP51A1 inhibitor (e.g., an increase in the patient's slow vital capacity within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient);

(iii) a reduction in decremental responses exhibited by the patient upon repetitive nerve stimulation, such as a reduction that is observed within one or more days, weeks, or months following administration of the CYP51A1 inhibitor (e.g., a reduction that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient);

(iv) an improvement in muscle strength, as assessed, for example, by way of the Medical Research Council muscle testing scale (as described, e.g., in Jagtap et al., Ann. Indian. Acad. Neurol. 17:336-339 (2014), the disclosure of which is incorporated herein by reference as it pertains to measuring patient response to neurological disease treatment), such as an improvement that is observed within one or more days, weeks, or months following administration of the CYP51A1 inhibitor (e.g., an improvement that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient);

(v) an improvement in quality of life, as assessed, for example, using the amyotrophic lateral sclerosis-specific quality of life (ALS-specific QOL) questionnaire, such as an improvement in the patient's quality of life that is observed within one or more days, weeks, or months following administration of the CYP51A1 inhibitor (e.g., an improvement in the subject's quality of life that is observed within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient);

(vi) a decrease in the frequency and/or severity of muscle cramps, such as a decrease in cramp frequency and/or severity within one or more days, weeks, or months following administration of the CYP51A1 inhibitor (e.g., a decrease in cramp frequency and/or severity within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient); and/or (vii) a decrease in TDP-43 aggregation, such as a decrease in TDP-43 aggregation within one or more days, weeks, or months following administration of the CYP51A1 inhibitor (e.g., a decrease in TDP-43 aggregation within from about 1 day to about 48 weeks (e.g., within from about 2 days to about 36 weeks, from about 4 weeks to about 24 weeks, from about 8 weeks to about 20 weeks, or from about 12 weeks to about 16 weeks), or more, following the initial administration of the CYP51A1 inhibitor to the patient, such as within 1 day, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or more, following the initial administration of the CYP51A1 inhibitor to the patient.

Routes of Administration and Dosing

CYP51A1 inhibitors (e.g., inhibitory small molecules, antibodies, antigen-binding fragments thereof, and interfering RNA molecules) described herein may be administered to a patient (e.g., a human patient having one or more neurological disorders described herein) by a variety of routes. Exemplary routes of administration are oral, transdermal, subcutaneous, intranasal, intravenous, intramuscular, intraocular, parenteral, topical, intrathecal, and intracerebroventricular administration. The most suitable route for administration in any given case will depend on the particular agent being administered, the patient, pharmaceutical formulation methods, administration methods (e.g., administration kinetics), the patient's age, body weight, sex, severity of the diseases being treated, the patient's diet, and the patient's excretion rate, among other factors.

Therapeutic compositions can be administered with medical devices known in the art. For example, therapeutic compositions described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of implants and modules useful in conjunction with the routes of administration described herein are those described in U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference as they pertain to devices suitable for administration of a therapeutic agent to a patient (e.g., a human patient). Various other such implants, delivery systems, and modules are known to those skilled in the art.

Pharmaceutical Compositions

The CYP51A1 inhibitors (e.g., small molecules, antibodies, antigen-binding fragments thereof, and interfering RNA molecules described herein) suitable for use with the compositions and methods described herein can be formulated into pharmaceutical compositions for administration to a patient, such as a human patient exhibiting or at risk of developing TDP-43 aggregation, in a biologically compatible form suitable for administration in vivo. A pharmaceutical composition containing, for example, a CYP51A1 inhibitor described herein, such as LEK-935, CP-320626, itraconazole, posaconazole, cyproconazole, voriconazole, fluconazole, clotrimazol, fenticonazole, epoxiconazole, ketoconazole, ravuconazole, isavuconazole, holothurin A, theasaponin, capsicosine, betulafolientriol, prochloraz, propiconazole, prothioconazole, prothioconazole-desthio, tebuconazole, triadimenol, azalanstat, or a variant thereof, or an antibody, antigen-binding fragment thereof, or interfering RNA molecule described herein, may additionally contain a suitable diluent, carrier, or excipient. CYP51A1 inhibitors can be formulated for administration to a subject, for example, by way of any one or more of the routes of administration described above. Under ordinary conditions of storage and use, a pharmaceutical composition may contain a preservative, e.g., to prevent the growth of microorganisms. Procedures and ingredients for the selection and preparation of suitable formulations are described, for example, in Remington: The Science and Practice of Pharmacy (2012, 22$^{nd}$ ed.) and in The United States Pharmacopeia: The National Formulary (2015, USP 38 NF 33).

Pharmaceutical compositions may include sterile aqueous solutions, dispersions, or powders, e.g., for the extemporaneous preparation of sterile solutions or dispersions. In all cases the form may be sterilized using techniques known in the art and may be fluidized to the extent that may be easily administered to a patient in need of treatment.

A pharmaceutical composition may be administered to a patient, e.g., a human patient, alone or in combination with one or more pharmaceutically acceptable carriers, e.g., as described herein, the proportion of which may be determined by the solubility of the compound, the chemical nature of the compound, and/or the chosen route of administration, among other factors.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regards as their invention.

Example 1. Inhibition of CYP51A1 Modulates TDP-43 Aggregation

Introduction

Amyotrophic lateral sclerosis (ALS), also known as Lou Gehrig's disease, is an aggressive, debilitating disease in which affected patients succumb within two to five years after diagnosis. ALS presents with heterogeneous clinical features but has a common underlying pathology of motor neuron loss that limits the central nervous system's ability to effectively regulate voluntary and involuntary muscle activity. Additionally, without neuronal trophic support muscles being to atrophy, further exacerbating motor deterioration. Cellular and tissue degeneration results in motor impairment such as fasciculations and weakening in the arms, legs and neck, difficulty swallowing, slurred speech and ultimately failure of the diaphragm muscles that control breathing.

At the cellular level, 97% of all ALS cases have the common pathological feature of misfolded and aggregated TAR-DNA binding protein (TDP)-43 in spinal motor neuron inclusions. TDP-43 is a DNA/RNA binding protein involved in RNA splicing and is typically localized to the nucleus but can be translocated to the cytoplasm under conditions of cell stress. Nuclear clearing and cytoplasmic accumulation of misfolded and aggregated TDP-43 are hallmarks of degenerating motor neurons in ALS, but it remains unclear if mechanism of toxicity is due to aggregation-dependent loss of TDP-43 function or if the aggregates acquire toxic gain of function. Aggregates of TDP-43 accumulate in discrete cellular domains known as stress granules, which are also enriched with translationally inactive mRNAs. Stress granules are observed in multiple cellular types and are thought to be directly related to TDP-43-dependent toxicity in ALS and FTD. Dysfunction in DNA/RNA binding protein activity plays a crucial role in susceptible motor neurons in ALS, as familial cases have also been traced to mutations in the protein Fused in Sarcoma (FUS), a DNA/RNA binding protein that recently has been shown to be involved in gene silencing. Preclinical studies suggest that FUS mutations promote a toxic gain of function that may be causative in motor neuron degeneration.

Mutations in the TDP-43 gene (TARDBP) have also been causally linked to familial forms of ALS. A common TDP-43 mutation is known as Q331K, in which glutamine (Q) 331 has been mutated to a lysine (K). This mutation results in a TDP-43 protein that is more aggregation prone and exhibits enhanced toxicity. A recent study has also demonstrated that the Q331K mutation can confer a toxic gain of function in a TDP-43 knock-in mouse, which exhibits cognitive deficits and histological abnormalities similar to that which occurs in frontotemporal dementia (FTD). FTD refers to a group of degenerative disorders that are characterized by atrophy in the frontal and temporal cortices due to progressive neuron loss. Due to the functional nature of the brain regions impacted in FTD, the most common symptoms involve noticeable alterations in personality, behavior and linguistic ability and can also present with loss of speech. The pathological basis of FTD appears to be multifactorial involving mutations in genes such as C9orf72, progranulin (GRN) and MAPT, but intracellular inclusions of aggregated TDP-43, FUS and tau have been observed. Although ALS and FTD may have different genetic and molecular triggers and occur in different cell types, similar protein misfolding and degenerative mechanisms may operate in multiple diseases.

The toxic gain of function features of TDP-43 can be faithfully recapitulated in the simple model organism, budding yeast, where the protein also localizes to stress granules. Human disease mutations in TDP-43 enhance toxicity and yeast genetic screens have revealed key connections that are conserved to humans. The yeast model thus provides a robust cell-based screening platform for small molecules capable of ameliorating toxicity. To validate compounds from such phenotypic screens, it is imperative to test compounds in a mammalian neuronal context. In an effort to develop TDP-43-related mammalian models of neuron loss that occurs in ALS and FTD, primary cultures of rat cortical neurons were transfected with human wild type or Q331K mutant TDP-43. These cells were compared to cells which received an empty expression vector control. Validation studies have demonstrated that cells expressing either wild type or Q331K TDP-43 have are more susceptible to dying over time in culture. In the experiments described in this example, this model system is used to interrogate new therapeutic approaches to ameliorate TDP-43 toxicity.

Results

Figure 1B:
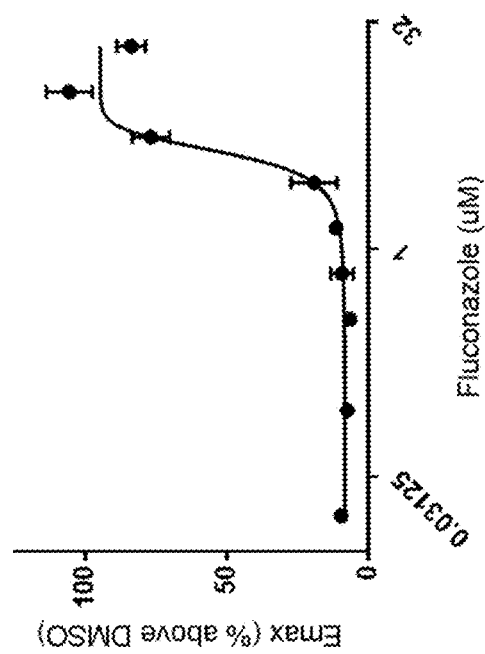

From the TDP-43 yeast model, a compound with known mode of action was identified that restored viability to TDP-43-expressing yeast (FIG. 1A). Fluconazole is an antifungal known to inhibit Erg11, the yeast lanosterol 14-alpha demethylase (FIG. 1B). Inhibition of Erg11 reduces ergosterol synthesis (yeast equivalent of cholesterol), while increasing lanosterol levels, the substrate of Erg11 (FIG. 1C). The human homolog of Erg11 is Cyp51A1, a member of the cytochrome P450 superfamily of enzymes but does not appear to have a role in detoxification of xenobiotics. CYP51A1 has also been known as lanosterol 14-alpha demethylase, which describes its function in removing the 14-alpha-methyl group from lanosterol to generate 4,4-dimethylcholesta-8(9),14,24-trien-3β-ol, which is a critical step in the cholesterol biosynthetic pathway.

Figure 2:
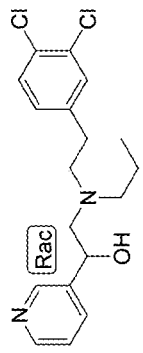
FIG. 2 shows the structures of compounds used in primary rat cortical neuron TDP-43 wild type and Q331K mutant survival studies.
Figure 3A:
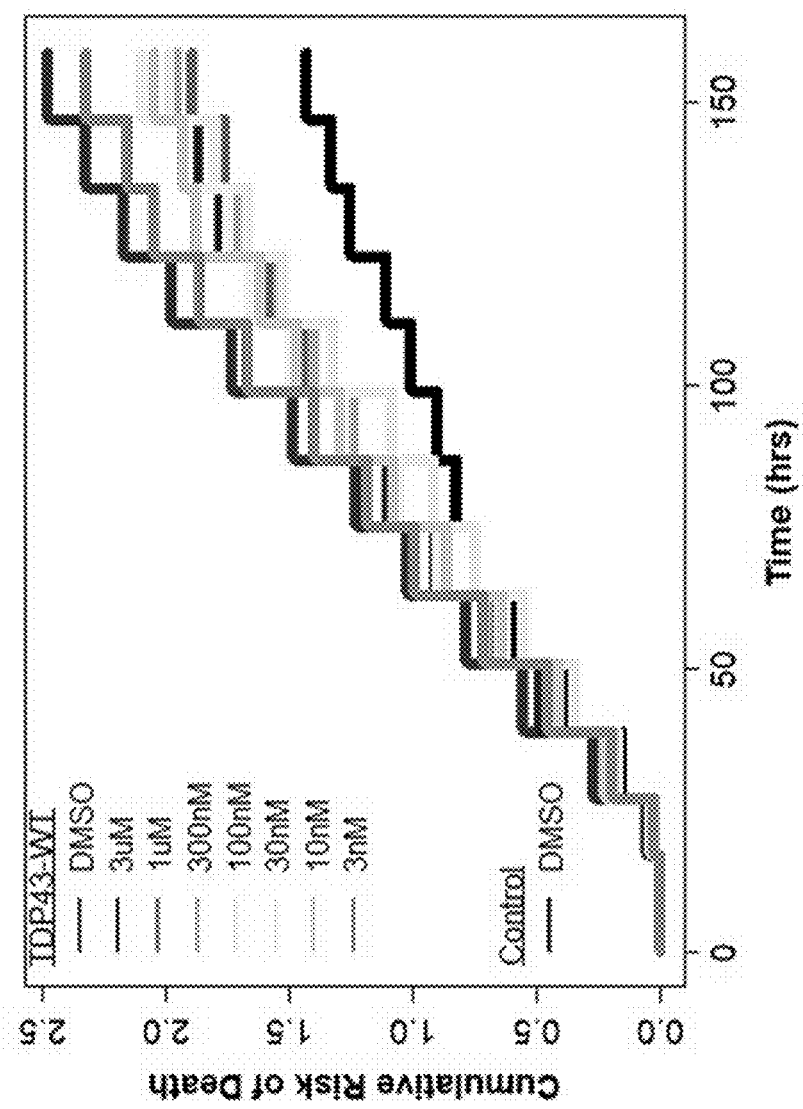
FIGS. 3A and 3B demonstrate that compound (3) promotes survival in primary rat cortical neurons transfected with wild-type TDP-43. Rat primary cortical neurons were co-transfected with a red fluorescent protein (RFP) as a morphological marker and either control (empty vector) or wild-type TDP-43 expression plasmids and treated with vehicle (DMSO) or a titration of compound (3).
Figure 3B:
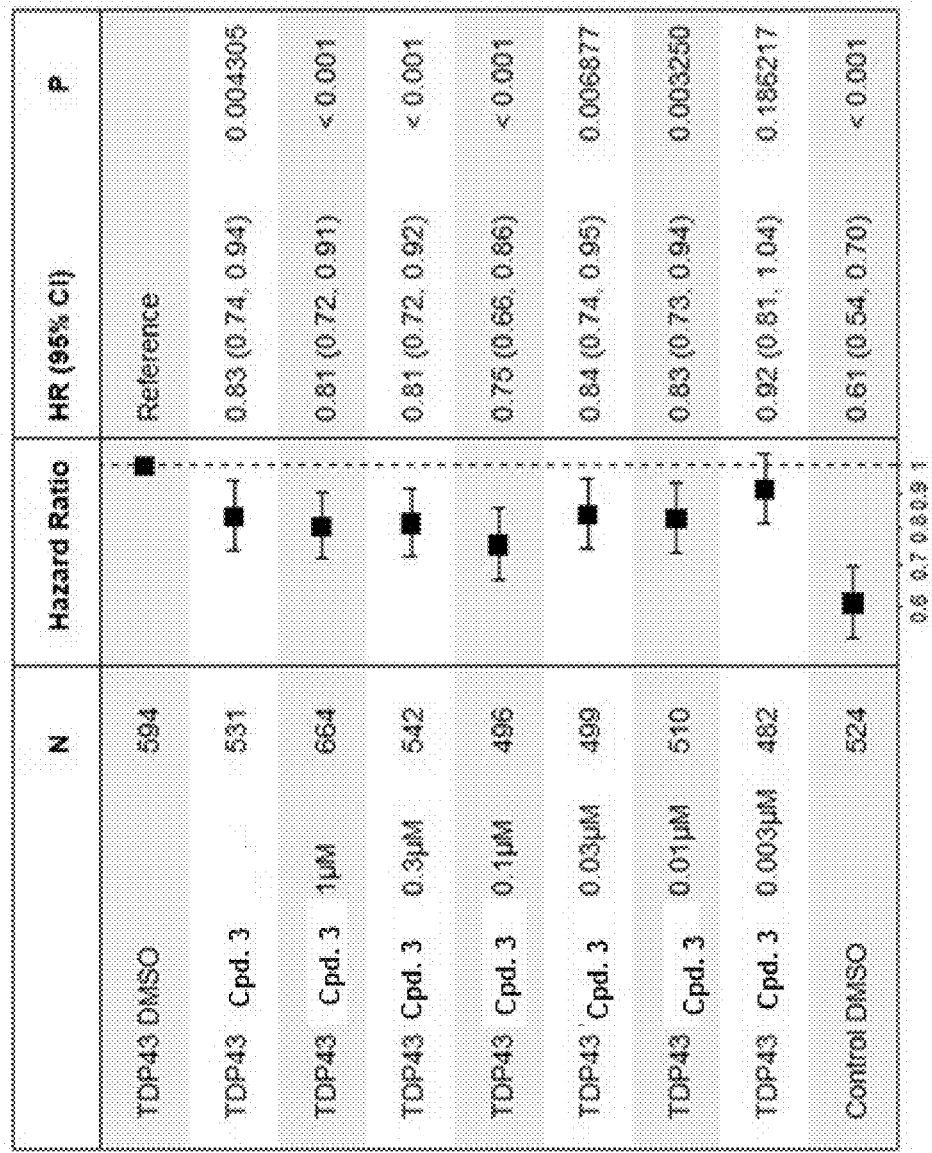
Figure 4A:
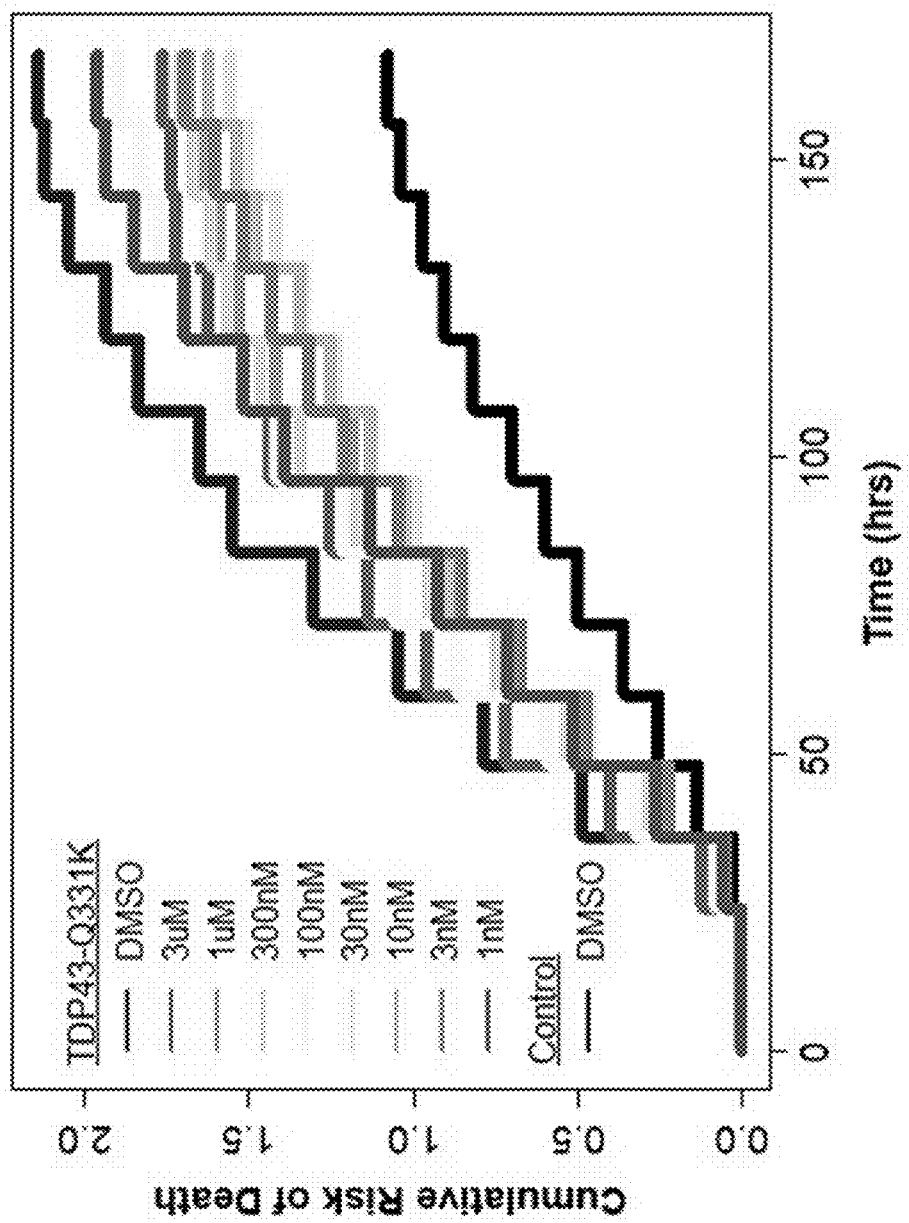
FIGS. 4A and 4B demonstrate that compound (3) promotes survival in primary rat cortical neurons transfected with Q331K Mutant TDP-43. Rat primary cortical neurons were co-transfected with a red fluorescent protein (RFP) as a morphological marker and either control (empty vector) or Q331K mutant TDP-43 expression plasmids and treated with vehicle (DMSO) or a titration of compound (3).
Figure 4B:
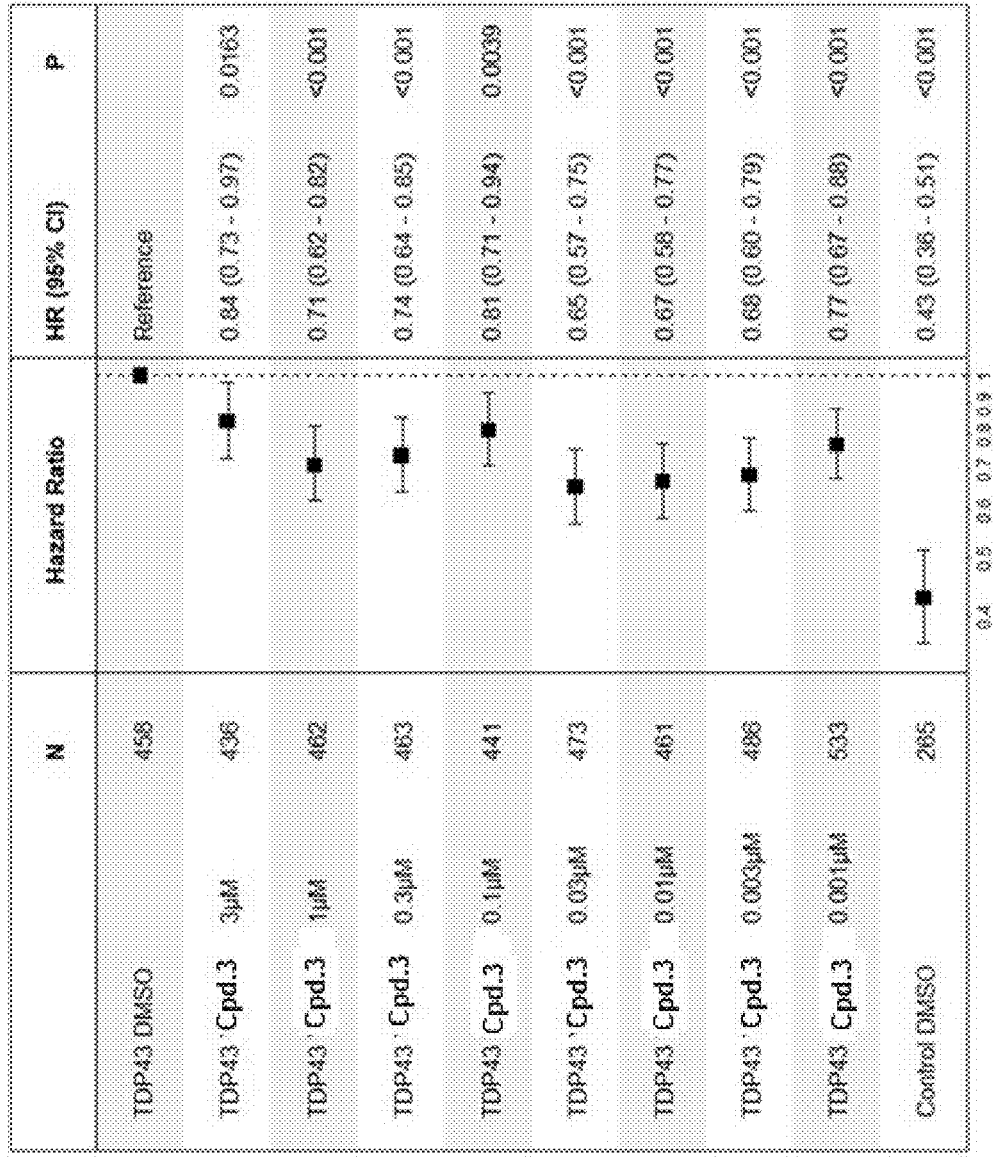
Figure 5A:
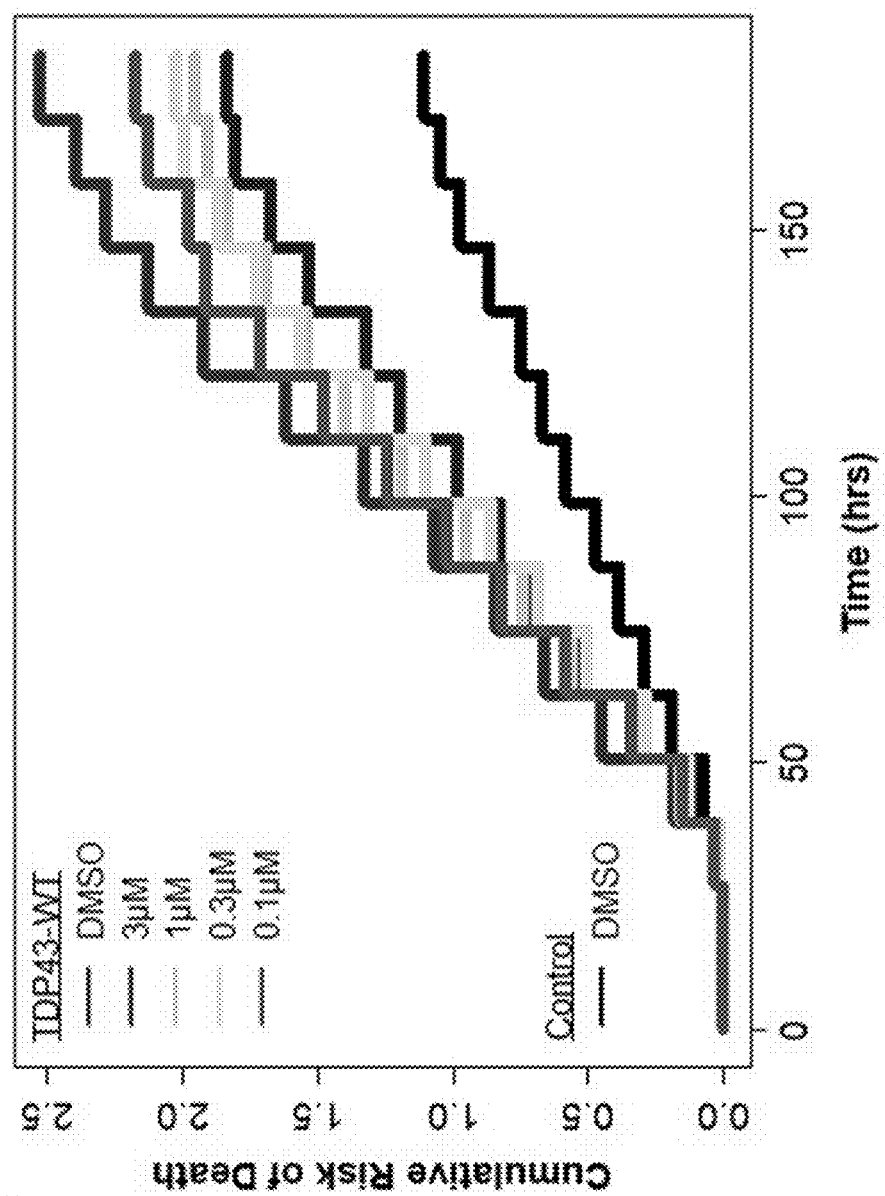
FIGS. 5A and 5B demonstrate that compound (4) promotes survival in primary rat cortical neurons transfected with wild-type TDP-43. Rat primary cortical neurons were co-transfected with a red fluorescent protein (RFP) as a morphological marker and either control (empty vector) or wild type TDP-43 expression plasmids and treated with vehicle (DMSO) or a titration of compound (4).
Figure 5B:
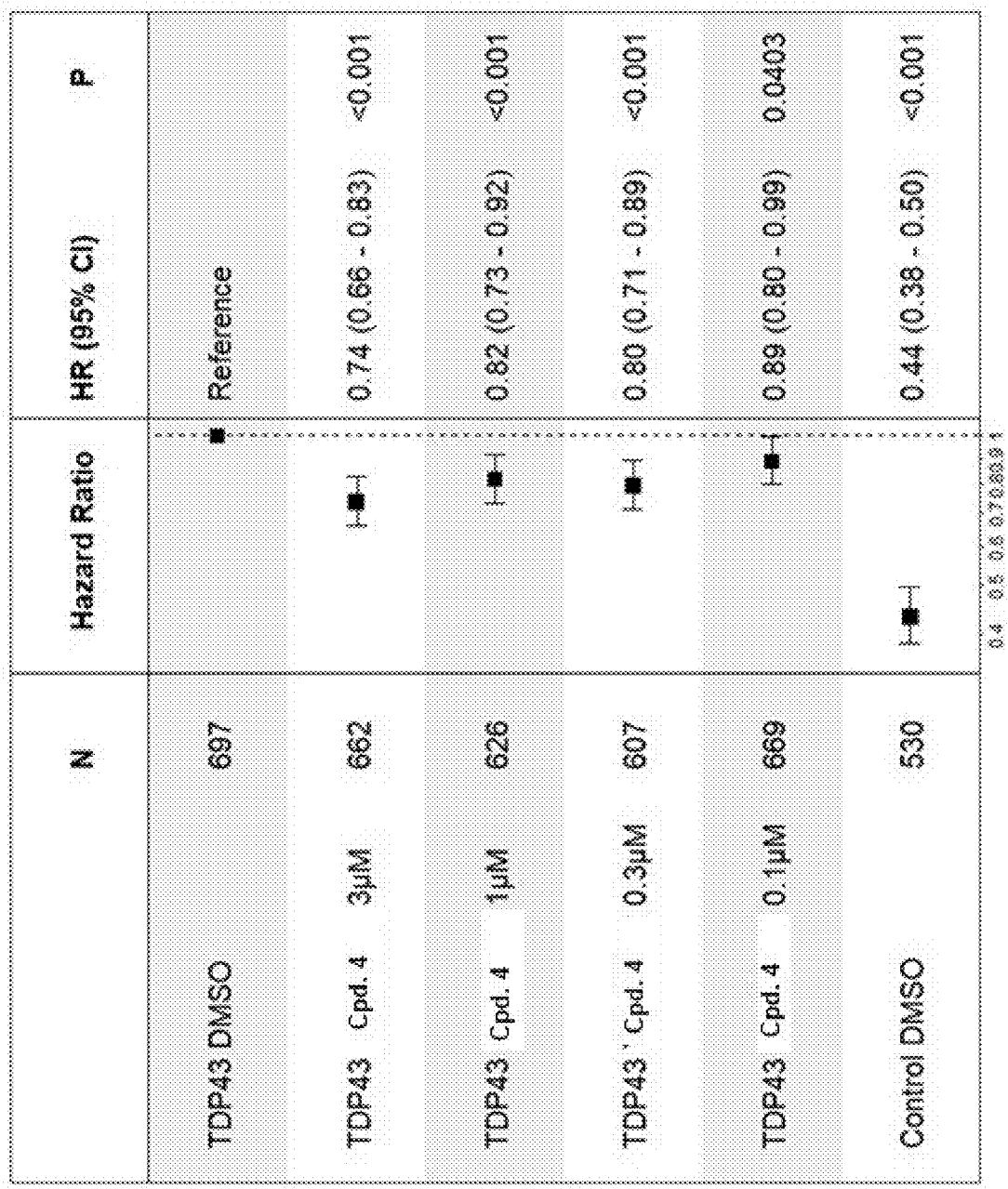

To evaluate the potential role of CYP51A1 in TDP-43 pathology, the aforementioned primary rat cortical neuron TDP-43 models were utilized to test the efficacy of published inhibitors (FIG. 2). Rat cortical neurons transfected with wild type human TDP-43 exhibited a significant reduction in survival compared to neurons transfected with empty vector control, and this reduction in survival was partially alleviated by treatment with compound (3) (FIGS. 3A and 3B). A similar survival befit was conferred by compound (3) when applied to cells transfected with Q331K mutant TDP-43 (FIGS. 4A and 4B). A similar effect in rescuing a survival deficit was observed for a structurally differentiated compound (4) when applied to cells transfected with wild type TDP-43 (FIGS. 5A and 5B). These studies demonstrate that inhibition of Erg11 in yeast and inhibition of Cyp51A1 has a beneficial effect of rescuing cells from wild type and mutant TDP-43 toxicity and promotes cell survival. This is the first demonstration that inhibition of CYP51A1 is beneficial in treating and preventing TDP-43 pathological processes and represents a novel therapeutic approach for the treatment of ALS.

Example 2. Use of a CYP51A1 Inhibitor for the Treatment or Prevention of a Neurological Disorder in a Human Patient Using the compositions and methods described herein, a patient suffering from or at risk of developing a neurological disorder, such as amyotrophic lateral sclerosis, frontotemporal degeneration, Alzheimer's disease, Parkinson's disease, dementia with Lewy Bodies, corticobasal degeneration, progressive supranuclear palsy, dementia parkinsonism ALS complex of Guam, Huntington's disease, Inclusion body myopathy with early-onset Paget disease and frontotemporal dementia (IBMPFD), sporadic inclusion body myositis, myofibrillar myopathy, dementia pugilistica, chronic traumatic encephalopathy, Alexander disease, or hereditary inclusion body myopathy, may be administered a CYP51A1 inhibitor so as to treat the disease, alleviate one or more symptoms of the disease, or slow or prevent the onset of the disease. The CYP51A1 inhibitor may be, for example, a small molecule that specifically binds to an/or inhibits the enzymatic activity of CYP51A1, an antibody or antigen-binding fragment thereof that specifically binds to and/or inhibits the activity of CYP51A1, or substance that reduces expression of functional CYP51A1, such as an interfering RNA molecule (for example, a siRNA, miRNA, or shRNA molecule described herein).

Prior to treatment, the patient may be subjected to one or more analytical tests in order to determine their initial quality of life, muscle strength, muscle function, slow vital capacity, decremental responses exhibited upon repetitive nerve stimulation, among other parameters that describe the patient's initial disease state. The patient may then be administered a CYP51A1 inhibitor, such as by way of oral, transdermal, subcutaneous, intranasal, intravenous, intramuscular, intraocular, parenteral, topical, intrathecal, and/or intracerebroventricular administration. The CYP51A1 inhibitor may be administered to the patient in combination with one or more pharmaceutically acceptable excipients, carriers, or diluents. The CYP51A1 inhibitor may be administered to the patient once or a plurality of times, such as periodically over the course of a treatment period of one or more days, weeks, months, or years.

To determine the responsiveness of the patient to CYP51A1 inhibitor therapy, a physician may perform one or more tests in order to evaluate whether the patient exhibits any of the following indications of clinical benefit:

(i) an improvement in condition as assessed using the amyotrophic lateral sclerosis functional rating scale (ALSFRS) or the revised ALSFRS (ALSFRS-R);

(ii) an increase in slow vital capacity, such as an increase in the patient's slow vital capacity within one or more days, weeks, or months following administration of the CYP51A1 inhibitor;

(iii) a reduction in decremental responses exhibited by the patient upon repetitive nerve stimulation, such as a reduction that is observed within one or more days, weeks, or months following administration of the CYP51A1 inhibitor;

(iv) an improvement in muscle strength, as assessed, for example, by way of the Medical Research Council muscle testing scale (as described, e.g., in Jagtap et al., Ann. Indian. Acad. Neurol. 17:336-339 (2014), the disclosure of which is incorporated herein by reference as it pertains to measuring patient response to neurological disease treatment);

(v) an improvement in quality of life, as assessed, for example, using the amyotrophic lateral sclerosis-specific quality of life (ALS-specific QOL) questionnaire;

(vi) a decrease in the frequency and/or severity of muscle cramps, such as a decrease in cramp frequency and/or severity within one or more days, weeks, or months following administration of the CYP51A1 inhibitor; and/or (vii) a decrease in TDP-43 aggregation, such as a decrease in TDP-43 aggregation within one or more days, weeks, or months following administration of the CYP51A1 inhibitor.

Example 3. Determining the Likelihood of a Patient to Respond to CYP51A1 Inhibitor Therapy Using the compositions and methods described herein, one may determine the propensity of a patient (e.g., a human patient) suffering from a neurological disease to respond to CYP51A1 inhibitor therapy. For example, a physician may obtain a sample from a patient having a neurological disease, such as amyotrophic lateral sclerosis or another neurological disorder described herein. The physician may then determine whether the patient expresses an isoform of TDP-43 having a mutation selected from Q331K, M337V, Q343R, N345K, R361S, and N390D, among others, as these mutations are associated with elevated TDP-43 aggregation and toxicity. This may be done, for example, by determining the patient's genotype at the TDP-43 locus and/or by isolating TDP-43 protein from a biological sample obtained from the patient and sequencing the protein using molecular biology techniques known in the art. A finding that the patient exhibits TDP-43 aggregation and/or expresses a mutant TDP-43 protein having a Q331K, M337V, Q343R, N345K, R361S, or N390D mutation may be taken as an indication that the patient is likely to respond to CYP51A1 inhibitor therapy.

Upon determining that the patient is likely to respond to treatment with a CYP51A1 inhibitor, the patient may be administered one or more CYP51A1 inhibitors, for example, as described in Example Two, above. The inhibitor of CYP51A1 may be a small molecule, such as LEK-935, CP-320626, itraconazole, posaconazole, cyproconazole, voriconazole, fluconazole, clotrimazol, fenticonazole, epoxiconazole, ketoconazole, ravuconazole, isavuconazole, holothurin A, theasaponin, capsicosine, betulafolientriol, prochloraz, propiconazole, prothioconazole, prothioconazole-desthio, tebuconazole, triadimenol, azalanstat, or a variant thereof. In some embodiments, the CYP51A1 inhibitor is an anti-CYP51A1 antibody or antigen-binding fragment thereof, or a compound, such as an interfering RNA molecule, that attenuates CYP51A1 expression.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

What is claimed is:

1. A method of treating a neurological disorder associated with TDP-43 aggregation in a human patient, the method comprising administering to the patient a therapeutically effective amount of a CYP51A1 inhibitor represented by formula (XLIII):

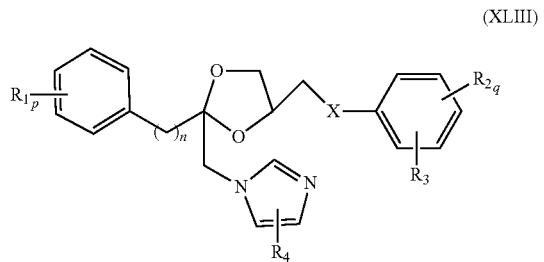

wherein n is 2 or 3;
p is 0, 1, or 2;
q is 0, 1, or 2;
X is oxygen or $S(O)_t$ wherein t is 0, 1, or 2;
each $R_1$ is independently halo, lower alkyl, lower alkoxy, or trifluoromethyl;
each $R_2$ is independently halo or lower alkyl;
$R_3$ is nitro or $-N(R_5)R_6$, where $R_5$ is hydrogen or lower alkyl, and $R_6$ is hydrogen, lower alkyl, lower alkylsulfonyl or $-C(Y)R_7$ where Y is oxygen or sulfur and $R_7$ is hydrogen, lower alkyl, lower alkoxy or $-N(R_8)R_9$ where $R_8$ is hydrogen or lower alkyl and $R_9$ is hydrogen, lower alkyl or lower alkoxycarbonyl; or $R_5$ and $R_6$ together with N is pyrrolidino, piperidino, morpholino, thiomorpholino or piperazino, wherein the piperazino is optionally substituted at the 4-position by $-C(O)R_{10}$ where $R_{10}$ is hydrogen, lower alkyl, lower alkoxy or amino; and
$R_4$ is hydrogen or optionally substituted lower alkyl;
or a pharmaceutically acceptable salt thereof.

2. The method of claim 1, the method comprising:
(i) determining that the patient is susceptible to developing TAR-DNA binding protein (TDP)-43 aggregation; and
(ii) administering to the patient the therapeutically effective amount of the CYP51A1 inhibitor.

3. The method of claim 1, wherein the patient has previously been determined to be susceptible to developing TDP-43 aggregation.

4. The method of claim 1, the method comprising:
(i) determining that the patient expresses a mutant form of TDP-43 having a mutation associated with TDP-43 aggregation; and
(ii) administering to the patient the therapeutically effective amount of the CYP51A1 inhibitor.

5. The method of claim 1, wherein the patient has previously been determined to express a mutant form of TDP-43 having a mutation associated with TDP-43 aggregation.

6. The method of claim 5, wherein the mutation is selected from the group consisting of Q331K, M337V, Q343R, N345K, R361S, and N390D.

7. The method of claim 1, wherein the neuromuscular disorder is amyotrophic lateral sclerosis.

8. The method of claim 1, wherein the CYP51A1 inhibitor is azalanstat.

* * * * *